(12) United States Patent
Silva et al.

(10) Patent No.: US 9,540,623 B2
(45) Date of Patent: Jan. 10, 2017

(54) METHOD FOR INCREASING THE EFFICIENCY OF DOUBLE-STRAND-BREAK INDUCED MUTAGENESIS

(75) Inventors: George H. Silva, Le Plessis Trevise (FR); Rachel Macmaster, Paris (FR)

(73) Assignee: CELLECTIS, Paris (FR)

( * ) Notice: Subject to any disclaimer, the term of this patent is extended or adjusted under 35 U.S.C. 154(b) by 304 days.

(21) Appl. No.: 14/131,210

(22) PCT Filed: Jul. 3, 2012

(86) PCT No.: PCT/US2012/045338
§ 371 (c)(1),
(2), (4) Date: Mar. 5, 2014

(87) PCT Pub. No.: WO2013/009525
PCT Pub. Date: Jan. 17, 2013

(65) Prior Publication Data
US 2014/0234975 A1    Aug. 21, 2014

Related U.S. Application Data

(60) Provisional application No. 61/505,793, filed on Jul. 8, 2011, provisional application No. 61/551,169, filed on Oct. 25, 2011, provisional application No. 61/579,939, filed on Dec. 23, 2011.

(51) Int. Cl.
  *C12N 15/87* (2006.01)
  *C12N 9/22* (2006.01)
  *C12N 15/82* (2006.01)

(52) U.S. Cl.
  CPC ............. *C12N 9/22* (2013.01); *C12N 15/82* (2013.01); *C12N 15/8213* (2013.01); *C12N 15/87* (2013.01); *C07K 2319/00* (2013.01); *C07K 2319/80* (2013.01)

(58) Field of Classification Search
  CPC ............ C07K 2319/00; C07K 2319/09; C07K 2319/80; C07K 2319/81; C12N 15/8213; C12N 15/902–15/907
  See application file for complete search history.

(56) References Cited

FOREIGN PATENT DOCUMENTS

WO  2007/049095 A1  5/2007
WO  2011/064751 A1  6/2011

OTHER PUBLICATIONS

Perrino et al. (The Human TREX2 3'→5'-Exonuclease Structure Suggests a Mechanism for Efficient Nonprocessive DNA Catalysis, J Biol Chem. Apr. 15, 2005;280(15):15212-8. Epub Jan. 19, 2005).*
Chen et al. Biochemical and cellular characteristics of the 3'→5' exonuclease TREX2. Nucleic Acids Research, vol. 35, No. 8, pp. 2682-2694, Apr. 2007.*
Manils et al. Multifaceted role of TREX2 in the skin defense against UV-induced skin carcinogenesis. Oncotarget, vol. 6, No. 26, pp. 22375-22396, Jun. 2015.*
Bennardo et al., Limiting the Persistence of a Chromosome Break Diminishes Its Mutagenic Potential, PLoS Genet 5(10): e1000683 (2009).
De Silva et al., DNA binding induces active site conformational change in the human TREX2 3'-exonuclease, Nucleic Acids Research, 2009, vol. 37, No. 7 2411-2417 (2009).
Bennardo et al., ATM Limits Incorrect End Utilization during Non-Homologous End Joining of Multiple Chromosome Breaks, PLoS Genet 6(11): e1001194 (2010).

* cited by examiner

*Primary Examiner* — Jennifer Dunston
(74) *Attorney, Agent, or Firm* — Law Office of Salvatore Arrigo and Scott Lee, LLP

(57) ABSTRACT

The present invention relates to a method for increasing double-strand-break induced mutagenesis at a genomic locus of interest in a cell, thereby giving new tools for genome engineering, including therapeutic applications and cell line engineering. More specifically, the present invention concerns the combined use of TALEN or meganucleases with TREX2, especially under the form of single-chain proteins.

22 Claims, 11 Drawing Sheets

METHOD FOR INCREASING THE EFFICIENCY OF DOUBLE-STRAND-BREAK INDUCED MUTAGENESIS

This application is the U.S. National Stage of International Application No. PCT/US2012/045338 filed Jul. 3, 2012, which claims priority to U.S. Ser. No. 61/505,793 filed Jul. 8, 2011, U.S. Ser. No. 61/551,169 filed Oct. 25, 2011, and U.S. Ser. No. 61/579,939 filed Dec. 23, 2011, the entire contents of each is incorporated herein by reference.

FIELD OF THE INVENTION

The present invention relates to a method for increasing double-strand break-induced mutagenesis at a genomic locus of interest in a cell, thereby giving new tools for genome engineering, including therapeutic applications and cell line engineering. More specifically, the present invention concerns a method for increasing double-strand break-induced mutagenesis at a genomic locus of interest, leading to a loss of genetic information. The present invention also relates to engineered endonucleases combining dimeric exonucleases, more especially TREX2 and rare-cutting endonucleases such as TALEN and Homing endonucleases, and vectors encoding such nucleases. These novel enzymes are particularly useful for inactivating genes in plants without resorting to chromosomal insertion of exogenous DNA.

BACKGROUND OF THE INVENTION

Mammalian genomes constantly suffer from various types of damage, of which double-strand breaks (DSB) are considered the most dangerous (Haber, 2000). For example, DSBs can arise when the replication fork encounters a nick or when ionizing radiation particles create clusters of reactive oxygen species along their path. These reactive oxygen species may in turn themselves cause DSBs. For cultured mammalian cells that are dividing, 5-10% appear to have at least one chromosomal break (or chromatid gap) at any one time (Lieber & Karanjawala, 2004). Hence, the need to repair DSBs arises commonly (Li et al, 2007) and is critical for cell survival (Haber, 2000). Failure or incorrect repair can result in deleterious genomic rearrangements, cell cycle arrest, or cell death.

Repair of DSBs can occur through diverse mechanisms that can depend on cellular context. Repair via homologous recombination, the most accurate process, is able to restore the original sequence at the break. Because of its strict dependence on extensive sequence homology, this mechanism is suggested to be active mainly during the S and G2 phases of the cell cycle where the sister chromatids are in close proximity (Sonoda et al, 2006). Single-strand annealing is another homology-dependent process that can repair DSB between direct repeats and thereby promotes deletions (Paques & Haber, 1999). Finally, non-homologous end joining (NHEJ) of DNA is a major pathway for the repair of DSBs because it can function throughout the cell cycle and because it does not require a homologous chromosome (Moore & Haber, 1996).

NHEJ comprises at least two different processes (Feldmann et al, 2000). The main and best characterized mechanism involves rejoining of what remains of the two DNA ends through direct re-ligation (Critchlow & Jackson, 1998) or via the so-called microhomology-mediated end joining (MMEJ) (Ma et al, 2003). Although perfect re-ligation of the broken ends is probably the most frequent event, it could be accompanied by the loss or gain of several nucleotides.

Like most DNA repair processes, there are three enzymatic activities required for repair of DSBs by the NHEJ pathway: (i) nucleases to remove damaged DNA; (ii) polymerases to aid in the repair, and; (iii) a ligase to restore the phosphodiester backbone. Depending on the nature of the DNA ends, DNA can be simply re-ligated or terminal nucleotides can be modified or removed by inherent enzymatic activities, such as phosphokinases and exonucleases. Missing nucleotides can also be added by polymerase μ or λ. In addition, an alternative or so-called back-up pathway has been described that does not depend on ligase IV and Ku components and has been involved in class switch and V(D)J recombination (Ma et al, 2003). Overall, NHEJ can be viewed as a flexible pathway wherein the goal is to restore the chromosomal integrity, even at the cost of nucleotide excisions or insertions.

DNA repair can be triggered by both physical and chemical means. Several chemicals are known to cause DNA lesions and are used routinely. Radiomimetic agents, for example, work through free-radical attack on the sugar moieties of DNA (Povirk, 1996). A second group of drugs inducing DNA damage includes inhibitors of topoisomerase I (TopoI) and II (TopoII) (Burden & N., 1998; Teicher, 2008). Other classes of chemicals bind covalently to the DNA and form bulky adducts that are repaired by the nucleotide excision repair (NER) system (Nouspikel, 2009). Chemicals inducing DNA damage have a diverse range of applications, however, although certain agents are more commonly applied in studying a particular repair pathway (e.g. cross-linking agents are favored for NER studies), most drugs simultaneously provoke a variety of lesions (Nagy & Soutoglou, 2009). Furthermore, using these classical strategies the overall yield of induced mutations is quite low, and the DNA damage leading to mutagenesis cannot be targeted to precise genomic DNA sequence.

The most widely used site-directed mutagenesis strategy is gene targeting (GT) via homologous recombination (HR). Efficient GT procedures in yeast and mouse have been available for more than 20 years (Capecchi, 1989; Rothstein, 1991). Successful GT has also been achieved in *Arabidopsis* and rice plants (Endo et al, 2006; Endo et al, 2007; Hanin et al, 2001; Terada et al, 2002). Typically, GT events occur in a fairly small population of treated mammalian cells and are extremely low in higher plant cells, in the range of 0.01-0.1% of the total number of random integration events (Terada et al, 2007). The low GT frequencies reported in various organisms are thought to result from competition between HR and NHEJ for repair of DSBs. There are extensive data indicating that DSB repair by NHEJ is error-prone due to end-joining processes that generate insertions and/or deletions (Britt, 1999). Thus, these NHEJ-based strategies might be more effective than HR-based strategies for targeted mutagenesis into cells.

Expression of I-SceI, a rare cutting endonuclease, has been shown to introduce mutations at I-SceI cleavage sites in mammalian cells (Liang et al, 1998), *Arabidopsis* and tobacco (Endo et al, 2006; Endo et al, 2007; Hanin et al, 2001; Kirik et al, 2000; Terada et al, 2007). However, the use of endonucleases is limited to rarely occurring natural recognition sites or to artificially introduced target sites. To overcome this problem, meganucleases with engineered specificity towards a chosen sequence have been developed (Arnould et al, 2006a; Arnould et al, 2007; Grizot et al, 2009; Smith et al, 2006). Meganucleases show high specificity to their DNA target, these proteins being able to cleave a unique chromosomal sequence and therefore do not affect global genome integrity. Natural meganucleases are essentially represented by homing endonucleases, a widespread class of proteins found in eukaryotes, bacteria and archae (Chevalier & Stoddard, 2001). Homing endonucleases can be classified in five different families, the largest and best characterized one being the LAGLIDAG homing endonuclease family, named after a conserved sequence motif (Stoddard, 2005). LAGLIDADG homing endonucleases can be dimeric (possessing a single LAGLIDADG motif per polypeptide), or monomeric (possessing two LAGLIDADG motifs per polypeptide).

Early studies of the I-SceI and HO homing endonucleases illustrated how the cleavage activities of these proteins could be used to initiate HR events in living cells and demonstrated the recombinogenic properties of chromosomal DSBs (Dujon et al, 1986; Haber, 1995). Since then, I-SceI-induced HR has been successfully used for genome engineering purposes in bacteria (Posfai et al, 1999b), mammalian cells (Cohen-Tannoudji et al, 1998; Donoho et al, 1998; Grizot et al, 2009; Sargent et al, 1997), mice (Gouble et al, 2006) and plants (Puchta et al, 1996; Siebert & Puchta, 2002). Meganucleases have emerged as the scaffolds of choice for deriving genome engineering tools cutting a desired target sequence (Paques & Duchateau, 2007b). Combinatorial assembly processes allowing for the engineering of meganucleases with modified specificities have been described (Arnould et al, 2006a; Arnould et al, 2007; Grizot et al, 2009; Smith et al, 2006). Briefly, these processes rely on the identification of locally engineered variants with a substrate specificity that differs from that of the wild-type meganuclease by only a few nucleotides.

Zinc-finger nucleases (ZFNs) represent another type of specific nuclease. ZFNs are chimeric proteins composed of a synthetic zinc-finger-based DNA binding domain fused to a DNA cleavage domain. By modification of the zinc-finger DNA binding domain, ZFNs can be specifically designed to cleave virtually any long stretch of dsDNA sequence (Cathomen & Joung, 2008; Kim et al, 1996). A NHEJ-based targeted mutagenesis strategy was recently developed for several organisms by using synthetic ZFNs to generate DSBs at specific genomic sites (Beumer et al, 2008; Doyon et al, 2008a; Holt et al, 2010; Lloyd et al, 2005; Meng et al, 2008; Perez et al, 2008; Santiago et al, 2008). Subsequent repair of the DSBs by NHEJ frequently produces deletions and/or insertions at the joining site. For example, in zebrafish embryos the injection of mRNA coding for engineered ZFNs led to animals carrying the desired heritable mutations (Doyon et al, 2008b). In plant, similar NHEJ-based targeted mutagenesis has also been successfully applied (Lloyd et al, 2005). Although these powerful tools are available, there is still a need to further improve double-strand break-induced mutagenesis.

Recent studies suggest that co-expressing TREX2 exonuclease with I-SceI meganuclease modify gene repair activity in mouse ES cells, thereby causing partial degradation of chromosomal DNA by I-SceI (Bennardo et al, 2009). However, it was found in these studies that limiting the persistence of a chromosome break with TREX 2, diminishes the mutagenic potential of the meganuclease.

In this context, the inventors have developed an original approach to increase the efficiency of targeted DSB-induced mutagenesis based on the use of single-chain proteins combining TREX2 exonuclease with different rare-cutting endonucleases, such LAGLIDADG homing endonucleases and TALENs.

This approach has proven particular efficiency for gene mutagenesis, especially in plant transformation.

BRIEF SUMMARY OF THE INVENTION

The present invention relates to single-chain molecules of dimeric exonuclease, typically TREX2, preferably coupled with a dimeric endonuclease, such as a TALEN or a LAGLIDAG homing endonuclease. These molecules enhance the frequency of NHEJ-based targeted mutagenesis into chromosomal genes without insertion of exogeneous DNA.

The present invention also relates to specific nucleic acids or vectors encoding these single-chain molecules, as well as compositions and kits comprising those.

The above polypeptides and polynucleotides according to the invention are useful for targeted mutagenesis into cells, especially in plant cells.

The above objects highlight certain aspects of the invention. Additional objects, aspects and embodiments of the invention are found in the following detailed description of the invention.

BRIEF DESCRIPTION OF THE DRAWINGS

In addition to the preceding features, the invention further comprises other features that will emerge from the description and appended drawings that follow. A more complete appreciation of the invention and many of the attendant advantages thereof will be readily obtained as the same becomes better understood by reference to the following figures in conjunction with the detailed description below.

Cells were co-transfected with 1 μg of expression vector for the SC_GS meganuclease and increasing amounts of plasmids coding for TREX2 protein taken as a control (pCLS7673, SEQ ID NO: 14), and the four following TREX2 single-chain molecules: scTrex1 (pCLS8981, SEQ ID NO: 9), scTrex2 (pCLS8982, SEQ ID NO: 10), scTrex3 (pCLS8983, SEQ ID NO: 11) and scTrex4 (pCLS8986, SEQ ID NO: 12). The percentage of GFP-positive cells induced in a NHEJ model was measured by flow cytometry three days post transfection.

Figure 2:
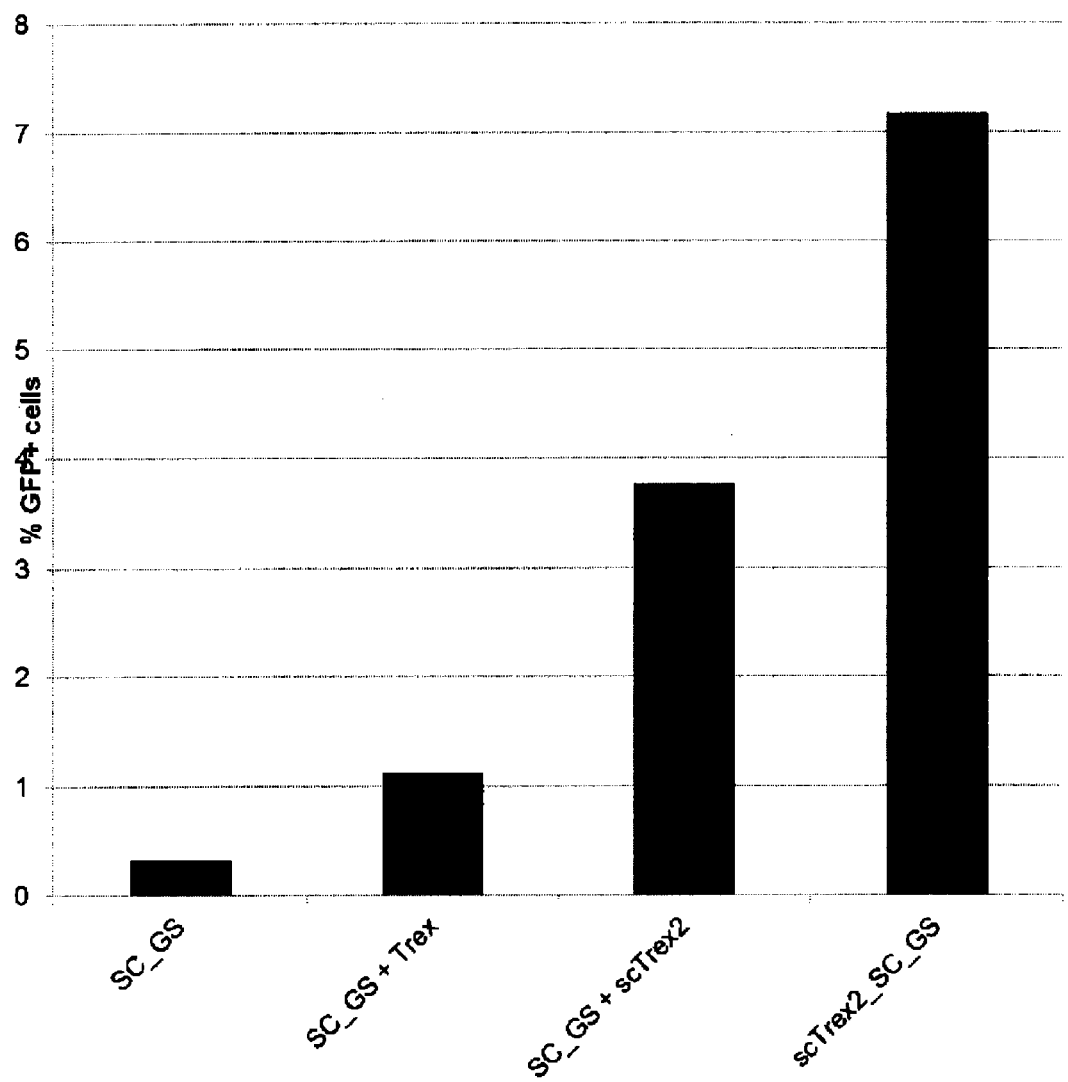

FIG. 2: Cells were co-transfected with 3 μg of plasmid encoding the SC_GS meganuclease (either alone or in fusion) as follows: SC_GS (pCLS2690, SEQ ID NO: 13), SC_GS (pCLS2690, SEQ ID NO: 13)+2 μg TREX (pCLS7673, SEQ ID NO: 14), SC_GS (pCLS2690, SEQ ID NO: 13)+2 μg scTrex2 (pCLS8982, SEQ ID NO: 10) and scTrex2-10-SC_GS (pCLS9572, SEQ ID NO: 39). The percentage of GFP-positive cells was measured four days post transfection by flow cytometry analysis using Guava instrumentation (Millipore).

Figure 3:
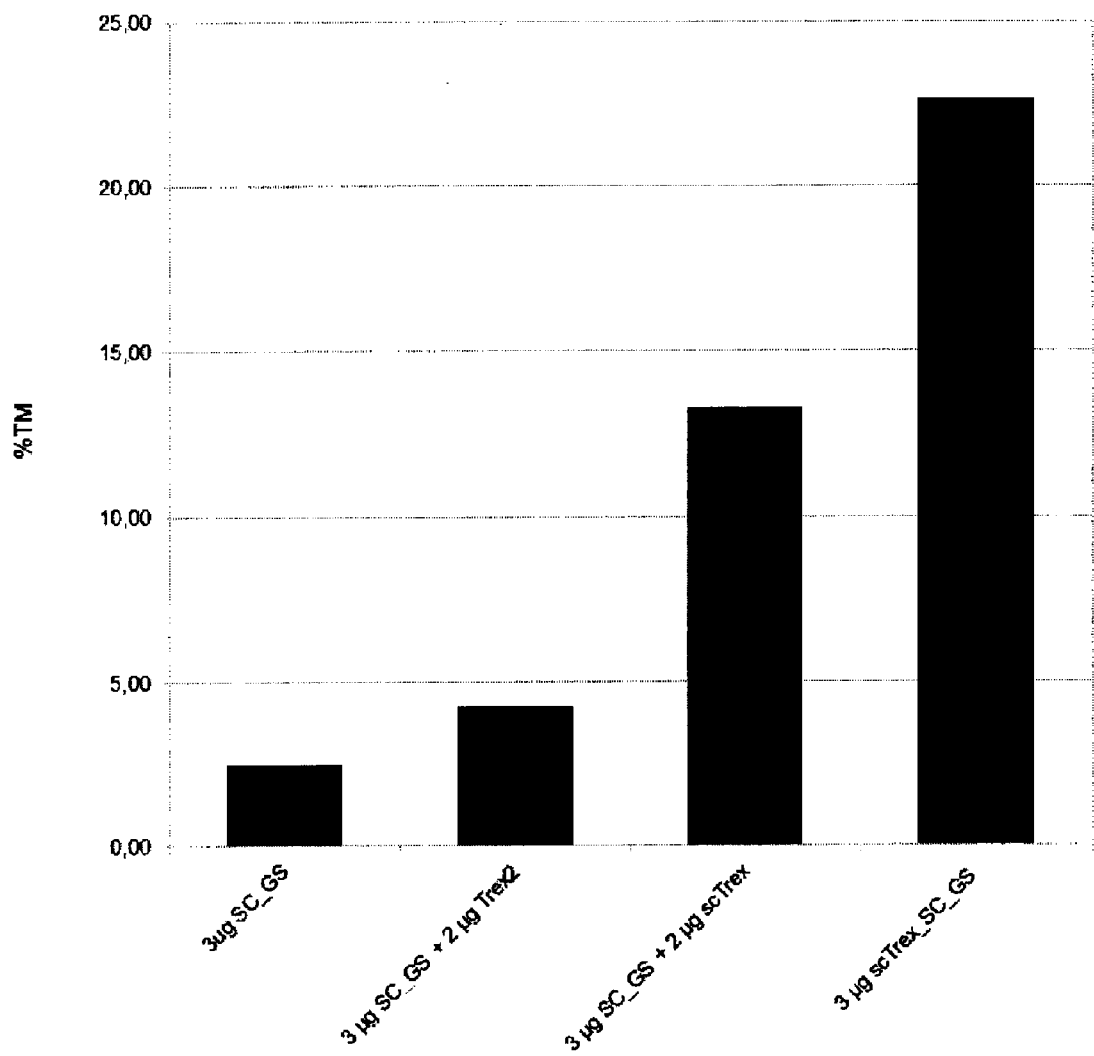

FIG. 3: Percentage of targeted mutagenesis events (insertions and deletions) generated by SC_GS (SEQ ID NO: 60), SC_GS (SEQ ID NO: 60)+TREX (SEQ ID NO: 26), SC_GS (SEQ ID NO: 60)+scTrex2 (SEQ ID NO: 6) or scTrex2-10-SC_GS (SEQ ID NO: 56) and detected in the vicinity of the GS_CHO1 site using deep sequencing analysis (454 Life Sciences).

Figure 4:
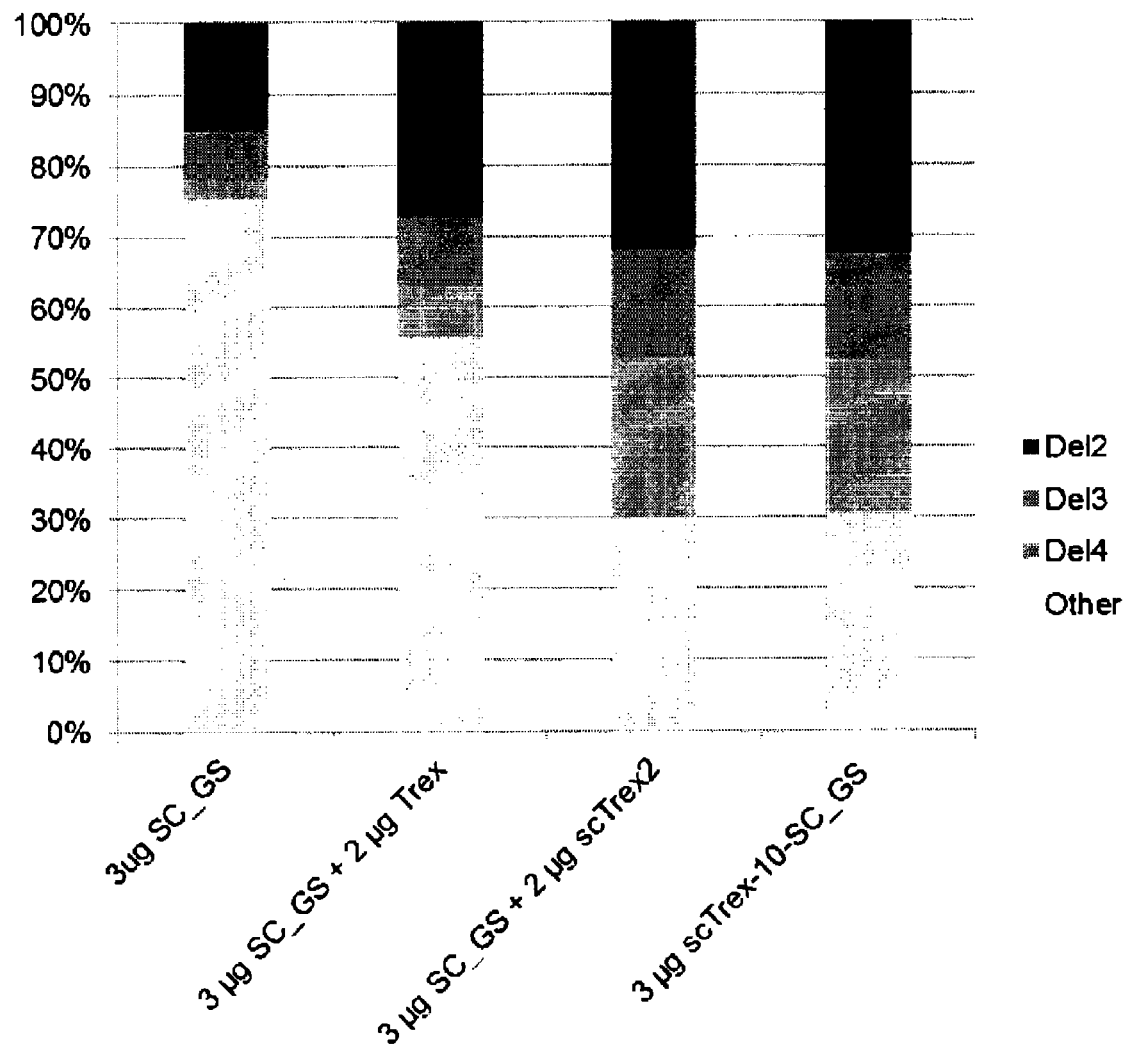

FIG. 4: Percentage of events corresponding to a deletion of 2 (Del2), 3 (Del3) or 4 (Del4) nucleotides at the end of double-strand break (corresponding to the loss of the 3' overhang), generated by SC_GS (SEQ ID NO: 60), SC_GS (SEQ ID NO: 60)+TREX (SEQ ID NO: 26), SC_GS (SEQ ID NO: 60)+scTrex2 (SEQ ID NO: 6) or scTrex2-10-SC_GS (SEQ ID NO: 56); Other indicates any other mutagenic NHEJ events (e.g. insertions or extended deletions).

Figure 5:
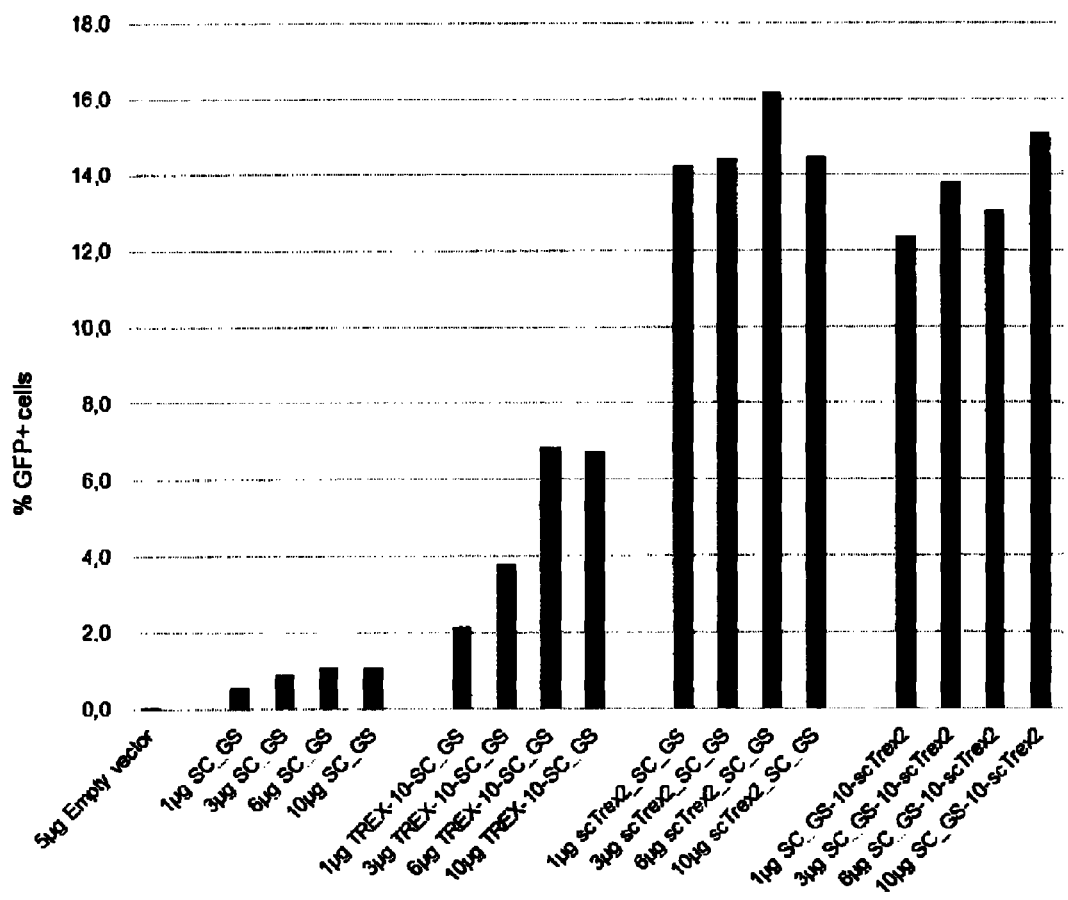

FIG. 5: Dose response measured using the GFP model at the GS CHO1 target. Cells were transfected with increasing amounts (1, 3, 6 or 10 μg) of SC_GS (SEQ ID NO: 60), Trex-10-SC_GS (SEQ ID NO: 53), scTrex2-10-SC_GS (SEQ ID NO: 56) or SC_GS-10-scTrex2 (SEQ ID NO: 57) as indicated. The percentage of GFP-positive cells was measured four days post transfection.

Figure 6:
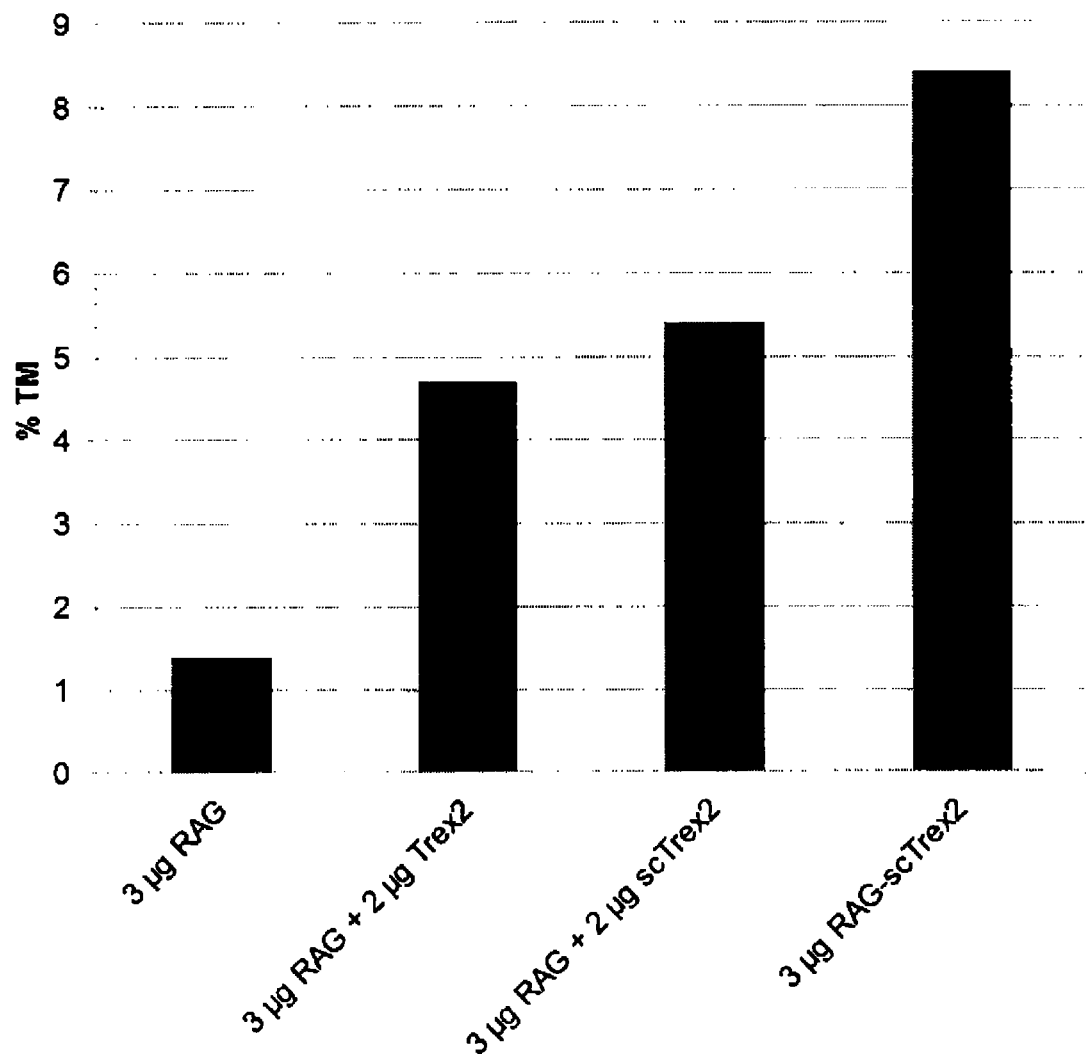

FIG. 6: Percentage of targeted mutagenesis events (insertions and deletions) generated by SC_RAG (SEQ ID NO: 47), SC_RAG (SEQ ID NO: 47)+TREX (SEQ ID NO: 26), SC_RAG (SEQ ID NO: 47)+scTrex2 (SEQ ID NO: 6) or scTrex2-10-SC_RAG (SEQ ID NO: 59) and detected in the vicinity of the RAG site using deep sequencing analysis (454 Life Sciences).

Figure 7:
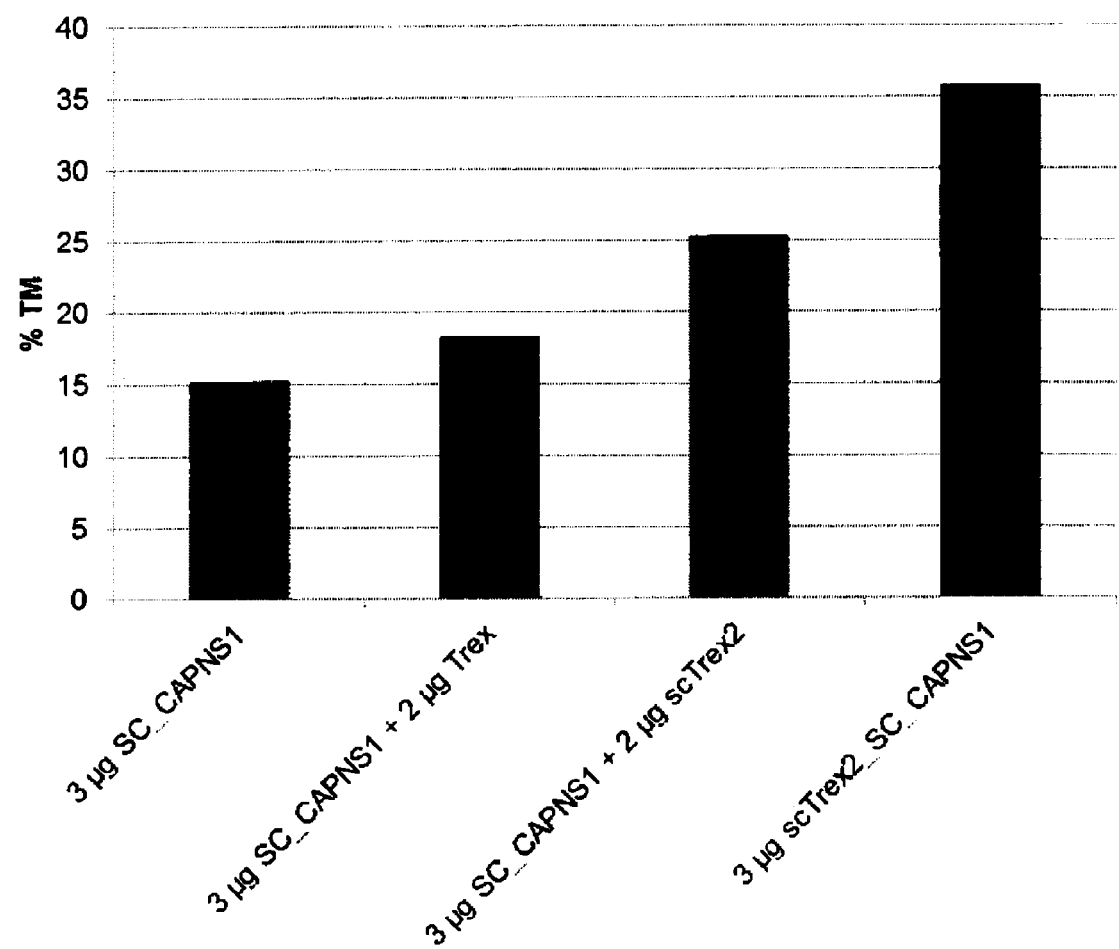

FIG. 7: Percentage of targeted mutagenesis events (insertions and deletions) generated by SC_CAPNS1 (SEQ ID NO: 45), SC_CAPNS1 (SEQ ID NO: 45)+TREX (SEQ ID NO: 26), SC_CAPNS1 (SEQ ID NO: 45)+scTrex2 (SEQ ID NO: 6) or scTrex2-10-SC_CAPNS1 (SEQ ID NO: 58) and detected in the vicinity of the CAPNS1 site using deep sequencing analysis (454 Life Sciences).

Figure 8:
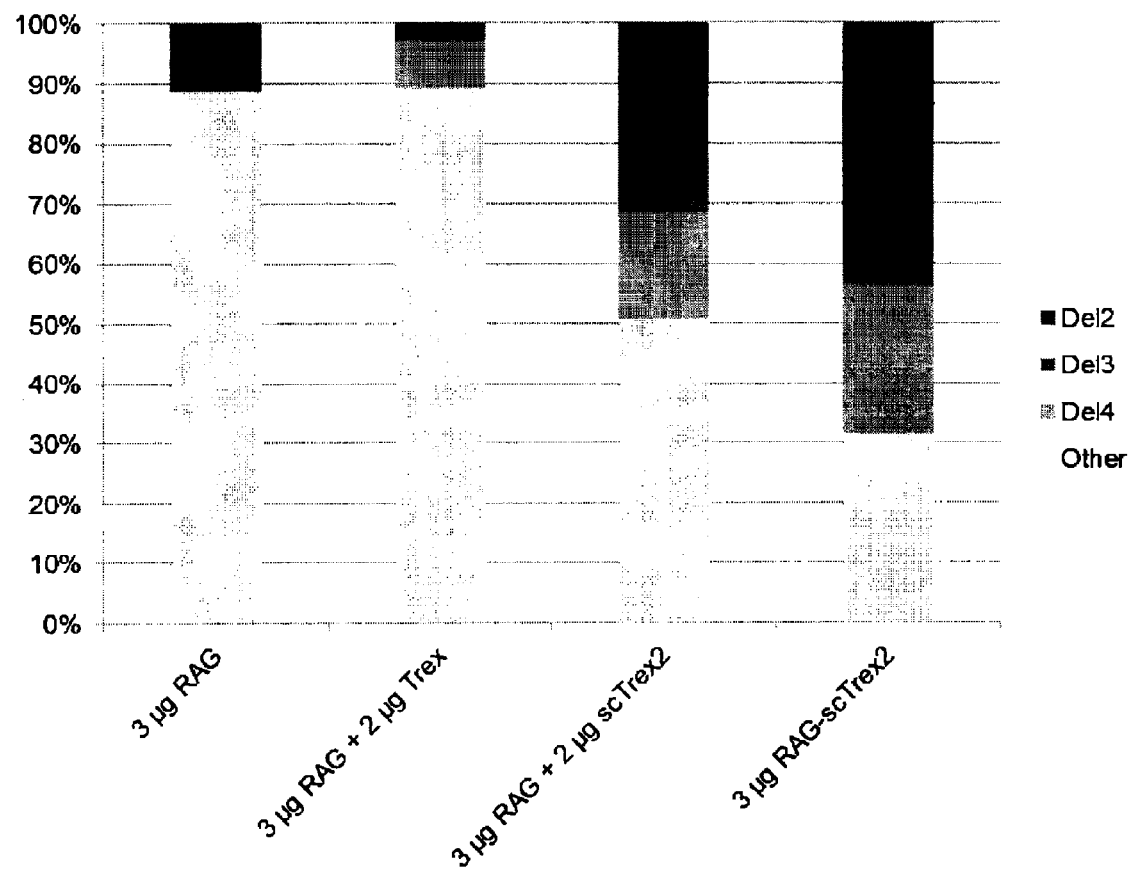

FIG. 8: Percentage of events corresponding to a deletion of 2 (Del2), 3 (Del3) or 4 (Del4) nucleotides at the end of double-strand break (corresponding to the loss of the 3' overhang), generated by SC_RAG (SEQ ID NO: 47), SC_RAG (SEQ ID NO: 47)+TREX (SEQ ID NO: 26), SC_RAG (SEQ ID NO: 47)+scTrex2 (SEQ ID NO: 6) or scTrex2-10-SC_RAG (SEQ ID NO: 59); Other indicates any other mutagenic NHEJ events (e.g. insertions or extended deletions).

Figure 9:
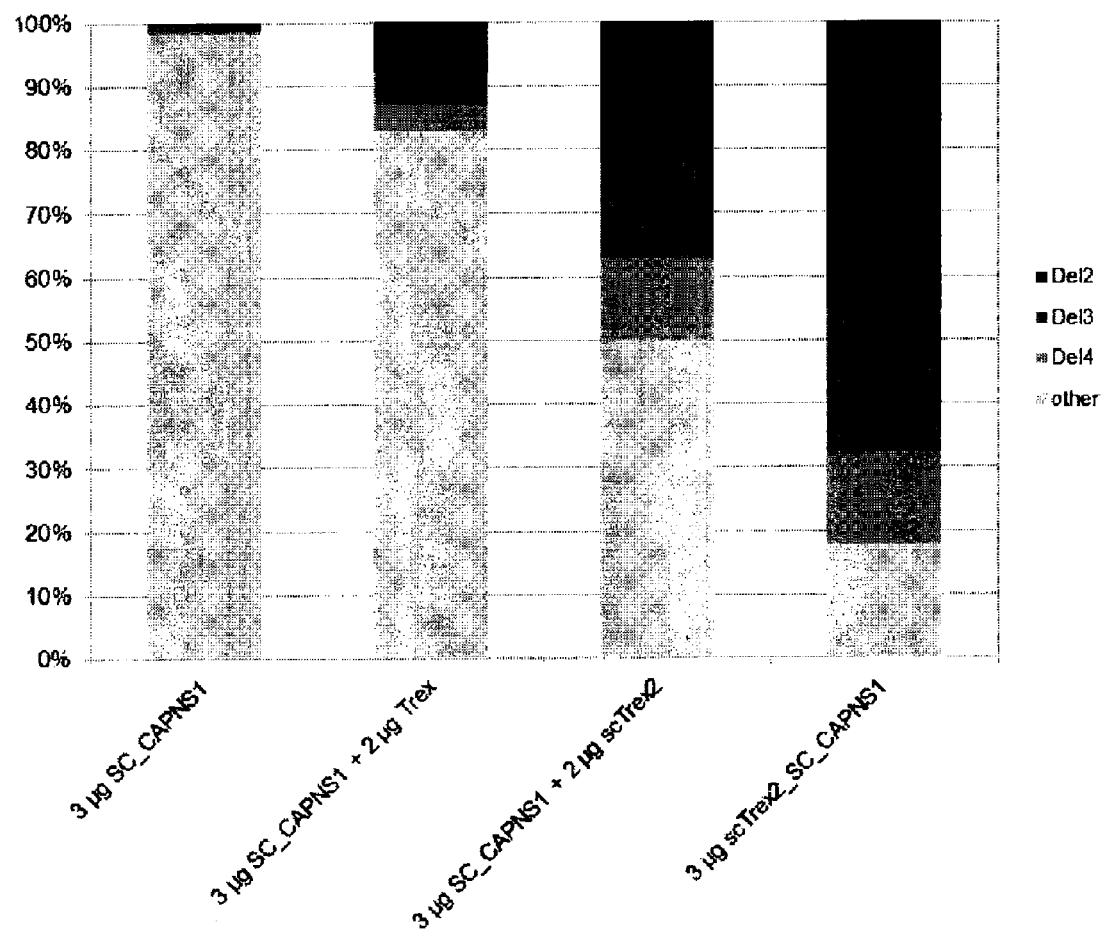

FIG. 9: Percentage of events corresponding to a deletion of 2 (Del2), 3 (Del3) or 4 (Del4) nucleotides at the end of double-strand break (corresponding to the loss of the 3' overhang), generated by SC_CAPNS1 (SEQ ID NO: 45), SC_CAPNS1 (SEQ ID NO: 45)+TREX (SEQ ID NO: 26), SC_CAPNS1 (SEQ ID NO: 45)+scTrex2 (SEQ ID NO: 6) or scTrex2-10-SC_CAPNS1 (SEQ ID NO: 58); Other indicates any other mutagenic NHEJ events (e.g. insertions or extended deletions).

Figure 10:
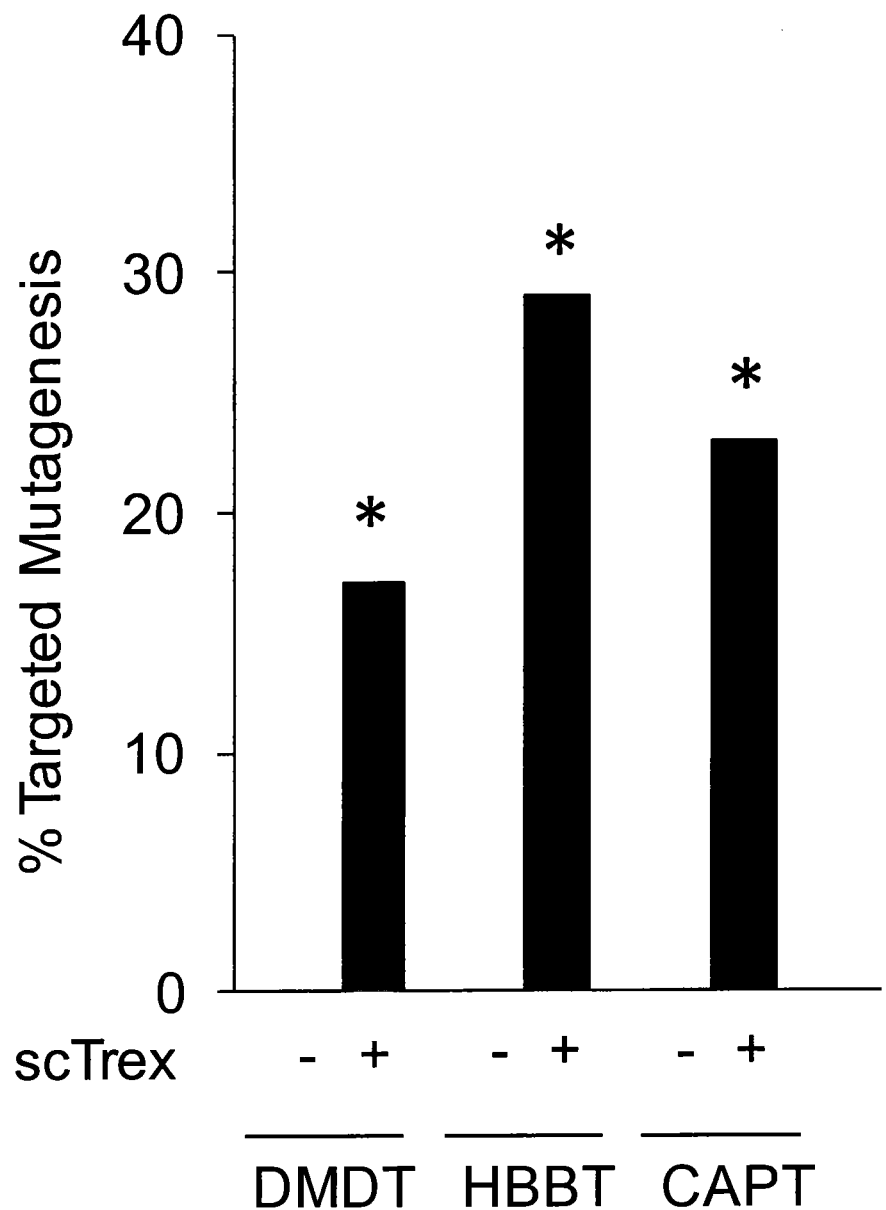

FIG. 10: Mutagenesis frequency induced by TALEN in presence of scTrex2. The TALENs DMDT, HBBT and CAPT targeting the DMD, HBBT and CAPT_target DNA sequences, respectively, were tested for their ability to induce mutagenesis in presence or absence of the DNA processing enzyme scTrex2. The percentage of mutagenesis frequency induced by TALEN in presence (+) or absence (−) of scTrex2 was determined 3 days post-transfection by deep sequencing analysis of amplicons surrounding a specific target. *represents the significant difference ($p<10^{-16}$) between the two conditions (with or without scTrex2).

Figure 11:
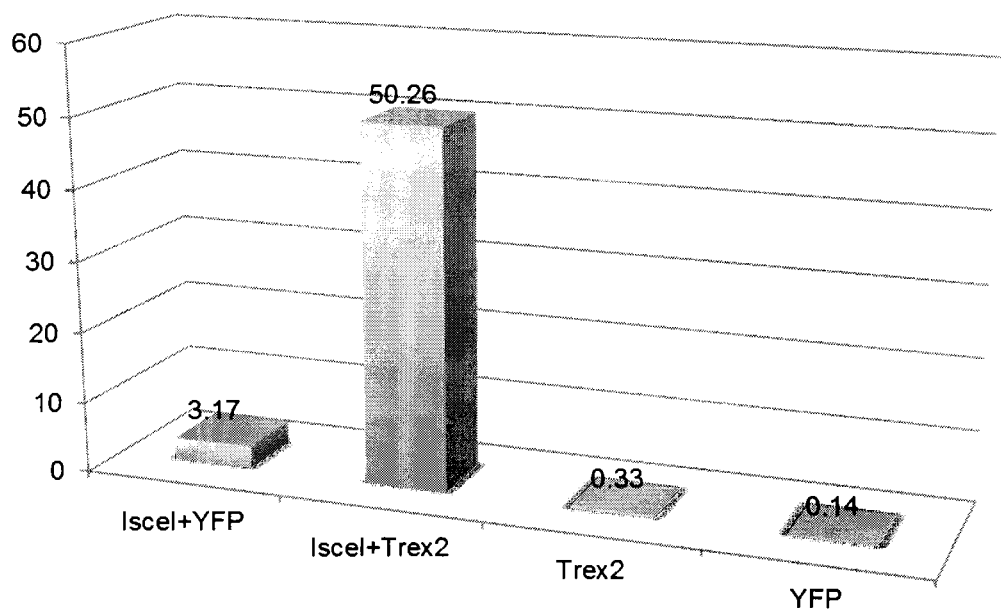

FIG. 11: Mutagenesis frequency obtained in example 4 with co-delivery of TREX2 and I-sceI in protoplasts derived from a tobacco line with an intergrated I-sceI recognition site. YFP: yellow fluorescent protein (transformation control).

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

According to a first aspect of the invention is a single-chain molecule of a dimeric exonuclease (scExo) to be co-transfected with a gene encoding a rare-cutting endonuclease. Such single-chain exonuclease, when expressed in a cell comprising a nucleic acid sequence encoding a rare-cutting endonuclease and including in ite genome a site recognized by said rare-cutting endonuclease, has been found to stimulate the frequency of induced NHEJ-based targeted mutagenesis at this site. Without being bound by theory, the exonuclease is believed to prevent scarless re-ligation of the site of interest recognized by the rare-cutting endonuclease thereby channeling more DSBs into an error-prone DSB repair pathway, but it could also act by other mechanisms (Dumitrache et al. 2011). Such scExo has generally a higher stimulatory effect than when the exonuclease is expressed under a dimeric form as reported in the prior art. Therefore, the co-expression of said scExo with said rare-cutting endonuclease represents a significant advantage when compared with models where a dimeric exonuclease is used, as described by Bennardo et al. (Bennardo et al, 2009).

In a preferred embodiment, said scExo is a polypeptide comprising:
(i) a first polypeptide sharing at least 80% similarity with the human TREX2 exonuclease protomer (SEQ ID NO: 26), a functional mutant, a variant or derivative thereof;
(ii) a second polypeptide sharing at least 80% similarity with the human TREX2 exonuclease protomer (SEQ ID NO: 26), a functional mutant, a variant or derivative thereof;

(iii) a peptidic linker connecting said first and second polypeptides

In a preferred embodiment, said scExo comprises a sequence selected from the group consisting of SEQ ID NO: 5-8.

In a preferred embodiment, said scExo is a single-chained version of the dimeric TREX2 exonuclease comprising:
(i) a first polypeptide sharing at least 80% similarity with the human TREX2 exonuclease protomer (SEQ ID NO: 26), a functional mutant, a variant or derivative thereof;
(ii) a peptidic linker;
(iii) a second polypeptide sharing at least 80% similarity with the human TREX2 exonuclease protomer (SEQ ID NO: 26), a functional mutant, a variant or derivative thereof;

According to a further embodiment of the invention said single-chain exonuclease as described above is fused with a rare-cutting endonuclease, in particular a meganuclease or a TALEN.

When said single-chain exonuclease is fused to a meganuclease, it can give rise to a polypeptide comprising:
(i) a first polypeptide sharing at least 80% similarity with the human TREX2 exonuclease protomer (SEQ ID NO: 26), a functional mutant, a variant or derivative thereof;
(ii) a second polypeptide sharing at least 80% similarity with the human TREX2 exonuclease protomer (SEQ ID NO: 26), a functional mutant, a variant or derivative thereof;
(iii) a peptidic linker connecting said first and second polypeptides
(iv) a third polypeptide sharing at least 80% similarity with a wild type LAGLIDADG meganuclease.

Said single chain exonuclease-meganuclease can include additional peptidic linkers to link the different polypeptides, especially between the exonuclease monomers.

Said wild type LAGLIDADG meganuclease can be selected, for instance, from the group consisting of I-SceI, I-ChuI, I-CreI, I-CsmI, PI-SceI, PI-TliI, PI-MtuI, I-CeuI, I-SceII, I-SceIII, HO, PI-CivI, PI-CtrI, PI-AaeI, PI-BsuI, PI-DhaI, PI-DraI, PI-MavI, PI-MchI, PI-MfuI, PI-MflI, PI-MgaI, PI-MgoI, PI-MinI, PI-MkaI, PI-MleI, PI-MmaI, PI-MshI, PI-MsmI, PI-MthI, PI-MtuI, PI-MxeI, PI-NpuI, PI-PfuI, PI-RmaI, PI-SpbI, PI-SspI, PI-FacI, PI-MjaI, PI-PhoI, PI-TagI, PI-ThyI, PI-TkoI, PI-TspI, I-MsoI; or can be a functional mutant or variant thereof, whether homodimeric, heterodimeric or monomeric. In a preferred embodiment, said LAGLIDADG meganuclease is a I-CreI derivative.

In a preferred embodiment, said LAGLIDADG meganuclease shares at least 80% similarity with the natural I-CreI LAGLIDADG meganuclease.

In a preferred embodiment, said LAGLIDADG meganuclease shares at least 80% similarity with residues 1-152 of the natural I-CreI LAGLIDADG meganuclease. Also the above third polypeptide may consists of two monomers sharing at least 80% similarity with residues 1-152 of the natural I-CreI LAGLIDADG meganuclease linked together, with or without a linker peptide.

In a preferred embodiment, said single-chain TREX2 exonuclease fused with a LAGLIDADG meganuclease comprises a sequence selected from the group consisting of SEQ ID NO: 56-59, a functional mutant, a variant or a derivative thereof.

In a second aspect the present invention relates to a method for increasing double-strand break-induced mutagenesis at a genomic locus of interest, leading to a loss of genetic information at said genomic locus of interest by NHEJ.

In a preferred embodiment, said method for increasing double-strand-break induced mutagenesis at a genomic locus of interest in a cell comprises the steps of:
(i) Identifying at said genomic locus of interest at least one DNA target sequence cleavable by one natural or engineered LAGLIDADG meganuclease;
(ii) Introducing said LAGLIDADG meganuclease into the cell together with a single-chained version of the dimeric TREX2 exonuclease;
thereby obtaining a cell in which double-strand-break induced mutagenesis at said genomic locus of interest is increased.

In another preferred embodiment, said method for increasing double-strand-break induced mutagenesis at a genomic locus of interest in a cell comprises the steps of:
(i) Identifying at said genomic locus of interest at least one DNA target sequence cleavable by one natural or engineered LAGLIDADG meganuclease
(ii) Introducing said natural or engineered meganuclease fused with a single-chained version of the dimeric TREX2 exonuclease wherein said polypeptide recognizes said target DNA
thereby obtaining a cell in which double-strand break-induced mutagenesis at said genomic locus of interest is increased.

In a third aspect, the present invention relates to a single-chain version of a dimeric exonuclease, which enhances the frequency of NHEJ based targeted mutagenesis induced by a rare-cutting endonuclease whose action on DNA liberates 3'-OH overhangs.

When said single-chain exonuclease is fused to a TALEN, it can give rise to a polypeptide comprising:
(i) a first polypeptide sharing at least 80% similarity with the human TREX2 exonuclease protomer (SEQ ID NO: 26), a functional mutant, a variant or derivative thereof;
(ii) a peptidic linker;
(iii) a second polypeptide sharing at least 80% similarity with the human TREX2 exonuclease protomer (SEQ ID NO: 26), a functional mutant, a variant or derivative thereof;
(iv) a peptidic linker;
(v) a third polypeptide sharing at least 80% similarity with a TALEN.

In a preferred embodiment, said single-chain TREX2 exonuclease is fused to the N-terminus of said rare-cutting endonuclease. In another preferred embodiment, said single-chain TREX2 exonuclease is fused to the C-terminus of said said rare-cutting endonuclease, especially when it is a LAGLIDADG meganuclease.

In another embodiment, said method for increasing double-strand-break induced mutagenesis at a genomic locus of interest in a cell comprises the steps of:
(i) identifying at said genomic locus of interest at least one DNA target sequence cleavable by one natural or engineered rare-cutting endonuclease;
(ii) introducing said natural or engineered rare-cutting endonuclease into the cell together with a single-chained version of the dimeric TREX2 exonuclease;
thereby obtaining a cell in which double-strand-break induced mutagenesis at said genomic locus of interest is increased.

In a preferred embodiment, said method for increasing double-strand-break induced mutagenesis at a genomic locus of interest in a cell comprises the steps of:
(i) identifying at said genomic locus of interest at least one DNA target sequence cleavable by one TAL nuclease (TALEN);

(ii) introducing said TALEN into the cell together with a single-chained version of the dimeric TREX2 exonuclease;

thereby obtaining a cell in which double-strand-break induced mutagenesis at said genomic locus of interest is increased.

As shown hereafter, the invention more particularly relates to the use of the single chain polypeptides and polynucleotides described above for performing targeted mutagenesis in plants, especially in tobacco. According to a preferred embodiment of this method, a plant expressible plasmid encoding a single chain of TREX2, such as that described previously, is co-transfected with at least one nucleic acid encoding a rare-cutting endonuclease into a protoplast. Preferably, TREX2 and the rare cutting endonucleases sequences are co-delivered on the same nucleic acid, and more preferably by expression of a single chain molecule. The single chain of Trex2 and the endonuclease are then co-expressed in the protoplast, such that NHEJ based targeted mutagenesis is induced as the result of the collaborative effect of TREX and the rare-cutting endonuclease.

Such a method has the advantage to create stable deletions into the gene sequence at the cleavage site of the rare cutting endonuclease, without necessarily involving selection markers or insertion of exogeneous DNA into the plant genome. The method is particularly useful for plants of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medic* and *Citrus reticulata*.

The present invention also relates to polynucleotides encoding the endonuclease proteins of the invention, specific vectors (polynucleotidic or not) encoding and/or vectorizing them, compositions and/or kits comprising them, all of them being used or part of a whole to implement methods of the present invention for increasing double-strand break-induced mutagenesis at a genomic locus of interest in a cell.

DEFINITIONS

Amino acid residues in a polypeptide sequence are designated herein according to the one-letter code, in which, for example, Q means a Gln or Glutamine residue, R means an Arg or Arginine residue and D means an Asp or Aspartic acid residue.

Amino acid substitution means the replacement of one amino acid residue with another, for instance the replacement of an Arginine residue with a Glutamine residue in a peptide sequence is an amino acid substitution.

Altered/enhanced/increased/improved activity, refers to an increase in the detected level of rare-cutting endonuclease activity against a target DNA sequence when said endonuclease is expressed together with a single-chain TREX2 exonuclease, or in fusion with a TREX2 exonuclease (see below), in comparison to the activity against the target DNA sequence of said rare-cutting endonuclease expressed alone.

Nucleotides are designated as follows: a one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

By "meganuclease" is intended an endonuclease having a double-stranded DNA target sequence of 12 to 45 bp. Said meganuclease is either a dimeric enzyme, wherein each meganuclease domain is on a monomer, or a monomeric enzyme comprising the two domains on a single polypeptide.

By "meganuclease domain" is intended the region that interacts with one half of the DNA target of a meganuclease and is able to associate with another domain of a meganuclease that interacts with the other half of the DNA target to form a functional meganuclease able to cleave said DNA target.

By "variant" it is intended a recombinant protein obtained by replacement of at least one residue in the amino acid sequence of the parent protein with a different amino acid.

By "LAGLIDADG meganuclease", is intended a homing endonuclease from the LAGLIDADG family, as defined in Stoddard et al (Stoddard, 2005), or an engineered variant comprising a polypeptide sharing at least 80%, 85%, 90%, 95%, 97.5%, 99% or more identity or similarity with said natural homing endonuclease. Such engineered LAGLIDADG meganucleases can be derived from monomeric or dimeric meganucleases. When derived from dimeric meganucleases, such engineered LAGLIDADG meganucleases can be single-chain or dimeric endonucleases, as described in Grizot et al. (Grizot et al, 2009).

By "peptide linker", "peptidic linker" or "peptide spacer" it is intended to mean a peptide sequence that allows the connection of different monomers in a fusion protein and the adoption of the correct conformation for said fusion protein activity and which does not alter the activity of either of the monomers. Peptide linkers can be of various sizes from 1, 2, 3, 4, 5, 10, 15, 20, 30, 40 to 50 amino acids as a non limiting indicative range or any intermediate value within this range.

By "related to", particularly in the expression "one cell type related to the chosen cell type or organism", is intended a cell type or an organism sharing characteristics with said chosen cell type or said chosen organism; this cell type or organism related to the chosen cell type or organism, can be derived from said chosen cell type or organism or not.

By "subdomain" it is intended the region of a LAGLIDADG homing endonuclease core domain that interacts with a distinct part of a DNA target half-site.

By "targeting DNA construct/minimal repair matrix/repair matrix" it is intended to mean a DNA construct comprising a first and second portions that are homologous to regions 5' and 3' of the DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and the repair matrix, wherein the genomic sequence containing the DNA target is replaced by the third portion of the repair matrix and a variable part of the first and second portions of the repair matrix.

By "functional variant", as related to meganucleases, is intended a variant that is able to cleave a DNA target sequence, preferably said target is a new target that is not cleaved by the parent meganuclease. For example, such variants have amino acid variations at positions contacting the DNA target sequence or interacting directly or indirectly with said DNA target. As related to a generic protein scaffold having a particular function, for example an exonuclease, a "functional variant" is intended as a variant that is able to retain its primary activity (e.g. exonuclease) to a measurable extent but having changes (amino acid substitutions and/or truncations) elsewhere in the polypeptide.

By "selection" or "selecting" it is intended to mean the isolation of one or more meganuclease variants based upon an observed specified phenotype, for instance altered cleavage activity. This selection can be of the variant in a peptide form upon which the observation is made or alternatively the selection can be of a nucleotide coding for selected meganuclease variant.

By "screening" it is intended to mean the sequential or simultaneous selection of one or more meganuclease variant (s) that exhibits a specified phenotype such as altered cleavage activity.

By "derived from" it is intended to mean a protein variant that is created from a parent protein and hence the peptide sequence of the protein variant is related to (primary sequence level) but derived from (mutations) the peptide sequence of the parent protein.

By "I-CreI" is intended the natural wild-type I-CreI meganuclease having the sequence of pdb accession code 1g9y, corresponding to sequence SEQ ID NO: 35 in the sequence listing.

By "I-CreI variant with novel specificity" is intended a variant having a pattern of cleaved targets different from that of the parent meganuclease. The terms "novel specificity", "modified specificity", "novel cleavage specificity", "novel substrate specificity" which are equivalent and used indifferently, refer to the specificity of the variant towards the nucleotides of the DNA target sequence. In the present patent application the I-CreI variants described can comprise an additional alanine after the first methionine of the wild-type I-CreI sequence as shown in SEQ ID NO: 36. These variants also comprise two additional alanine residues and an aspartic acid residue after the final proline of the wild-type I-CreI sequence. These additional residues do not affect the properties of the enzyme and to avoid confusion these additional residues do not affect the numeration of the residues in I-CreI or a variant referred in the present patent application, as these references exclusively refer to residues of the wild type I-CreI enzyme (SEQ ID NO: 35) as present in the variant, so for instance residue 2 of I-CreI is in fact residue 3 of a variant which comprises an additional alanine after the first methionine.

By "I-CreI site" is intended a 22 to 24 base pair double-stranded DNA sequence that is cleaved by I-CreI. I-CreI sites include the wild-type non-palindromic I-CreI homing site and the derived palindromic sequences such as the sequence 5'-t−12c−11a−10a−9a−8a−7c−6g−5t−4−c−3g−2t−1a+1c+2g+3a+4c+5g+6t+7t+8t+9t+10g+11a+12 (SEQ ID NO: 37), also called C1221.

By "domain" or "core domain" is intended the "LAGLIDADG homing endonuclease core domain", which is the characteristic αββαββα fold of the homing endonucleases of the LAGLIDADG family, corresponding to a sequence of about one hundred amino acid residues. Said domain comprises four beta-strands ($\beta_1\beta_2\beta_3\beta_4$) folded in an anti-parallel beta-sheet that interacts with one half of the DNA target. This domain is able to associate with another LAGLIDADG homing endonuclease core domain that interacts with the other half of the DNA target to form a functional endonuclease able to cleave said DNA target. For example, in the case of the homodimeric homing endonuclease I-CreI (163 amino acids), the LAGLIDADG homing endonuclease core domain corresponds to the residues 6 to 94.

By "subdomain" is intended the region of a LAGLIDADG homing endonuclease core domain that interacts with a distinct part of a homing endonuclease DNA target half-site.

By "DNA target", "DNA target sequence", "target sequence", "target-site", "target", "site", "site of interest", "recognition site", "polynucleotide recognition site", "recognition sequence", "homing recognition site", "homing site", "cleavage site" is intended a 20 to 24 bp double-stranded palindromic, partially palindromic (pseudo-palindromic) or non-palindromic polynucleotide sequence that is recognized and cleaved by a LAGLIDADG homing endonuclease such as I-CreI, or a variant, or a single-chain chimeric meganuclease derived from I-CreI. Said DNA target sequence is qualified of "cleavable" by an endonuclease, when recognized within a genomic sequence and known to correspond to the DNA target sequence of a given endonuclease or a variant of such endonuclease. These terms refer to a distinct DNA location, preferably a genomic location, at which a double-strand break (cleavage) is to be induced by the meganuclease. The DNA target is defined by the 5' to 3' sequence of one strand of the double-stranded polynucleotide, as indicate above for C1221. Cleavage of the DNA target occurs at nucleotides at positions +2 and −2, respectively for the sense and the antisense strand. Unless otherwise indicated, the position at which cleavage of the DNA target by an I-CreI meganuclease variant occurs, corresponds to the cleavage site on the sense strand of the DNA target. For a rare-cutting endonuclease such as a TALEN, or a rare-cutting endonuclease derived from a TALEN, in a functional layout of a FokI-based TALEN, a "DNA target", "DNA target sequence", "target DNA sequence", "nucleic acid target sequence", "target sequence", or "processing site" requires two DNA recognition regions flanking an unspecific central region, i.e. the spacer.

By spacer is meant the nucleic acid area that separates the two nucleic acid sequences recognized and bound by each monomer constituting a rare-cutting endonuclease such as a TALEN according to the invention. By spacer length is meant the nucleic acid distance that separates the two nucleic acid sequences recognized and bound by each monomer constituting the rare-cutting endonuclease according to the invention.

By "DNA target half-site", "half cleavage site" or half-site" is intended the portion of the DNA target which is bound by each LAGLIDADG homing endonuclease core domain.

By "chimeric DNA target" or "hybrid DNA target" is intended the fusion of different halves of two parent meganuclease target sequences. In addition at least one half of said target may comprise the combination of nucleotides which are bound by at least two separate subdomains (combined DNA target).

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Choulika et al, 1995; Pingoud & Silva, 2007; Rouet et al, 1994a; Rouet et al, 1994b). Rare-cutting endonucleases can for example be a homing endonuclease (Paques & Duchateau, 2007b), a chimeric Zinc-Finger nuclease (ZFN) resulting from the fusion of engineered zinc-finger domains with the catalytic domain of a restriction enzyme such as FokI (Porteus & Carroll, 2005) or a chemical endonuclease (Arimondo et al, 2006; Eisenschmidt et al, 2005). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish & Glazer, 2005). Such chemical endonucleases are comprised in the term "endonuclease" according to the present invention.

Rare-cutting endonucleases can also be for example TAL-ENs, a new class of chimeric nucleases using a FokI catalytic domain and a DNA binding domain derived from Transcription Activator Like Effector (TALE), a family of proteins used in the infection process by plant pathogens of the *Xanthomonas* genus (Boch et al, 2009; Christian et al, 2010; Li et al, 2010; Moscou & Bogdanove, 2009). The functional layout of a FokI-based TALE-nuclease (TALEN) is essentially that of a ZFN, with the Zinc-finger DNA binding domain being replaced by the TALE domain. As such, DNA cleavage by a TALEN requires two DNA recognition regions flanking an unspecific central region. Rare-cutting endonucleases encompassed in the present invention can also be derived from TALENs.

Rare-cutting endonuclease can be a homing endonuclease, also known under the name of meganuclease. Such homing endonucleases are well-known to the art (Stoddard, 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease.

In the wild, meganucleases are essentially represented by homing endonucleases. Homing Endonucleases (HEs) are a widespread family of natural meganucleases including hundreds of proteins families (Chevalier & Stoddard, 2001). These proteins are encoded by mobile genetic elements that propagate by a process called "homing": the endonuclease cleaves a cognate allele from which the mobile element is absent, thereby stimulating a homologous recombination event that duplicates the mobile DNA into the recipient locus. Given their exceptional cleavage properties in terms of efficacy and specificity, they could represent ideal scaffolds to derive novel, highly specific endonucleases.

HEs belong to five major families. The LAGLIDADG family, named after a conserved sequence motif involved in the catalytic center, is the most widespread and the best characterized group. Several structures are now available. Whereas most proteins from this family are monomeric and display two LAGLIDADG motifs, a few have only one motif, and thus dimerize to cleave palindromic or pseudo-palindromic target sequences.

Although the LAGLIDADG motif is the only conserved region among members of the family, these proteins share a very similar architecture. The catalytic core is flanked by two DNA-binding domains with a perfect two-fold symmetry for homodimers such as I-CreI (Chevalier et al, 2001), I-MsoI (Chevalier et al, 2003) and I-CeuI (Spiegel et al, 2006) and with a pseudo symmetry for monomers such as I-SceI (Moure et al, 2003), I-DmoI (Silva et al, 1999) or I-AniI (Bolduc et al, 2003). Both monomers and both domains (for monomeric proteins) contribute to the catalytic core, organized around divalent cations. Just above the catalytic core, the two LAGLIDADG peptides also play an essential role in the dimerization interface. DNA binding depends on two typical saddle-shaped αββαββα folds, positioned in the DNA major groove. Other domains can be found, for example in inteins such as PI-PfuI (Ichiyanagi et al, 2000) and PI-SceI (Moure et al, 2002), whose protein splicing domain is also involved in DNA binding.

The making of functional chimeric meganucleases, by fusing the N-terminal I-DmoI domain with an I-CreI monomer (Chevalier et al, 2002; Epinat et al, 2003); International PCT Application WO 03/078619 (Cellectis) and WO 2004/031346 (Fred Hutchinson Cancer Research Center, Stoddard et al)) have demonstrated the plasticity of LAGLIDADG proteins.

Different groups have also used a semi-rational approach to locally alter the specificity of the I-CreI (Seligman et al, 1997; Sussman et al, 2004); International PCT Applications WO 2006/097784, WO 2006/097853, WO 2007/060495 and WO 2007/049156 (Cellectis); (Arnould et al, 2006a; Rosen et al, 2006; Smith et al, 2006), I-SceI (Doyon et al, 2006), PI-SceI (Gimble et al, 2003) and I-MsoI (Ashworth et al, 2006).

In addition, hundreds of I-CreI derivatives with locally altered specificity were engineered by combining the semi-rational approach and High Throughput Screening.

Residues Q44, R68 and R70 or Q44, R68, D75 and 177 of I-CreI were mutagenized and a collection of variants with altered specificity towards positions ±3 to 5 of the DNA target (5NNN DNA target) were identified by screening (International PCT Applications WO 2006/097784 and WO 2006/097853 (Cellectis); (Arnould et al, 2006a; Smith et al, 2006).

Residues K28, N30 and Q38 or N30, Y33 and Q38 or K28, Y33, Q38 and S40 of I-CreI were mutagenized and a collection of variants with altered specificity towards positions ±8 to 10 of the DNA target (10NNN DNA target) were identified by screening (Arnould et al, 2006a; Smith et al, 2006); International PCT Applications WO 2007/060495 and WO 2007/049156 (Cellectis)).

Two different variants were combined and assembled in a functional heterodimeric endonuclease able to cleave a chimeric target resulting from the fusion of two different halves of each variant DNA target sequence ((Arnould et al, 2006a; Smith et al, 2006); International PCT Applications WO 2006/097854 and WO 2007/034262).

Furthermore, residues 28 to 40 and 44 to 77 of I-CreI were shown to form two partially separable functional clusters, able to bind distinct parts of a homing endonuclease target half-site (Smith et al, 2006); International PCT Applications WO 2007/049095 and WO 2007/057781 (Cellectis)).

The combination of mutations from the two clusters of I-CreI within the same monomer allowed the design of novel chimeric molecules (homodimers) able to cleave a palindromic combined DNA target sequence comprising the nucleotides at positions ±3 to 5 and ±8 to 10 which are bound by each cluster ((Smith et al, 2006); International PCT Applications WO 2007/049095 and WO 2007/057781 (Cellectis)).

The method for producing meganuclease variants and the assays based on cleavage-induced recombination in mammal or yeast cells, which are used for screening variants with altered specificity are described in the International PCT Application WO 2004/067736; (Arnould et al, 2006a; Chames et al, 2005; Epinat et al, 2003). These assays result in a functional LacZ reporter gene which can be monitored by standard methods.

The combination of the two former steps allows a larger combinatorial approach, involving four different clusters. The different clusters can be modified separately and combined to obtain an entirely redesigned meganuclease variant (heterodimer or single-chain molecule) with chosen specificity. In a first step, couples of novel meganucleases are combined in new molecules ("half-meganucleases") cleaving palindromic targets derived from the target one wants to cleave. Then, the combination of such "half-meganucleases" can result in a heterodimeric species cleaving the target of interest. The assembly of four sets of mutations into heterodimeric endonucleases cleaving a model target sequence or a sequence from different genes has been described in the following Cellectis International patent applications: XPC gene (WO2007/093918), RAG gene (WO2008/010093), HPRT gene (WO2008/059382), beta-2 microglobulin gene (WO2008/102274), Rosa26 gene (WO2008/152523), Human hemoglobin beta gene (WO2009/13622) and Human interleukin-2 receptor gamma chain gene (WO2009019614).

These variants can be used to cleave genuine chromosomal sequences and have paved the way for novel perspectives in several fields, including gene therapy.

A homing endonuclease can be a LAGLIDADG endonuclease such as I-SceI, I-CreI, I-CeuI, I-MsoI, and I-DmoI.

Said LAGLIDADG endonuclease can be I-SceI, a member of the family that contains two LAGLIDADG motifs and functions as a monomer, its molecular mass being approximately twice the mass of other family members like I-CreI which contains only one LAGLIDADG motif and functions as homodimers.

Endonucleases mentioned in the present application encompass both wild-type (naturally-occurring) and variant endonucleases. Endonucleases according to the invention can be a "variant" endonuclease, i.e. an endonuclease that does not naturally exist in nature and that is obtained by genetic engineering or by random mutagenesis, i.e. an engineered endonuclease. This variant endonuclease can for example be obtained by substitution of at least one residue in the amino acid sequence of a wild-type, naturally-occurring, endonuclease with a different amino acid. Said substitution(s) can for example be introduced by site-directed mutagenesis and/or by random mutagenesis. In the frame of the present invention, such variant endonucleases remain functional, i.e. they retain the capacity of recognizing and specifically cleaving a target sequence to initiate gene targeting process.

The variant endonuclease according to the invention cleaves a target sequence that is different from the target sequence of the corresponding wild-type endonuclease. Methods for obtaining such variant endonucleases with novel specificities are well-known in the art.

Endonucleases variants may be homodimers (meganuclease comprising two identical monomers) or heterodimers (meganuclease comprising two non-identical monomers).

Endonuclease variants may also be single-chain meganucleases. Such single-chain meganucleases may be derivatives of natural monomeric LAGLIDADG homing endonucleases or derivatives of dimeric LAGLIDADG homing endonucleases.

In this last case, the single-chain meganuclease comprises
(i) two LAGLIDADG homing endonuclease domains (containing at least a single LAGLIDADG motif each) linked by a peptidic linker, or
(ii) two polypeptides, each one sharing at least 80%, 90%, 95%, 99% or more similarity with a LAGLIDADG homing endonuclease domain, and linked by a peptidic linker.

The single-chain meganuclease is able to cleave a chimeric DNA target sequence comprising one different half of each parent meganuclease target sequence.

Endonucleases with novel specificities can be used in the method according to the present invention for gene targeting and thereby integrating a transgene of interest into a genome at a predetermined location.

By "delivery vector" or "delivery vectors" is intended any vector that can be used in the present invention to put into cell contact or delivered inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses for example include Norwalk virus, togavirus, flavivirus, reoviruses, papovavirus, hepadnavirus, and hepatitis virus. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is linear double-strand viral DNA, which is the substrate for viral integration in the DNA of infected cells.

By "integrative lentiviral vectors (or LV)", is meant such vectors, as non limiting example, that are able to integrate into the genome of a target cell.

By "non integrative lentiviral vectors (or NILV)" is meant efficient gene delivery vectors that do not integrate into the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevi-siae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-□-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Inducible promoters may be induced by pathogens or stress, more preferably by stress like cold, heat, UV light, or high ionic concentrations (reviewed in Potenza C et al. 2004, In vitro Cell Dev Biol 40:1-22). Inducible promoter may be induced by chemicals (reviewed in (Moore et al, 2006); (Padidam, 2003); (Wang et al, 2003); (Zuo & Chua, 2000).

Delivery vectors and vectors can be associated or combined with any cellular permeabilization techniques such as sonoporation or electroporation or derivatives of these techniques.

By cell or cells is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*.

More preferably the plant is of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana*,

*Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata.*

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans.*

- by "homologous" is intended a sequence with enough identity to each other to lead to homologous recombination between sequences, more particularly having at least 95% identity, preferably at least 97% identity and more preferably at least 99% identity.

- "Identity" refers to sequence identity between two nucleic acid molecules or polypeptides. Identity can be determined by comparing a position in each sequence which may be aligned for purposes of comparison. When a position in the compared sequence is occupied by the same residue, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. When it is mentioned in the present disclosure that a polynucleotide or polypeptide shares at least 80% identity, it means that these generally share at least 90%, preferably at least 95%, more preferably at least 97%, even more preferably 99% identity with the reference indicated sequence.

- by "mutation" is intended the substitution, deletion, insertion of one, two, three, four five, six, seven, eight, nine, ten, fifteen, twenty, thirty or more nucleotides or amino acids in a polynucleotide (cDNA, gene) or a polypeptide sequence, respectively. Said mutation can affect the coding sequence of a gene or its regulatory sequence. It may also affect the structure of the genomic sequence or the structure/stability of the encoded mRNA.

- In the frame of the present invention, the expression "double-strand break induced mutagenesis" (DSB-induced mutagenesis) refers to a mutagenesis event consecutive to an NHEJ event following an endonuclease-induced DSB, leading to insertion/deletion at the cleavage site of an endonuclease.

- By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

- As used herein, the term "transgene" refers to a DNA sequence introduced into a cell of interest, tissue or individual. When inserted, said transgene could be used for generating RNA and/or a polypeptide. Most preferably, the transgene encodes a therapeutic polypeptide useful for the treatment of an individual.

- The term "gene of interest" or "GOI" refers to any nucleotide sequence encoding a known or putative gene product.

- As used herein, the term "locus" is the specific physical location of a DNA sequence (e.g., of a gene) on a chromosome. The term "locus" usually refers to the specific physical location of an endonuclease's target sequence on a chromosome. Such a locus, which comprises a target sequence that is recognized and cleaved by an endonuclease according to the invention, is referred to as "locus according to the invention". Also, the expression "genomic locus of interest" is used to qualify a nucleic acid sequence in a genome that can be a putative target for a double-strand break according to the invention. By "endogenous genomic locus of interest" is intended a native nucleic acid sequence in a genome, i.e. a sequence or allelic variations of this sequence that is naturally present at this genomic locus. It is understood that the considered genomic locus of interest of the present invention can be between two overlapping genes the considered endonuclease's target sequences are located in two different genes.

- By the expression "loss of genetic information" is understood the elimination or addition of at least one given DNA fragment (at least one nucleotide) or sequence, bordering the recognition sites of the endonucleases of the present invention and leading to a change of the original sequence around said endonuclease-cut sites, within the genomic locus of interest. This loss of genetic information can be, as a non-limiting example, the elimination of an intervening sequence between two endonuclease-cut sites; it can also be, in another non-limiting example, the result of an exonuclease DNA-ends processing activity after a unique endonuclease DNA double-strand break. In this last case, loss of genetic information within the genomic locus of interest is generated "around said DNA target sequence", i.e. around the endonuclease-cut site (DSB), taken as reference. It can also be, in other non-limiting examples, the result of DNA-ends processing activities by other enzymes, after a unique endonuclease DNA double-strand break, such as polymerase activity (TdT . . . ), dephosphatase activity . . . .

- By "scarless re-ligation" is intended the perfect re-ligation event, without loss of genetic information (no insertion/deletion events) of the DNA broken ends through NHEJ process after the creation of a double-strand break event.

- By "fusion protein" is intended the result of a well-known process in the art consisting in the joining of two or more genes that originally encode separate proteins, the translation of said "fusion gene" resulting in a single polypeptide with functional properties derived from each of the original proteins.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Effect of Single-Chain TREX2 (scTrex) Molecules on the Meganuclease-Induced Mutagenesis Human TREX2 protein (SEQ ID NO: 26) is known to function as a homodimer (Perrino, de Silva et al., 2008). We hypothesized that the creation of a TREX2 single-chain molecule can enhance the exonucleolytic activity. Four single-chain TREX2 molecules were designed and tested in co-expression experiments with an engineered meganuclease to evaluate their effect on meganuclease-induced mutagenesis. A set of four linkers (Link1 to Link4) consisting of 8, 11, 12 and 14 amino acids (SEQ ID NO: 1 to 4) were designed to create a bridge between the C-terminal alanine of one TREX2 molecule and the serine located at the N-terminus of the second TREX2 molecule of the homodimer. This creates a single-chain protein with a molecular weight of 53 kDa. Residues were chosen to create a flexible linker to tether the homodimer, without being restrictive. The four single-chain TREX2 (scTrex) molecular constructions were named scTrex1 to scTrex4 (SEQ ID NO: 5 to 8).

Co-Transfection of Single-Chain TREX2 (scTrex) with Meganucleases

Stimulation of mutagenesis induced by scTrex has been compared to stimulation of mutagenesis induced by wild-type TREX2 when co-transfected with a single-chain meganuclease (SC-MN). Plasmids encoding scTrex1 to scTrex4 (SEQ ID NO: 9 to 12), respectively, and the plasmid encoding SC_GS meganuclease (pCLS2690, SEQ ID NO: 13) were co-transfected into the cellular model described below and established to monitor SC_GS-induced mutagenesis.

Material and Methods a) Cellular Model to Monitor Meganuclease-Induced Mutagenesis The plasmid pCLS6810 (SEQ ID NO: 25) was designed to quantify the NHEJ repair frequency induced by the SC_GS meganuclease (pCLS2690, SEQ ID NO: 13). The SC_GS meganuclease is a single-chain protein where two I-CreI variants have been fused. It recognizes a 22 bp DNA sequence (5'-TGCCCCAGGGTGAGAAAGTCCA-3': GS_CHO.1 target, SEQ ID NO: 32) located in the first exon of *Cricetulus griseus* glutamine synthetase gene. The sequence used to measure SC_GS-induced mutagenesis is made of an ATG start codon followed by (i) 2 codons for alanine; (ii) an HA-tag sequence; (iii) the SC_GS recognition site; (iv) a stretch of glycine-serine di-residues; (v) an additional 2 codons for alanine as in (i), and finally; (vi) a GFP reporter gene lacking its ATG start codon. The GFP reporter gene is inactive due to a frame-shift introduced by the GS recognition site. The creation of a DNA double-strand break (DSB) by the SC_GS meganuclease followed by error-prone NHEJ events can lead to restoration of the GFP gene expression in frame with the ATG start codon. The final construct was introduced at the RAG1 locus in 293H cell line using the hsRAG1 Integration Matrix CMV Neo from cGPS® Custom Human Full Kit DD (Cellectis Bioresearch) following the provider's instructions. Using this kit, a stable cell line containing a single copy of the transgene at the RAG1 locus was obtained. Thus, after transfection of this cell line by SC_GS meganuclease expressing plasmid with or without a plasmid encoding scTrex1-4 (SEQ ID NO: 5 to 8) or encoding TREX2 taken as a control (pCLS7673, SEQ ID NO: 14), the percentage of GFP-positive cells is directly correlated to the mutagenic NHEJ repair frequency induced by the transfected molecular entity/ies.

b) Transfection in a Cellular Model Monitoring Meganuclease-Induced Mutagenesis

Cells (~10⁶), seeded one day prior to transfection, were co-transfected with 1 µg of SC_GS encoding vector (pCLS2690, SEQ ID NO: 13) and either 0, 2.8, 5.6 or 10 µg of plasmid encoding scTrex1-4 (SEQ ID NO: 9 to 12) or control plasmid encoding TREX2 (pCLS7673 SEQ ID NO: 14) using 25 µl of LIPOFECTAMINE® (Invitrogen) according to the manufacturer's instructions. Total DNA transfected was adjusted to 11 µg with a pUC vector (pCLS0002, SEQ ID NO: 31). Four days post transfection, cells were harvested for flow cytometry analysis using a GUAVA® system (Millipore). Genomic DNA was extracted from transfected cell populations and locus specific PCRs were performed using the following primers: 5'-CCATCTCATC-CCTGCGTGTCTCCGACTCAG (forward adaptor sequence)-10N-(sequences needed for PCR product identification)-GCTCTCTGGCTAACTAGAGAACCC (transgenic locus specific forward sequence)-3' (SEQ ID NO: 33) and 5'-CCTATCCCCTGTGTGCCTTGGCAGTCTCAG-(reverse adaptor sequence)-TCGATCAGCACGGGCAC-GATGCC (transgenic locus specific reverse sequence) (SEQ ID NO: 34). PCR products were sequenced by a 454 sequencing system (454 Life Sciences). Approximately 10,000 sequences were obtained per PCR product and then analyzed for the presence of site-specific insertion or deletion events.

c) Making of Single Chain TREX2 (scTrex) Molecules

Making single-chain molecules, where two identical proteins are fused, is a difficult task as any gene amplification would result in the amplification of only one monomer. To bypass this difficulty, we developed an original strategy. Briefly, the TREX2 protein cloned into the mammalian expression vector (pCLS7673, SEQ ID NO: 14) was taken as a template and the unique PstI restriction site covering amino acids 101 (leucine) and 102 (glutamine) of the TREX2 protein was considered. For each single-chain construct, two independent PCRs were carried out using the either primers TrexPstFor/TrexLinkiRev (where "i" varies from 1 to 4) or primers TrexLinkiFor (where "i" varies from 1 to 4) and TrexPstRev. The two PCR fragments were then purified after migration on an agarose gel and an assembly PCR was performed using primers TrexPstFor/TrexPstRev. This PCR uses the linker sequence as the initial annealing region. The resulting PCR fragment was then digested by PstI and ligated into pCLS7673 (SEQ ID NO: 14) also digested by PstI. The following table indicates the oligonucleotide sequences.

torization issues as it is much easier to transfect only one molecular species into the cells. Second, the fusion protein has the advantage to concentrate the TREX2 exonucleolytic activity at the double-strand break created by the meganuclease, minimizing potential adverse effects. Therefore, each of the four scTrex molecules (scTrex1 to scTrex4) are independently fused to the N- or C-terminus of the SC_GS

TABLE 1

Oligonucleotides used to create single chain TREX molecules

| Name | Sequence | SEQ ID NO: | Final Linker Sequence |
|---|---|---|---|
| TrexPstFor | acgctgcaggccttcctgagccgcc | 15 | |
| TrexPstRev | ggcctgcagcgtccgcaccacggcgccat | 16 | |
| TrexLink1For | ccttctgagtctgaaggttccgaggcaccccgggccgag | 17 | SRPSESEG |
| TrexLink1Rev | agactcagaaggacgagacgcctccaggctggggtcatc | 18 | (SEQ ID NO: 1) |
| TrexLink2For | cagaccggtctggatgttccttactccgaggcacccgggccgag | 19 | TPPQTGLDVPY |
| TrexLink2Rev | aacatccagaccggtctgtggaggagtcgcctccaggctgggtcatc | 20 | (SEQ ID NO: 2) |
| TrexLink3For | tctgtttctaattctgagcatattgcttccgaggcaccccggccgag | 21 | GDSSVSNSEHIA |
| TrexLink3Rev | ctcagaattagaaacagaggaatcaccgcctccaggctgggtcatc | 22 | (SEQ ID NO: 3) |
| TrexLink4For | gctattggaggttctaaacctcgtgttgcttccgaggcacccgggccgag | 23 | IRPRAIGGSKPRVA |
| TrexLink4Rev | tttagaacctccaatagcacgaggacgaatcgcctccaggcggggtcatc | 24 | (SEQ ID NO: 4) |

Results

Figure 1:
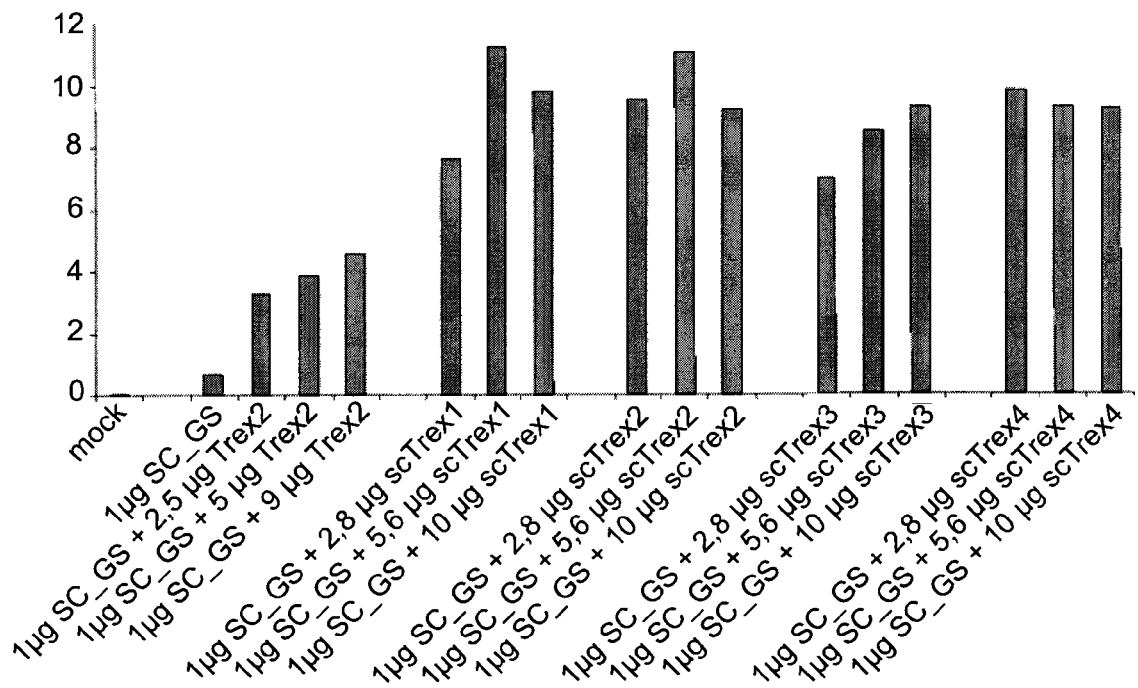
FIG. 1: Effect of different single-chain TREX2 molecules on the targeted mutagenesis frequency induced by the engineered SC_GS meganuclease.

The ability of the newly obtained scTrex molecules to increase meganuclease-induced mutagenesis was evaluated using the cellular model described above. The four single chain molecules (scTrex1 to scTrex4) wherein two TREX2 promoters have been fused using, respectively, the aforementioned linkers [SRPSESEG (SEQ ID NO: 1), TPPQT-GLDVPY (SEQ ID NO: 2), GDSSVSNSEHIA (SEQ ID NO: 3) and IRPRAIGGSKPRVA (SEQ ID NO: 4)] and cloned into a mammalian expression vector [pCLS8981 (SEQ ID NO: 9), pCLS8982 (SEQ ID NO: 10), pCLS8984 (SEQ ID NO: 11) and pCLS8986 (SEQ ID NO: 12)] were used in combination with the vector encoding for SC_GS meganuclease to co-transfect a cellular model measuring mutagenic NHEJ repair induced by SC_GS. 1 µg of the vector encoding for SC_GS meganuclease was transfected into the cells alone or with increasing amounts of pCLS7673 (TREX2 encoding vector, SEQ ID NO: 14) or pCLS8981 [(SEQ ID NO: 9), pCLS8982 (SEQ ID NO: 10), pCLS8984 (SEQ ID NO: 11) and pCLS8986 (SEQ ID NO: 12) encoding scTrex1 to scTrex4 (SEQ ID NO: 5 to 8)], respectively. The SC_GS meganuclease induces a mutagenesis frequency circa 0.7%. This frequency increased up to 5% when TREX2 protein is present (FIG. 1). In contrast, up to 11% mutagenic events could be achieved when single-chain TREX2 molecules were present.

Example 2

Fusion of Single-Chain TREX2 Molecules to the N- or C-Terminus of an Engineered Meganuclease Fusion of the TREX2 protein to an engineered meganuclease presents great advantages. First, it alleviates vecmeganuclease to evaluate the ability of these new chimeric rare-cutting endonucleases to increase targeted mutagenesis using the cell line previously described.

Material and Methods a) Creating Fusion Proteins of SC_GS Meganuclease and Single-Chain TREX2 Molecules.

The strategy developed to build such fusion molecules is almost identical to the one described in the previous example 1A to make the single-chain TREX2 molecules. The two fusion proteins SC_GS-10-TREX (pCLS8052, SEQ ID NO: 27) and TREX-10-SC_GS (pCLS8054, SEQ ID NO: 28) are taken as a template. Instead of considering the PstI restriction site that is no longer unique in these plasmids, the Tth111I restriction site (GACACTGTC), which covers amino acids 142 to 144 (DTV) of the TREX2 protein, is considered. Taking pCLS7673 (SEQ ID NO: 14) as a template, two independent PCRs are carried out using the either primers TrexTthFor (5'-cccgggacactgtctgcctgga-cacgc-3', SEQ ID NO: 29) and TrexLinkiRev (where "i" varies from 1 to 4) or primers and TrexLinkiFor (wherein i varies from 1 to 4) and TrexTthRev (5'-aggcagacagtgtc-ccggggcaggcgg-3', SEQ ID NO: 30). The two PCR fragments are then purified after migration on an agarose gel and an assembly PCR is performed using primers TrexTthFor/TrexTthRev. This PCR uses the linker sequence as the initial annealing region. The resulting PCR fragments are then digested by Tth111I and ligated into in either pCLS8052 (SEQ ID NO: 27) or pCLS8054 (SEQ ID NO: 28), also digested by Tth111I. Eight molecules (scTrex1-10-SC_GS, scTrex2-10-SC_GS, scTrex3-10-SC_GS, scTrex4-10-SC_GS and SC_GS-10-scTrex1, SC_GS-10-scTrex2, SC_GS-10-scTrex3, SC_GS-10-scTrex4) are obtained directly and cloned into the mammalian expression vector.

Taking pCLS7673 (SEQ ID NO: 14) as a template, two independent PCRs were carried out using either primers TrexTthFor (5'-cccgggacactgtctgcctggacacgc-3', SEQ ID NO: 29) and TrexLink2Rev (SEQ ID NO: 20), or primers TrexLink2For (SEQ ID NO: 19; see Table 1) and TrexTthRev (5'-aggcagacagtgtcccggggcaggcgg-3', SEQ ID NO: 30). The two PCR fragments were then purified after migration on an agarose gel and an assembly PCR was performed using primers TrexTthFor/TrexTthRev. This PCR used the linker sequence as the initial annealing region. The resulting PCR fragments were then digested by Tth111I and ligated into SC_GS-10_Trex (pCLS8052 of SEQ ID NO: 27, encoding protein of SEQ ID NO: 52), Trex-10-SC_GS (pCLS8054 of SEQ ID NO: 28, encoding protein of SEQ ID NO: 53), Trex-SC_CAPNS1 (pCLS8518 of SEQ ID NO: 42, encoding protein of SEQ ID NO: 54), or Trex-SC_RAG (pCLS8980 of SEQ ID NO: 38, encoding protein of SEQ ID NO: 55). Four molecules: scTrex2-10-SC_GS (pCLS9572 of SEQ ID NO: 39, encoding protein of SEQ ID NO: 56), SC_GS-10-scTrex2 (pCLS9570 of SEQ ID NO: 40, encoding protein of SEQ ID NO: 57), scTrex2_SC_CAPNS1 (pCLS9571 of SEQ ID NO: 43, encoding protein of SEQ ID NO: 58), and scTrex2_SC_RAG (pCLS9573 of SEQ ID NO: 41, encoding protein of SEQ ID NO: 59) were then obtained directly in the mammalian expression vector.

b) Mutagenesis Induced by SC_GS Fused to scTREX2

Using the cellular model as described in example 1a, one million cells were seeded one day prior to transfection. These cells were co-transfected with 3 µg of plasmid encoding SC_GS (pCLS2690 of SEQ ID NO: 13, encoding the protein of SEQ ID NO: 60), or scTrex2-10-SC_GS (pCLS9572, SEQ ID NO: 39), with 0 or 2 µg of plasmid encoding TREX or scTREX2 (respectively, pCSL7673, SEQ ID NO: 14; pCLS8982, SEQ ID NO: 10) in 5 µg of total DNA by complementation with a pUC vector (pCLS0002 SEQID NO: 31) using 25 µl of LIPOFECTAMINE® (Invitrogen) according to the manufacturer's instructions. Four days following transfection, cells were harvested and the percentage of GFP-positive cells was measured by flow cytometry analysis using GUAVA® instrumentation (Millipore). As mentioned in example 1a), the percentage of GFP-positive cells is directly correlated to the mutagenic NHEJ repair frequency induced by the transfected molecular entities.

The results show that in the absence of TREX, the mutagenic frequency is approximately 0.3%, increasing to 1.1% on addition of TREX2, and to 3.8% with scTREX2. In comparison to the addition of TREX alone, scTREX2 results in a 3-fold increase in mutagenic frequency if used in a co-transfection, or a 6-fold increase (7.1%) when fused to the GS meganuclease (FIG. 2).

Using the same samples as above, genomic DNA was extracted from cell populations and locus specific PCRs were performed using the following primers: 5'-CCATCT-CATCCCTGCGTGTCTCCGACTCAG (forward adaptor sequence)-10N-(sequences needed for PCR product identification)-GCTCTCTGGCTAACTAGAGAACCC (transgenic GS locus specific forward sequence)-3' (SEQ ID NO: 33) and 5'-CCTATCCCCTGTGTGCCTTGGCA-GTCTCAG-(reverse adaptor sequence)-TCGATCAG-CACGGGCACGATGCC (transgenic GS locus specific reverse sequence) (SEQ ID NO: 34). PCR products were sequenced by a 454 sequencing system (454 Life Sciences). Approximately 10,000 sequences were obtained per PCR product and then analyzed for the presence of site-specific insertion or deletion events.

Full analysis of the targeted mutagenesis (TM) revealed that using the GS meganuclease in the absence of TREX results in a mutagenic frequency of approximately 2.5%. This increases to 4% on addition of TREX, 13% with scTREX2 and 22% when the N-terminal fusion of scTREX2 to the GS meganuclease is used (FIG. 3).

Analysis of the nature of the mutagenic events in the presence of TREX2 revealed a modification in the pattern of mutagenesis (FIG. 4). In the absence of TREX2, approximately 24% of the mutagenic events correspond to the complete or partial loss of the 3' overhang generated by SC_GS meganuclease (e.g. deletions of 2, 3 or 4 bases; respectively Del2, Del3 and Del4). In contrast, addition of scTREX2 either co-transfected or fused to the GS meganuclease increased the frequency of these deletion events to 70% (FIG. 4).

Dose Response

Cells ($10^6$) of the cellular model described in example 1a, seeded one day prior transfection, were transfected with increasing amounts of plasmid (1 µg, 3 µg, 6 µg, 10 µg) encoding SC_GS (pCLS2690, SEQ ID NO: 13), Trex-10-SC_GS (pCLS8054, SEQ ID NO: 28), scTrex2-10-SC_GS (pCLS9572, SEQ ID NO: 39), or SC_GS-10-scTrex2 (pCLS9570, SEQ ID NO: 40) wherein a single-chain TREX2 molecule has been linked N- or C-terminally to the SC_GS meganuclease. The transfection was performed with 10 µg of total DNA (complemented with a pUC vector (pCLS0002 of SEQ ID NO: 31) as needed) using 25 µl of LIPOFECTAMINE® (Invitrogen) according to the manufacturer's instructions. GS locus specific PCR was carried out as above using the same primers, and the PCR products were sequenced and analysed in the same manner.

In accordance with results of example 1c, the SC-GS meganuclease alone induced a mutagenic frequency circa 0.6-1% and circa 2-7% when fused to Trex (FIG. 5). Higher levels of mutagenic events were achieved when fusions between scTREX2 and SC-GS were used. Up to 16% mutagenic events could be achieved when scTREX2 has been linked N-terminally to SC_GS and up to 15% when linked C-terminally to SC_GS (FIG. 5). Fusion of scTREX2 to the SC_GS meganuclease also resulted in a higher frequency of mutagenesis using a lower dose.

Transfection on 293H Cells to Monitor Meganuclease-Induced Mutagenesis at Endogenous Loci One million cells were seeded one day prior to transfection. Cells were co-transfected with 3 µg of plasmid expressing SC_Meganuclease (respectively, SC_CAPNS1 in pCLS6163 of SEQ ID NO: 44, the expression vector encoding SC_CAPNS1 of SEQ ID NO: 45 and SC_RAG in pCLS2222 of SEQ ID NO: 46, the expression vector encoding SC_RAG of SEQ ID NO: 47), or scTREX2_SC_Meganuclease (respectively, scTrex2-SC_CAPNS1 in pCLS9571 of SEQ ID NO: 43, encoding the protein of SEQ ID NO: 58 and scTrex2-SC_RAG in pCLS9573 of SEQ ID NO: 41, encoding the protein of SEQ ID NO: 59) and with 0 or 2 µg of plasmid encoding TREX or scTREX2 (respectively, pCSL7673 of SEQ ID NO: 14, encoding the protein of SEQ ID NO: 26 and pCLS8982 of SEQ ID NO: 10, encoding the protein of SEQ ID NO: 6) in 5 µg of total DNA by complementation with a pUC vector (pCLS0002, SEQID NO: 31) using 251 of LIPOFECTAMINE® (Invitrogen) according to the manufacturer's instructions. Locus specific PCRs were performed using the following primers: 5'-CCATCTCATCCCTGCGT-GTCTCCGACTCAG-(forward adaptor sequence)-10N-(sequences needed for PCR product identification)-locus specific forward sequence for CAPNS1:-

CGAGTCAGGGCGGGATTAAG-3' (SEQ ID NO: 48), or for RAG1:-GGCAAAGATGAATCAAAGATTCTGTCC-3' (SEQ ID NO: 49), and the reverse primer 5'-CCTATCCCCTGTGTGCCTTGGCAGTCTCAG-(reverse adaptor sequence)-endogenous locus specific reverse sequence for CAPNS1:-CGAGACTTCACGGTTTCGCC-3' (SEQ ID NO: 50), or RAG1:-GATCTCACCCGGAACAGCTTAAATTTC-3' (SEQ ID NO: 51). PCR products were sequenced by a 454 sequencing system (454 Life Sciences). Approximately 10,000 sequences were obtained per PCR product and then analyzed for the presence of site-specific insertion or deletion events.

At the RAG1 locus, co-transfection of scTREX2 resulted in a targeted mutagenesis frequency of 5.4%, increasing to 8.4% using the scTREX2 fusion, in contrast to 1.4% in the absence of TREX (Table 2, and FIG. 6). At the CAPNS1 locus, the meganuclease alone gave rise to a frequency of targeted mutagenesis (TM) of 15%, increasing to 25% when co-transfected with scTREX2, and 36% when C-terminally fused to scTREX2 (Table 2, and FIG. 7).

TABLE 2

Percentage of targeted mutagenesis at endogenous locus RAG1 or CAPNS1; stimulation factors relative to the meganuclease alone are shown in parenthesis.

|  | Meganuclease alone | Meganuclease + TREX | Meganuclease + scTREX2 | Meganuclease – scTREX2 (fusion) |
| --- | --- | --- | --- | --- |
| RAG1 | 1.4 (1.0) | 4.69 (3.4) | 5.41 (3.9) | 8.42 (6.0) |
| CAPNS1 | 15.2 (1.0) | 18.25 (1.2) | 25.4 (1.7) | 35.8 (2.4) |

The nature of the mutagenic events was also analysed, revealing that the frequency of small deletions corresponding to the complete or partial removal of the 3' overhang (Del2, Del3 or Del4) is increased on addition of scTREX2. The percentage of small deletions was increased from 11% using the RAG1 meganuclease alone, to 49% on co-transfection with scTREX2 and 68% using the scTrex2_SC_RAG fusion protein (FIG. 8). The percentage of small deletions using the CAPNS1 meganuclease alone was 2%, increasing to 50% using scTREX2 in a co-transfection experiment, and 82% when the scTrex_SC_CAPNS1 fusion was used (FIG. 9).

Example 3

Impact of scTrex2 on Mutagenesis Induced by TALEN

Three heterodimeric TALENs called DMDT, HBBT and CAPT were designed to target the human genes DMD, HBB and CAPNS1 respectively. DMDT is encoded by plasmids pCLS9027 (SEQ ID NO: 61) and pCLS9028 (SEQ ID NO: 62), HBBT is an heterodimeric protein encoded by pCLS9235 (SEQ ID NO: 63) and pCLS9241 (SEQ ID NO: 64) and CAPT is encoded by pCLS9025 (SEQ ID NO: 65) and pCLS9026 (SEQ ID NO: 66). Proteins respectively encoded by these plasmids are given in SEQ ID NO: 85-90. DMDT is designed to cleave the target DNA sequences DMD_target: TGTATTCCTTTATGGATcagttaacattataaATGATAACTTTAGCTCA (SEQ ID NO: 67), HBBT is designed to cleave the target DNA sequence HBB_target: TCTGACACAACTGTGTTcactagcaacctcaaACAGACACCATGGTGCA (SEQ ID NO: 68), and CAPT is designed to cleave the target DNA sequence CAPT_target: TCCGGGAACCCAGAGCTcacagccacgatcttAGACCCGAGCCCACAGA (SEQ ID NO: 69).

Co-transfection of the DMDT, HBBT and CAPT expressing plasmids were performed in presence of plasmid pCLS8982 (SEQ ID NO: 10) coding for a single-chain variant of TREX2 (scTrex2) and in the presence of plasmids pCLS8940 (SEQ ID NO: 70) or pCLS8943 (SEQ ID NO: 71) or pCLS9893 (SEQ ID NO: 72) encoding repair matrices respectively. Targeted mutagenesis was measured by molecular analysis of a specific locus using PCR amplification followed by Deep sequencing.

Cells Transfection

The human 293H cells (ATCC) were plated at a density of 1.2×10⁶ cells per 10 cm dish in complete medium (DMEM supplemented with 2 mM L-glutamine, penicillin (100 IU/ml), streptomycin (100 µg/ml), amphotericin B (Fongizone: 0.25 µg/ml, Invitrogen-Life Science) and 10% FBS). The next day, cells were co-transfected with 15 µg of total DNA containing 2.5 µg of each monomer of TALENS, 5 µg of scTREX2 or empty vector, and 5 µg of pCLS8940 (SEQ ID NO: 70) or pCLS8943 (SEQ ID NO: 71), or pCLS9893 (SEQ ID NO: 72) as mentioned above, with LIPOFECTAMINE® 2000 transfection reagent (Invitrogen) according to the manufacturer's protocol. As negative control, cells were transfected with 10 µg of empty vector and 5 µg of scTREX2. Three days after transfection, genomic DNA was extracted and the region surrounding the target site was amplified by specific PCR. The first PCR was performed using the primers F1 and R1 and was followed by a nested PCR using the primers F2 and R2 flanked by specific adaptator needed for HTS sequencing on the 454 sequencing system (454 Life Sciences).

DMDT_F1:
(SEQ ID NO: 73)
5'-AGGCCTCCATTCCTTTGAAGGAATTGG-3'

DMDT_R1:
(SEQ ID NO: 74)
5'-TTAAACACTGCTATTCAGTAGGACACACACC-3'

DMDT_F2:
(SEQ ID NO: 75)
5'-CCATCTCATCCCTGCGTGTCTCCGACTCAG-Tag-
<u>CCTGATATTTCTCCTATTAATATTG</u> -3'

DMDT_R2:
(SEQ ID NO: 76)
5'- CCTATCCCCTGTGTGCCTTGGCAGTCTCAG-
<u>GGAGTGTGGTACTTCATCATGTCAGA</u> -3'

HBBT_F1:
(SEQ ID NO: 77)
5'-GAAGAGTAAATTTTAGTAAAGGAGG-3'

HBBT_R1:
(SEQ ID NO: 78)
5'-GCCTAGCTTGGACTCAGAATAATC-3'

HBBT_F2:
(SEQ ID NO: 79):
5'-CCATCTCATCCCTGCGTGTCTCCGACTCAG-Tag-
<u>CCACACCCTAGGGTTGGCCAATCTACTCCC</u> -3'

HBBT_R2:
(SEQ ID NO: 80)
5'- CCTATCCCCTGTGTGCCTTGGCAGTCTCAG-
<u>CCCACCCTTAGGCTGCTGGTGGTCTAC</u> -3'

```
CAPT_F1:
                                          (SEQ ID NO: 81)
5'- CTTCTCCACCCTCTGTCTCATGATC-3'

CAPT_R1:
                                          (SEQ ID NO: 82)
5'- CCTTGGCAGGTCATGGGCGCGGAGC-3'

CAPT_F2:
                                          (SEQ ID NO: 83)
5'-CCATCTCATCCCTGCGTGTCTCCGACTCAG-tag-

CTTCTCCACCCTCTGTCTCATGATC -3'

CAPT_R2:
                                          (SEQ ID NO: 84)
5'- CCTATCCCCTGTGTGCCTTGGCAGTCTCAG-

CCTTGGCAGGTCATGGGCGCGGAGC -3'.
```

5000 to 10000 sequences per sample were analyzed.

Results

The frequency of mutagenesis induced by TALE nucleases alone or in the presence of the scTREX2 molecule was determined by molecular analysis after specific amplification of each locus followed by deep sequencing analysis of the amplicons. Results are presented in FIG. 10. In absence of scTREX2, 9.98%, 13.06% and 9.75% of PCR fragments carries mutations in samples corresponding to cells transfected with plasmids expressing respectively DMDT, HBBT and CAPT. In contrast, in sample corresponding to cells co-transfected with these TALENs and scTREX2 expressing plasmids (FIG. 10) these frequencies increase significantly ($p<10^{-16}$) for all the TALENs tested to 16.76%, 27.07% and 22.50% respectively.

Thus, co-transfection of TALEN nuclease with the DNA processing enzyme scTREX2 stimulates the mutagenesis frequency.

Example 4

Trex2 Increases the Mutagenic Potential of Meganucleases in Plant Cells

Experiments were performed to test whether co-expression of a meganuclease with Trex2 increases frequencies of targeted mutagenesis in plant cells. I-SceI and Trex2 were each cloned downstream of a promoter that provides high levels of constitutive expression in plant cells. Plasmids encoding I-SceI and Trex2 (pCLS8982, SEQ ID NO: 10) were then introduced into tobacco protoplasts by PEG-mediated transformation. The protoplasts were derived from a tobacco line with an integrated I-SceI recognition site.

Four batches of protoplasts, each with 1×106 cells, were transformed with different combinations of plasmids. One batch was transformed with 15 μg each of plasmids encoding I-SceI and YFP; a second batch was transformed with 15 μg each of plasmids encoding I-SceI and Trex2; a third batch was transformed with 15 μg each of plasmids encoding Trex2 and YFP, and the fourth batch was transformed with 15 μg of a plasmid encoding YFP. Twenty-four hours after transformation, genomic DNA was prepared from the protoplasts. An approximately 350 bp encompassing the I-SceI recognition site was then amplified by PCR. The PCR product was subjected to 454 pyro-sequencing. Sequencing reads with insertion/deletion (indel) mutations at the cleavage site were considered as having been derived from imprecise repair of a cleaved target site by non-homologous end-joining.

The sequencing results provided clear evidence that Trex2, in combination with a meganuclease, greatly increases frequencies of targeted mutagenesis in plants (FIG. 11). Indels were recovered from cells expressing both I-SceI and Trex2 at a frequency 16-fold greater than with I-SceI alone. In addition to increasing the mutation frequency, the expression of Trex2 also changed the mutation spectrum. For example, the occurrence of insertions in cells expressing Trex2 (7 out of 1238; 0.57%) was significantly lower than in cells expressing I-SceI alone (9 out 46; 19.5%). Furthermore, the size of the deletions created by co-expression of I-SceI and Trex2 was smaller than what was observed with I-SceI alone. In the former case, 96.6% of the deletions were less than 10 bp, whereas in the latter, the number of deletions less than 10 bp was 81.1%.

We conclude that co-expression of Trex2 with a meganuclease in plant cells greatly stimulates the frequency of mutagenesis and promotes the formation of small deletions at the cleavage site.

LIST OF CITED REFERENCES

Arimondo, P. B., C. J. Thomas, et al. (2006). "Exploring the cellular activity of camptothecin-triple-helix-forming oligonucleotide conjugates." *Mol Cell Biol* 26(1): 324-33.

Arnould, S., P. Chames, et al. (2006). "Engineering of large numbers of highly specific homing endonucleases that induce recombination on novel DNA targets." *J Mol Biol* 355(3): 443-58.

Arnould, S., C. Perez, et al. (2007). "Engineered I-CreI derivatives cleaving sequences from the human XPC gene can induce highly efficient gene correction in mammalian cells." *J Mol Biol* 371(1): 49-65.

Ashworth, J., J. J. Havranek, et al. (2006). "Computational redesign of endonuclease DNA binding and cleavage specificity." *Nature* 441(7093): 656-9.

Beumer, K. J., J. K. Trautman, et al. (2008). "Efficient gene targeting in *Drosophila* by direct embryo injection with zinc-finger nucleases." *Proc Natl Acad Sci USA* 105(50): 19821-6.

Boch, J., H. Scholze, et al. (2009). "Breaking the code of DNA binding specificity of TAL-type III effectors." *Science* 326(5959): 1509-12.

Bolduc, J. M., P. C. Spiegel, et al. (2003). "Structural and biochemical analyses of DNA and RNA binding by a bifunctional homing endonuclease and group I intron splicing factor." *Genes Dev* 17(23): 2875-88.

Britt, A. B. (1999). "Molecular genetics of DNA repair in higher plants." *Trends Plant Sci* 4(1): 20-25.

Burden and O. N. (1998). "Mechanism of action of eukaryotic topoisomerase II and drugs targeted to the enzyme." *Biochim Biophys Acta.* 1400(1-3): 139-154.

Capecchi, M. R. (1989). "The new mouse genetics: altering the genome by gene targeting."*Trends Genet.* 5(3): 70-6.

Cathomen, T. and J. K. Joung (2008). "Zinc-finger nucleases: the next generation emerges." *Mol Ther* 16(7): 1200-7.

Chames, P., J. C. Epinat, et al. (2005). "In vivo selection of engineered homing endonucleases using double-strand break induced homologous recombination."*Nucleic Acids Res* 33(20): e178.

Chevalier, B., M. Turmel, et al. (2003). "Flexible DNA target site recognition by divergent homing endonuclease isoschizomers I-CreI and I-MsoI." *J Mol Biol* 329(2): 253-69.

Chevalier, B. S., T. Kortemme, et al. (2002). "Design, activity, and structure of a highly specific artificial endonuclease." *Mol Cell* 10(4): 895-905.

Chevalier, B. S., R. J. Monnat, Jr., et al. (2001). "The homing endonuclease I-CreI uses three metals, one of which is shared between the two active sites." *Nat Struct Biol* 8(4): 312-6.

Chevalier, B. S, and B. L. Stoddard (2001). "Homing endonucleases: structural and functional insight into the catalysts of intron/intein mobility." *Nucleic Acids Res* 29(18): 3757-74.

Choulika, A., A. Perrin, et al. (1995). "Induction of homologous recombination in mammalian chromosomes by using the I-SceI system of *Saccharomyces cerevisiae*." *Mol Cell Biol* 15(4): 1968-73.

Christian, M., T. Cermak, et al. (2010). "Targeting DNA double-strand breaks with TAL effector nucleases." *Genetics* 186(2): 757-61.

Cohen-Tannoudji, M., S. Robine, et al. (1998). "I-SceI-induced gene replacement at a natural locus in embryonic stem cells." *Mol Cell Biol* 18(3): 1444-8.

Critchlow, S. E. and S. P. Jackson (1998). "DNA end-joining: from yeast to man." *Trends Biochem Sci* 23(10): 394-8.

Donoho, G., M. Jasin, et al. (1998). "Analysis of gene targeting and intrachromosomal homologous recombination stimulated by genomic double-strand breaks in mouse embryonic stem cells." *Mol Cell Biol* 18(7): 4070-8.

Doyon, J. B., V. Pattanayak, et al. (2006). "Directed evolution and substrate specificity profile of homing endonuclease I-SceI." *J Am Chem Soc* 128(7): 2477-84.

Doyon, Y., J. M. McCammon, et al. (2008). "Heritable targeted gene disruption in zebrafish using designed zinc-finger nucleases." *Nat Biotechnol* 26(6): 702-8.

Dujon, B., L. Colleaux, et al. (1986). "Mitochondrial introns as mobile genetic elements: the role of intron-encoded proteins." *Basic Life Sci* 40: 5-27.

Eisenschmidt, K., T. Lanio, et al. (2005). "Developing a programmed restriction endonuclease for highly specific DNA cleavage." *Nucleic Acids Res* 33(22): 7039-47.

Endo, M., K. Osakabe, et al. (2006). "Molecular characterization of true and ectopic gene targeting events at the acetolactate synthase gene in *Arabidopsis*." *Plant Cell Physiol* 47(3): 372-9.

Endo, M., K. Osakabe, et al. (2007). "Molecular breeding of a novel herbicide-tolerant rice by gene targeting." *Plant J* 52(1): 157-66.

Epinat, J. C., S. Arnould, et al. (2003). "A novel engineered meganuclease induces homologous recombination in yeast and mammalian cells." *Nucleic Acids Res* 31(11): 2952-62.

Feldmann, E., V. Schmiemann, et al. (2000). "DNA double-strand break repair in cell-free extracts from Ku80-deficient cells: implications for Ku serving as an alignment factor in non-homologous DNA end joining." *Nucleic Acids Res* 28(13): 2585-96.

Gimble, F. S., C. M. Moure, et al. (2003). "Assessing the plasticity of DNA target site recognition of the PI-SceI homing endonuclease using a bacterial two-hybrid selection system." *J Mol Biol* 334(5): 993-1008.

Gouble, A., J. Smith, et al. (2006). "Efficient in toto targeted recombination in mouse liver by meganuclease-induced double-strand break." *J Gene Med* 8(5): 616-22.

Grizot, S., J. Smith, et al. (2009). "Efficient targeting of a SCID gene by an engineered single-chain homing endonuclease." *Nucleic Acids Res* 37(16): 5405-19.

Haber, J. (2000). "Partners and pathways repairing a double-strand break." *Trends Genet.* 16(6): 259-264.

Haber, J. E. (1995). "In vivo biochemistry: physical monitoring of recombination induced by site-specific endonucleases." *Bioessays* 17(7): 609-20.

Hanin, M., S. Volrath, et al. (2001). "Gene targeting in *Arabidopsis*." *Plant J* 28(6): 671-7.

Ichiyanagi, K., Y. Ishino, et al. (2000). "Crystal structure of an archaeal intein-encoded homing endonuclease PI-PfuI." *J Mol Biol* 300(4): 889-901.

Kalish, J. M. and P. M. Glazer (2005). "Targeted genome modification via triple helix formation." *Ann NY Acad Sci* 1058: 151-61.

Kim, Y. G., J. Cha, et al. (1996). "Hybrid restriction enzymes: zinc finger fusions to Fok I cleavage domain." *Proc Natl Acad Sci USA* 93(3): 1156-60.

Kirik, A., S. Salomon, et al. (2000). "Species-specific double-strand break repair and genome evolution in plants." *Embo J* 19(20): 5562-6.

Li, H., H. Vogel, et al. (2007). "Deletion of Ku70, Ku80, or both causes early aging without substantially increased cancer." *Mol Cell Biol* 27(23): 8205-14.

Li, T., S. Huang, et al. (2010). "TAL nucleases (TALNs): hybrid proteins composed of TAL effectors and FokI DNA-cleavage domain." *Nucleic Acids Res* 39(1): 359-72.

Lieber, M. R. and Z. E. Karanjawala (2004). "Ageing, repetitive genomes and DNA damage." *Nat Rev Mol Cell Biol.* 5(1): 69-75.

Lloyd, A., C. L. Plaisier, et al. (2005). "Targeted mutagenesis using zinc-finger nucleases in *Arabidopsis*." *Proc Natl Acad Sci USA* 102(6): 2232-7.

Ma, J., E. Kim, et al. (2003). "Yeast Mre11 and Rad1 proteins define a Ku-independent mechanism to repair double-strand breaks lacking overlapping end sequences." *Mol Cell Biol.* 23(23): 8820-8828.

Meng, X., M. B. Noyes, et al. (2008). "Targeted gene inactivation in zebrafish using engineered zinc-finger nucleases." *Nat Biotechnol* 26(6): 695-701.

Moore, I., M. Samalova, et al. (2006). "Transactivated and chemically inducible gene expression in plants." *Plant J* 45(4): 651-83.

Moore, J. K. and J. E. Haber (1996). "Cell cycle and genetic requirements of two pathways of nonhomologous end-joining repair of double-strand breaks in *Saccharomyces cerevisiae*." *Mol Cell Biol* 16(5): 2164-73.

Moscou, M. J. and A. J. Bogdanove (2009). "A simple cipher governs DNA recognition by TAL effectors." *Science* 326(5959): 1501.

Moure, C. M., F. S. Gimble, et al. (2002). "Crystal structure of the intein homing endonuclease PI-SceI bound to its recognition sequence." *Nat Struct Biol* 9(10): 764-70.

Moure, C. M., F. S. Gimble, et al. (2003). "The crystal structure of the gene targeting homing endonuclease I-SceI reveals the origins of its target site specificity." *J Mol Biol* 334(4): 685-95.

Nagy, Z. and E. Soutoglou (2009). "DNA repair: easy to visualize, difficult to elucidate."*Trends Cell Biol* 19(11): 617-29.

Nouspikel, T. (2009). "DNA repair in mammalian cells: Nucleotide excision repair: variations on versatility." *Cell Mol Life Sci* 66(6): 994-1009.

Padidam, M. (2003). "Chemically regulated gene expression in plants." *Curr Opin Plant Biol* 6(2): 169-77.

Paques, F. and P. Duchateau (2007). "Meganucleases and DNA double-strand break-induced recombination: perspectives for gene therapy." *Curr Gene Ther* 7(1): 49-66.

Paques, F. and J. E. Haber (1999). "Multiple pathways of recombination induced by double-strand breaks in *Saccharomyces cerevisiae.*" *Microbiol Mol Biol Rev* 63(2): 349-404.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Posfai, G., V. Kolisnychenko, et al. (1999). "Markerless gene replacement in *Escherichia coli* stimulated by a double-strand break in the chromosome." *Nucleic Acids Res* 27(22): 4409-15.

Povirk, L. F. (1996). "DNA damage and mutagenesis by radiomimetic DNA-cleaving agents: bleomycin, neocarzinostatin and other enediynes." *Mutat Res* 355(1-2): 71-89.

Puchta, H., B. Dujon, et al. (1996). "Two different but related mechanisms are used in plants for the repair of genomic double-strand breaks by homologous recombination." *Proc Natl Acad Sci USA* 93(10): 5055-60.

Rosen, L. E., H. A. Morrison, et al. (2006). "Homing endonuclease I-CreI derivatives with novel DNA target specificities." *Nucleic Acids Res.*

Rothstein, R. (1991). "Targeting, disruption, replacement, and allele rescue: integrative DNA transformation in yeast." *Methods Enzymol* 194: 281-301.

Rouet, P., F. Smih, et al. (1994). "Expression of a site-specific endonuclease stimulates homologous recombination in mammalian cells." *Proc Natl Acad Sci USA* 91(13): 6064-8.

Rouet, P., F. Smih, et al. (1994). "Introduction of double-strand breaks into the genome of mouse cells by expression of a rare-cutting endonuclease." *Mol Cell Biol* 14(12): 8096-106.

Sargent, R. G., M. A. Brenneman, et al. (1997). "Repair of site-specific double-strand breaks in a mammalian chromosome by homologous and illegitimate recombination." *Mol Cell Biol* 17(1): 267-77.

Seligman, L. M., K. M. Stephens, et al. (1997). "Genetic analysis of the *Chlamydomonas* reinhardtii I-CreI mobile intron homing system in *Escherichia coli.*" *Genetics* 147(4): 1653-64.

Siebert, R. and H. Puchta (2002). "Efficient Repair of Genomic Double-Strand Breaks by Homologous Recombination between Directly Repeated Sequences in the Plant Genome." *Plant Cell* 14(5): 1121-31.

Silva, G. H., J. Z. Dalgaard, et al. (1999). "Crystal structure of the thermostable archaeal intron-encoded endonuclease I-DmoI." *J Mol Biol* 286(4): 1123-36.

Simon, P., F. Cannata, et al. (2008). "Sequence-specific DNA cleavage mediated by bipyridine polyamide conjugates." *Nucleic Acids Res* 36(11): 3531-8.

Smith, J., S. Grizot, et al. (2006). "A combinatorial approach to create artificial homing endonucleases cleaving chosen sequences." *Nucleic Acids Res* 34(22): e149.

Sonoda, E., H. Hochegger, et al. (2006). "Differential usage of non-homologous end-joining and homologous recombination in double strand break repair." *DNA Repair (Amst)* 5(9-10): 1021-9.

Spiegel, P. C., B. Chevalier, et al. (2006). "The structure of I-CeuI homing endonuclease: Evolving asymmetric DNA recognition from a symmetric protein scaffold."*Structure* 14(5): 869-80.

Stoddard, B. L. (2005). "Homing endonuclease structure and function." *Q Rev Biophys* 38(1): 49-95.

Sussman, D., M. Chadsey, et al. (2004). "Isolation and characterization of new homing endonuclease specificities at individual target site positions." *J Mol Biol* 342(1): 31-41.

Teicher, B. A. (2008). "Next generation topoisomerase I inhibitors: Rationale and biomarker strategies." *Biochem Pharmacol* 75(6): 1262-71.

Terada, R., Y. Johzuka-Hisatomi, et al. (2007). "Gene targeting by homologous recombination as a biotechnological tool for rice functional genomics." *Plant Physiol* 144(2): 846-56.

Terada, R., H. Urawa, et al. (2002). "Efficient gene targeting by homologous recombination in rice." *Nat Biotechnol* 20(10): 1030-4.

Wang, R., X. Zhou, et al. (2003). "Chemically regulated expression systems and their applications in transgenic plants." *Transgenic Res* 12(5): 529-40.

Zuo, J. and N. H. Chua (2000). "Chemical-inducible systems for regulated expression of plant genes." *Curr Opin Biotechnol* 11(2): 146-51.

Mazur, D. J. and F. W. Perrino (2001). "Structure and expression of the TREX1 and TREX2 3'→5' exonuclease genes." *J Biol Chem* 276(18): 14718-27.

Perrino, F. W., de Silva U, Harvey S, Pryor E. E. Jr., Cole D. W. and Hollis T (2008). "Cooperative DNA binding and communication across the dimer interface in the TREX2 3'→5'-exonuclease." J Biol Chem 283 (31): 21441-52.

Dumitrache, L. C. et al. Trex2 Enables Spontaneous Sister Chromatid Exchanges without Facilitating DNA Double Strand Break Repair. (2011, May 31). *Genetics.*

Bennardo, N., Gunn, A., Cheng, A., Hasty, P. & Stark, J. M. (2009). Limiting the persistence of a chromosome break diminishes its mutagenic potential. *PLoS Genet.* 5, e1000683 (2009).

The invention claimed is:

1. A method for increasing double-strand-break induced mutagenesis at a genomic locus of interest in a cell comprising the steps of:
   (i) identifying at said genomic locus of interest at least one DNA target sequence cleavable by one natural or engineered rare-cutting endonuclease;
   (ii) expressing said rare-cutting endonuclease in the cell together with a polynucleotide encoding a fusion protein that comprises:
   a first polypeptide that is a human TREX2 exonuclease protomer of SEQ ID NO: 26 or functional mutant thereof that shares at least 80% identity with the human TREX2 exonuclease protomer;
   a second polypeptide that is a human TREX2 exonuclease protomer of SEQ ID NO: 26 or functional mutant thereof that shares at least 80% identity with the human TREX2 exonuclease protomer; and
   a peptidic linker connecting said first and second polypeptides;
   (iii) thereby obtaining, by expression of said fusion protein in said cell, increased double strand-break-induced mutagenesis at said genomic locus of interest.

2. The method of claim 1, wherein the polynucleotide further encodes the rare-cutting endonuclease.

3. The method of claim 1, wherein the rare-cutting endonuclease is encoded by a second polynucleotide.

4. The method of claim 2, wherein the rare-cutting endonuclease is a meganuclease.

5. The method of claim 2, wherein the rare-cutting endonuclease is selected from the group consisting of I-SceI, I-ChuI, I-CreI, I-CsmI, PI-SceI, PI-TliI, PI-MtuI, I-CeuI, I-SceII, I-SceIII, HO, PI-CivI, PI-CtrI, PI-AaeI, PI-BsuI, PI-DhaI, PI-DraI, PI-MavI, PI-MchI, PI-MfuI, PI-MflI, PI-MgaI, PI-MgoI, PI-MinI, PI-MkaI, PI-MleI, PI-MmaI, PI-MshI, PI-MsmI, PI-MthI, PI-MtuI, PI-MxeI, PI-NpuI, PI-PfuI, PI-RmaI, PI-SpbI, PI-SspI, PI-FacI, PI-MjaI, PI-PhoI, PI-TagI, PI-ThyI, PI-TkoI, PI-TspI, and I-MsoI.

6. The method of claim 4, wherein the meganuclease shares at least 80% identity with residues 1-152 of the natural I-CreI LAGLIDADG meganuclease of SEQ ID NO: 35.

7. The method of claim 4, wherein the meganuclease is the natural I-CreI LAGLIDADG meganuclease of SEQ ID NO: 35.

8. The method of claim 2, wherein the rare-cutting endonuclease is a TAL nuclease (TALEN).

9. The method of claim 2, wherein said cell is a plant cell.

10. The method of claim 2, wherein said cell is a mammalian cell.

11. The method of claim 2, wherein said cell is a human cell.

12. The method of claim 3, wherein the rare-cutting endonuclease is a meganuclease.

13. The method of claim 3, wherein the rare-cutting endonuclease is selected from the group consisting of I-SceI, I-ChuI, I-CreI, I-CsmI, PI-SceI, PI-TliI, PI-MtuI, I-CeuI, I-SceII, I-SceIII, HO, PI-CivI, PI-CtrI, PI-AaeI, PI-BsuI, PI-DhaI, PI-DraI, PI-MavI, PI-MchI, PI-MfuI, PI-MflI, PI-MgaI, PI-MgoI, PI-MinI, PI-MkaI, PI-MleI, PI-MmaI, PI-MshI, PI-MsmI, PI-MthI, PI-MtuI, PI-MxeI, PI-NpuI, PI-PfuI, PI-RmaI, PI-SpbI, PI-SspI, PI-FacI, PI-MjaI, PI-PhoI, PI-TagI, PI-ThyI, PI-TkoI, PI-TspI, and I-MsoI.

14. The method of claim 12, wherein the meganuclease shares at least 80% identity with residues 1-152 of the natural I-CreI LAGLIDADG of SEQ ID NO: 35.

15. The method of claim 12, wherein the meganuclease is the natural I-CreI LAGLIDADG meganuclease of SEQ ID NO: 35.

16. The method of claim 3, wherein the rare-cutting endonuclease is a TAL nuclease (TALEN).

17. The method of claim 3, wherein said cell is a plant cell.

18. The method of claim 3, wherein said cell is a mammalian cell.

19. The method of claim 3, wherein said cell is a human cell.

20. The method of claim 1, wherein the first and second polypeptides are functional mutants of the human TREX2 exonuclease protomer of SEQ ID NO: 26 that share at least 90% identity with the human TREX2 exonuclease protomer.

21. The method of claim 1, wherein the first and second polypeptides are functional mutants of the human TREX2 exonuclease protomer of SEQ ID NO: 26 that share at least 95% identity with the human TREX2 exonuclease protomer.

22. The method of claim 1, wherein the first and second polypeptides are functional mutants of the human TREX2 exonuclease protomer of SEQ ID NO: 26 that share at least 97% identity with the human TREX2 exonuclease protomer.

* * * * *

SEQUENCE LISTING

```
<160> NUMBER OF SEQ ID NOS: 90

<210> SEQ ID NO 1
<211> LENGTH: 8
<212> TYPE: PRT
<213> ORGANISM: Artificial sequence
<220> FEATURE:
<223> OTHER INFORMATION: scTrex Linker1

<400> SEQUENCE: 1

Ser Arg Pro Ser Glu Ser Glu Gly
1               5
```

```
<210> SEQ ID NO 2
<211> LENGTH: 11
<212> TYPE: PRT
<213> ORGANISM: Artificial sequence
<220> FEATURE:
<223> OTHER INFORMATION: scTrex Linker2

<400> SEQUENCE: 2

Thr Pro Pro Gln Thr Gly Leu Asp Val Pro Tyr
1               5                   10

<210> SEQ ID NO 3
<211> LENGTH: 12
<212> TYPE: PRT
<213> ORGANISM: Artificial sequence
<220> FEATURE:
<223> OTHER INFORMATION: scTrex Linker3

<400> SEQUENCE: 3

Gly Asp Ser Ser Val Ser Asn Ser Glu His Ile Ala
1               5                   10

<210> SEQ ID NO 4
<211> LENGTH: 14
<212> TYPE: PRT
<213> ORGANISM: Artificial sequence
<220> FEATURE:
<223> OTHER INFORMATION: scTrex Linker4

<400> SEQUENCE: 4

Ile Arg Pro Arg Ala Ile Gly Gly Ser Lys Pro Arg Val Ala
1               5                   10

<210> SEQ ID NO 5
<211> LENGTH: 482
<212> TYPE: PRT
<213> ORGANISM: Artificial sequence
<220> FEATURE:
<223> OTHER INFORMATION: scTrex1

<400> SEQUENCE: 5

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
                20                  25                  30

Leu Phe Ala Val His Arg Ser Ser Leu Glu Asn Pro Glu His Asp Glu
            35                  40                  45

Ser Gly Ala Leu Val Leu Pro Arg Val Leu Asp Lys Leu Thr Leu Cys
        50                  55                  60

Met Cys Pro Glu Arg Pro Phe Thr Ala Lys Ala Ser Glu Ile Thr Gly
65                  70                  75                  80

Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
    130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
```

165                 170                 175
Phe His Arg Tyr Phe Arg Ala Glu Pro Ser Ala Ala His Ser Ala Glu
            180                 185                 190

Gly Asp Val His Thr Leu Leu Leu Ile Phe Leu His Arg Ala Ala Glu
        195                 200                 205

Leu Leu Ala Trp Ala Asp Glu Gln Ala Arg Gly Trp Ala His Ile Glu
    210                 215                 220

Pro Met Tyr Leu Pro Pro Asp Asp Pro Ser Leu Glu Ala Ser Arg Pro
225                 230                 235                 240

Ser Glu Ser Glu Gly Ser Glu Ala Pro Arg Ala Glu Thr Phe Val Phe
            245                 250                 255

Leu Asp Leu Glu Ala Thr Gly Leu Pro Ser Val Glu Pro Glu Ile Ala
        260                 265                 270

Glu Leu Ser Leu Phe Ala Val His Arg Ser Ser Leu Glu Asn Pro Glu
    275                 280                 285

His Asp Glu Ser Gly Ala Leu Val Leu Pro Arg Val Leu Asp Lys Leu
290                 295                 300

Thr Leu Cys Met Cys Pro Glu Arg Pro Phe Thr Ala Lys Ala Ser Glu
305                 310                 315                 320

Ile Thr Gly Leu Ser Ser Glu Gly Leu Ala Arg Cys Arg Lys Ala Gly
            325                 330                 335

Phe Asp Gly Ala Val Val Arg Thr Leu Gln Ala Phe Leu Ser Arg Gln
        340                 345                 350

Ala Gly Pro Ile Cys Leu Val Ala His Asn Gly Phe Asp Tyr Asp Phe
    355                 360                 365

Pro Leu Leu Cys Ala Glu Leu Arg Arg Leu Gly Ala Arg Leu Pro Arg
370                 375                 380

Asp Thr Val Cys Leu Asp Thr Leu Pro Ala Leu Arg Gly Leu Asp Arg
385                 390                 395                 400

Ala His Ser His Gly Thr Arg Ala Arg Gly Arg Gln Gly Tyr Ser Leu
            405                 410                 415

Gly Ser Leu Phe His Arg Tyr Phe Arg Ala Glu Pro Ser Ala Ala His
        420                 425                 430

Ser Ala Glu Gly Asp Val His Thr Leu Leu Leu Ile Phe Leu His Arg
    435                 440                 445

Ala Ala Glu Leu Leu Ala Trp Ala Asp Glu Gln Ala Arg Gly Trp Ala
    450                 455                 460

His Ile Glu Pro Met Tyr Leu Pro Pro Asp Asp Pro Ser Leu Glu Ala
465                 470                 475                 480

Ala Asp

<210> SEQ ID NO 6
<211> LENGTH: 485
<212> TYPE: PRT
<213> ORGANISM: Artificial sequence
<220> FEATURE:
<223> OTHER INFORMATION: scTrex2

<400> SEQUENCE: 6

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
            20                  25                  30

Leu Phe Ala Val His Arg Ser Ser Leu Glu Asn Pro Glu His Asp Glu
        35                  40                  45

```
Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
 65                  70                  75                  80

Leu Ser Ser Glu Gly Leu Ala Arg Cys Arg Lys Ala Gly Phe Asp Gly
                 85                  90                  95

Ala Val Val Arg Thr Leu Gln Ala Phe Leu Ser Arg Gln Ala Gly Pro
                100                 105                 110

Ile Cys Leu Val Ala His Asn Gly Phe Asp Tyr Asp Phe Pro Leu Leu
                115                 120                 125

Cys Ala Glu Leu Arg Arg Leu Gly Ala Arg Leu Pro Arg Asp Thr Val
    130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
                180                 185                 190

Gly Asp Val His Thr Leu Leu Leu Ile Phe Leu His Arg Ala Ala Glu
                195                 200                 205

Leu Leu Ala Trp Ala Asp Glu Gln Ala Arg Gly Trp Ala His Ile Glu
    210                 215                 220

Pro Met Tyr Leu Pro Pro Asp Asp Pro Ser Leu Glu Ala Thr Pro Pro
225                 230                 235                 240

Gln Thr Gly Leu Asp Val Pro Tyr Ser Glu Ala Pro Arg Ala Glu Thr
                245                 250                 255

Phe Val Phe Leu Asp Leu Glu Ala Thr Gly Leu Pro Ser Val Glu Pro
                260                 265                 270

Glu Ile Ala Glu Leu Ser Leu Phe Ala Val His Arg Ser Ser Leu Glu
                275                 280                 285

Asn Pro Glu His Asp Glu Ser Gly Ala Leu Val Leu Pro Arg Val Leu
    290                 295                 300

Asp Lys Leu Thr Leu Cys Met Cys Pro Glu Arg Pro Phe Thr Ala Lys
305                 310                 315                 320

Ala Ser Glu Ile Thr Gly Leu Ser Ser Glu Gly Leu Ala Arg Cys Arg
                325                 330                 335

Lys Ala Gly Phe Asp Gly Ala Val Val Arg Thr Leu Gln Ala Phe Leu
                340                 345                 350

Ser Arg Gln Ala Gly Pro Ile Cys Leu Val Ala His Asn Gly Phe Asp
    355                 360                 365

Tyr Asp Phe Pro Leu Leu Cys Ala Glu Leu Arg Arg Leu Gly Ala Arg
    370                 375                 380

Leu Pro Arg Asp Thr Val Cys Leu Asp Thr Leu Pro Ala Leu Arg Gly
385                 390                 395                 400

Leu Asp Arg Ala His Ser His Gly Thr Arg Ala Arg Gly Arg Gln Gly
                405                 410                 415

Tyr Ser Leu Gly Ser Leu Phe His Arg Tyr Phe Arg Ala Glu Pro Ser
                420                 425                 430

Ala Ala His Ser Ala Glu Gly Asp Val His Thr Leu Leu Leu Ile Phe
                435                 440                 445

Leu His Arg Ala Ala Glu Leu Leu Ala Trp Ala Asp Glu Gln Ala Arg
    450                 455                 460
```

Gly Trp Ala His Ile Glu Pro Met Tyr Leu Pro Pro Asp Asp Pro Ser
465                 470                 475                 480

Leu Glu Ala Ala Asp
            485

<210> SEQ ID NO 7
<211> LENGTH: 486
<212> TYPE: PRT
<213> ORGANISM: Artificial sequence
<220> FEATURE:
<223> OTHER INFORMATION: scTrex3

<400> SEQUENCE: 7

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
            20                  25                  30

Leu Phe Ala Val His Arg Ser Leu Glu Asn Pro Glu His Asp Glu
        35                  40                  45

Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
65                  70                  75                  80

Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Leu Ile Phe Leu His Arg Ala Ala Glu
        195                 200                 205

Leu Leu Ala Trp Ala Asp Glu Gln Ala Arg Gly Trp Ala His Ile Glu
210                 215                 220

Pro Met Tyr Leu Pro Pro Asp Asp Pro Ser Leu Glu Ala Gly Asp Ser
225                 230                 235                 240

Ser Val Ser Asn Ser Glu His Ile Ala Ser Glu Ala Pro Arg Ala Glu
                245                 250                 255

Thr Phe Val Phe Leu Asp Leu Glu Ala Thr Gly Leu Pro Ser Val Glu
            260                 265                 270

Pro Glu Ile Ala Glu Leu Ser Leu Phe Ala Val His Arg Ser Ser Leu
        275                 280                 285

Glu Asn Pro Glu His Asp Glu Ser Gly Ala Leu Val Leu Pro Arg Val
    290                 295                 300

Leu Asp Lys Leu Thr Leu Cys Met Cys Pro Glu Arg Pro Phe Thr Ala
305                 310                 315                 320

Lys Ala Ser Glu Ile Thr Gly Leu Ser Ser Glu Gly Leu Ala Arg Cys
                325                 330                 335

```
Arg Lys Ala Gly Phe Asp Gly Ala Val Val Arg Thr Leu Gln Ala Phe
                340                 345                 350

Leu Ser Arg Gln Ala Gly Pro Ile Cys Leu Val Ala His Asn Gly Phe
        355                 360                 365

Asp Tyr Asp Phe Pro Leu Leu Cys Ala Glu Leu Arg Arg Leu Gly Ala
370                 375                 380

Arg Leu Pro Arg Asp Thr Val Cys Leu Asp Thr Leu Pro Ala Leu Arg
385                 390                 395                 400

Gly Leu Asp Arg Ala His Ser His Gly Thr Arg Ala Arg Gly Arg Gln
                405                 410                 415

Gly Tyr Ser Leu Gly Ser Leu Phe His Arg Tyr Phe Arg Ala Glu Pro
            420                 425                 430

Ser Ala Ala His Ser Ala Glu Gly Asp Val His Thr Leu Leu Leu Ile
                435                 440                 445

Phe Leu His Arg Ala Ala Glu Leu Leu Ala Trp Ala Asp Glu Gln Ala
            450                 455                 460

Arg Gly Trp Ala His Ile Glu Pro Met Tyr Leu Pro Pro Asp Asp Pro
465                 470                 475                 480

Ser Leu Glu Ala Ala Asp
                485

<210> SEQ ID NO 8
<211> LENGTH: 488
<212> TYPE: PRT
<213> ORGANISM: Artificial sequence
<220> FEATURE:
<223> OTHER INFORMATION: scTrex4

<400> SEQUENCE: 8

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
            20                  25                  30

Leu Phe Ala Val His Arg Ser Ser Leu Glu Asn Pro Glu His Asp Glu
        35                  40                  45

Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
65                  70                  75                  80

Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
    130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Leu Ile Phe Leu His Arg Ala Ala Glu
        195                 200                 205
```

```
Leu Leu Ala Trp Ala Asp Glu Gln Ala Arg Gly Trp Ala His Ile Glu
    210                 215                 220

Pro Met Tyr Leu Pro Pro Asp Asp Pro Ser Leu Glu Ala Ile Arg Pro
225                 230                 235                 240

Arg Ala Ile Gly Gly Ser Lys Pro Arg Val Ala Ser Glu Ala Pro Arg
                245                 250                 255

Ala Glu Thr Phe Val Phe Leu Asp Leu Glu Ala Thr Gly Leu Pro Ser
            260                 265                 270

Val Glu Pro Glu Ile Ala Glu Leu Ser Leu Phe Ala Val His Arg Ser
        275                 280                 285

Ser Leu Glu Asn Pro Glu His Asp Glu Ser Gly Ala Leu Val Leu Pro
    290                 295                 300

Arg Val Leu Asp Lys Leu Thr Leu Cys Met Cys Pro Glu Arg Pro Phe
305                 310                 315                 320

Thr Ala Lys Ala Ser Glu Ile Thr Gly Leu Ser Ser Glu Gly Leu Ala
                325                 330                 335

Arg Cys Arg Lys Ala Gly Phe Asp Gly Ala Val Val Arg Thr Leu Gln
            340                 345                 350

Ala Phe Leu Ser Arg Gln Ala Gly Pro Ile Cys Leu Val Ala His Asn
        355                 360                 365

Gly Phe Asp Tyr Asp Phe Pro Leu Leu Cys Ala Glu Leu Arg Arg Leu
    370                 375                 380

Gly Ala Arg Leu Pro Arg Asp Thr Val Cys Leu Asp Thr Leu Pro Ala
385                 390                 395                 400

Leu Arg Gly Leu Asp Arg Ala His Ser His Gly Thr Arg Ala Arg Gly
                405                 410                 415

Arg Gln Gly Tyr Ser Leu Gly Ser Leu Phe His Arg Tyr Phe Arg Ala
            420                 425                 430

Glu Pro Ser Ala Ala His Ser Ala Glu Gly Asp Val His Thr Leu Leu
        435                 440                 445

Leu Ile Phe Leu His Arg Ala Ala Glu Leu Leu Ala Trp Ala Asp Glu
    450                 455                 460

Gln Ala Arg Gly Trp Ala His Ile Glu Pro Met Tyr Leu Pro Pro Asp
465                 470                 475                 480

Asp Pro Ser Leu Glu Ala Ala Asp
                485

<210> SEQ ID NO 9
<211> LENGTH: 6617
<212> TYPE: DNA
<213> ORGANISM: Artificial sequence
<220> FEATURE:
<223> OTHER INFORMATION: pCLS8981

<400> SEQUENCE: 9
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
```

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca caagtttgta caaaaaagca ggctggcgcg cctacacagc ggccttgcca    960
ccatgggttc cgaggcaccc cgggccgaga cctttgtctt cctggacctg aagccactg    1020
ggctccccag tgtggagccc gagattgccg agctgtccct ctttgctgtc caccgctcct   1080
ccctggagaa cccggagcac gacgagtctg gtgccctagt attgccccgg gtcctggaca   1140
agctcacgct gtgcatgtgc ccggagcgcc ccttcactgc caaggccagc gagatcaccg   1200
gcctgagcag tgagggcctg gcgcgatgcc ggaaggctgg ctttgatggc gccgtggtgc   1260
ggacgctgca ggccttcctg agccgccagg cagggcccat ctgccttgtg cccacaatg    1320
gctttgatta tgatttcccc ctgctgtgtg ccgagctgcg gcgcctgggt gcccgcctgc   1380
cccgggacac tgtctgcctg gacacgctgc cggccctgcg gggcctggac cgcgcccaca   1440
gccacggcac ccgggcccgg ggccgccagg ttacagcct cggcagcctc ttccaccgct    1500
acttccgggc agagccaagc gcagcccact cagccgaggg cgacgtgcac accctgctcc   1560
tgatcttcct gcaccgcgcc gcagagctgc tcgcctgggc cgatgagcag gcccgtgggt   1620
gggcccacat cgagcccatg tacttgccgc ctgatgaccc cagcctggag gcgtctcgtc   1680
cttctgagtc tgaaggttcc gaggcacccc gggccgagac cttttgtcttc ctggacctgg   1740
aagccactgg gctccccagt gtggagcccg agattgccga gctgtccctc tttgctgtcc   1800
accgctcctc cctggagaac ccggagcacg acgagtctgg tgccctagta ttgccccggg   1860
tcctggacaa gctcacgctg tgcatgtgcc cggagcgccc cttcactgcc aaggccagcg   1920
agatcaccgg cctgagcagt gagggcctgg cgcgatgcc gaaggctggc tttgatggcg    1980
ccgtggtgcg gacgctgcag gccttcctga gccgccaggc agggcccatc tgccttgtgg   2040
cccacaatgg ctttgattat gatttccccc tgctgtgtgc cgagctgcgg cgcctgggtg   2100
cccgcctgcc ccgggacact gtctgcctgg acacgctgcc ggccctgcgg ggcctggacc   2160
gcgcccacag ccacggcacc cgggcccggg gccgccaggt tacagcctc ggcagcctct    2220
tccaccgcta cttccgggca gagccaagcg cagcccactc agccgagggc gacgtgcaca   2280
ccctgctcct gatcttcctg caccgcgccg cagagctgct cgcctgggcc gatgagcagg   2340
cccgtgggtg ggcccacatc gagcccatgt acttgccgcc tgatgacccc agcctggagg   2400
cggccgactg ataactcgag cgctagcacc cagctttctt gtacaaagtg gtgatctaga   2460
gggcccgcgg ttcgaaggta agcctatccc taaccctctc ctcggtctcg attctacgcg   2520
taccggttag taatgagttt aaacggggga ggctaactga aacacggaag gagacaatac   2580
cggaaggaac ccgcgctatg acggcaataa aaagacagaa taaaacgcac gggtgttggg   2640
tcgtttgttc ataaacgcgg ggttcggtcc cagggctggc actctgtcga taccccaccg   2700
agaccccatt ggggccaata cgcccgcgtt tcttcctttt ccccaccccca ccccccaagt   2760
tcgggtgaag gcccagggct cgcagccaac gtcgggcgg caggccctgc catagcagat    2820
```

```
ctgcgcagct ggggctctag ggggtatccc cacgcgccct gtagcggcgc attaagcgcg    2880
gcgggtgtgg tggttacgcg cagcgtgacc gctacacttg ccagcgccct agcgcccgct    2940
cctttcgctt tcttcccttc ctttctcgcc acgttcgccg gctttccccg tcaagctcta    3000
aatcggggca tccctttagg gttccgattt agtgctttac ggcacctcga ccccaaaaaa    3060
cttgattagg gtgatggttc acgtagtggg ccatcgccct gatagacggt ttttcgccct    3120
ttgacgttgg agtccacgtt ctttaatagt ggactcttgt tccaaactgg aacaacactc    3180
aaccctatct cggtctattc ttttgattta aagggatttt ggggatttc ggcctattgg    3240 ttaaaaaatg agctgattta acaaaaattt aacgcgaatt aattctgtgg aatgtgtgtc    3300
agttagggtg tggaaagtcc ccaggctccc cagcaggcag aagtatgcaa agcatgcatc    3360
tcaattagtc agcaaccagg tgtggaaagt ccccaggctc cccagcaggc agaagtatgc    3420
aaagcatgca tctcaattag tcagcaacca tagtcccgcc cctaactccg cccatcccgc    3480
ccctaactcc gcccagttcc gcccattctc cgccccatgg ctgactaatt ttttttattt    3540
atgcagaggc cgaggccgcc tctgcctctg agctattcca gaagtagtga ggaggctttt    3600
ttggaggcct aggcttttgc aaaaagctcc cgggagcttg tatatccatt ttcggatctg    3660
atcagcacgt gttgacaatt aatcatcggc atagtatatc ggcatagtat aatacgacaa    3720
ggtgaggaac taaaccatgg ccaagccttt gtctcaagaa gaatccaccc tcattgaaag    3780
agcaacggct acaatcaaca gcatccccat ctctgaagac tacagcgtcg ccagcgcagc    3840
tctctctagc gacggccgca tcttcactgg tgtcaatgta tatcatttta ctgggggacc    3900
ttgtgcagaa ctcgtggtgc tgggcactgc tgctgctgcg gcagctggca acctgacttg    3960
tatcgtcgcg atcggaaatg agaacagggg catcttgagc ccctgcggac ggtgccgaca    4020
ggtgcttctc gatctgcatc ctgggatcaa agccatagtg aaggacagtg atggacagcc    4080
gacggcagtt gggattcgtg aattgctgcc ctctggttat gtgtgggagg ctaagcact    4140 tcgtggccga ggagcaggac tgacacgtgc tacgagattt cgattccacc gccgccttct    4200
atgaaaggtt gggcttcgga atcgttttcc gggacgccgg ctggatgatc ctccagcgcg    4260
gggatctcat gctggagttc ttcgcccacc ccaacttgtt tattgcagct tataatggtt    4320
acaaataaag caatagcatc acaaatttca caaataaagc atttttttca ctgcattcta    4380
gttgtggttt gtccaaactc atcaatgtat cttatcatgt ctgtataccg tcgacctcta    4440
gctagagctt ggcgtaatca tggtcatagc tgtttcctgt gtgaaattgt tatccgctca    4500
caattccaca acatacga gccggaagca taaagtgtaa agcctggggt gcctaatgag    4560
tgagctaact cacattaatt gcgttgcgct cactgcccgc tttccagtcg ggaaacctgt    4620
cgtgccagct gcattaatga atcggccaac gcgcggggag aggcggtttg cgtattgggc    4680
gctcttccgc ttcctcgctc actgactcgc tgcgctcggt cgttcggctg cggcgagcgg    4740
tatcagctca ctcaaaggcg gtaatacggt tatccacaga atcaggggat aacgcaggaa    4800
agaacatgtg agcaaaaggc cagcaaaagg ccaggaaccg taaaaaggcc gcgttgctgg    4860
cgttttccca taggctccgc cccctgacg agcatcacaa aaatcgacgc tcaagtcaga    4920
ggtggcgaaa cccgacagga ctataaagat accaggcgtt tccccctgga agctccctcg    4980
tgcgctctcc tgttccgacc ctgccgctta ccggatacct gtccgccttt ctcccttcgg    5040
gaagcgtggc gctttctcat agctcacgct gtaggtatct cagttcggtg taggtcgttc    5100
gctccaagct gggctgtgtg cacgaacccc cgttcagcc cgaccgctgc gccttatccg    5160
gtaactatcg tcttgagtcc aacccggtaa gacacgactt atcgccactg gcagcagcca    5220
```

```
ctggtaacag gattagcaga gcgaggtatg taggcggtgc tacagagttc ttgaagtggt    5280
ggcctaacta cggctacact agaagaacag tatttggtat ctgcgctctg ctgaagccag    5340
ttaccttcgg aaaaagagtt ggtagctctt gatccggcaa acaaaccacc gctggtagcg    5400
gtttttttgt ttgcaagcag cagattacgc gcagaaaaaa aggatctcaa gaagatcctt    5460
tgatcttttc tacggggtct gacgctcagt ggaacgaaaa ctcacgttaa gggattttgg    5520
tcatgagatt atcaaaaagg atcttcacct agatcctttt aaattaaaaa tgaagtttta    5580
aatcaatcta agtatatatg agtaaacttg gtctgacagt taccaatgct taatcagtg    5640 aggcacctat ctcagcgatc tgtctatttc gttcatccat agttgcctga ctccccgtcg    5700
tgtagataac tacgatacgg gagggcttac catctggccc cagtgctgca atgataccgc    5760
gagacccacg ctcaccggct ccagatttat cagcaataaa ccagccagcc ggaagggccg    5820
agcgcagaag tggtcctgca actttatccg cctccatcca gtctattaat tgttgccggg    5880
aagctagagt aagtagttcg ccagttaata gtttgcgcaa cgttgttgcc attgctacag    5940
gcatcgtggt gtcacgctcg tcgtttggta tggcttcatt cagctccggt tcccaacgat    6000
caaggcgagt tacatgatcc cccatgttgt gcaaaaaagc ggttagctcc ttcggtcctc    6060
cgatcgttgt cagaagtaag ttggccgcag tgttatcact catggttatg gcagcactgc    6120
ataattctct tactgtcatg ccatccgtaa gatgcttttc tgtgactggt gagtactcaa    6180
ccaagtcatt ctgagaatag tgtatgcggc gaccgagttg ctcttgcccg gcgtcaatac    6240
gggataatac cgcgccacat agcagaactt taaaagtgct catcattgga aaacgttctt    6300
cggggcgaaa actctcaagg atcttaccgc tgttgagatc cagttcgatg taacccactc    6360
gtgcacccaa ctgatcttca gcatctttta ctttcaccag cgtttctggg tgagcaaaaa    6420
caggaaggca aaatgccgca aaaagggaa taagggcgac acggaaatgt tgaatactca    6480
tactcttcct ttttcaatat tattgaagca tttatcaggg ttattgtctc atgagcggat    6540
acatatttga atgtatttag aaaaataaac aaataggggt tccgcgcaca tttccccgaa    6600
aagtgccacc tgacgtc                                                  6617
```

<210> SEQ ID NO 10
<211> LENGTH: 6626
<212> TYPE: DNA
<213> ORGANISM: Artificial sequence
<220> FEATURE:
<223> OTHER INFORMATION: pCLS8982

<400> SEQUENCE: 10

```
gacggatcgg gagatctccc gatccccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca caagtttgta caaaaaagca ggctggcgcg cctacacagc ggccttgcca    960
ccatgggttc cgaggcaccc cgggccgaga cctttgtctt cctggacctg gaagccactg   1020
ggctccccag tgtggagccc gagattgccg agctgtccct ctttgctgtc caccgctcct   1080
ccctggagaa cccggagcac gacgagtctg gtgccctagt attgccccgg gtcctggaca   1140
agctcacgct gtgcatgtgc ccggagcgcc ccttcactgc caaggccagc gagatcaccg   1200
gcctgagcag tgagggcctg cgcgatgcc ggaaggctgg ctttgatggc gccgtggtgc   1260
ggacgctgca ggccttcctg agccgccagg cagggcccat ctgccttgtg cccacaatg   1320 gctttgatta tgatttcccc ctgctgtgtg ccgagctgcg gcgcctgggt gcccgcctgc   1380
cccgggacac tgtctgcctg gacacgctgc cggccctgcg gggcctggac cgcgcccaca   1440
gccacggcac ccgggcccgg ggccgccagg gttacagcct cggcagcctc ttccaccgct   1500
acttccgggc agagccaagc gcagcccact cagccgaggg cgacgtgcac accctgctcc   1560
tgatcttcct gcaccgcgcc gcagagctgc tcgcctgggc cgatgagcag gcccgtgggt   1620
gggcccacat cgagcccatg tacttgccgc ctgatgaccc cagcctggag gcgactcctc   1680
cacagaccgg tctggatgtt ccttactccg aggcaccccg ggccgagacc tttgtcttcc   1740
tggacctgga agccactggg ctccccagtg tggagcccga gattgccgag ctgtccctct   1800
ttgctgtcca ccgctcctcc ctggagaacc cggagcacga cgagtctggt gccctagtat   1860
tgccccgggt cctggacaag ctcacgctgt gcatgtgccc ggagcgcccc ttcactgcca   1920 aggcagcga gatcaccggc ctgagcagtg agggcctggc gcgatgccgg aaggctggct   1980 tgatggcgc cgtggtgcgg acgctgcagg ccttcctgag ccgccaggca gggcccatct   2040
gccttgtggc ccacaatggc tttgattatg atttcccct gctgtgtgcc gagctgcggc   2100
gcctgggtgc ccgcctgccc cgggacactg tctgcctgga cacgctgccg gccctgcggg   2160
gcctggaccg cgcccacagc cacggcaccc gggcccgggg ccgccagggt tacagcctcg   2220
gcagcctctt ccaccgctac ttccgggcag agccaagcgc agcccactca gccgagggcg   2280
acgtgcacac cctgctcctg atcttcctgc accgcgccgc agagctgctc gcctgggccg   2340
atgagcaggc ccgtgggtgg gcccacatcg agcccatgta cttgccgcct gatgacccca   2400
gcctggaggc ggccgactga taactcgagc gctagcaccc agcttttctt gtacaaagtgg   2460 tgatctagag ggcccgcggt tcgaaggtaa gcctatccct aaccctctcc tcggtctcga   2520
ttctacgcgt accggttagt aatgagttta acggggagg ctaactgaa acacggaagg   2580 agacaatacc ggaaggaacc cgcgctatga cggcaataaa aagacagaat aaaacgcacg   2640
ggtgttgggt cgtttgttca taaacgcggg gttcggtccc agggctggca ctctgtcgat   2700
accccaccga gaccccattg gggccaatac gcccgcgttt cttccttttc cccaccccac   2760
cccccaagtt cgggtgaagg cccagggctc gcagccaacg tcgggcggc aggccctgcc   2820 atagcagatc tgcgcagctg gggctctagg gggtatcccc acgcgccctg tagcggcgca   2880
ttaagcgcgg cgggtgtggt ggttacgcgc agcgtgaccg ctacacttgc cagcgcccta   2940
gcgcccgctc cttttcgctt tcttcccttc tttctcgcca cgttcgccgg ctttccccgt   3000
```

```
caagctctaa atcggggcat ccctttaggg ttccgattta gtgctttacg gcacctcgac    3060
cccaaaaaac ttgattaggg tgatggttca cgtagtgggc catcgccctg atagacggtt    3120
tttcgccctt tgacgttgga gtccacgttc tttaatagtg gactcttgtt ccaaactgga    3180
acaacactca accctatctc ggtctattct tttgatttat aagggatttt ggggatttcg    3240
gcctattggt taaaaaatga gctgatttaa caaaaattta acgcgaatta attctgtgga    3300
atgtgtgtca gttagggtgt ggaaagtccc caggctcccc agcaggcaga agtatgcaaa    3360
gcatgcatct caattagtca gcaaccaggt gtggaaagtc cccaggctcc ccagcaggca    3420
gaagtatgca aagcatgcat ctcaattagt cagcaaccat agtcccgccc ctaactccgc    3480
ccatcccgcc cctaactccg cccagttccg cccattctcc gccccatggc tgactaattt    3540
tttttattta tgcagaggcc gaggccgcct ctgcctctga gctattccag aagtagtgag    3600 gaggctttttt tggaggccta ggcttttgca aaaagctccc gggagcttgt atatccattt    3660
tcggatctga tcagcacgtg ttgacaatta atcatcggca tagtatatcg gcatagtata    3720
atacgacaag gtgaggaact aaaccatggc caagcctttg tctcaagaag aatccaccct    3780
cattgaaaga gcaacggcta caatcaacag catccccatc tctgaagact acagcgtcgc    3840
cagcgcagct ctctctagcg acggccgcat cttcactggt gtcaatgtat atcattttac    3900
tgggggacct tgtgcagaac tcgtggtgct gggcactgct gctgctgcgg cagctggcaa    3960
cctgacttgt atcgtcgcga tcggaaatga gaacaggggc atcttgagcc cctgcggacg    4020
gtgccgacag gtgcttctcg atctgcatcc tgggatcaaa gccatagtga aggacagtga    4080
tggacagccg acggcagttg ggattcgtga attgctgccc tctggttatg tgtgggaggg    4140
ctaagcactt cgtggccgag gagcaggact gacacgtgct acgagatttc gattccaccg    4200
ccgccttcta tgaaaggttg gcttcggaa tcgttttccg ggacgccggc tggatgatcc    4260
tccagcgcgg ggatctcatg ctggagttct tcgcccaccc caacttgttt attgcagctt    4320
ataatggtta caaataaagc aatagcatca caaatttcac aaataaagca ttttttttcac    4380 tgcattctag ttgtggtttg tccaaactca tcaatgtatc ttatcatgtc tgtataccgt    4440
cgacctctag ctagagcttg gcgtaatcat ggtcatagct gtttcctgtg tgaaattgtt    4500
atccgctcac aattccacac aacatacgag ccggaagcat aaagtgtaaa gcctggggtg    4560
cctaatgagt gagctaactc acattaattg cgttgcgctc actgcccgct ttccagtcgg    4620
gaaacctgtc gtgccagctg cattaatgaa tcggccaacg cgcggggaga ggcggtttgc    4680
gtattgggcg ctcttccgct tcctcgctca ctgactcgct gcgctcggtc gttcggctgc    4740
ggcgagcggt atcagctcac tcaaaggcgg taatacggtt atccacagaa tcaggggata    4800
acgcaggaaa gaacatgtga gcaaaaggcc agcaaaaggc caggaaccgt aaaaaggccg    4860
cgttgctggc gtttttccat aggctccgcc cccctgacga gcatcacaaa aatcgacgct    4920
caagtcagag gtggcgaaac ccgacaggac tataaagata ccaggcgttt ccccctggaa    4980
gctccctcgt gcgctctcct gttccgaccc tgccgcttac cggatacctg tccgcctttc    5040
tcccttcggg aagcgtggcg ctttctcata gctcacgctg taggtatctc agttcggtgt    5100
aggtcgttcg ctccaagctg ggctgtgtgc acgaaccccc cgttcagccc gaccgctgcg    5160
ccttatccgg taactatcgt cttgagtcca acccggtaag acacgactta tcgccactgg    5220
cagcagccac tggtaacagg attagcagag cgaggtatgt aggcggtgct acagagttct    5280
tgaagtggtg gcctaactac ggctacacta agaacagt atttggtatc tgcgctctgc    5340
```

| | |
|---|---|
| tgaagccagt taccttcgga aaaagagttg gtagctcttg atccggcaaa caaaccaccg | 5400 |
| ctggtagcgg ttttttttgtt tgcaagcagc agattacgcg cagaaaaaaa ggatctcaag | 5460 |
| aagatccttt gatcttttct acggggtctg acgctcagtg aacgaaaac tcacgttaag | 5520 |
| ggattttggt catgagatta tcaaaaagga tcttcaccta gatccttta aattaaaaat | 5580 |
| gaagttttaa atcaatctaa agtatatatg agtaaacttg gtctgacagt taccaatgct | 5640 |
| taatcagtga ggcacctatc tcagcgatct gtctatttcg ttcatccata gttgcctgac | 5700 |
| tccccgtcgt gtagataact acgatacggg agggcttacc atctggcccc agtgctgcaa | 5760 |
| tgataccgcg agacccacgc tcaccggctc cagatttatc agcaataaac cagccagccg | 5820 |
| gaagggccga gcgcagaagt ggtcctgcaa ctttatccgc ctccatccag tctattaatt | 5880 |
| gttgccggga agctagagta agtagttcgc cagttaatag tttgcgcaac gttgttgcca | 5940 |
| ttgctacagg catcgtggtg tcacgctcgt cgtttggtat ggcttcattc agctccggtt | 6000 |
| cccaacgatc aaggcgagtt acatgatccc ccatgttgtg caaaaaagcg gttagctcct | 6060 |
| tcggtcctcc gatcgttgtc agaagtaagt tggccgcagt gttatcactc atggttatgg | 6120 |
| cagcactgca taattctctt actgtcatgc catccgtaag atgcttttct gtgactggtg | 6180 |
| agtactcaac caagtcattc tgagaatagt gtatgcggcg accgagttgc tcttgcccgg | 6240 |
| cgtcaatacg ggataatacc gcgccacata gcagaacttt aaaagtgctc atcattggaa | 6300 |
| aacgttcttc ggggcgaaaa ctctcaagga tcttaccgct gttgagatcc agttcgatgt | 6360 |
| aacccactcg tgcacccaac tgatcttcag catcttttac tttcaccagc gtttctgggt | 6420 |
| gagcaaaaac aggaaggcaa aatgccgcaa aaaagggaat aagggcgaca cggaaatgtt | 6480 |
| gaatactcat actcttcctt tttcaatatt attgaagcat ttatcagggt tattgtctca | 6540 |
| tgagcggata catatttgaa tgtatttaga aaaataaaca ataggggtt ccgcgcacat | 6600 |
| ttccccgaaa agtgccacct gacgtc | 6626 |

<210> SEQ ID NO 11
<211> LENGTH: 6629
<212> TYPE: DNA
<213> ORGANISM: Artificial sequence
<220> FEATURE:
<223> OTHER INFORMATION: pCLS8984

<400> SEQUENCE: 11

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |

```
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca caagtttgta caaaaaagca ggctggcgcg cctacacagc ggccttgcca    960
ccatgggttc cgaggcaccc cgggccgaga cctttgtctt cctggacctg aagccactg    1020 ggctccccag tgtggagccc gagattgccg agctgtccct ctttgctgtc caccgctcct   1080
ccctggagaa cccggagcac gacgagtctg gtgccctagt attgccccgg gtcctggaca   1140
agctcacgct gtgcatgtgc ccggagcgcc ccttcactgc caaggccagc gagatcaccg   1200
gcctgagcag tgagggcctg gcgcgatgcc ggaaggctgg ctttgatggc gccgtggtgc   1260
ggacgctgca ggccttcctg agccgccagg cagggcccat ctgccttgtg gcccacaatg   1320
gctttgatta tgatttcccc ctgctgtgtg ccgagctgcg gcgcctgggt gcccgcctgc   1380
cccgggacac tgtctgcctg gacacgctgc cggcctgcg ggcctggac cgcgcccaca   1440 gccacggcac ccgggcccgg ggcgccagg gttacagcct cggcagcctc ttccaccgct   1500
acttccgggc agagccaagc gcagcccact cagccgaggg cgacgtgcac accctgctcc   1560
tgatcttcct gcaccgcgcc gcagagctgc tcgcctgggc cgatgagcag gcccgtgggt   1620
gggcccacat cgagcccatg tacttgccgc ctgatgaccc cagcctggag gcgggtgatt   1680
cctctgtttc taattctgag catattgctt ccgaggcacc ccgggccgag acctttgtct   1740
tcctggacct ggaagccact gggctcccca gtgtggagcc cgagattgcc gagctgtccc   1800
tctttgctgt ccaccgctcc tccctggaga acccggagca cgacgagtct ggtgccctag   1860
tattgccccg ggtcctggac aagctcacgc tgtgcatgtg cccggagcgc ccttcactg    1920 ccaaggccag cgagatcacc ggcctgagca gtgagggcct ggcgcgatgc cggaaggctg   1980
gctttgatgg cgccgtggtg cggacgctgc aggccttcct gagccgccag gcagggccca   2040
tctgccttgt ggcccacaat ggctttgatt atgatttccc cctgctgtgt gccgagctgc   2100
ggcgcctggg tgcccgcctg ccccgggaca ctgtctgcct ggacacgctg ccggccctgc   2160
gggcctggac cgcgcccac agccacggca cccgggcccg gggcgccag gttacagcc    2220 tcggcagcct cttccaccgc tacttccggg cagagccaag cgcagcccac tcagccgagg   2280
gcgacgtgca caccctgctc ctgatcttcc tgcaccgcgc cgcagagctg ctcgcctggg   2340
ccgatgagca ggcccgtggg tgggcccaca tcgagcccat gtacttgccg cctgatgacc   2400
ccagcctgga ggcggccgac tgataactcg agcgctagca cccagctttc ttgtacaaag   2460
tggtgatcta gagggcccgc ggttcgaagg taagcctatc cctaaccctc tcctcggtct   2520
cgattctacg cgtaccggtt agtaatgagt ttaaacgggg gaggctaact gaaacacgga   2580
aggagacaat accggaagga acccgcgcta tgacggcaat aaaagacag aataaaacgc    2640 acgggtgttg ggtcgtttgt tcataaacgc ggggttcggt cccagggctg cactctgtc    2700 gatacccac cgagacccca ttggggccaa tacgcccgcg tttcttcctt ttccccaccc    2760 cacccccaa gttcgggtga aggcccaggg ctcgcagcca acgtcgggc ggcaggccct     2820 gccatagcag atctgcgcag ctggggctct aggggggtatc cccacgcgcc ctgtagcggc   2880
gcattaagcg cggcgggtgt ggtggttacg cgcagcgtga ccgctacact tgccagcgcc   2940
ctagcgcccg ctcctttcgc tttcttccct tcctttctcg ccacgttcgc cggctttccc   3000
cgtcaagctc taaatcgggg catcccttta gggttccgat ttagtgcttt acggcacctc   3060
gaccccaaaa aacttgatta gggtgatggt tcacgtagtg gccatcgcc ctgatagacg    3120
```

```
gttttttcgcc ctttgacgtt ggagtccacg ttctttaata gtggactctt gttccaaact   3180
ggaacaacac tcaaccctat ctcggtctat tcttttgatt tataagggat tttggggatt   3240
tcggcctatt ggttaaaaaa tgagctgatt taacaaaaat ttaacgcgaa ttaattctgt   3300
ggaatgtgtg tcagttaggg tgtggaaagt ccccaggctc cccagcaggc agaagtatgc   3360
aaagcatgca tctcaattag tcagcaacca ggtgtggaaa gtccccaggc tccccagcag   3420
gcagaagtat gcaaagcatg catctcaatt agtcagcaac catagtcccg cccctaactc   3480
cgcccatccc gcccctaact ccgcccagtt ccgcccattc tccgcccat ggctgactaa    3540 ttttttttat ttatgcagag gccgaggccg cctctgcctc tgagctattc cagaagtagt   3600
gaggaggctt ttttggaggc ctaggctttt gcaaaaagct cccgggagct tgtatatcca   3660
ttttcggatc tgatcagcac gtgttgacaa ttaatcatcg gcatagtata tcggcatagt   3720
ataatacgac aaggtgagga actaaaccat ggccaagcct ttgtctcaag aagaatccac   3780
cctcattgaa agagcaacgg ctacaatcaa cagcatcccc atctctgaag actacagcgt   3840
cgccagcgca gctctctcta cgacggccg catcttcact ggtgtcaatg tatatcattt   3900
tactggggga ccttgtgcag aactcgtggt gctgggcact gctgctgctg cggcagctgg   3960
caacctgact tgtatcgtcg cgatcggaaa tgagaacagg gcatcttga gccctgcgg    4020 acggtgccga caggtgcttc tcgatctgca tcctgggatc aaagccatag tgaaggacag   4080
tgatggacag ccgacggcag ttgggattcg tgaattgctg ccctctggtt atgtgtggga   4140
gggctaagca cttcgtggcc gaggagcagg actgacacgt gctacgagat ttcgattcca   4200
ccgccgcctt ctatgaaagg ttgggcttcg gaatcgtttt ccgggacgcc ggctggatga   4260
tcctccagcg cggggatctc atgctggagt tcttcgccca ccccaacttg tttattgcag   4320
cttataatgg ttacaaataa agcaatagca tcacaaattt cacaaataaa gcatttttt    4380 cactgcattc tagttgtggt ttgtccaaac tcatcaatgt atcttatcat gtctgtatac   4440
cgtcgacctc tagctagagc ttggcgtaat catggtcata gctgtttcct gtgtgaaatt   4500
gttatccgct cacaattcca cacaacatac gagccggaag cataaagtgt aaagcctggg   4560
gtgcctaatg agtgagctaa ctcacattaa ttgcgttgcg ctcactgccc gctttccagt   4620
cgggaaacct gtcgtgccag ctgcattaat gaatcggcca acgcgcgggg agaggcggtt   4680
tgcgtattgg gcgctcttcc gcttcctcgc tcactgactc gctgcgctcg tcgttcggc    4740 tgcggcgagc ggtatcagct cactcaaagg cggtaatacg ttatccaca gaatcagggg    4800 ataacgcagg aaagaacatg tgagcaaaag gccagcaaaa ggccaggaac cgtaaaaagg   4860
ccgcgttgct ggcgtttttc cataggctcc gcccccctga cgagcatcac aaaaatcgac   4920
gctcaagtca gaggtggcga aacccgacag gactataaag ataccaggcg tttccccctg   4980
gaagctccct cgtgcgctct cctgttccga ccctgccgct taccggatac ctgtccgcct   5040
ttctcccttc gggaagcgtg gcgctttctc atagctcacg ctgtaggtat ctcagttcgg   5100
tgtaggtcgt tcgctccaag ctgggctgtg tgcacgaacc cccgttcag cccgaccgct    5160 gcgccttatc cggtaactat cgtcttgagt ccaacccggt aagacacgac ttatcgccac   5220
tggcagcagc cactggtaac aggattagca gagcgaggta tgtaggcggt gctacagagt   5280
tcttgaagtg gtggcctaac tacggctaca ctagaagaac agtatttggt atctgcgctc   5340
tgctgaagcc agttaccttc ggaaaaagag ttggtagctc ttgatccggc aaacaaacca   5400
ccgctggtag cggtttttt gtttgcaagc agcagattac gcgcagaaaa aaggatctc    5460 aagaagatcc tttgatcttt tctacggggt ctgacgctca gtggaacgaa aactcacgtt   5520
```

```
aagggatttt ggtcatgaga ttatcaaaaa ggatcttcac ctagatcctt ttaaattaaa    5580
aatgaagttt taaatcaatc taaagtatat atgagtaaac ttggtctgac agttaccaat    5640
gcttaatcag tgaggcacct atctcagcga tctgtctatt tcgttcatcc atagttgcct    5700 gactcccgt cgtgtagata actacgatac gggagggctt accatctggc cccagtgctg     5760
caatgatacc gcgagaccca cgctcaccgg ctccagattt atcagcaata aaccagccag    5820
ccggaagggc cgagcgcaga agtggtcctg caactttatc cgcctccatc cagtctatta    5880
attgttgccg ggaagctaga gtaagtagtt cgccagttaa tagtttgcgc aacgttgttg    5940
ccattgctac aggcatcgtg gtgtcacgct cgtcgtttgg tatggcttca ttcagctccg    6000
gttcccaacg atcaaggcga gttacatgat ccccatgtt gtgcaaaaaa gcggttagct     6060
ccttcggtcc tccgatcgtt gtcagaagta agttggccgc agtgttatca ctcatggtta    6120
tggcagcact gcataattct cttactgtca tgccatccgt aagatgcttt tctgtgactg    6180
gtgagtactc aaccaagtca ttctgagaat agtgtatgcg gcgaccgagt tgctcttgcc    6240
cggcgtcaat acgggataat accgcgccac atagcagaac tttaaaagtg ctcatcattg    6300
gaaaacgttc ttcggggcga aaactctcaa ggatcttacc gctgttgaga tccagttcga    6360
tgtaacccac tcgtgcaccc aactgatctt cagcatcttt tactttcacc agcgtttctg    6420
ggtgagcaaa aacaggaagg caaaatgccg caaaaaaggg aataagggcg acacggaaat    6480
gttgaatact catactcttc cttttcaat attattgaag catttatcag ggttattgtc      6540
tcatgagcgg atacatattt gaatgtattt agaaaaataa acaaataggg gttccgcgca    6600
catttccccg aaaagtgcca cctgacgtc                                       6629
```

<210> SEQ ID NO 12
<211> LENGTH: 6635
<212> TYPE: DNA
<213> ORGANISM: Artificial sequence
<220> FEATURE:
<223> OTHER INFORMATION: pCLS8986

<400> SEQUENCE: 12

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa atgaattcga ctcactgttg ggagacccaa gctggctagt    900
```

```
taagctatca caagtttgta caaaaaagca ggctggcgcg cctacacagc ggccttgcca      960
ccatgggttc cgaggcaccc cgggccgaga cctttgtctt cctggacctg gaagccactg     1020
ggctccccag tgtggagccc gagattgccg agctgtccct ctttgctgtc caccgctcct     1080
ccctggagaa cccggagcac gacgagtctg gtgccctagt attgcccegg gtcctggaca     1140
agctcacgct gtgcatgtgc ccggagcgcc ccttcactgc caaggccagc gagatcaccg     1200
gcctgagcag tgagggcctg cgcgcgatgcc ggaaggctgg cttgtgatggc gccgtggtgc   1260
ggacgctgca ggccttcctg agccgccagg cagggcccat ctgccttgtg cccacaatg     1320
gctttgatta tgatttcccc ctgctgtgtg ccgagctgcg cgcctgggt gcccgcctgc     1380
cccgggacac tgtctgcctg gacacgctgc cggccctgcg gggcctggac cgcgcccaca    1440
gccacggcac ccgggcccgg ggccgccagg gttacagcct cggcagcctc ttccaccgct     1500
acttccgggc agagccaagc gcagcccact cagccgaggg cgacgtgcac accctgctcc    1560
tgatcttcct gcaccgcgcc gcagagctgc tcgcctgggc cgatgagcag gcccgtgggt    1620
gggcccacat cgagcccatg tacttgccgc ctgatgaccc cagcctggag gcgattcgtc     1680
ctcgtgctat tggaggttct aaacctcgtg ttgcttccga ggcaccccgg gccgagacct     1740
ttgtcttcct ggacctggaa gccactgggc tccccagtgt ggagcccgag attgccgagc    1800
tgtccctctt tgctgtccac cgctcctccc tggagaaccc ggagcacgac gagtctggtg    1860
ccctagtatt gccccgggtc ctggacaagc tcacgctgtg catgtgcccg gagcgccct     1920
tcactgccaa ggccagcgag atcaccggcc tgagcagtga gggcctggcg cgatgccgga    1980
aggctggctt tgatggcgcc gtggtgcgga cgctgcaggc cttcctgagc cgccaggcag    2040
ggcccatctg ccttgtggcc cacaatggct ttgattatga tttccccctg ctgtgtgccg    2100
agctgcggcg cctgggtgcc cgcctgcccc gggacactgt ctgcctggac acgctgccgg    2160
ccctgcgggg cctggaccgc gcccacagcc acggcacccg ggcccggggc cgccagggtt    2220
acagcctcgg cagcctcttc caccgctact tccgggcaga gccaagcgca gcccactcag    2280
ccgagggcga cgtgcacacc ctgctcctga tcttcctgca ccgcgccgca gagctgctcg    2340
cctgggccga tgagcaggcc cgtgggtggg cccacatcga gcccatgtac ttgccgcctg    2400
atgaccccag cctggaggcg gccgactgat aactcgagcg ctagcaccca gctttcttgt    2460
acaaagtggt gatctagagg gcccgcggtt cgaaggtaag cctatcccta accctctcct    2520
cggtctcgat tctacgcgta ccggttagta atgagtttaa acggggagg ctaactgaaa     2580
cacggaagga acaataccg gaaggaaccc gcgctatgac ggcaataaaa agacagaata    2640
aaacgcacgg gtgttgggtc gtttgttcat aaacgcgggg ttcggtccca gggctggcac   2700
tctgtcgata ccccaccgag acccccattgg gccaatacg cccgcgtttc ttccttttcc    2760
ccaccccacc ccccaagttc gggtgaaggc ccagggctcg cagccaacgt cggggcggca    2820
ggccctgcca tagcagatct gcgcagctgg ggctctaggg ggtatcccca cgcgccctgt    2880
agcggcgcat taagcgcggc gggtgtggtg gttacgcgca gcgtgaccgc tacacttgcc    2940
agcgccctag cgcccgctcc tttcgctttc ttcccttcct ttctcgccac gttcgccggc    3000
tttccccgtc aagctctaaa tcggggcatc cctttagggt tccgatttag tgctttacgg    3060
cacctcgacc ccaaaaaact tgattagggt gatggttcac gtagtgggcc atcgccctga    3120
tagacggttt ttcgcccttt gacgttggag tccacgttct ttaatagtgg actcttgttc    3180
caaactggaa caacactcaa ccctatctcg gtctattctt ttgatttata agggattttg    3240
gggatttcgg cctattggtt aaaaaatgag ctgatttaac aaaaatttaa cgcgaattaa    3300
```

```
ttctgtggaa tgtgtgtcag ttagggtgtg gaaagtcccc aggctcccca gcaggcagaa    3360
gtatgcaaag catgcatctc aattagtcag caaccaggtg tggaaagtcc ccaggctccc    3420
cagcaggcag aagtatgcaa agcatgcatc tcaattagtc agcaaccata gtcccgcccc    3480
taactccgcc catcccgccc ctaactccgc ccagttccgc ccattctccg ccccatggct    3540
gactaatttt ttttatttat gcagaggccg aggccgcctc tgcctctgag ctattccaga    3600
agtagtgagg aggcttttt ggaggcctag gcttttgcaa aaagctcccg ggagcttgta    3660
tatccatttt cggatctgat cagcacgtgt tgacaattaa tcatcggcat agtatatcgg    3720
catagtataa tacgacaagg tgaggaacta aaccatggcc aagcctttgt ctcaagaaga    3780
atccaccctc attgaaagag caacggctac aatcaacagc atccccatct ctgaagacta    3840
cagcgtcgcc agcgcagctc tctctagcga cggccgcatc ttcactggtg tcaatgtata    3900
tcattttact gggggacctt gtgcagaact cgtggtgctg ggcactgctg ctgctgcggc    3960
agctggcaac ctgacttgta tcgtcgcgat cggaaatgag aacaggggca tcttgagccc    4020
ctgcggacgg tgccgacagg tgcttctcga tctgcatcct gggatcaaag ccatagtgaa    4080
ggacagtgat ggacagccga cggcagttgg gattcgtgaa ttgctgccct ctggttatgt    4140
gtgggagggc taagcacttc gtggccgagg agcaggactg acacgtgcta cgagatttcg    4200
attccaccgc cgccttctat gaaaggttgg gcttcggaat cgttttccgg gacgccggct    4260
ggatgatcct ccagcgcggg gatctcatgc tggagttctt cgcccacccc aacttgttta    4320
ttgcagctta taatggttac aaataaagca atagcatcac aaatttcaca aataaagcat    4380 tttttttcact gcattctagt tgtggtttgt ccaaactcat caatgtatct tatcatgtct    4440
gtataccgtc gacctctagc tagagcttgg cgtaatcatg gtcatagctg tttcctgtgt    4500
gaaattgtta tccgctcaca attccacaca acatacgagc cggaagcata agtgtaaag    4560 cctggggtgc ctaatgagtg agctaactca cattaattgc gttgcgctca ctgcccgctt    4620
tccagtcggg aaacctgtcg tgccagctgc attaatgaat cggccaacgc gcggggagag    4680
gcggtttgcg tattgggcgc tcttccgctt cctcgctcac tgactcgctg cgctcggtcg    4740
ttcggctgcg gcgagcggta tcagctcact caaaggcggt aatacggtta tccacagaat    4800
caggggataa cgcaggaaag aacatgtgag caaaaggcca gcaaaaggcc aggaaccgta    4860
aaaaggccgc gttgctggcg tttttccata ggctccgccc ccctgacgag catcacaaaa    4920
atcgacgctc aagtcagagg tggcgaaacc cgacaggact ataaagatac caggcgtttc    4980
cccctggaag ctccctcgtg cgctctcctg ttccgaccct gccgcttacc ggatacctgt    5040
ccgcctttct cccttcggga agcgtggcgc tttctcatag ctcacgctgt aggtatctca    5100
gttcggtgta ggtcgttcgc tccaagctgg gctgtgtgca cgaaccccc gttcagcccg    5160 accgctgcgc cttatccggt aactatcgtc ttgagtccaa cccggtaaga cacgacttat    5220
cgccactggc agcagccact ggtaacagga ttagcagagc gaggtatgta ggcggtgcta    5280
cagagttctt gaagtggtgg cctaactacg gctacactag aagaacagta tttggtatct    5340
gcgctctgct gaagccagtt accttcggaa aaagagttgg tagctcttga tccggcaaac    5400
aaaccaccgc tggtagcggt ttttttgttt gcaagcagca gattacgcgc agaaaaaaag    5460
gatctcaaga agatcctttg atcttttcta cggggtctga cgctcagtgg aacgaaaact    5520
cacgttaagg gattttggtc atgagattat caaaaaggat cttcacctag atccttttaa    5580
attaaaaatg aagttttaaa tcaatctaaa gtatatatga gtaaacttgg tctgacagtt    5640
```

| | |
|---|---|
| accaatgctt aatcagtgag gcacctatct cagcgatctg tctatttcgt tcatccatag | 5700 |
| ttgcctgact ccccgtcgtg tagataacta cgatacggga gggcttacca tctggcccca | 5760 |
| gtgctgcaat gataccgcga gacccacgct caccggctcc agatttatca gcaataaacc | 5820 |
| agccagccgg aagggccgag cgcagaagtg gtcctgcaac tttatccgcc tccatccagt | 5880 |
| ctattaattg ttgccgggaa gctagagtaa gtagttcgcc agttaatagt ttgcgcaacg | 5940 |
| ttgttgccat tgctacaggc atcgtggtgt cacgctcgtc gtttggtatg gcttcattca | 6000 |
| gctccggttc ccaacgatca aggcgagtta catgatcccc catgttgtgc aaaaaagcgg | 6060 |
| ttagctcctt cggtcctccg atcgttgtca aagtaagtt ggccgcagtg ttatcactca | 6120 |
| tggttatggc agcactgcat aattctctta ctgtcatgcc atccgtaaga tgcttttctg | 6180 |
| tgactggtga gtactcaacc aagtcattct gagaatagtg tatgcggcga ccgagttgct | 6240 |
| cttgcccggc gtcaatacgg gataataccg cgccacatag cagaacttta aaagtgctca | 6300 |
| tcattggaaa acgttcttcg gggcgaaaac tctcaaggat cttaccgctg ttgagatcca | 6360 |
| gttcgatgta acccactcgt gcacccaact gatcttcagc atcttttact ttcaccagcg | 6420 |
| tttctgggtg agcaaaaaca ggaaggcaaa atgccgcaaa aaagggaata agggcgacac | 6480 |
| ggaaatgttg aatactcata ctcttccttt ttcaatatta ttgaagcatt tatcagggtt | 6540 |
| attgtctcat gagcggatac atatttgaat gtatttagaa aaataaacaa ataggggttc | 6600 |
| cgcgcacatt tccccgaaaa gtgccacctg acgtc | 6635 |

<210> SEQ ID NO 13
<211> LENGTH: 6101
<212> TYPE: DNA
<213> ORGANISM: Artificial sequence
<220> FEATURE:
<223> OTHER INFORMATION: pCLS2690

<400> SEQUENCE: 13

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa atgaattccg tcgaccatgg ccaataccaa atataacgaa | 900 |
| gagttcctgc tgtacctggc cggctttgtg gacgctgacg gtagcatcat cgctcagatt | 960 |
| aaaccaagac agtctcggaa gtttaaacat gagctaagct tgacctttga tgtgactcaa | 1020 |
| aagacccagc gccgttggtt tctggacaag ctagtggatg aaattggcgt tggttacgta | 1080 |

```
tatgattctg gatccgtttc ctattaccag ttaagcgaaa tcaagccgct gcacaacttc    1140
ctgactcaac tgcagccgtt tctggaactg aaacagaaac aggcaaacct ggttctgaaa    1200
attatcgaac agctgccgtc tgcaaaagaa tccccggcca aattcctgga agtttgtacc    1260
tgggtggatc agattgcagc tctgaacgat tctaagacgc gtaaaaccac ttctgaaacc    1320
gttcgtgctg tgctggacag cctgagcgag aagaagaaat cctccccggc ggccggtgga    1380
tctgataagt ataatcaggc tctgtctaaa tacaaccaag cactgtccaa gtacaatcag    1440
gccctgtctg gtggaggcgg ttccaacaaa aagttcctgc tgtatcttgc tggatttgtg    1500
gatggtgatg gctccatcat tgctcagata aaaccacgtc aagggtataa gttcaaacac    1560
cagctctcct tgacttttca ggtcactcag aagacacaaa gaaggtggtt cttggacaaa    1620
ttggttgatc gtattggtgt gggctatgtc gctgaccgtg gctctgtgtc agactaccgc    1680
ctgtctgaaa ttaagcctct tcataacttt ctcacccaac tgcaacccct cttgaagctc    1740
aaacagaagc aagcaaatct ggttttgaaa atcatcgagc aactgccatc tgccaaggag    1800
tccctggaca gtttcttga agtgtgtact tgggtggatc agattgctgc cttgaatgac    1860
tccaagacca gaaaaaccac ctctgagact gtgagggcag ttctggatag cctctctgag    1920
aagaaaaagt cctctcctta gccatggccc gcggttcgaa ggtaagccta ccctaacccc    1980
tctcctcggt ctcgattcta cgcgtaccgg ttagtaatga gtttaaacgg gggaggctaa    2040
ctgaaacacg gaaggagaca ataccggaag gaacccgcgc tatgacggca ataaaaagac    2100
agaataaaac gcacgggtgt tgggtcgttt gttcataaac gcggggttcg gtcccagggc    2160
tggcactctg tcgataccccc accgagaccc cattggggcc aatacgcccg cgtttcttcc    2220
ttttccccac cccaccccccc aagttcgggt gaaggcccag ggctcgcagc caacgtcggg    2280
gcggcaggcc ctgccatagc agatctgcgc agctggggct cttaggggggta tccccacgcg    2340 ccctgtagcg gcgcattaag cgcggcgggt gtggtggtta cgcgcagcgt gaccgctaca    2400
cttgccagcg ccctagcgcc cgctccttt c gctttcttcc cttcctttct cgccacgttc    2460
gccggctttc cccgtcaagc tctaaatcgg ggcatccctt tagggttccg atttagtgct    2520
ttacggcacc tcgaccccaa aaaacttgat tagggtgatg gttcacgtag tgggccatcg    2580
ccctgataga cggttttttcg ccccttttgacg ttggagtcca cgttctttaa tagtggactc    2640
ttgttccaaa ctggaacaac actcaaccct atctcggtct attcttttga tttataaggg    2700
attttgggga tttcggccta ttggttaaaa aatgagctga tttaacaaaa atttaacgcg    2760
aattaattct gtggaatgtg tgtcagttag ggtgtggaaa gtccccaggc tccccagcag    2820
gcagaagtat gcaaagcatg catctcaatt agtcagcaac caggtgtgga agtccccag    2880 gctcccagc aggcagaagt atgcaaagca tgcatctcaa ttagtcagca accatagtcc    2940
cgcccctaac tccgcccatc ccgcccctaa ctccgcccag ttccgcccat tctccgcccc    3000
atggctgact aatttttttt atttatgcag aggccgaggc cgcctctgcc tctgagctat    3060
tccagaagta gtgaggaggc ttttttggag gcctaggctt ttgcaaaaag ctcccgggag    3120
cttgtatatc cattttcgga tctgatcagc acgtgttgac aattaatcat cggcatagta    3180
tatcggcata gtataatacg acaaggtgag gaactaaacc atggccaagc ctttgtctca    3240
agaagaatcc accctcattg aaagagcaac ggctacaatc aacagcatcc ccatctctga    3300
agactacagc gtcgccagcg cagctctctc tagcgacggc cgcatcttca ctggtgtcaa    3360
tgtatatcat tttactgggg gaccttgtgc agaactcgtg gtgctgggca ctgctgctgc    3420
```

```
tgcggcagct ggcaacctga cttgtatcgt cgcgatcgga aatgagaaca ggggcatctt    3480
gagcccctgc ggacggtgcc gacaggtgct tctcgatctg catcctggga tcaaagccat    3540
agtgaaggac agtgatggac agccgacggc agttgggatt cgtgaattgc tgccctctgg    3600
ttatgtgtgg gagggctaag cacttcgtgg ccgaggagca ggactgacac gtgctacgag    3660
atttcgattc caccgccgcc ttctatgaaa ggttgggctt cggaatcgtt ttccgggacg    3720
ccggctggat gatcctccag cgcggggatc tcatgctgga gttcttcgcc cacccccaact   3780 tgtttattgc agcttataat ggttacaaat aaagcaatag catcacaaat ttcacaaata    3840
aagcattttt ttcactgcat tctagttgtg gtttgtccaa actcatcaat gtatcttatc    3900
atgtctgtat accgtcgacc tctagctaga gcttggcgta atcatggtca tagctgtttc    3960
ctgtgtgaaa ttgttatccg ctcacaattc cacacaacat acgagccgga agcataaagt    4020
gtaaagcctg gggtgcctaa tgagtgagct aactcacatt aattgcgttg cgctcactgc    4080
ccgctttcca gtcgggaaac ctgtcgtgcc agctgcatta atgaatcggc caacgcgcgg    4140
ggagaggcgg tttgcgtatt gggcgctctt ccgcttcctc gctcactgac tcgctgcgct    4200
cggtcgttcg gctgcggcga gcggtatcag ctcactcaaa ggcggtaata cggttatcca    4260
cagaatcagg ggataacgca ggaaagaaca tgtgagcaaa aggccagcaa aaggccagga    4320
accgtaaaaa ggccgcgttg ctggcgtttt tccataggct ccgcccccct gacgagcatc    4380
acaaaaatcg acgctcaagt cagaggtggc gaaacccgac aggactataa agataccagg    4440
cgtttccccc tggaagctcc ctcgtgcgct ctcctgttcc gaccctgccg cttaccggat    4500
acctgtccgc ctttctccct tcgggaagcg tggcgctttc tcatagctca cgctgtaggt    4560
atctcagttc ggtgtaggtc gttcgctcca agctgggctg tgtgcacgaa ccccccgttc    4620
agcccgaccg ctgcgcctta tccggtaact atcgtcttga gtccaacccg gtaagacacg    4680
acttatcgcc actggcagca gccactggta acaggattag cagagcgagg tatgtaggcg    4740
gtgctacaga gttcttgaag tggtggccta actacggcta cactagaaga acagtatttg    4800
gtatctgcgc tctgctgaag ccagttacct tcggaaaaag agttggtagc tcttgatccg    4860
gcaaacaaac caccgctggt agcggttttt tgtttgcaa gcagcagatt acgcgcagaa    4920
aaaaaggatc tcaagaagat cctttgatct tttctacggg gtctgacgct cagtggaacg    4980
aaaactcacg ttaagggatt ttggtcatga gattatcaaa aaggatcttc acctagatcc    5040
ttttaaatta aaaatgaagt tttaaatcaa tctaaagtat atatgagtaa acttggtctg    5100
acagttacca atgcttaatc agtgaggcac ctatctcagc gatctgtcta tttcgttcat    5160
ccatagttgc ctgactcccc gtcgtgtaga taactacgat acgggagggc ttaccatctg    5220
gccccagtgc tgcaatgata ccgcgagacc cacgctcacc ggctccagat ttatcagcaa    5280
taaaccagcc agccggaagg gccgagcgca gaagtggtcc tgcaacttta tccgcctcca    5340
tccagtctat taattgttgc cgggaagcta gagtaagtag ttcgccagtt aatagtttgc    5400
gcaacgttgt tgccattgct acaggcatcg tggtgtcacg ctcgtcgttt ggtatggctt    5460
cattcagctc cggttcccaa cgatcaaggc gagttacatg atcccccatg ttgtgcaaaa    5520
aagcggttag ctccttcggt cctccgatcg ttgtcagaag taagttggcc gcagtgttat    5580
cactcatggt tatggcagca ctgcataatt ctcttactgt catgccatcc gtaagatgct    5640
tttctgtgac tggtgagtac tcaaccaagt cattctgaga atagtgtatg cggcgaccga    5700
gttgctcttg cccggcgtca atacgggata ataccgcgcc acatagcaga actttaaaag    5760
tgctcatcat tggaaaacgt tcttcggggc gaaaactctc aaggatctta ccgctgttga    5820
```

```
gatccagttc gatgtaaccc actcgtgcac ccaactgatc ttcagcatct tttactttca    5880
ccagcgtttc tgggtgagca aaacaggaa ggcaaaatgc cgcaaaaaag ggaataaggg    5940
cgacacggaa atgttgaata ctcatactct tccttttca atattattga agcatttatc    6000
agggttattg tctcatgagc ggatacatat ttgaatgtat ttagaaaaat aaacaaatag    6060
gggttccgcg cacatttccc cgaaaagtgc cacctgacgt c                       6101
```

<210> SEQ ID NO 14
<211> LENGTH: 5885
<212> TYPE: DNA
<213> ORGANISM: Artificial sequence
<220> FEATURE:
<223> OTHER INFORMATION: pCLS7673

<400> SEQUENCE: 14

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca caaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa atgaattcga ctcactgttg ggagacccaa gctggctagt    900
taagctatca caagtttgta caaaaaagca ggctggcgcg cctacacagc ggccttgcca    960
ccatgggttc cgaggcaccc cgggccgaga cctttgtctt cctggacctg gaagccactg   1020
ggctccccag tgtggagccc gagattgccg agctgtccct ctttgctgtc caccgctcct   1080
ccctggagaa cccggagcac gacgagtctg gtgcccagt attgcccgg gtcctggaca   1140 agctcacgct gtgcatgtgc ccggagcgcc ccttcactgc caaggccagc gagatcaccg   1200
gcctgagcag tgagggcctg cgcgatgcc ggaaggctgg ctttgatggc gccgtggtgc   1260
ggacgctgca ggccttcctg agccgccagg cagggcccat ctgccttgtg gcccacaatg   1320
gctttgatta tgatttcccc ctgctgtgtg ccgagctgcg cgcgtgggt gccgcctgc   1380 cccgggacac tgtctgcctg gacacgctgc cggccctgcg gggcctggac gcgccaca    1440 gccacggcac ccgggccgg ggccgccagg gttacagcct cggcagcctc ttccaccgct   1500
acttccggga gagccaagc gcagcccact cagccgaggg cgacgtgcac accctgctcc   1560
tgatcttcct gcaccgcgcc gcagagctgc tcgcctgggc cgatgagcag gcccgtgggt   1620
gggcccacat cgagcccatg tacttgccgc ctgatgaccc cagcctggag gcggccgact   1680
gactcgagcg ctagcaccca gctttcttgt acaaagtggt gatctagagg gcccgcggtt   1740
```

-continued

```
cgaaggtaag cctatcccta accctctcct cggtctcgat tctacgcgta ccggttagta    1800
atgagtttaa acgggggagg ctaactgaaa cacggaagga acaataccg aaggaaccc      1860 gcgctatgac ggcaataaaa agacagaata aaacgcacgg gtgttgggtc gtttgttcat    1920
aaacgcgggg ttcggtccca gggctggcac tctgtcgata ccccaccgag accccattgg    1980
ggccaatacg cccgcgtttc ttccttttcc ccaccccacc ccccaagttc gggtgaaggc    2040
ccagggctcg cagccaacgt cggggcggca ggccctgcca tagcagatct gcgcagctgg    2100
ggctctaggg ggtatcccca cgcgccctgt agcggcgcat taagcgcggc gggtgtggtg    2160
gttacgcgca gcgtgaccgc tacacttgcc agcgccctag cgcccgctcc tttcgctttc    2220
ttcccttcct ttctcgccac gttcgccggc tttccccgtc aagctctaaa tcggggcatc    2280
cctttagggt tccgatttag tgctttacgg cacctcgacc ccaaaaaact tgattagggt    2340
gatggttcac gtagtgggcc atcgccctga tagacggttt ttcgcccttt gacgttggag    2400
tccacgttct ttaatagtgg actcttgttc caaactggaa caacactcaa ccctatctcg    2460
gtctattctt ttgatttata agggattttg ggatttcgg cctattggtt aaaaaatgag    2520
ctgatttaac aaaaatttaa cgcgaattaa ttctgtggaa tgtgtgtcag ttagggtgtg    2580
gaaagtcccc aggctcccca gcaggcagaa gtatgcaaag catgcatctc aattagtcag    2640
caaccaggtg tggaaagtcc ccaggctccc cagcaggcag aagtatgcaa agcatgcatc    2700
tcaattagtc agcaaccata gtcccgcccc taactccgcc catcccgccc ctaactccgc    2760
ccagttccgc ccattctccg ccccatggct gactaatttt ttttatttat gcagaggccg    2820
aggccgcctc tgcctctgag ctattccaga agtagtgagg aggcttttt ggaggcctag    2880 gcttttgcaa aaagctcccg ggagcttgta tatccatttt cggatctgat cagcacgtgt    2940
tgacaattaa tcatcggcat agtatatcgg catagtataa tacgacaagg tgaggaacta    3000
aaccatggcc aagcctttgt ctcaagaaga atccaccctc attgaaagag caacggctac    3060
aatcaacagc atccccatct ctgaagacta cagcgtcgcc agcgcagctc tctctagcga    3120
cggccgcatc ttcactggtg tcaatgtata tcattttact gggggaccttt gtgcagaact    3180 cgtggtgctg ggcactgctg ctgctgcggc agctggcaac ctgacttgta tcgtcgcgat    3240
cggaaatgag aacaggggca tcttgagccc ctgcggacgg tgccgacagg tgcttctcga    3300
tctgcatcct gggatcaaag ccatagtgaa ggacagtgat ggacagccga cggcagttgg    3360
gattcgtgaa ttgctgccct ctggttatgt gtgggagggc taagcacttc gtggccgagg    3420
agcaggactg acacgtgcta cgagatttcg attccaccgc cgccttctat gaaaggttgg    3480
gcttcggaat cgttttccgg gacgccggct ggatgatcct ccagcgcggg gatctcatgc    3540
tggagttctt cgcccacccc aacttgttta ttgcagctta taatggttac aaataaagca    3600
atagcatcac aaatttcaca aataaagcat ttttttcact gcattctagt tgtggtttgt    3660
ccaaactcat caatgtatct tatcatgtct gtataccgtc gacctctagc tagagcttgg    3720
cgtaatcatg gtcatagctg tttcctgtgt gaaattgtta tccgctcaca attccacaca    3780
acatacgagc cggaagcata aagtgtaaag cctggggtgc ctaatgagtg agctaactca    3840
cattaattgc gttgcgctca ctgcccgctt tccagtcggg aaacctgtcg tgccagctgc    3900
attaatgaat cggccaacgc gcggggagag gcggtttgcg tattgggcgc tcttccgctt    3960
cctcgctcac tgactcgctg cgctcggtcg ttcggctgcg gcgagcggta tcagctcact    4020
caaaggcggt aatacggtta tccacagaat caggggataa cgcaggaaag aacatgtgag    4080
caaaaggcca gcaaaaggcc aggaaccgta aaaaggccgc gttgctggcg ttttccata    4140
```

```
ggctccgccc ccctgacgag catcacaaaa atcgacgctc aagtcagagg tggcgaaacc    4200
cgacaggact ataaagatac caggcgtttc ccctggaag ctccctcgtg cgctctcctg    4260
ttccgaccct gccgcttacc ggatacctgt ccgcctttct cccttcggga agcgtggcgc    4320
tttctcatag ctcacgctgt aggtatctca gttcggtgta ggtcgttcgc tccaagctgg    4380
gctgtgtgca cgaacccccc gttcagcccg accgctgcgc cttatccggt aactatcgtc    4440
ttgagtccaa cccggtaaga cacgacttat cgccactggc agcagccact ggtaacagga    4500
ttagcagagc gaggtatgta ggcggtgcta cagagttctt gaagtggtgg cctaactacg    4560
gctacactag aagaacagta tttggtatct gcgctctgct gaagccagtt accttcggaa    4620
aaagagttgg tagctcttga tccggcaaac aaaccaccgc tggtagcggt ttttttgttt    4680
gcaagcagca gattacgcgc agaaaaaaag gatctcaaga agatcctttg atcttttcta    4740
cggggtctga cgctcagtgg aacgaaaact cacgttaagg gattttggtc atgagattat    4800
caaaaaggat cttcacctag atccttttaa attaaaaatg aagttttaaa tcaatctaaa    4860
gtatatatga gtaaacttgg tctgacagtt accaatgctt aatcagtgag gcacctatct    4920
cagcgatctg tctatttcgt tcatccatag ttgcctgact ccccgtcgtg tagataacta    4980
cgatacggga gggcttacca tctggcccca gtgctgcaat gataccgcga acccacgct    5040 caccggctcc agatttatca gcaataaacc agccagccgg aagggccgag cgcagaagtg    5100
gtcctgcaac tttatccgcc tccatccagt ctattaattg ttgccgggaa gctagagtaa    5160
gtagttcgcc agttaatagt ttgcgcaacg ttgttgccat tgctacaggc atcgtggtgt    5220
cacgctcgtc gtttggtatg gcttcattca gctccggttc ccaacgatca aggcgagtta    5280
catgatcccc catgttgtgc aaaaaagcgg ttagctcctt cggtcctccg atcgttgtca    5340
gaagtaagtt ggccgcagtg ttatcactca tggttatggc agcactgcat aattctctta    5400
ctgtcatgcc atccgtaaga tgcttttctg tgactggtga gtactcaacc aagtcattct    5460
gagaatagtg tatgcggcga ccgagttgct cttgcccggc gtcaatacgg ataataccg    5520 cgccacatag cagaacttta aaagtgctca tcattggaaa acgttcttcg ggcgaaaac    5580 tctcaaggat cttaccgctg ttgagatcca gttcgatgta acccactcgt gcacccaact    5640
gatcttcagc atcttttact ttcaccagcg tttctgggtg agcaaaaaca ggaaggcaaa    5700
atgccgcaaa aaagggaata agggcgacac ggaaatgttg aatactcata ctcttccttt    5760
ttcaatatta ttgaagcatt tatcagggtt attgtctcat gagcggatac atatttgaat    5820
gtatttagaa aaataaacaa ataggggttc cgcgcacatt tccccgaaaa gtgccacctg    5880
acgtc                                                                5885
```

<210> SEQ ID NO 15
<211> LENGTH: 25
<212> TYPE: DNA
<213> ORGANISM: Artificial sequence
<220> FEATURE:
<223> OTHER INFORMATION: TrexPstFor primer

<400> SEQUENCE: 15
acgctgcagg ccttcctgag ccgcc                                          25

<210> SEQ ID NO 16
<211> LENGTH: 29
<212> TYPE: DNA
<213> ORGANISM: Artificial sequence
<220> FEATURE:

<223> OTHER INFORMATION: TrexPstRev primer

<400> SEQUENCE: 16
ggcctgcagc gtccgcacca cggcgccat                                              29

<210> SEQ ID NO 17
<211> LENGTH: 39
<212> TYPE: DNA
<213> ORGANISM: Artificial sequence
<220> FEATURE:
<223> OTHER INFORMATION: TrexLink1For primer

<400> SEQUENCE: 17
ccttctgagt ctgaaggttc cgaggcaccc cgggccgag                                   39

<210> SEQ ID NO 18
<211> LENGTH: 39
<212> TYPE: DNA
<213> ORGANISM: Artificial sequence
<220> FEATURE:
<223> OTHER INFORMATION: TrexLink1Rev primer

<400> SEQUENCE: 18
agactcagaa ggacgagacg cctccaggct ggggtcatc                                   39

<210> SEQ ID NO 19
<211> LENGTH: 45
<212> TYPE: DNA
<213> ORGANISM: Artificial sequence
<220> FEATURE:
<223> OTHER INFORMATION: TrexLink2For primer

<400> SEQUENCE: 19
cagaccggtc tggatgttcc ttactccgag gcaccccggg ccgag                            45

<210> SEQ ID NO 20
<211> LENGTH: 48
<212> TYPE: DNA
<213> ORGANISM: Artificial sequence
<220> FEATURE:
<223> OTHER INFORMATION: TrexLink2Rev primer

<400> SEQUENCE: 20
aacatccaga ccggtctgtg gaggagtcgc ctccaggctg ggtcatc                          48

<210> SEQ ID NO 21
<211> LENGTH: 48
<212> TYPE: DNA
<213> ORGANISM: Artificial sequence
<220> FEATURE:
<223> OTHER INFORMATION: TrexLink3For primer

<400> SEQUENCE: 21
tctgtttcta attctgagca tattgcttcc gaggcacccc gggccgag                         48

<210> SEQ ID NO 22
<211> LENGTH: 48
<212> TYPE: DNA
<213> ORGANISM: Artificial sequence
<220> FEATURE:
<223> OTHER INFORMATION: TrexLink3Rev primer

<400> SEQUENCE: 22
ctcagaatta gaaacagagg aatcaccccgc ctccaggctg ggtcatc                         48

<210> SEQ ID NO 23
<211> LENGTH: 51
<212> TYPE: DNA
<213> ORGANISM: Artificial sequence
<220> FEATURE:
<223> OTHER INFORMATION: TrexLink4For primer

<400> SEQUENCE: 23
gctattggag gttctaaacc tcgtgttgct tccgaggcac cccgggccga g    51

<210> SEQ ID NO 24
<211> LENGTH: 51
<212> TYPE: DNA
<213> ORGANISM: Artificial sequence
<220> FEATURE:
<223> OTHER INFORMATION: TrexLink4Rev primer

<400> SEQUENCE: 24
tttagaacct ccaatagcac gaggacgaat cgcctccagg ctggggtcat c    51

<210> SEQ ID NO 25
<211> LENGTH: 11446
<212> TYPE: DNA
<213> ORGANISM: Artificial sequence
<220> FEATURE:
<223> OTHER INFORMATION: pCLS6810

<400> SEQUENCE: 25

| | |
|---|---|
| tcatggtcat agctgtttcc tgtgtgaaat tgttatccgc tcacaattcc acacaacata | 60 |
| caggatccac tagcgatgta cgggccagat atacgcgttg acattgatta ttgactagtt | 120 |
| attaatagta atcaattacg gggtcattag ttcatagccc atatatggag ttccgcgtta | 180 |
| cataacttac ggtaaatggc ccgcctggct gaccgcccaa cgacccccgc ccattgacgt | 240 |
| caataatgac gtatgttccc atagtaacgc caatagggac tttccattga cgtcaatggg | 300 |
| tggagtattt acggtaaact gcccacttgg cagtacatca agtgtatcat atgccaagta | 360 |
| cgccccctat tgacgtcaat gacggtaaat ggcccgcctg gcattatgcc cagtacatga | 420 |
| ccttatggga ctttcctact tggcagtaca tctacgtatt agtcatcgct attaccatgg | 480 |
| tgatgcggtt ttggcagtac atcaatgggc gtggatagcg gtttgactca cggggatttc | 540 |
| caagtctcca ccccattgac gtcaatggga gtttgttttg gcaccaaaat caacgggact | 600 |
| ttccaaaatg tcgtaacaac tccgccccat tgacgcaaat gggcggtagg cgtgtacggt | 660 |
| gggaggtcta taagcaga gctctctggc taactagaga acccactgct tactggctta | 720 |
| tcgaaattaa tacgactcac tatagggaga cccaagctgg ctagccttag gcgcgcctcg | 780 |
| cgagtttaaa ccgccaccat ggccgcttat ccttatgacg ttcctgatta cgctggattt | 840 |
| atagctgccc cagggtgaga aagtccaagg aggctccgga tccggcggtt ctggatccgg | 900 |
| cggttctggt tccgccgcta gcgggggcga ggagctgttc gccggcatcg tgcccgtgct | 960 |
| gatcgagctg gacggcgacg tgcacggcca agttcagc gtgcgcggcg agggcgaggg | 1020 |
| cgacgccgac tacggcaagc tggagatcaa gttcatctgc accaccggca agctgcccgt | 1080 |
| gccctggccc accctggtga ccaccctctg ctacggcatc cagtgcttcg cccgctaccc | 1140 |
| cgagcacatg aagatgaacg acttcttcaa gagcgccatg cccgagggct acatccagga | 1200 |
| gcgcaccatc cagttccagg acgacggcaa gtacaagacc cgcggcgagg tgaagttcga | 1260 |
| gggcgacacc ctggtgaacc gcatcgagct gaagggcaag gacttcaagg aggacggcaa | 1320 |
| catcctgggc cacaagctgg agtacagctt caacagccac aacgtgtaca tccgccccga | 1380 |

```
caaggccaac aacggcctgg aggctaactt caagacccgc cacaacatcg agggcggcgg   1440
cgtgcagctg gccgaccact accagaccaa cgtgcccctg ggcgacggcc ccgtgctgat   1500
ccccatcaac cactacctga gcactcagac caagatcagc aaggaccgca acgaggcccg   1560
cgaccacatg tgtgctcctgg agtccttcag cgcctgctgc cacacccacg gcatggacga   1620
gctgtacagg taacccgggg agcggccgct cgagtctaga gggcccgttt aaacccgctg   1680
atcagcctcg actgtgcctt ctagttgcca gccatctgtt gtttgcccct cccccgtgcc   1740
ttccttgacc ctggaaggtg ccactcccac tgtccttttcc taataaaatg aggaaattgc   1800
atcgcattgt ctgagtaggt gtcattctat tctgggggt ggggtggggc aggacagcaa   1860
gggggaggat tgggaagaca atagcaggca tgctggggat gcggtgggct ctatggcttc   1920
tgaggcggaa agaacggatc cgcagcctct ttcccaccca ccttgggact cagttctgcc   1980
ccagatgaaa ttcagcaccc acatattaaa ttttcagaat ggaaatttaa gctgttccgg   2040
gtgagatcct ttgaaaagac acctgaagaa gctcaaaagg aaaagaagga ttccttgag   2100 gggaaacccct ctctggagca atctccagca gtcctggaca aggctgatgg tcagaagcca   2160
gtcccaactc agccattgtt aaaagcccac cctaagtttt cgaagaaatt tcacgacaac   2220
gagaaagcaa gaggcaaagc gatccatcaa gccaaccttc gacatctctg ccgcatctgt   2280
gggaattctt ttagagctga tgagcacaac aggagatatc cagtccatgg tcctgtggat   2340
ggtaaaaccc taggccttttt acgaaagaag gaaaagagag ctacttcctg gccggacctc   2400
attgccaagg ttttccggat cgatgtgaag gcagatgttg actcgatcca ccccactgag   2460
ttctgccata actgctggag catcatgcac aggaagttta gcagtgcccc atgtgaggtt   2520
tacttcccga ggaacgtgac catggagtgg caccccccaca caccatcctg tgacatctgc   2580
aacactgccc gtcggggact caagaggaag agtcttcagc caaacttgca gctcagcaaa   2640
aaactcaaaa ctgtgcttga ccaagcaaga caagcccgtc agcacaagag aagagctcag   2700
gcaaggatca gcagcaagga tgtcatgaag aagatcgcca actgcagtaa gatacatctt   2760
agtaccaagc tccttgcagt ggacttccca gagcactttg tgaaatccat ctcctgccag   2820
atctgtgaac acattctggc tgaccctgtg gagaccaact gtaagcatgt cttttgccgg   2880
gtctgcattc tcagatgcct caaagtcatg gcagctatt gtccctcttg ccgatatcca   2940
tgcttcccta ctgacctgga gagtccagtg aagtcctttc tgagcgtctt gaattccctg   3000
atggtgaaat gtccagcaaa agagtgcaat gaggaggtca gtttggaaaa atataatcac   3060
cacatctcaa gtcacaagga atcaaaagag attttttgtgc acattaataa aggggggtcga   3120 gtaacgcgtg caggcatgca agctggccgc aataaaatat ctttattttc attacatctg   3180
tgtgttggtt ttttgtgtga atcgtaacta acatacgctc tccatcaaaa caaaacgaaa   3240
caaaacaaac tagcaaaata ggctgtcccc agtgcaagtg caggtgccag aacatttctc   3300
tatcgaagga tctgcgatcg ctccggtgcc cgtcagtggg cagagcgcac atcgcccaca   3360
gtccccgaga agttggggg aggggtcggc aattgaaccg gtgcctagag aaggtggcgc   3420
ggggtaaact gggaaagtga tgtcgtgtac tggctccgcc tttttcccga gggtggggga   3480
gaaccgtata taagtgcagt agtcgccgtg aacgttcttt ttcgcaacgg gtttgccgcc   3540
agaacacagc tgaagcttcg aggggctcgc atctctcctt cacgcgcccg ccgccctacc   3600
tgaggccgcc atccacgccg gttgagtcgc gttctgccgc ctcccgcctg tggtgcctcc   3660
tgaactgcgt ccgccgtcta ggtaagttta agctcaggt cgagacccgg cctttgtccg   3720
gcgctccctt ggagcctacc tagactcagc cggctctcca cgctttgcct gaccctgctt   3780
```

```
gctcaactct acgtctttgt ttcgttttct gttctgcgcc gttacagatc caagctgtga   3840
ccggcgccta cgtaagtgat atctactaga tttatcaaaa agagtgttga cttgtgagcg   3900
ctcacaattg atacttagat tcatcgagag ggacacgtcg actactaacc ttcttctctt   3960
tcctacagct gagatcaccg gcgaaggagg gccaccatgg cttcttaccc tggacaccag   4020
catgcttctg cctttgacca ggctgccaga tccaggggcc actccaacag gagaactgcc   4080
ctaagaccca agacagca ggaagccact gaggtgaggc tgagcagaa gatgccaacc      4140 ctgctgaggg tgtacattga tggacctcat ggcatgggca agaccaccac cactcaactg   4200
ctggtggcac tgggctccag ggatgacatt gtgtatgtgc ctgagccaat gacctactgg   4260
agagtgctag gagcctctga gaccattgcc aacatctaca ccacccagca caggctggac   4320
cagggagaaa tctctgctgg agatgctgct gtggtgatga cctctgccca gatcacaatg   4380
ggaatgccct atgctgtgac tgatgctgtt ctggctcctc acattggagg agaggctggc   4440
tcttctcatg cccctccacc tgccctgacc ctgatctttg acagacaccc cattgcagcc   4500
ctgctgtgct acccagcagc aaggtacctc atgggctcca tgaccccaca ggctgtgctg   4560
gcttttgtgg ccctgatccc tccaaccctc cctggcacca acattgttct gggagcactg   4620
cctgaagaca gacacattga caggctggca aagaggcaga gacctggaga gagactggac   4680
ctggccatgc tggctgcaat cagaagggtg tatggactgc tggcaaacac tgtgagatac   4740
ctccagtgtg gaggctcttg gagagaggac tggggacagc tctctggaac agcagtgccc   4800
cctcaaggag ctgagcccca gtccaatgct ggtccaagac ccacattgg ggacaccctg    4860 ttcaccctgt tcagagcccc tgagctgctg gctcccaatg gagacctgta caatgtgttt   4920
gcctgggctc tggatgttct agccaagagg ctgaggtcca tgcatgtgtt catcctggac   4980
tatgaccagt cccctgctgg atgcagagat gctctgctgc aactaacctc tggcatggtg   5040
cagacccatg tgaccacccc tggcagcatc cccaccatct gtgacctagc cagaaccttt   5100
gccagggaga tgggagaggc caactaaacc tgagctagct cgacatgata agatacattg   5160
atgagtttgg acaaaccaca actagaatgc agtgaaaaaa atgctttatt tgtgaaattt   5220
gtgatgctat tgctttattt gtgaaatttg tgatgctatt gctttatttg taaccattat   5280
aagctgcaat aaacaagtta acaacaacaa ttgcattcat tttatgtttc aggttcaggg   5340
ggaggtgtgg gaggttttt aaagcaagta aaacctctac aaatgtggta gatccatttt    5400
tggcgtaatc atggtcatag ctgtttcctg tgtgaaattg ttatccgctc acaattccac   5460
acaacatacg agccggaagc ataaagtgta aagcctgggg tgcctaatga gtgagctaac   5520
tcacattaat tgcgttgcgc tcactgcccg ctttccagtc gggaaacctg tcgtgccagc   5580
tgcattaatg aatcggccaa cgcgcgggga gaggcggttt gcgtattggg cgctcttccg   5640
cttcctcgct cactgactcg ctgcgctcgg tcgttcggct gcggcgagcg gtatcagctc   5700
actcaaaggc ggtaatacgg ttatccacag aatcagggga taacgcagga aagaacatgt   5760
gagcaaaagg ccagcaaaag gccaggaacc gtaaaaaggc cgcgttgctg gcgttttcc    5820 ataggctccg ccccccctgac gagcatcaca aaaatcgacg ctcaagtcag aggtggcgaa   5880
acccgacagg actataaaga taccaggcgt ttccccctgg aagctccctc gtgcgctctc   5940
ctgttccgac cctgccgctt accggatacc tgtccgcctt tctcccttcg ggaagcgtgg   6000
cgctttctca tagctcacgc tgtaggtatc tcagttcggt gtaggtcgtt cgctccaagc   6060
tgggctgtgt gcacgacccc cccgttcagc ccgaccgctg cgccttatcc ggtaactatc   6120
```

```
gtcttgagtc caacccggta agacacgact tatcgccact ggcagcagcc actggtaaca   6180
ggattagcag agcgaggtat gtaggcggtg ctacagagtt cttgaagtgg tggcctaact   6240
acggctacac tagaagaaca gtatttggta tctgcgctct gctgaagcca gttaccttcg   6300
gaaaaagagt tggtagctct tgatccggca aacaaccac cgctggtagc ggtggttttt    6360
ttgtttgcaa gcagcagatt acgcgcagaa aaaaggatc tcaagaagat cctttgatct   6420
tttctacggg gtctgacgct cagtggaacg aaaactcacg ttaagggatt ttggtcatga   6480
gattatcaaa aaggatcttc acctagatcc ttttaaatta aaaatgaagt tttaaatcaa   6540
tctaaagtat atatgagtaa acttggtctg acagttacca atgcttaatc agtgaggcac   6600
ctatctcagc gatctgtcta tttcgttcat ccatagttgc ctgactcccc gtcgtgtaga   6660
taactacgat acgggagggc ttaccatctg gccccagtgc tgcaatgata ccgcgagacc   6720
cacgctcacc ggctccagat ttatcagcaa taaaccagcc agccggaagg gccgagcgca   6780
gaagtggtcc tgcaacttta tccgcctcca tccagtctat taattgttgc cgggaagcta   6840
gagtaagtag ttcgccagtt aatagtttgc gcaacgttgt tgccattgct acaggcatcg   6900
tggtgtcacg ctcgtcgttt ggtatggctt cattcagctc cggttcccaa cgatcaaggc   6960
gagttacatg atccccatg ttgtgcaaaa aagcggttag ctccttcggt cctccgatcg    7020
ttgtcagaag taagttggcc gcagtgttat cactcatggt tatggcagca ctgcataatt   7080
ctcttactgt catgccatcc gtaagatgct tttctgtgac tggtgagtac tcaaccaagt   7140
cattctgaga atagtgtatg cggcgaccga gttgctcttg cccggcgtca atacgggata   7200
ataccgcgcc acatagcaga actttaaaag tgctcatcat tggaaaacgt tcttcggggc   7260
gaaaactctc aaggatctta ccgctgttga tccagttc gatgtaaccc actcgtgcac    7320
ccaactgatc ttcagcatct tttactttca ccagcgtttc tgggtgagca aaaacaggaa   7380
ggcaaaatgc cgcaaaaaag gaataaggg cgacacggaa atgttgaata ctcatactct    7440
tcctttttca atattattga agcatttatc agggttattg tctcatgagc ggatacatat   7500
ttgaatgtat ttagaaaaat aaacaaatag gggttccgcg cacatttccc cgaaaagtgc   7560
cacctgacgt ctaagaaacc attattatca tgacattaac ctataaaaat aggcgtatca   7620
cgaggccctt tcgtctcgcg cgtttcggtg atgacggtga aaacctctga cacatgcagc   7680
tcccggagac ggtcacagct tgtctgtaag cggatgccgg gagcagacaa gcccgtcagg   7740
gcgcgtcagc gggtgttggc gggtgtcggg gctggcttaa ctatgcggca tcagagcaga   7800
ttgtactgag agtgcaccat atgcggtgtg aaataccgca cagatgcgta aggagaaaat   7860
accgcatcag gcgccaatat taaacttgat gagctctaga gatggtcatg cattttaaaa   7920
agaattactc aaaatattgt cttggaatac cagagagcaa gtgctttaag tataggctgg   7980
gaagtaaaat gctaaaggaa tgagaaggca tttggggttg agttcaacct aagaggcagg   8040
ggagccacag ggaaagacct agcacctgcc acagaagaga attaggaagc agaattgaac   8100
tataagcaat tttgaggtgt tcgttgggct gcagttgaaa tatttttga ggttaatgag    8160 acatttgaaa tggccgtgta ttgtttaact cttgcatagt cctgcatagg aacaatcta    8220 ataggatttc tctgtgaatc aagtcttaga aatttgcttt taattttat gaaaaacgcc    8280 catttctttg ttttgagac agagtcctgc tctgtcatcc aggctgggtt gcagtggcgt    8340
gatcttggcc cactgcaatc tctgcctcct gggttcaggc aatttcctg tctcagcctc    8400 ccgagtagct gggatttcaa gtgcctgcca ccatgcccgg ctaaattttt ttgtattttt   8460
ggtacagatg gagtatcacc atgttggcca ggctggtctc gaactcctga cctcaagtga   8520
```

```
ttcaccagcc ttgacctccc aaagtgttgg gatcacaggc atgagccact gtgcctgtgc   8580
cccaaaacac caatttctga tgtgtgatgc atgtaagata gaacaaactt cagtaaagcg   8640
gggacttgaa aagaggcttt ggtaacagct gtcagcatta acccttgccc ctccgtacct   8700
cctaatccca cccctgctca aagtatgttc atctgagaat ttgtctccat aactatgtga   8760
ctataaaaat tctcatcgat tttgttagtt gatcaattga gggaaaaaca tatgttactt   8820 gataaactg gtgggtcaaa agaattaacc caggcaaatt tgagataggt ggatgggatg    8880
atggattgaa atacagctg ctctcttttcc aatcatgtac taagtaattt gggaaagatt   8940
gatctaattg ggtctagaga gtacacttca catggcattg tttgactttt tttctgcatc   9000
gctagcgatc tgtgcattac aactcaaatc agtcgggttt cctggcatat gtaattgcca   9060 atgttttta ccagaagaga aacattactc ccacctcttc ttattatgtt acaaactata   9120
gtgctaatga ccatcgacca acagtgactt tcaggatgac ctgtgtgagt tttatctgaa   9180
accatgtgaa tttttcatct taaaagtccc ttagaatctc agtctatgta cactcaggtt   9240
tgttgcaggt ttagagttcc gtgttttttg tttctaatgt agacacagcc ttataattta   9300
caacagcatt cactaattaa aattgtaagc ataattacta tccacgatac ttattattag   9360
tttgcattca taaagctcaa aattcacttc atcctttcaa gtagtgaata attagtttct   9420
ttgggtttgc agcttttatca tcctttatg acccatttgg aagaaataaa caaccaaccc    9480
cctggaagac tgctttaaaa agctggaaat acattgtcca gctagtacaa tgaggctaat   9540
acaatgtgga aaatattact tttctttgat tttagtagcc tgtttatctt tacatttact   9600
gaacaaataa ctattgagca cctaatgtat actgggaccc ttggggaggc aaagatgaat   9660
caaagattct gtccttaaag accttaagac gcgttgacat tgattattga ctagttatta   9720
atagtaatca attacggggt cattagttca tagcccatat atggagttcc gcgttacata   9780
acttacggta aatggcccgc ctggctgacc gcccaacgac ccccgcccat tgacgtcaat   9840
aatgacgtat gttcccatag taacgccaat agggactttc cattgacgtc aatgggtgga   9900
gtatttacgg taaactgccc acttggcagt acatcaagtg tatcatatgc caagtacgcc   9960
ccctattgac gtcaatgacg gtaaatggcc cgcctggcat tatgcccagt acatgacctt  10020
atgggacttt cctacttggc agtacatcta cgtattagtc atcgctatta ccatggtgat  10080
gcggttttgg cagtacatca atgggcgtgg atagcggttt gactcacggg gatttccaag  10140
tctccacccc attgacgtca atgggagttt gttttggcac caaaatcaac gggactttcc  10200
aaaatgtcgt aacaactccg ccccattgac gcaaatgggc ggtaggcgtg tacggtggga  10260
ggtctatata agcagagctc cccgggagct tgtatatcca ttttcggatc tgatcaagag  10320
acaggatgag gatcgtttcg catgattgaa caagatggat tgcacgcagg ttctccggcc  10380
gcttgggtgg agaggctatt cggctatgac tgggcacaac agacaatcgg ctgctctgat  10440
gccgccgtgt tccggctgtc agcgcagggg cgcccggttc tttttgtcaa gaccgacctg  10500
tccggtgccc tgaatgaact gcaggacgag gcagcgcggc tatcgtggct ggccacgacg  10560
ggcgttcctt gcgcagctgt gctcgacgtt gtcactgaag cgggaaggga ctggctgcta  10620
ttgggcgaag tgccggggca ggatctcctg tcatctcacc ttgctcctgc cgagaaagta  10680
tccatcatgg ctgatgcaat gcggcggctg catacgcttg atccggctac ctgcccattc  10740
gaccaccaag cgaaacatcg catcgagcga gcacgtactc ggatggaagc cggtcttgtc  10800
gatcaggatg atctggacga agagcatcag gggctcgcgc cagccgaact gttcgccagg  10860
```

```
ctcaaggcgc gcatgcccga cggcgaggat ctcgtcgtga cccatggcga tgcctgcttg    10920
ccgaatatca tggtggaaaa tggccgcttt tctggattca tcgactgtgg ccggctgggt    10980
gtggcggacc gctatcagga catagcgttg gctacccgtg atattgctga agagcttggc    11040
ggcgaatggg ctgaccgctt cctcgtgctt tacggtatcg ccgctcccga ttcgcagcgc    11100
atcgccttct atcgccttct tgacgagttc ttctgattaa ttaacaggac tgaccgtgct    11160
acgagatttc gattccaccg ccgccttcta tgaaaggttg ggcttcggaa tcgtttttccg   11220 ggacgccggc tggatgatcc tccagcgcgg ggatctcatg ctggagttct tcgcccaccc    11280
caacttgttt attgcagctt ataatggtta caaataaagc aatagcatca caaatttcac    11340
aaataaagca ttttttttcac tgcattctag ttgtggtttg tccaaactca tcaatgtatc    11400
ttatcatgtc tgtataccgt cgacctctag ctagagcttg gcgtaa                   11446
```

<210> SEQ ID NO 26
<211> LENGTH: 236
<212> TYPE: PRT
<213> ORGANISM: Artificial sequence
<220> FEATURE:
<223> OTHER INFORMATION: Trex2 (236 aa)

<400> SEQUENCE: 26

```
Met Ser Glu Ala Pro Arg Ala Glu Thr Phe Val Phe Leu Asp Leu Glu
  1               5                  10                  15

Ala Thr Gly Leu Pro Ser Val Glu Pro Glu Ile Ala Glu Leu Ser Leu
             20                  25                  30

Phe Ala Val His Arg Ser Ser Leu Glu Asn Pro Glu His Asp Glu Ser
         35                  40                  45

Gly Ala Leu Val Leu Pro Arg Val Leu Asp Lys Leu Thr Leu Cys Met
     50                  55                  60

Cys Pro Glu Arg Pro Phe Thr Ala Lys Ala Ser Glu Ile Thr Gly Leu
 65                  70                  75                  80

Ser Ser Glu Gly Leu Ala Arg Cys Arg Lys Ala Gly Phe Asp Gly Ala
                 85                  90                  95

Val Val Arg Thr Leu Gln Ala Phe Leu Ser Arg Gln Ala Gly Pro Ile
            100                 105                 110

Cys Leu Val Ala His Asn Gly Phe Asp Tyr Asp Phe Pro Leu Leu Cys
        115                 120                 125

Ala Glu Leu Arg Arg Leu Gly Ala Arg Leu Pro Arg Asp Thr Val Cys
    130                 135                 140

Leu Asp Thr Leu Pro Ala Leu Arg Gly Leu Asp Arg Ala His Ser His
145                 150                 155                 160

Gly Thr Arg Ala Arg Gly Arg Gln Gly Tyr Ser Leu Gly Ser Leu Phe
                165                 170                 175

His Arg Tyr Phe Arg Ala Glu Pro Ser Ala Ala His Ser Ala Glu Gly
            180                 185                 190

Asp Val His Thr Leu Leu Leu Ile Phe Leu His Arg Ala Ala Glu Leu
        195                 200                 205

Leu Ala Trp Ala Asp Glu Gln Ala Arg Gly Trp Ala His Ile Glu Pro
    210                 215                 220

Met Tyr Leu Pro Pro Asp Asp Pro Ser Leu Glu Ala
225                 230                 235
```

<210> SEQ ID NO 27
<211> LENGTH: 6882
<212> TYPE: DNA

<213> ORGANISM: Artificial sequence
<220> FEATURE:
<223> OTHER INFORMATION: pCLS8052

<400> SEQUENCE: 27

| | | | | | |
|---|---|---|---|---|---|
| ctcgagcgct | agcacccagc | tttcttgtac | aaagtggtga | tctagagggc | ccgcggttcg | 60 |
| aaggtaagcc | tatccctaac | cctctcctcg | gtctcgattc | tacgcgtacc | ggttagtaat | 120 |
| gagtttaaac | gggggaggct | aactgaaaca | cggaaggaga | caataccgga | aggaacccgc | 180 |
| gctatgacgg | caataaaaag | acagaataaa | acgcacgggt | gttggtcgt | ttgttcataa | 240 |
| acgcggggtt | cggtcccagg | gctggcactc | tgtcgatacc | ccaccgagac | cccattgggg | 300 |
| ccaatacgcc | cgcgtttctt | cctttttccc | accccacccc | ccaagttcgg | gtgaaggccc | 360 |
| agggctcgca | gccaacgtcg | gggcggcagg | ccctgccata | gcagatctgc | gcagctgggg | 420 |
| ctctaggggg | tatccccacg | cgccctgtag | cggcgcatta | gcgcggcgg | gtgtggtggt | 480 |
| tacgcgcagc | gtgaccgcta | cacttgccag | cgccctagcg | cccgctcctt | tcgctttctt | 540 |
| cccttccttt | ctcgccacgt | tcgccggctt | tccccgtcaa | gctctaaatc | ggggcatccc | 600 |
| tttagggttc | cgatttagtg | ctttacggca | cctcgacccc | aaaaaacttg | attagggtga | 660 |
| tggttcacgt | agtgggccat | cgccctgata | gacggttttt | cgccctttga | cgttggagtc | 720 |
| cacgttcttt | aatagtggac | tcttgttcca | aactggaaca | acactcaacc | ctatctcggt | 780 |
| ctattctttt | gatttataag | ggattttggg | gatttcggcc | tattggttaa | aaatgagct | 840 |
| gatttaacaa | aaatttaacg | cgaattaatt | ctgtggaatg | tgtgtcagtt | agggtgtgga | 900 |
| aagtccccag | gctccccagc | aggcagaagt | atgcaaagca | tgcatctcaa | ttagtcagca | 960 |
| accaggtgtg | gaaagtcccc | aggctcccca | gcaggcagaa | gtatgcaaag | catgcatctc | 1020 |
| aattagtcag | caaccatagt | cccgccccta | actccgccca | tcccgcccct | aactccgccc | 1080 |
| agttccgccc | attctccgcc | ccatggctga | ctaatttttt | ttatttatgc | agaggccgag | 1140 |
| gccgcctctg | cctctgagct | attccagaag | tagtgaggag | gcttttttgg | aggcctaggc | 1200 |
| ttttgcaaaa | agctcccggg | agcttgtata | tccattttcg | gatctgatca | gcacgtgttg | 1260 |
| acaattaatc | atcggcatag | tatatcggca | tagtataata | cgacaaggtg | aggaactaaa | 1320 |
| ccatggccaa | gcctttgtct | caagaagaat | ccaccctcat | tgaaagagca | acggctacaa | 1380 |
| tcaacagcat | ccccatctct | gaagactaca | gcgtcgccag | cgcagctctc | tctagcgacg | 1440 |
| gccgcatctt | cactggtgtc | aatgtatatc | attttactgg | gggaccttgt | gcagaactcg | 1500 |
| tggtgctggg | cactgctgct | gctgcggcag | ctggcaacct | gacttgtatc | gtcgcgatcg | 1560 |
| gaaatgagaa | caggggcatc | ttgagcccct | gcggacggtg | ccgacaggtg | cttctcgatc | 1620 |
| tgcatcctgg | gatcaaagcc | atagtgaagg | acagtgatgg | acagccgacg | gcagttggga | 1680 |
| ttcgtgaatt | gctgccctct | ggttatgtgt | gggagggcta | agcacttcgt | ggccgaggag | 1740 |
| caggactgac | acgtgctacg | agatttcgat | tccaccgccg | ccttctatga | aaggttgggc | 1800 |
| ttcggaatcg | ttttccggga | cgccggctgg | atgatcctcc | agcgcgggga | tctcatgctg | 1860 |
| gagttcttcg | cccacccaa | cttgtttatt | gcagcttata | atggttacaa | ataaagcaat | 1920 |
| agcatcacaa | atttcacaaa | taaagcattt | ttttcactgc | attctagttg | tggtttgtcc | 1980 |
| aaactcatca | atgtatctta | tcatgtctgt | ataccgtcga | cctctagcta | gagcttggcg | 2040 |
| taatcatggt | catagctgtt | tcctgtgtga | aattgttatc | cgctcacaat | tccacacaac | 2100 |
| atacgagccg | gaagcataaa | gtgtaaagcc | tggggtgcct | aatgagtgag | ctaactcaca | 2160 |
| ttaattgcgt | tgcgctcact | gcccgctttc | cagtcgggaa | acctgtcgtg | ccagctgcat | 2220 |

```
taatgaatcg gccaacgcgc ggggagaggc ggtttgcgta ttgggcgctc ttccgcttcc    2280
tcgctcactg actcgctgcg ctcggtcgtt cggctgcggc gagcggtatc agctcactca    2340
aaggcggtaa tacggttatc cacagaatca ggggataacg caggaaagaa catgtgagca    2400
aaaggccagc aaaaggccag gaaccgtaaa aaggccgcgt tgctggcgtt tttccatagg    2460
ctccgccccc ctgacgagca tcacaaaaat cgacgctcaa gtcagaggtg gcgaaacccg    2520
acaggactat aaagatacca ggcgtttccc cctggaagct ccctcgtgcg ctctcctgtt    2580
ccgaccctgc cgcttaccgg atacctgtcc gcctttctcc cttcgggaag cgtggcgctt    2640
tctcatagct cacgctgtag gtatctcagt tcggtgtagg tcgttcgctc caagctgggc    2700
tgtgtgcacg aaccccccgt tcagcccgac cgctgcgcct tatccggtaa ctatcgtctt    2760
gagtccaacc cggtaagaca cgacttatcg ccactggcag cagccactgg taacaggatt    2820
agcagagcga ggtatgtagg cggtgctaca gagttcttga agtggtggcc taactacggc    2880
tacactagaa gaacagtatt tggtatctgc gctctgctga agccagttac cttcggaaaa    2940
agagttggta gctcttgatc cggcaaacaa accaccgctg gtagcggttt ttttgtttgc    3000
aagcagcaga ttacgcgcag aaaaaaagga tctcaagaag atcctttgat cttttctacg    3060
gggtctgacg ctcagtggaa cgaaaactca cgttaaggga ttttggtcat gagattatca    3120
aaaaggatct tcacctagat ccttttaaat taaaaatgaa gttttaaatc aatctaaagt    3180
atatatgagt aaacttggtc tgacagttac caatgcttaa tcagtgaggc acctatctca    3240
gcgatctgtc tatttcgttc atccatagtt gcctgactcc ccgtcgtgta gataactacg    3300
atacgggagg gcttaccatc tggccccagt gctgcaatga taccgcgaga cccacgctca    3360
ccggctccag atttatcagc aataaaccag ccagccggaa gggccgagcg cagaagtggt    3420
cctgcaactt tatccgcctc catccagtct attaattgtt gccgggaagc tagagtaagt    3480
agttcgccag ttaatagttt gcgcaacgtt gttgccattg ctacaggcat cgtggtgtca    3540
cgctcgtcgt ttggtatggc ttcattcagc tccggttccc aacgatcaag gcgagttaca    3600
tgatccccca tgttgtgcaa aaaagcggtt agctccttcg gtcctccgat cgttgtcaga    3660
agtaagttgg ccgcagtgtt atcactcatg gttatggcag cactgcataa ttctcttact    3720
gtcatgccat ccgtaagatg cttttctgtg actggtgagt actcaaccaa gtcattctga    3780
gaatagtgta tgcggcgacc gagttgctct tgcccggcgt caatacggga taataccgcg    3840
ccacatagca gaactttaaa agtgctcatc attggaaaac gttcttcggg gcgaaaactc    3900
tcaaggatct taccgctgtt gagatccagt tcgatgtaac ccactcgtgc acccaactga    3960
tcttcagcat cttttacttt caccagcgtt tctgggtgag caaaaacagg aaggcaaaat    4020
gccgcaaaaa agggaataag ggcgacacgg aaatgttgaa tactcatact cttcctttt    4080 caatattatt gaagcattta tcagggttat tgtctcatga gcggatacat atttgaatgt    4140
atttagaaaa ataaacaaat aggggttccg cgcacatttc cccgaaaagt gccacctgac    4200
gtcgacggat cgggagatct cccgatcccc tatggtgcac tctcagtaca atctgctctg    4260
atgccgcata gttaagccag tatctgctcc ctgcttgtgt gttggaggtc gctgagtagt    4320
gcgcgagcaa aatttaagct acaacaaggc aaggcttgac cgacaattgc atgaagaatc    4380
tgcttagggt taggcgtttt gcgctgcttc gcgatgtacg ggccagatat acgcgttgac    4440
attgattatt gactagttat taatagtaat caattacggg gtcattagtt catagcccat    4500
atatggagtt ccgcgttaca taacttacgg taaatggccc gcctggctga ccgcccaacg    4560
```

| | |
|---|---|
| acccccgccc attgacgtca ataatgacgt atgttcccat agtaacgcca atagggactt | 4620 |
| tccattgacg tcaatgggtg gagtatttac ggtaaactgc ccacttggca gtacatcaag | 4680 |
| tgtatcatat gccaagtacg cccnctattg acgtcaatga cggtaaatgg cccgcctggc | 4740 |
| attatgccca gtacatgacc ttatgggact ttcctacttg gcagtacatc tacgtattag | 4800 |
| tcatcgctat taccatggtg atgcggtttt ggcagtacat caatgggcgt ggatagcggt | 4860 |
| ttgactcacg gggatttcca agtctccacc ccattgacgt caatgggagt ttgttttggc | 4920 |
| accaaaatca acgggacttt ccaaaatgtc gtaacaactc cgccccattg acgcaaatgg | 4980 |
| gcggtaggcg tgtacggtgg gaggtctata taagcagagc tctctggcta actagagaac | 5040 |
| ccactgctta ctggcttatc gaaatgaatt ccgtcgacca tggccaatac caaatataac | 5100 |
| gaagagttcc tgctgtacct ggccggcttt gtggacgctg acggtagcat catcgctcag | 5160 |
| attaaaccaa gacagtctcg gaagtttaaa catgagctaa gcttgacctt tgatgtgact | 5220 |
| caaaagaccc agcgccgttg gtttctggac aagctagtgg atgaaattgg cgttggttac | 5280 |
| gtatatgatt ctggatccgt ttcctattac cagttaagcg aaatcaagcc gctgcacaac | 5340 |
| ttcctgactc aactgcagcc gtttctggaa ctgaaacaga aacaggcaaa cctggttctg | 5400 |
| aaaattatcg aacagctgcc gtctgcaaaa gaatccccgg ccaaattcct ggaagtttgt | 5460 |
| acctgggtgg atcagattgc agctctgaac gattctaaga cgcgtaaaac cacttctgaa | 5520 |
| accgttcgtg ctgtgctgga tagcctgagc gagaagaaga atcctcccc ggcggccggt | 5580 |
| ggatctgata agtataatca ggctctgtct aaatacaacc aagcactgtc caagtacaat | 5640 |
| caggccctgt ctggtggagg cggttccaac aaaaagttcc tgctgtatct tgctggattt | 5700 |
| gtggatggtg atggctccat cattgctcag ataaaaccac gtcaagggta aagttcaaa | 5760 |
| caccagctct ccttgacttt tcaggtcact cagaagacac aaagaaggtg gttcttggac | 5820 |
| aaattggttg atcgtattgg tgtgggctat gtcgctgacc gtggctctgt gtcagactac | 5880 |
| cgcctgtctg aaattaagcc tcttcataac tttctcaccc aactgcaacc cttcttgaag | 5940 |
| ctcaaacaga agcaagcaaa tctggttttg aaaatcatcg agcaactgcc atctgccaag | 6000 |
| gagtccctgg acaagtttct tgaagtgtgt acttgggtgg atcagattgc tgccttgaat | 6060 |
| gactccaaga ccagaaaaac cacctctgag actgtgaggg cagttctgga tagcctctct | 6120 |
| gagaagaaaa agtcctctcc tggaggtggc ggatctggag gtggaggttc cgaggcaccc | 6180 |
| cgggccgaga ccttttgtctt cctggacctg gaagccactg gctccccag tgtggagccc | 6240 |
| gagattgccg agctgtccct cttttgctgtc caccgctcct ccctggagaa cccggagcac | 6300 |
| gacgagtctg gtgccctagt attgccccgg gtcctggaca agctcacgct gtgcatgtgc | 6360 |
| ccggagcgcc ccttcactgc caaggccagc gagatcaccg gcctgagcag tgagggcctg | 6420 |
| gcgcgatgcc ggaaggctgg ctttgatggc gccgtggtgc ggacgctgca ggccttcctg | 6480 |
| agccgccagg cagggcccat ctgccttgtg gcccacaatg gctttgatta tgatttcccc | 6540 |
| ctgctgtgtg ccgagctgcg cgcgctgggt gcccgcctgc ccgggacac tgtctgcctg | 6600 |
| gacacgctgc cggccctgcg gggcctggac cgcgcccaca gccacggcac ccgggcccgg | 6660 |
| ggccgccagg gttacagcct cggcagcctc ttccaccgct acttccgggc agagccaagc | 6720 |
| gcagcccact cagccgaggg cgacgtgcac accctgctcc tgatcttcct gcaccgcgcc | 6780 |
| gcagagctgc tcgcctgggc cgatgagcag gccgtgggt gggcccacat cgagcccatg | 6840 |
| tacttgccgc ctgatgaccc cagcctggag gcggccgact ga | 6882 |

<210> SEQ ID NO 28
<211> LENGTH: 6922
<212> TYPE: DNA
<213> ORGANISM: Artificial sequence
<220> FEATURE:
<223> OTHER INFORMATION: pCLS8054

<400> SEQUENCE: 28

| | | | | | |
|---|---|---|---|---|---|
| gacggatcgg | gagatctccc | gatccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | atgaattcga | ctcactgttg | ggagacccaa | gctggctagt | 900 |
| taagctatca | caagtttgta | caaaaaagca | ggctggcgcg | cctacacagc | ggccttgcca | 960 |
| ccatgggttc | cgaggcaccc | cgggccgaga | cctttgtctt | cctggacctg | aagccactg | 1020 |
| ggctccccag | tgtggagccc | gagattgccg | agctgtccct | cttctgtgtc | caccgctcct | 1080 |
| ccctggagaa | cccggagcac | gacgagtctg | gtgccctagt | attgccccgg | gtcctggaca | 1140 |
| agctcacgct | gtgcatgtgc | ccggagcgcc | ccttcactgc | caaggccagc | gagatcaccg | 1200 |
| gcctgagcag | tgagggcctg | gcgcgatgcc | ggaaggctgg | ctttgatggc | gccgtggtgc | 1260 |
| ggacgctgca | ggccttcctg | agccgccagg | cagggcccat | ctgccttgtg | gcccacaatg | 1320 |
| gctttgatta | tgatttcccc | ctgctgtgtg | ccgagctgcg | gcgcctgggt | gcccgcctgc | 1380 |
| cccgggacac | tgtctgcctg | gacacgctgc | cggccctgcg | gggcctggac | gcgcccacab | 1440 |
| gccacggcac | ccgggcccgg | ggccgccagg | gttacagcct | cggcagcctc | ttccaccgct | 1500 |
| acttccgggc | agagccaagc | gcagcccact | cagccgaggg | cgacgtgcac | accctgctcc | 1560 |
| tgatcttcct | gcaccgcgcc | gcagagctgc | tcgcctgggc | cgatgagcag | gcccgtgggt | 1620 |
| gggcccacat | cgagcccatg | tacttgccgc | ctgatgaccc | cagcctggag | gcgggaggtg | 1680 |
| gaggttctgg | aggtggaggt | tccaatacca | aatataacga | agagttcctg | ctgtacctgg | 1740 |
| ccggctttgt | ggacgctgac | ggtagcatca | tcgctcagat | taaaccaaga | cagtctcgga | 1800 |
| agttttaaaca | tgagctaagc | ttgacttttg | atgtgactca | aaagacccag | cgccgttggt | 1860 |
| ttctggacaa | gctagtggat | gaaattgcg | ttggttacgt | atatgattct | ggatccgttt | 1920 |
| cctattacca | gttaagcgaa | atcaagccgc | tgcacaactt | cctgactcaa | ctgcagccgt | 1980 |
| ttctggaact | gaaacagaaa | caggcaaacc | tggttctgaa | aattatcgaa | cagctgccgt | 2040 |
| ctgcaaaaga | atccccggcc | aaattcctgg | aagtttgtac | ctgggtggat | cagattgcag | 2100 |

-continued

```
ctctgaacga ttctaagacg cgtaaaacca cttctgaaac cgttcgtgct gtgctggata    2160
gcctgagcga gaagaagaaa tcctccccgg cggccggtgg atctgataag tataatcagg    2220
ctctgtctaa atacaaccaa gcactgtcca agtacaatca ggccctgtct ggtggaggcg    2280
gttccaacaa aaagttcctg ctgtatcttg ctggatttgt ggatggtgat ggctccatca    2340
ttgctcagat aaaaccacgt caagggtata agttcaaaca ccagctctcc ttgacttttc    2400
aggtcactca gaagacacaa agaaggtggt tcttggacaa attggttgat cgtattggtg    2460
tgggctatgt cgctgaccgt ggctctgtgt cagactaccg cctgtctgaa attaagcctc    2520
ttcataactt tctcacccaa ctgcaaccct tcttgaagct caaacagaag caagcaaatc    2580
tggttttgaa aatcatcgag caactgccat ctgccaagga gtccctggac aagtttcttg    2640
aagtgtgtac ttgggtggat cagattgctg ccttgaatga ctccaagacc agaaaaacca    2700
cctctgagac tgtgagggca gttctggata gcctctctga agaaaaaag tcctctcctt    2760
agccatggcc cgcggttcga aggtaagcct atccctaacc ctctcctcgg tctcgattct    2820
acgcgtaccg gttagtaatg agtttaaacg ggggaggcta actgaaacac ggaaggagac    2880
aataccggaa ggaacccgcg ctatgacggc aataaaaaga cagaataaaa cgcacgggtg    2940
ttgggtcgtt tgttcataaa cgcggggttc ggtcccaggg ctggcactct gtcgataccc    3000
caccgagacc ccattgggc caatacgccc gcgtttcttc cttttcccca ccccaccccc    3060
caagttcggg tgaaggccca gggctcgcag ccaacgtcgg ggcggcaggc cctgccatag    3120
cagatctgcg cagctggggc tctagggggt atccccacgc gccctgtagc ggcgcattaa    3180
gcgcggcggg tgtggtggtt acgcgcagcg tgaccgctac acttgccagc gccctagcgc    3240
ccgctccttt cgctttcttc ccttcctttc tcgccacgtt cgccggcttt ccccgtcaag    3300
ctctaaatcg gggcatccct ttagggttcc gatttagtgc tttacggcac ctcgaccca    3360
aaaaacttga ttagggtgat ggttcacgta gtgggccatc gccctgatag acggttttc     3420
gccctttgac gttggagtcc acgttcttta atagtggact cttgttccaa actggaacaa    3480
cactcaaccc tatctcggtc tattctttg atttataagg gattttgggg atttcggcct    3540
attggttaaa aaatgagctg atttaacaaa aatttaacgc gaattaattc tgtggaatgt    3600
gtgtcagtta gggtgtggaa agtccccagg ctccccagca ggcagaagta tgcaaagcat    3660
gcatctcaat tagtcagcaa ccaggtgtgg aaagtcccca ggctccccag caggcagaag    3720
tatgcaaagc atgcatctca attagtcagc aaccatagtc ccgcccctaa ctccgcccat    3780
cccgcccta actccgccca gttccgccca ttctccgccc catggctgac taatttttttt    3840
tatttatgca gaggccgagg ccgcctctgc ctctgagcta ttccagaagt agtgaggagg    3900
ctttttttgga ggcctaggct tttgcaaaaa gctcccggga gcttgtatat ccattttcgg    3960
atctgatcag cacgtgttga caattaatca tcggcatagt atatcggcat agtataatac    4020
gacaaggtga ggaactaaac catggccaag cctttgtctc aagaagaatc caccctcatt    4080
gaaagagcaa cggctacaat caacagcatc cccatctctg aagactacag cgtcgccagc    4140
gcagctctct ctagcgacgg ccgcatcttc actggtgtca atgtatatca ttttactggg    4200
ggaccttgtg cagaactcgt ggtgctgggc actgctgctg ctgcggcagc tggcaacctg    4260
acttgtatcg tcgcgatcgg aaatgagaac aggggcatct tgagccctg cggacggtgc    4320
cgacaggtgc ttctcgatct gcatcctggg atcaaagcca tagtgaagga cagtgatgga    4380
cagccgacgg cagttgggat tcgtgaattg ctgccctctg ttatgtgtg ggagggctaa    4440
gcacttcgtg gccgaggagc aggactgaca cgtgctacga gatttcgatt ccaccgccgc    4500
```

| | |
|---|---|
| cttctatgaa aggttgggct tcggaatcgt tttccgggac gccggctgga tgatcctcca | 4560 |
| gcgcggggat ctcatgctgg agttcttcgc ccacccaac ttgtttattg cagcttataa | 4620 |
| tggttacaaa taaagcaata gcatcacaaa tttcacaaat aaagcatttt tttcactgca | 4680 |
| ttctagttgt ggtttgtcca aactcatcaa tgtatcttat catgtctgta taccgtcgac | 4740 |
| ctctagctag agcttggcgt aatcatggtc atagctgttt cctgtgtgaa attgttatcc | 4800 |
| gctcacaatt ccacacaaca tacgagccgg aagcataaag tgtaaagcct ggggtgccta | 4860 |
| atgagtgagc taactcacat taattgcgtt gcgctcactg cccgctttcc agtcgggaaa | 4920 |
| cctgtcgtgc cagctgcatt aatgaatcgg ccaacgcgcg gggagaggcg gtttgcgtat | 4980 |
| tgggcgctct tccgcttcct cgctcactga ctcgctgcgc tcggtcgttc ggctgcggcg | 5040 |
| agcggtatca gctcactcaa aggcggtaat acgttatcc acagaatcag gggataacgc | 5100 |
| aggaaagaac atgtgagcaa aaggccagca aaaggccagg aaccgtaaaa aggccgcgtt | 5160 |
| gctggcgttt ttccataggc tccgcccccc tgacgagcat cacaaaaatc gacgctcaag | 5220 |
| tcagaggtgg cgaaacccga caggactata agataccag gcgtttcccc ctggaagctc | 5280 |
| cctcgtgcgc tctcctgttc cgaccctgcc gcttaccgga tacctgtccg cctttctccc | 5340 |
| ttcgggaagc gtggcgcttt ctcatagctc acgctgtagg tatctcagtt cggtgtaggt | 5400 |
| cgttcgctcc aagctgggct gtgtgcacga accccccgtt cagcccgacc gctgcgcctt | 5460 |
| atccggtaac tatcgtcttg agtccaaccc ggtaagacac gacttatcgc cactggcagc | 5520 |
| agccactggt aacaggatta gcagagcgag gtatgtaggc ggtgctacag agttcttgaa | 5580 |
| gtggtggcct aactacggct acactagaag aacagtattt ggtatctgcg ctctgctgaa | 5640 |
| gccagttacc ttcggaaaaa gagttggtag ctcttgatcc ggcaaacaaa ccaccgctgg | 5700 |
| tagcggtttt tttgtttgca agcagcagat tacgcgcaga aaaaaggat ctcaagaaga | 5760 |
| tcctttgatc ttttctacgg ggtctgacgc tcagtggaac gaaaactcac gttaagggat | 5820 |
| tttggtcatg agattatcaa aaaggatctt cacctagatc cttttaaatt aaaaatgaag | 5880 |
| ttttaaatca atctaaagta tatatgagta aacttggtct gacagttacc aatgcttaat | 5940 |
| cagtgaggca cctatctcag cgatctgtct atttcgttca tccatagttg cctgactccc | 6000 |
| cgtcgtgtag ataactacga tacgggaggg cttaccatct ggccccagtg ctgcaatgat | 6060 |
| accgcgagac ccacgctcac cggctccaga tttatcagca ataaaccagc cagccggaag | 6120 |
| ggccgagcgc agaagtggtc ctgcaacttt atccgcctcc atccagtcta ttaattgttg | 6180 |
| ccgggaagct agagtaagta gttcgccagt taatagtttg cgcaacgttg ttgccattgc | 6240 |
| tacaggcatc gtggtgtcac gctcgtcgtt tggtatggct tcattcagct ccggttccca | 6300 |
| acgatcaagg cgagttacat gatccccat gttgtgcaaa aaagcggtta gctccttcgg | 6360 |
| tcctccgatc gttgtcagaa gtaagttggc cgcagtgtta tcactcatgg ttatggcagc | 6420 |
| actgcataat tctcttactg tcatgccatc cgtaagatgc ttttctgtga ctggtgagta | 6480 |
| ctcaaccaag tcattctgag aatagtgtat gcggcgaccg agttgctctt gcccggcgtc | 6540 |
| aatacgggat aataccgcgc cacatagcag aactttaaaa gtgctcatca ttggaaaacg | 6600 |
| ttcttcgggg cgaaaactct caaggatctt accgctgttg agatccagtt cgatgtaacc | 6660 |
| cactcgtgca cccaactgat cttcagcatc ttttactttc accagcgttt ctgggtgagc | 6720 |
| aaaaacagga aggcaaaatg ccgcaaaaaa gggaataagg gcgacacgga aatgttgaat | 6780 |
| actcatactc ttcctttttc aatattattg aagcatttat cagggttatt gtctcatgag | 6840 |

| cggatacata tttgaatgta tttagaaaaa taaacaaata ggggttccgc gcacatttcc | 6900 |
| ccgaaaagtg ccacctgacg tc | 6922 |

<210> SEQ ID NO 29
<211> LENGTH: 27
<212> TYPE: DNA
<213> ORGANISM: Artificial sequence
<220> FEATURE:
<223> OTHER INFORMATION: TrexTthFor

<400> SEQUENCE: 29

| cccgggacac tgtctgcctg gacacgc | 27 |

<210> SEQ ID NO 30
<211> LENGTH: 27
<212> TYPE: DNA
<213> ORGANISM: Artificial sequence
<220> FEATURE:
<223> OTHER INFORMATION: TrexTthRev

<400> SEQUENCE: 30

| aggcagacag tgtcccgggg caggcgg | 27 |

<210> SEQ ID NO 31
<211> LENGTH: 2686
<212> TYPE: DNA
<213> ORGANISM: Artificial sequence
<220> FEATURE:
<223> OTHER INFORMATION: pCLS0002

<400> SEQUENCE: 31

| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acccggggat | 420 |
| cctctagagt cgacctgcag gcatgcaagc ttggcgtaat catggtcata gctgtttcct | 480 |
| gtgtgaaatt gttatccgct cacaattcca cacaacatac gagccggaag cataaagtgt | 540 |
| aaagcctggg gtgcctaatg agtgagctaa ctcacattaa ttgcgttgcg ctcactgccc | 600 |
| gctttccagt cgggaaacct gtcgtgccag ctgcattaat gaatcggcca acgcgcgggg | 660 |
| agaggcggtt tgcgtattgg gcgctcttcc gcttcctcgc tcactgactc gctgcgctcg | 720 |
| gtcgttcggc tgcggcgagc ggtatcagct cactcaaagg cggtaatacg ttatccaca | 780 |
| gaatcagggg ataacgcagg aaagaacatg tgagcaaaag gccagcaaaa ggccaggaac | 840 |
| cgtaaaaagg ccgcgttgct ggcgtttttc cataggctcc gcccccctga cgagcatcac | 900 |
| aaaaatcgac gctcaagtca gaggtggcga aacccgacag gactataaag ataccaggcg | 960 |
| tttccccctg gaagctccct cgtgcgctct cctgttccga cctgccgct taccggatac | 1020 |
| ctgtccgcct ttctcccttc gggaagcgtg gcgctttctc atagctcacg ctgtaggtat | 1080 |
| ctcagttcgg tgtaggtcgt tcgctccaag ctgggctgtg tgcacgaacc ccccgttcag | 1140 |
| cccgaccgct gcgccttatc cggtaactat cgtcttgagt ccaacccggt aagacacgac | 1200 |
| ttatcgccac tggcagcagc cactggtaac aggattagca gagcgaggta tgtaggcggt | 1260 |

```
gctacagagt tcttgaagtg gtggcctaac tacggctaca ctagaaggac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatccccat gttgtgcaaa    2040 aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttcctttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                  2686
```

<210> SEQ ID NO 32
<211> LENGTH: 22
<212> TYPE: DNA
<213> ORGANISM: Artificial sequence
<220> FEATURE:
<223> OTHER INFORMATION: GS target sequence

<400> SEQUENCE: 32
tgccccaggg tgagaaagtc ca                                              22

<210> SEQ ID NO 33
<211> LENGTH: 64
<212> TYPE: DNA
<213> ORGANISM: Artificial sequence
<220> FEATURE:
<223> OTHER INFORMATION: GS Locus specific forward primer
<220> FEATURE:
<221> NAME/KEY: misc_feature
<222> LOCATION: (31)..(40)
<223> OTHER INFORMATION: n is a or c or t or g

<400> SEQUENCE: 33
ccatctcatc cctgcgtgtc tccgactcag nnnnnnnnnn gctctctggc taactagaga    60
accc                                                                  64

<210> SEQ ID NO 34
<211> LENGTH: 53
<212> TYPE: DNA
<213> ORGANISM: Artificial sequence
<220> FEATURE:
<223> OTHER INFORMATION: GS Locus specific reverse primer

<400> SEQUENCE: 34
cctatcccct gtgtgccttg gcagtctcag tcgatcagca cgggcacgat gcc     53

<210> SEQ ID NO 35
<211> LENGTH: 163
<212> TYPE: PRT
<213> ORGANISM: Chlamydomonas reinhardtii

<400> SEQUENCE: 35

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 36
<211> LENGTH: 167
<212> TYPE: PRT
<213> ORGANISM: artificial sequence
<220> FEATURE:
<223> OTHER INFORMATION: I-CreI

<400> SEQUENCE: 36

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 37
<211> LENGTH: 22
<212> TYPE: DNA
<213> ORGANISM: Artificial
<220> FEATURE:
<223> OTHER INFORMATION: C1221 target

<400> SEQUENCE: 37
caaaacgtcg tacgacgttt tg                                              22

<210> SEQ ID NO 38
<211> LENGTH: 6922
<212> TYPE: DNA
<213> ORGANISM: Artificial sequence
<220> FEATURE:
<223> OTHER INFORMATION: pCLS8980

<400> SEQUENCE: 38
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata agataccagg cgtttccccc tggaagctcc ctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag aacagtattt ggtatctgcg ctctgctgaa gccagttacc     540
ttcggaaaaa gagttggtag ctcttgatcc ggcaaacaaa ccaccgctgg tagcggtttt     600
tttgtttgca agcagcagat tacgcgcaga aaaaaaggat ctcaagaaga tcctttgatc     660
ttttctacgg ggtctgacgc tcagtggaac gaaaactcac gttaagggat tttggtcatg     720
agattatcaa aaaggatctt cacctagatc cttttaaatt aaaaatgaag ttttaaatca     780
atctaaagta tatatgagta aacttggtct gacagttacc aatgcttaat cagtgaggca     840
cctatctcag cgatctgtct atttcgttca tccatagttg cctgactccc cgtcgtgtag     900
ataactacga tacgggaggg cttaccatct ggccccagtg ctgcaatgat accgcgagac     960
ccacgctcac cggctccaga tttatcagca ataaaccagc cagccggaag ggccgagcgc    1020
agaagtggtc ctgcaacttt atccgcctcc atccagtcta ttaattgttg ccgggaagct    1080
agagtaagta gttcgccagt taatagtttg cgcaacgttg ttgccattgc tacaggcatc    1140
gtggtgtcac gctcgtcgtt tggtatggct tcattcagct ccggttccca acgatcaagg    1200
cgagttacat gatcccccat gttgtgcaaa aaagcggtta gctccttcgg tcctccgatc    1260
```

```
gttgtcagaa gtaagttggc cgcagtgtta tcactcatgg ttatggcagc actgcataat    1320
tctcttactg tcatgccatc cgtaagatgc ttttctgtga ctggtgagta ctcaaccaag    1380
tcattctgag aatagtgtat gcggcgaccg agttgctctt gcccggcgtc aatacgggat    1440
aataccgcgc cacatagcag aactttaaaa gtgctcatca ttggaaaacg ttcttcgggg    1500
cgaaaactct caaggatctt accgctgttg agatccagtt cgatgtaacc cactcgtgca    1560
cccaactgat cttcagcatc ttttactttc accagcgttt ctgggtgagc aaaaacagga    1620
aggcaaaatg ccgcaaaaaa gggaataagg gcgacacgga aatgttgaat actcatactc    1680 ttccttttc aatattattg aagcatttat cagggttatt gtctcatgag cggatacata    1740
tttgaatgta tttagaaaaa taaacaaata ggggttccgc gcacatttcc ccgaaaagtg    1800
ccacctgacg tcgacggatc gggagatctc ccgatcccct atggtgcact ctcagtacaa    1860
tctgctctga tgccgcatag ttaagccagt atctgctccc tgcttgtgtg ttggaggtcg    1920
ctgagtagtg cgcgagcaaa atttaagcta caacaaggca aggcttgacc gacaattgca    1980
tgaagaatct gcttagggtt aggcgttttg cgctgcttcg cgatgtacgg gccagatata    2040
cgcgttgaca ttgattattg actagttatt aatagtaatc aattacgggg tcattagttc    2100
atagcccata tatggagttc cgcgttacat aacttacggt aaatggcccg cctggctgac    2160
cgcccaacga ccccgccca ttgacgtcaa taatgacgta tgttcccata gtaacgccaa    2220
tagggacttt ccattgacgt caatgggtgg agtatttacg gtaaactgcc cacttggcag    2280
tacatcaagt gtatcatatg ccaagtacgc cccctattga cgtcaatgac ggtaaatggc    2340
ccgcctggca ttatgcccag tacatgacct tatgggactt tcctacttgg cagtacatct    2400
acgtattagt catcgctatt accatggtga tgcggttttg gcagtacatc aatgggcgtg    2460
gatagcggtt tgactcacgg ggatttccaa gtctccaccc cattgacgtc aatgggagtt    2520
tgttttggca ccaaaatcaa cgggactttc caaaatgtcg taacaactcc gccccattga    2580
cgcaaatggg cggtaggcgt gtacggtggg aggtctatat aagcagagct ctctggctaa    2640
ctagagaacc cactgcttac tggcttatcg aaatgaattc gactcactgt tgggagaccc    2700
aagctggcta gttaagctat cacaagtttg tacaaaaaag caggctggcg cgcctacaca    2760
gcggccttgc caccatgggt tccgaggcac ccgggccga acctttgtc ttcctggacc    2820 tggaagccac tgggctcccc agtgtggagc ccgagattgc cgagctgtcc ctctttgctg    2880
tccaccgctc ctccctggag aacccggagc acgacgagtc tggtgcccta gtattgcccc    2940
gggtcctgga caagctcacg ctgtgcatgt cccggagcg ccccttcact gccaaggcca    3000
gcgagatcac cggcctgagc agtgagggcc tggcgcgatg ccggaaggct ggctttgatg    3060
gcgccgtggt gcggacgctg caggccttcc tgagccgcca gcagggccc atctgccttg    3120 tggcccacaa tggctttgat tatgatttcc ccctgctgtg tgccgagctg cggcgcctgg    3180
gtgcccgcct gccccgggac actgtctgcc tggacacgct gccggccctg cggggcctgg    3240
accgcgccca cagccacggc acccggcccc ggggccgcca gggttacagc ctcggcagcc    3300
tcttccaccg ctacttccgg gcagagccaa gcgcagccca ctcagccgag ggcgacgtgc    3360
acacccctgc tcctgatctt ctgcaccgcg ccgcagagct gctcgcctgg gccgatgagc    3420
aggcccgtgg gtgggcccac atcgagccca tgtacttgcc gcctgatgac cccagcctgg    3480 aggcggagg tggaggttct ggaggtggag gttccaatac caaatataac gaagagttcc    3540
tgctgtacct ggccggcttt gtggacggtg acggtagcat catcgctcag attaatccaa    3600
```

```
accagtcttc taagttttaaa catcgtctac gtttgacctt ttatgtgact caaaagaccc    3660
agcgccgttg gtttctggac aaactagtgg atgaaattgg cgttggttac gtacgtgatt    3720
ctggatccgt ttcccagtac gttttaagcg aaatcaagcc gctgcacaac ttcctgactc    3780
aactgcagcc gtttctggaa ctgaaacaga acaggcaaa cctggttctg aaaattatcg    3840
aacagctgcc gtctgcaaaa gaatccccgg acaaattcct ggaagtttgt acctgggtgg    3900
atcagattgc agctctgaac gattctaaga cgcgtaaaac cacttctgaa accgttcgtg    3960
ctgtgctgga cagcctgagc gggaagaaga atcctcccc ggcggccggt ggatctgata    4020
agtataatca ggctctgtct aaatacaacc aagcactgtc caagtacaat caggccctgt    4080
ctggtggagg cggttccaac aaaaagttcc tgctgtatct tgctggattt gtggattctg    4140
atggctccat cattgctcag ataaaaccac gtcaatctaa caagttcaaa caccagctct    4200
ccttgacttt tgcagtcact cagaagacac aaagaaggtg gttcttggac aaattggttg    4260
ataggattgg tgtgggctat gtctatgaca gtggctctgt gtcagactac cgcctgtctg    4320
aaattaagcc tcttcataac tttctcaccc aactgcaacc cttcttgaag ctcaaacaga    4380
agcaagcaaa tctggttttg aaaatcatcg agcaactgcc atctgccaag gagtcccctg    4440
acaagtttct tgaagtgtgt acttgggtgg atcagattgc tgccttgaat gactccaaga    4500
ccagaaaaac cacctctgag actgtgaggg cagttctgga tagcctctct gagaagaaaa    4560
agtcctctcc ttagccatgg cccgcggttc gaaggtaagc ctatccctaa ccctctcctc    4620
ggtctcgatt ctacgcgtac cggttagtaa tgagtttaaa cggggaggc taactgaaac    4680
acggaaggag acaataccgg aaggaacccg cgctatgacg gcaataaaaa gacagaataa    4740
aacgcacggg tgttgggtcg tttgttcata acgcggggt tcggtcccag ggctggcact    4800
ctgtcgatac cccaccgaga ccccattggg gccaatacgc ccgcgtttct tcctttttccc    4860
caccccaccc cccaagttcg ggtgaaggcc cagggctcgc agccaacgtc ggggcggcag    4920
gccctgccat agcagatctg cgcagctggg gctctagggg gtatccccac cgcccctgta    4980
gcggcgcatt aagcgcggcg ggtgtggtgg ttacgcgcag cgtgaccgct acacttgcca    5040
gcgccctagc gcccgctcct ttcgctttct tcccttcctt tctcgccacg ttcgccggct    5100
ttccccgtca gctctaaat cggggcatcc ctttagggtt ccgatttagt gctttacggc    5160
acctcgaccc caaaaaactt gattagggtg atggttcacg tagtgggcca tcgccctgat    5220
agacggtttt tcgccctttg acgttggagt ccacgttctt taatagtgga ctcttgttcc    5280
aaactggaac aacactcaac cctatctcgg tctattcttt tgatttataa gggattttgg    5340
ggatttcggc ctattggtta aaaaatgagc tgatttaaca aaaatttaac gcgaattaat    5400
tctgtggaat gtgtgtcagt tagggtgtgg aaagtcccca ggctcccag caggcagaag    5460
tatgcaaagc atgcatctca attagtcagc aaccaggtgt ggaaagtccc caggctcccc    5520
agcaggcaga gtatgcaaa gcatgcatct caattagtca gcaaccatag tcccgccccct    5580
aactccgccc atcccgcccc taactccgcc cagttccgcc cattctccgc cccatggctg    5640
actaattttt tttatttatg cagaggccga ggccgcctct gcctctgagc tattccagaa    5700
gtagtgagga ggcttttttg gaggcctagg cttttgcaaa aagctcccgg gagcttgtat    5760
atccattttc ggatctgatc agcacgtgtt gacaattaat catcggcata gtatatcggc    5820
atagtataat acgacaaggt gaggaactaa accatggcca agcctttgtc tcaagaagaa    5880
tccaccctca ttgaaagagc aacggctaca atcaacagca tccccatctc tgaagactac    5940
agcgtcgcca gcgcagctct ctctagcgac ggccgcatct tcactggtgt caatgtatat    6000
```

```
cattttactg ggggaccttg tgcagaactc gtggtgctgg gcactgctgc tgctgcggca    6060
gctggcaacc tgacttgtat cgtcgcgatc ggaaatgaga cagggggcat cttgagcccc    6120
tgcggacggt gccgacaggt gcttctcgat ctgcatcctg ggatcaaagc catagtgaag    6180
gacagtgatg gacagccgac ggcagttggg attcgtgaat tgctgccctc tggttatgtg    6240
tgggagggct aagcacttcg tggccgagga gcaggactga cacgtgctac gagatttcga    6300
ttccaccgcc gccttctatg aaaggttggg cttcggaatc gttttccggg acgccggctg    6360
gatgatcctc cagcgcgggg atctcatgct ggagttcttc gcccacccca acttgtttat    6420
tgcagcttat aatggttaca ataaagcaa tagcatcaca aatttcacaa ataaagcatt     6480
tttttcactg cattctagtt gtggtttgtc caaactcatc aatgtatctt atcatgtctg    6540
tataccgtcg acctctagct agagcttggc gtaatcatgg tcatagctgt ttcctgtgtg    6600
aaattgttat ccgctcacaa ttccacacaa catacgagcc ggaagcataa agtgtaaagc    6660
ctggggtgcc taatgagtga gctaactcac attaattgcg ttgcgctcac tgcccgcttt    6720
ccagtcggga aacctgtcgt gccagctgca ttaatgaatc ggccaacgcg cggggagagg    6780
cggtttgcgt attgggcgct cttccgcttc ctcgctcact gactcgctgc gctcggtcgt    6840
tcggctgcgg cgagcggtat cagctcactc aaaggcggta atacggttat ccacagaatc    6900 agggataac gcaggaaaga ac                                              6922

<210> SEQ ID NO 39
<211> LENGTH: 7660
<212> TYPE: DNA
<213> ORGANISM: Artificial sequence
<220> FEATURE:
<223> OTHER INFORMATION: pCLS9572

<400> SEQUENCE: 39
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata aagataccag gcgtttcccc ctggaagctc cctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag aacagtattt ggtatctgcg ctctgctgaa gccagttacc     540
ttcggaaaaa gagttggtag ctcttgatcc ggcaaacaaa ccaccgctgg tagcggtttt     600
tttgtttgca agcagcagat tacgcgcaga aaaaaggat ctcaagaaga tcctttgatc      660
ttttctacgg ggtctgacgc tcagtggaac gaaaactcac gttaagggat tttggtcatg     720
agattatcaa aaaggatctt cacctagatc cttttaaatt aaaaatgaag ttttaaatca     780
atctaaagta tatatgagta aacttggtct gacagttacc aatgcttaat cagtgaggca     840
cctatctcag cgatctgtct atttcgttca tccatagttg cctgactccc cgtcgtgtag     900
ataactacga tacgggaggg cttaccatct ggccccagtg ctgcaatgat accgcgagac     960
ccacgctcac cggctccaga tttatcagca ataaaccagc cagccggaag ggccgagcgc    1020
agaagtggtc ctgcaacttt atccgcctcc atccagtcta ttaattgttg ccgggaagct    1080
```

```
agagtaagta gttcgccagt taatagtttg cgcaacgttg ttgccattgc tacaggcatc    1140
gtggtgtcac gctcgtcgtt tggtatggct tcattcagct ccggttccca acgatcaagg    1200
cgagttacat gatcccccat gttgtgcaaa aaagcggtta gctccttcgg tcctccgatc    1260
gttgtcagaa gtaagttggc cgcagtgtta tcactcatgg ttatggcagc actgcataat    1320
tctcttactg tcatgccatc cgtaagatgc ttttctgtga ctggtgagta ctcaaccaag    1380
tcattctgag aatagtgtat gcggcgaccg agttgctctt gcccggcgtc aatacgggat    1440
aataccgcgc cacatagcag aactttaaaa gtgctcatca ttggaaaacg ttcttcgggg    1500
cgaaaactct caaggatctt accgctgttg agatccagtt cgatgtaacc cactcgtgca    1560
cccaactgat cttcagcatc ttttactttc accagcgttt ctgggtgagc aaaaacagga    1620
aggcaaaatg ccgcaaaaaa gggaataagg gcgacacgga atgttgaat  actcatactc    1680 ttcctttttc aatattattg aagcatttat cagggttatt gtctcatgag cggatacata    1740
tttgaatgta tttagaaaaa taaacaaata ggggttccgc gcacatttcc ccgaaaagtg    1800
ccacctgacg tcgacggatc gggagatctc ccgatcccct atggtgcact ctcagtacaa    1860
tctgctctga tgccgcatag ttaagccagt atctgctccc tgcttgtgtg ttggaggtcg    1920
ctgagtagtg cgcgagcaaa atttaagcta caacaaggca aggcttgacc gacaattgca    1980
tgaagaatct gcttagggtt aggcgttttg cgctgcttcg cgatgtacgg gccagatata    2040
cgcgttgaca ttgattattg actagttatt aatagtaatc aattacgggg tcattagttc    2100
atagcccata tatggagttc cgcgttacat aacttacggt aaatggcccg cctggctgac    2160
cgcccaacga ccccgccca ttgacgtcaa taatgacgta tgttcccata gtaacgccaa    2220
tagggacttt ccattgacgt caatgggtgg agtatttacg gtaaactgcc cacttggcag    2280
tacatcaagt gtatcatatg ccaagtacgc cccctattga cgtcaatgac ggtaaatggc    2340
ccgcctggca ttatgcccag tacatgacct tatgggactt tcctacttgg cagtacatct    2400
acgtattagt catcgctatt accatggtga tgcggttttg gcagtacatc aatgggcgtg    2460
gatagcggtt tgactcacgg ggatttccaa gtctccaccc cattgacgtc aatgggagtt    2520
tgttttggca ccaaaatcaa cgggactttc caaaatgtcg taacaactcc gccccattga    2580
cgcaaatggg cggtaggcgt gtacggtggg aggtctatat aagcagagct ctctggctaa    2640
ctagagaacc cactgcttac tggcttatcg aaatgaattc gactcactgt tgggagaccc    2700
aagctggcta gttaagctat cacaagtttg tacaaaaaag caggctggcg cgcctacaca    2760
gcggccttgc caccatgggt tccgaggcac cccgggccga gacctttgtc ttcctggacc    2820
tggaagccac tgggctcccc agtgtggagc ccgagattgc cgagctgtcc ctctttgctg    2880
tccaccgctc ctccctggag aacccggagc acgacgagtc tggtgcccta gtattgcccc    2940
gggtcctgga caagctcacg ctgtgcatgt gcccggagcg ccccttcact gccaaggcca    3000
gcgagatcac cggcctgagc agtgagggcc tggcgcgatg ccggaaggct ggctttgatg    3060
gcgccgtggt gcggacgctg caggccttcc tgagccgcca gcagggccc  atctgccttg    3120 tggcccacaa tggctttgat tatgatttcc ccctgctgtg tgccgagctg cggcgcctgg    3180
gtgcccgcct gccccgggac actgtctgcc tggacacgct gccggccctg cggggcctgg    3240
accgcgccca cagccacggc acccgggccc ggggccgcca gggttacagc ctcggcagcc    3300
tcttccaccg ctacttccgg gcagagccaa gcgcagccca ctcagccgag ggcgacgtgc    3360
acaccctgct cctgatcttc ctgcaccgcg ccgcagagct gctcgcctgg gccgatgagc    3420
aggcccgtgg gtgggcccac atcgagccca tgtacttgcc gcctgatgac cccagcctgg    3480
```

```
aggcgactcc tccacagacc ggtctggatg ttccttactc cgaggcaccc cgggccgaga   3540
cctttgtctt cctggacctg gaagccactg ggctccccag tgtggagccc gagattgccg   3600
agctgtccct ctttgctgtc caccgctcct ccctggagaa cccggagcac gacgagtctg   3660
gtgccctagt attgccccgg gtcctggaca agctcacgct gtgcatgtgc ccggagcgcc   3720
ccttcactgc caaggccagc gagatcaccg gcctgagcag tgagggcctg cgcgatgcc    3780
ggaaggctgg ctttgatggc gccgtggtgc ggacgctgca ggccttcctg agccgccagg   3840
cagggcccat ctgccttgtg gcccacaatg gctttgatta tgatttcccc ctgctgtgtg   3900
ccgagctgcg gcgcctgggt gcccgcctgc ccgggacac tgtctgcctg gacacgctgc   3960
cggccctgcg gggcctggac cgcgcccaca gccacggcac ccgggcccgg ggccgccagg   4020
gttacagcct cggcagcctc ttccaccgct acttccgggc agagccaagc gcagcccact   4080
cagccgaggg cgacgtgcac accctgctcc tgatcttcct gcaccgcgcc gcagagctgc   4140
tcgcctgggc cgatgagcag gcccgtgggg gggcccacat cgagcccatg tacttgccgc   4200
ctgatgaccc cagcctggag gcgggaggtg gaggttctgg aagtggaggt tccaatacca   4260
aatataacga agagttcctg ctgtacctgg ccggctttgt ggacgctgac ggtagcatca   4320
tcgctcagat taaaccaaga cagtctcgga agtttaaaca tgagctaagc ttgactttg    4380
atgtgactca aaagacccag cgccgttggt ttctggacaa gctagtggat gaaattggcg   4440
ttggttacgt atatgattct ggatccgttt cctattacca gttaagcgaa atcaagccgc   4500
tgcacaactt cctgactcaa ctgcagccgt ttctggaact gaaacagaaa caggcaaacc   4560
tggttctgaa aattatcgaa cagctgccgt ctgcaaaaga atccccggcc aaattcctgg   4620
aagtttgtac ctgggtggat cagattgcag ctctgaacga ttctaagacg cgtaaaacca   4680
cttctgaaac cgttcgtgct gtgctggata gcctgagcga agaagaaaa tcctccccgg    4740
cggccggtgg atctgataag tataatcagg ctctgtctaa atacaaccaa gcactgtcca   4800
agtacaatca ggccctgtct ggtggaggcg gttccaacaa aaagttcctg ctgtatcttg   4860
ctggatttgt ggatggtgat ggctccatca ttgctcagat aaaaccacgt caagggtata   4920
agttcaaaca ccagctctcc ttgactttc aggtcactca aagacacaa agaaggtggt    4980
tcttggacaa attggttgat cgtattggtg tgggctatgt cgctgaccgt ggctctgtgt   5040
cagactaccg cctgtctgaa attaagcctc ttcataactt tctcacccaa ctgcaaccct   5100
tcttgaagct caaacagaag caagcaaatc tggttttgaa aatcatcgag caactgccat   5160
ctgccaagga gtccctggac aagtttcttg aagtgtgtac ttgggtggat cagattgctg   5220
ccttgaatga ctccaagacc agaaaaacca cctctgagac tgtgagggca gttctggata   5280
gcctctctga gaagaaaaag tcctctcctt agccatggcc cgcggttcga aggtaagcct   5340
atccctaacc ctctcctcgg tctcgattct acgcgtaccg gttagtaatg agtttaaacg   5400
ggggaggcta actgaaacac ggaaggagac aataccggaa ggaacccgcg ctatgacggc   5460
aataaaaga cagaataaaa cgcacggtgt ttgggtcgtt tgttcataaa cgcggggttc     5520
ggtcccaggg ctggcactct gtcgataccc caccgagacc ccattgggc caatacgccc    5580
gcgtttcttc cttttcccca ccccaccccc caagttcggg tgaaggccca gggctcgcag   5640
ccaacgtcgg ggcggcaggc cctgccatag cagatctgcg cagctgggc tctaggggt     5700
atccccacgc gccctgtagc ggcgcattaa gcgcggcggg tgtggtggtt acgcgcagcg   5760
tgaccgctac acttgccagc gccctagcgc ccgctccttt cgctttcttc ccttcctttc   5820
```

```
tcgccacgtt cgccggcttt ccccgtcaag ctctaaatcg gggcatccct ttagggttcc      5880
gatttagtgc tttacggcac ctcgacccca aaaaacttga ttagggtgat ggttcacgta      5940
gtgggccatc gccctgatag acggttttc gccctttgac gttggagtcc acgttcttta      6000
atagtggact cttgttccaa actgaacaa cactcaaccc tatctcggtc tattcttttg      6060
atttataagg gattttgggg atttcggcct attggttaaa aaatgagctg atttaacaaa      6120
aatttaacgc gaattaattc tgtggaatgt gtgtcagtta gggtgtggaa agtccccagg      6180
ctccccagca ggcagaagta tgcaaagcat gcatctcaat tagtcagcaa ccaggtgtgg      6240
aaagtcccca ggctcccag caggcagaag tatgcaaagc atgcatctca attagtcagc      6300
aaccatagtc ccgcccctaa ctccgcccat cccgcccta actccgccca gttccgccca      6360
ttctccgccc catggctgac taatttttt tatttatgca gaggccgagg ccgcctctgc      6420
ctctgagcta ttccagaagt agtgaggagg cttttttgga ggcctaggct tttgcaaaaa      6480
gctcccggga gcttgtatat ccattttcgg atctgatcag cacgtgttga caattaatca      6540
tcggcatagt atatcggcat agtataatac gacaaggtga ggaactaaac catggccaag      6600
cctttgtctc aagaagaatc caccctcatt gaaagagcaa cggctacaat caacagcatc      6660
cccatctctg aagactacag cgtcgccagc gcagctctct ctagcgacgg ccgcatcttc      6720
actggtgtca atgtatatca ttttactggg ggaccttgtg cagaactcgt ggtgctgggc      6780
actgctgctg ctgcggcagc tggcaacctg acttgtatcg tcgcgatcgg aaatgagaac      6840
aggggcatct tgagcccctg cggacggtgc cgacaggtgc ttctcgatct gcatcctggg      6900
atcaaagcca tagtgaagga cagtgatgga cagccgacgg cagttgggat tcgtgaattg      6960
ctgccctctg gttatgtgtg ggagggctaa gcacttcgtg gccgaggagc aggactgaca      7020
cgtgctacga gatttcgatt ccaccgccgc cttctatgaa aggttgggct tcggaatcgt      7080
tttccgggac gccggctgga tgatcctcca gcgcgggat ctcatgctgg agttcttcgc      7140
ccaccccaac ttgtttattg cagcttataa tggttacaaa taagcaata gcatcacaaa      7200
tttcacaaat aaagcatttt tttcactgca ttctagttgt ggtttgtcca aactcatcaa      7260
tgtatcttat catgtctgta taccgtcgac ctctagctag agcttggcgt aatcatggtc      7320
atagctgttt cctgtgtgaa attgttatcc gctcacaatt ccacacaaca tacgagccgg      7380
aagcataaag tgtaaagcct ggggtgccta atgagtgagc taactcacat taattgcgtt      7440
gcgctcactg cccgctttcc agtcgggaaa cctgtcgtgc cagctgcatt aatgaatcgg      7500
ccaacgcgcg gggagaggcg gtttgcgtat tgggcgctct tccgcttcct cgctcactga      7560
ctcgctgcgc tcggtcgttc ggctgcggcg agcggtatca gctcactcaa aggcggtaat      7620
acggttatcc acagaatcag gggataacgc aggaaagaac                           7660
```

<210> SEQ ID NO 40
<211> LENGTH: 7620
<212> TYPE: DNA
<213> ORGANISM: Artificial sequence
<220> FEATURE:
<223> OTHER INFORMATION: pCLS9570

<400> SEQUENCE: 40

```
ctcgagcgct agcacccagc tttcttgtac aaagtggtga tctagagggc ccgcggttcg        60
aaggtaagcc tatccctaac cctctcctcg gtctcgattc tacgcgtacc ggttagtaat       120
gagtttaaac gggggaggct aactgaaaca cggaaggaga ataccggaa aggacccgc         180
gctatgacgg caataaaaag acagaataaa acgcacgggt gttgggtcgt tgttcataa        240
```

```
acgcggggtt cggtcccagg gctggcactc tgtcgatacc ccaccgagac cccattgggg    300
ccaatacgcc cgcgtttctt ccttttcccc accccacccc ccaagttcgg gtgaaggccc    360
agggctcgca gccaacgtcg gggcggcagg ccctgccata gcagatctgc gcagctgggg    420
ctctaggggg tatccccacg cgccctgtag cggcgcatta agcgcggcgg gtgtggtggt    480
tacgcgcagc gtgaccgcta cacttgccag cgccctagcg cccgctcctt tcgctttctt    540
cccttccttt ctcgccacgt tcgccggctt tccccgtcaa gctctaaatc ggggcatccc    600
tttagggttc cgatttagtg ctttacggca cctcgacccc aaaaaacttg attagggtga    660
tggttcacgt agtgggccat cgccctgata cggttttt cgcccttga cgttggagtc    720
cacgttcttt aatagtggac tcttgttcca aactggaaca cactcaacc ctatctcggt    780
ctattctttt gatttataag ggattttggg gatttcggcc tattggttaa aaaatgagct    840
gatttaacaa aaatttaacg cgaattaatt ctgtggaatg tgtgtcagtt agggtgtgga    900
aagtccccag gctccccagc aggcagaagt atgcaaagca tgcatctcaa ttagtcagca    960
accaggtgtg gaaagtcccc aggctcccca gcaggcagaa gtatgcaaag catgcatctc    1020
aattagtcag caaccatagt cccgcccta actccgccca tcccgcccct aactccgccc    1080
agttccgccc attctccgcc ccatggctga ctaattttt ttatttatgc agaggccgag    1140
gccgcctctg cctctgagct attccagaag tagtgaggag gcttttttgg aggcctaggc    1200
ttttgcaaaa agctcccggg agcttgtata tccatttcg gatctgatca gcacgtgttg    1260
acaattaatc atcggcatag tatatcggca tagtataata cgacaaggtg aggaactaaa    1320
ccatggccaa gcctttgtct caagaagaat ccaccctcat tgaaagagca acggctacaa    1380
tcaacagcat ccccatctct gaagactaca gcgtcgccag cgcagctctc tctagcgacg    1440
gccgcatctt cactggtgtc aatgtatatc atttactgg gggaccttgt gcagaactcg    1500
tggtgctggg cactgctgct gctgcggcag ctggcaacct gacttgtatc gtcgcgatcg    1560
gaaatgagaa cagggcatc ttgagcccct gcggacggtg ccgacaggtg cttctcgatc    1620
tgcatcctgg gatcaaagcc atagtgaagg acagtgatgg acagccgacg gcagttggga    1680
ttcgtgaatt gctgccctct ggttatgtgt gggagggcta agcacttcgt ggccgaggag    1740
caggactgac acgtgctacg agatttcgat tccaccgccg ccttctatga aaggttgggc    1800
ttcggaatcg ttttccggga cgccggctgg atgatcctcc agcgcgggga tctcatgctg    1860
gagttcttcg cccaccccaa cttgtttatt gcagcttata atggttacaa ataaagcaat    1920
agcatcacaa atttcacaaa taaagcattt ttttcactgc attctagttg tggtttgtcc    1980
aaactcatca atgtatctta tcatgtctgt ataccgtcga cctctagcta gagcttggcg    2040
taatcatggt catagctgtt tcctgtgtga aattgttatc cgctcacaat tccacacaac    2100
atacgagccg gaagcataaa gtgtaaagcc tggggtgcct aatgagtgag ctaactcaca    2160
ttaattgcgt tgcgctcact gcccgctttc cagtcgggaa acctgtcgtg ccagctgcat    2220
taatgaatcg gccaacgcgc ggggagaggc ggtttgcgta ttgggcgctc ttccgcttcc    2280
tcgctcactg actcgctgcg ctcggtcgtt cggctgcggc gagcggtatc agctcactca    2340
aaggcggtaa tacggttatc cacagaatca ggggataacg caggaaagaa catgtgagca    2400
aaaggccagc aaaaggccag gaaccgtaaa aaggccgcgt tgctggcgtt tttccatagg    2460
ctccgccccc ctgacgagca tcacaaaaat cgacgctcaa gtcagaggtg cgaaacccg    2520
acaggactat aaagatacca ggcgtttccc cctggaagct ccctcgtgcg ctctcctgtt    2580
```

```
ccgaccctgc cgcttaccgg atacctgtcc gcctttctcc cttcgggaag cgtggcgctt    2640
tctcatagct cacgctgtag gtatctcagt tcggtgtagg tcgttcgctc caagctgggc    2700
tgtgtgcacg aaccccccgt tcagcccgac cgctgcgcct tatccggtaa ctatcgtctt    2760
gagtccaacc cggtaagaca cgacttatcg ccactggcag cagccactgg taacaggatt    2820
agcagagcga ggtatgtagg cggtgctaca gagttcttga agtggtggcc taactacggc    2880
tacactagaa gaacagtatt tggtatctgc gctctgctga agccagttac cttcggaaaa    2940
agagttggta gctcttgatc cggcaaacaa accaccgctg gtagcggttt ttttgtttgc    3000
aagcagcaga ttacgcgcag aaaaaaagga tctcaagaag atcctttgat cttttctacg    3060
gggtctgacg ctcagtggaa cgaaaactca cgttaaggga ttttggtcat gagattatca    3120
aaaaggatct tcacctagat ccttttaaat taaaaatgaa gttttaaatc aatctaaagt    3180
atatatgagt aaacttggtc tgacagttac caatgcttaa tcagtgaggc acctatctca    3240
gcgatctgtc tatttcgttc atccatagtt gcctgactcc ccgtcgtgta gataactacg    3300
atacgggagg gcttaccatc tggccccagt gctgcaatga taccgcgaga cccacgctca    3360
ccggctccag atttatcagc aataaaccag ccagccggaa gggccgagcg cagaagtggt    3420
cctgcaactt tatccgcctc catccagtct attaattgtt gccgggaagc tagagtaagt    3480
agttcgccag ttaatagttt gcgcaacgtt gttgccattg ctacaggcat cgtggtgtca    3540
cgctcgtcgt ttggtatggc ttcattcagc tccggttccc aacgatcaag gcgagttaca    3600
tgatccccca tgttgtgcaa aaaagcggtt agctccttcg gtcctccgat cgttgtcaga    3660
agtaagttgg ccgcagtgtt atcactcatg gttatggcag cactgcataa ttctcttact    3720
gtcatgccat ccgtaagatg cttttctgtg actggtgagt actcaaccaa gtcattctga    3780
gaatagtgta tgcggcgacc gagttgctct tgcccggcgt caatacggga taataccgcg    3840
ccacatagca gaactttaaa agtgctcatc attggaaaac gttcttcggg gcgaaaactc    3900
tcaaggatct taccgctgtt gagatccagt tcgatgtaac ccactcgtgc acccaactga    3960
tcttcagcat cttttacttt caccagcgtt tctgggtgag caaaaacagg aaggcaaaat    4020
gccgcaaaaa agggaataag ggcgacacgg aaatgttgaa tactcatact cttcctttt    4080 caatattatt gaagcattta tcagggttat tgtctcatga gcggatacat atttgaatgt    4140
atttagaaaa ataaacaaat aggggttccg cgcacatttc cccgaaaagt gccacctgac    4200
gtcgacggat cgggagatct cccgatcccc tatggtgcac tctcagtaca atctgctctg    4260
atgccgcata gttaagccag tatctgctcc ctgcttgtgt gttggaggtc gctgagtagt    4320
gcgcgagcaa aatttaagct acaacaaggc aaggcttgac cgacaattgc atgaagaatc    4380
tgcttagggt taggcgtttt gcgctgcttc gcgatgtacg ggccagatat acgcgttgac    4440
attgattatt gactagttat taatagtaat caattacggg gtcattagtt catagcccat    4500
atatggagtt ccgcgttaca taacttacgg taaatggccc gcctggctga ccgcccaacg    4560
acccccgccc attgacgtca ataatgacgt atgttcccat agtaacgcca atagggactt    4620
tccattgacg tcaatgggtg gagtatttac ggtaaactgc ccacttggca gtacatcaag    4680
tgtatcatat gccaagtacg ccccctattg acgtcaatga cggtaaatgg cccgcctggc    4740
attatgccca gtacatgacc ttatgggact ttcctacttg gcagtacatc tacgtattag    4800
tcatcgctat taccatggtg atgcggtttt ggcagtacat caatgggcgt ggatagcggt    4860
ttgactcacg gggatttcca agtctccacc ccattgacgt caatgggagt ttgttttggc    4920
accaaaatca acgggacttt ccaaaatgtc gtaacaactc cgccccattg acgcaaatgg    4980
```

```
gcggtaggcg tgtacggtgg gaggtctata taagcagagc tctctggcta actagagaac      5040
ccactgctta ctggcttatc gaaatgaatt ccgtcgacca tggccaatac caaatataac      5100
gaagagttcc tgctgtacct ggccggcttt gtggacgctg acggtagcat catcgctcag      5160
attaaaccaa gacagtctcg gaagtttaaa catgagctaa gcttgacctt tgatgtgact      5220
caaaagaccc agcgccgttg gtttctggac aagctagtgg atgaaattgg cgttggttac      5280
gtatatgatt ctggatccgt ttcctattac cagttaagcg aaatcaagcc gctgcacaac      5340
ttcctgactc aactgcagcc gtttctggaa ctgaaacaga acaggcaaa cctggttctg       5400 aaaattatcg aacagctgcc gtctgcaaaa gaatccccgg ccaaattcct ggaagtttgt      5460
acctgggtgg atcagattgc agctctgaac gattctaaga cgcgtaaaac cacttctgaa      5520
accgttcgtg ctgtgctgga tagcctgagc gagaagaaga atcctcccc ggcggccggt       5580 ggatctgata agtataatca ggctctgtct aaatacaacc aagcactgtc caagtacaat      5640
caggccctgt ctggtggagg cggttccaac aaaaagttcc tgctgtatct tgctggattt      5700
gtggatggtg atggctccat cattgctcag ataaaaccac gtcaagggta taagttcaaa      5760
caccagctct ccttgacttt tcaggtcact cagaagacaa aaagaaggtg gttcttggac      5820
aaattggttg atcgtattgg tgtgggctat gtcgctgacc gtggctctgt gtcagactac      5880
cgcctgtctg aaattaagcc tcttcataac tttctcaccc aactgcaacc cttcttgaag      5940
ctcaaacaga agcaagcaaa tctggttttg aaaatcatcg agcaactgcc atctgccaag      6000
gagtccctgg acaagtttct tgaagtgtgt acttgggtgg atcagattgc tgccttgaat      6060
gactccaaga ccagaaaaac cacctctgag actgtgaggg cagttctgga tagcctctct      6120
gagaagaaaa agtcctctcc tggaggtggc ggatctggag gtggaggttc cgaggcaccc      6180
cgggccgaga cctttgtctt cctggacctg gaagccactg gctccccag tgtggagccc       6240 gagattgccg agctgtccct cttttgctgtc caccgctcct ccctggagaa cccggagcac      6300
gacgagtctg gtgccctagt attgccccgg gtcctggaca agctcacgct gtgcatgtgc      6360
ccggagcgcc ccttcactgc caaggccagc gagatcaccg gcctgagcag tgagggcctg      6420
gcgcgatgcc ggaaggctgg ctttgatggc gccgtggtgc ggacgctgca ggccttcctg      6480
agccgccagg cagggcccat ctgccttgtg gcccacaatg gctttgatta tgatttcccc      6540
ctgctgtgtg ccgagctgcg gcgcctgggt gcccgcctgc ccgggacac tgtctgcctg       6600 gacacgctgc cggccctgcg gggcctggac cgcgcccaca gccacggcac ccgggcccgg      6660
ggccgccagg gttacagcct cggcagcctc ttccaccgct acttccgggc agagccaagc      6720
gcagcccact cagccgaggg cgacgtgcac accctgctcc tgatcttcct gcaccgcgcc      6780
gcagagctgc tcgcctgggc cgatgagcag gccgtgggt gggcccacat cgagcccatg      6840
tacttgccgc ctgatgaccc cagcctggag gcgactcctc cacagaccgg tctggatgtt      6900
ccttactccg aggcacccg ggccgagacc tttgtcttcc tggacctgga agccactggg      6960
ctccccagtg tggagcccga gattgccgag ctgtccctct tgctgtccca ccgctcctcc      7020
ctggagaacc cggagcacga cgagtctggt gccctagtat tgccccgggt cctggacaag      7080
ctcacgctgt gcatgtgccc ggagcgcccc ttcactgcca aggccagcga gatcaccggc      7140
ctgagcagtg agggcctggc gcgatgccgg aaggctggct ttgatggcgc cgtggtgcgg      7200
acgctgcagg ccttcctgag ccgccaggca gggcccatct gccttgtggc ccacaatggc      7260
tttgattatg atttcccccct gctgtgtgcc gagctgcggc gcctgggtgc ccgcctgccc      7320
```

-continued

| | |
|---|---|
| cgggacactg tctgcctgga cacgctgccg gccctgcggg gcctggaccg cgcccacagc | 7380 |
| cacggcaccc gggcccgggg ccgccagggt tacagcctcg gcagcctctt ccaccgctac | 7440 |
| ttccgggcag agccaagcgc agcccactca gccgagggcg acgtgcacac cctgctcctg | 7500 |
| atcttcctgc accgcgccgc agagctgctc gcctgggccg atgagcaggc ccgtgggtgg | 7560 |
| gcccacatcg agcccatgta cttgccgcct gatgacccca gcctggaggc ggccgactga | 7620 |

<210> SEQ ID NO 41
<211> LENGTH: 7660
<212> TYPE: DNA
<213> ORGANISM: Artificial sequence
<220> FEATURE:
<223> OTHER INFORMATION: pCLS9573

<400> SEQUENCE: 41

| | |
|---|---|
| atgtgagcaa aaggccagca aaaggccagg aaccgtaaaa aggccgcgtt gctggcgttt | 60 |
| ttccataggc tccgcccccc tgacgagcat cacaaaaatc gacgctcaag tcagaggtgg | 120 |
| cgaaacccga caggactata agataccagg cgtttccccc tggaagctc cctcgtgcgc | 180 |
| tctcctgttc cgaccctgcc gcttaccgga tacctgtccg cctttctccc ttcgggaagc | 240 |
| gtggcgcttt ctcatagctc acgctgtagg tatctcagtt cggtgtaggt cgttcgctcc | 300 |
| aagctgggct gtgtgcacga accccccgtt cagcccgacc gctgcgcctt atccggtaac | 360 |
| tatcgtcttg agtccaaccc ggtaagacac gacttatcgc cactggcagc agccactggt | 420 |
| aacaggatta gcagagcgag gtatgtaggc ggtgctacag agttcttgaa gtggtggcct | 480 |
| aactacggct acactagaag aacagtattt ggtatctgcg ctctgctgaa gccagttacc | 540 |
| ttcggaaaaa gagttggtag ctcttgatcc ggcaaacaaa ccaccgctgg tagcggtttt | 600 |
| tttgtttgca agcagcagat tacgcgcaga aaaaaggat ctcaagaaga tcctttgatc | 660 |
| ttttctacgg ggtctgacgc tcagtggaac gaaaactcac gttaagggat tttggtcatg | 720 |
| agattatcaa aaaggatctt cacctagatc cttttaaatt aaaaatgaag ttttaaatca | 780 |
| atctaaagta tatatgagta aacttggtct gacagttacc aatgcttaat cagtgaggca | 840 |
| cctatctcag cgatctgtct atttcgttca tccatagttg cctgactccc cgtcgtgtag | 900 |
| ataactacga tacgggaggg cttaccatct ggccccagtg ctgcaatgat accgcgagac | 960 |
| ccacgctcac cggctccaga tttatcagca ataaaccagc cagccggaag ggccgagcgc | 1020 |
| agaagtggtc ctgcaacttt atccgcctcc atccagtcta ttaattgttg ccgggaagct | 1080 |
| agagtaagta gttcgccagt taatagtttg cgcaacgttg ttgccattgc tacaggcatc | 1140 |
| gtggtgtcac gctcgtcgtt tggtatggct tcattcagct ccggttccca acgatcaagg | 1200 |
| cgagttacat gatcccccat gttgtgcaaa aaagcggtta gctccttcgg tcctccgatc | 1260 |
| gttgtcagaa gtaagttggc cgcagtgtta tcactcatgg ttatggcagc actgcataat | 1320 |
| tctcttactg tcatgccatc cgtaagatgc ttttctgtga ctggtgagta ctcaaccaag | 1380 |
| tcattctgag aatagtgtat gcggcgaccg agttgctctt gcccggcgtc aatacgggat | 1440 |
| aataccgcgc cacatagcag aactttaaaa gtgctcatca ttggaaaacg ttcttcgggg | 1500 |
| cgaaaactct caaggatctt accgctgttg agatccagtt cgatgtaacc cactcgtgca | 1560 |
| cccaactgat cttcagcatc ttttactttc accagcgttt ctgggtgagc aaaaacagga | 1620 |
| aggcaaaatg ccgcaaaaaa gggaataagg gcgacacgga aatgttgaat actcatactc | 1680 |
| ttcctttttc aatattattg aagcatttat cagggttatt gtctcatgag cggatacata | 1740 |
| tttgaatgta tttagaaaaa taaacaaata ggggttccgc gcacatttcc ccgaaaagtg | 1800 |

```
ccacctgacg tcgacggatc gggagatctc ccgatcccct atggtgcact ctcagtacaa   1860
tctgctctga tgccgcatag ttaagccagt atctgctccc tgcttgtgtg ttggaggtcg   1920
ctgagtagtg cgcgagcaaa atttaagcta caacaaggca aggcttgacc gacaattgca   1980
tgaagaatct gcttagggtt aggcgttttg cgctgcttcg cgatgtacgg gccagatata   2040
cgcgttgaca ttgattattg actagttatt aatagtaatc aattacgggg tcattagttc   2100
atagcccata tatggagttc cgcgttacat aacttacggt aaatggcccg cctggctgac   2160
cgcccaacga ccccgccca ttgacgtcaa taatgacgta tgttcccata gtaacgccaa   2220
tagggacttt ccattgacgt caatgggtgg agtatttacg gtaaactgcc cacttggcag   2280
tacatcaagt gtatcatatg ccaagtacgc cccctattga cgtcaatgac ggtaaatggc   2340
ccgcctggca ttatgcccag tacatgacct tatgggactt tcctacttgg cagtacatct   2400
acgtattagt catcgctatt accatggtga tgcggttttg gcagtacatc aatgggcgtg   2460
gatagcggtt tgactcacgg ggatttccaa gtctccaccc cattgacgtc aatgggagtt   2520
tgttttggca ccaaaatcaa cgggactttc caaaatgtcg taacaactcc gccccattga   2580
cgcaaatggg cggtaggcgt gtacggtggg aggtctatat aagcagagct ctctggctaa   2640
ctagagaacc cactgcttac tggcttatcg aaatgaattc gactcactgt gggagaccc   2700 aagctggcta gttaagctat cacaagtttg tacaaaaaag caggctggcg cgcctacaca   2760
gcggccttgc caccatgggt tccgaggcac cccgggccga dacctttgtc ttcctggacc   2820
tggaagccac tgggctcccc agtgtggagc ccgagattgc cgagctgtcc ctctttgctg   2880
tccaccgctc ctccctggag aacccggagc acgacgagtc tggtgcccta gtattgcccc   2940
gggtcctgga caagctcacg ctgtgcatgt gccggagcg ccccttcact gccaaggcca   3000
gcgagatcac cggcctgagc agtgagggcc tggcgcgatg ccggaaggct ggctttgatg   3060
gcgccgtggt gcggacgctg caggccttcc tgagccgcca ggcagggccc atctgccttg   3120
tggcccacaa tggctttgat tatgattttc ccctgctgtg tgccgagctg cggcgcctgg   3180
gtgcccgcct gccccgggac actgtctgcc tggacacgct gccggccctg cggggcctgg   3240
accgcgccca cagccacggc acccgggccc ggggccgcca gggttacagc ctcggcagcc   3300
tcttccaccg ctacttccgg gcagagccaa gcgcagccca ctcagccgag ggcgacgtgc   3360
acaccctgct cctgatcttc ctgcaccgcg ccgcagagct gctcgcctgg gccgatgagc   3420
aggcccgtgg gtgggcccac atcgagccca tgtacttgcc gcctgatgac cccagcctgg   3480
aggcgactcc tccacagacc ggtctggatg ttccttactc cgaggcaccc cgggccgaga   3540
cctttgtctt cctggacctg gaagccactg ggctccccag tgtggagccc gagattgccg   3600
agctgtccct ctttgctgtc accgctcct ccctggagaa cccggagcac gacgagtctg   3660
gtgccctagt attgccccgg gtcctggaca agctcacgct gtgcatgtgc ccggagcgcc   3720
ccttcactgc caaggccagc gagatcaccg gcctgagcag tgagggcctg gcgcgatgcc   3780
ggaaggctgg ctttgatggc gccgtggtgc ggacgctgca ggccttcctg agccgccagg   3840
cagggcccat ctgccttgtg cccacaatg gctttgatta tgatttcccc ctgctgtgtg   3900
ccgagctgcg gcgcctgggt gccgcctgc ccgggacac tgtctgcctg gacacgctgc   3960
cggccctgcg gggcctggac cgcgcccaca gccacggcac ccgggccgg ggcgccagg   4020 gttacagcct cggcagcctc ttccaccgct acttccgggc agagccaagc gcagcccact   4080
cagccgaggg cgacgtgcac accctgctcc tgatcttcct gcaccgcgcc gcagagctgc   4140
```

```
tcgcctgggc cgatgagcag gcccgtgggt gggcccacat cgagcccatg tacttgccgc    4200
ctgatgaccc cagcctggag gcgggaggtg gaggttctgg aggtggaggt tccaatacca    4260
aatataacga agagttcctg ctgtacctgg ccggctttgt ggacggtgac ggtagcatca    4320
tcgctcagat taatccaaac cagtcttcta agtttaaaca tcgtctacgt ttgaccttt    4380 atgtgactca aaagacccag cgccgttggt ttctggacaa actagtggat gaaattggcg    4440
ttggttacgt acgtgattct ggatccgttt cccagtacgt tttaagcgaa atcaagccgc    4500
tgcacaactt cctgactcaa ctgcagccgt ttctggaact gaaacagaaa caggcaaacc    4560
tggttctgaa aattatcgaa cagctgccgt ctgcaaaaga atccccggac aaattcctgg    4620
aagtttgtac ctgggtggat cagattgcag ctctgaacga ttctaagacg cgtaaaacca    4680
cttctgaaac cgttcgtgct gtgctggaca gcctgagcgg gaagaagaaa tcctccccgg    4740
cggccggtgg atctgataag tataatcagg ctctgtctaa atacaaccaa gcactgtcca    4800
agtacaatca ggccctgtct ggtggaggcg gttccaacaa aaagttcctg ctgtatcttg    4860
ctggatttgt ggattctgat ggctccatca ttgctcagat aaaaccacgt caatctaaca    4920
agttcaaaca ccagctctcc ttgactttg cagtcactca gaagacacaa agaaggtggt    4980
tcttggacaa attggttgat aggattggtg tgggctatgt ctatgacagt ggctctgtgt    5040
cagactaccg cctgtctgaa attaagcctc ttcataactt tctcacccaa ctgcaaccct    5100
tcttgaagct caaacagaag caagcaaatc tggttttgaa atcatcgag caactgccat    5160 ctgccaagga gtcccctgac aagtttcttg aagtgtgtac ttgggtggat cagattgctg    5220
ccttgaatga ctccaagacc agaaaaacca cctctgagac tgtgagggca gttctggata    5280
gcctctctga agagaaaaag tcctctcctt agccatggcc cgcggttcga aggtaagcct    5340
atccctaacc ctcctcgg tctcgattct acgcgtaccg ttagtaatg agttaaacg    5400 ggggaggcta actgaaacac ggaaggagac aataccggaa ggaacccgcg ctatgacggc    5460
aataaaaaga cagaataaaa cgcacgggtg ttgggtcgtt tgttcataaa cgcggggttc    5520
ggtcccaggg ctggcactct gtcgatacc caccgagacc ccattggggc caatacgccc    5580
gcgtttcttc cttttcccca ccccacccc caagttcggg tgaaggccca gggctcgcag    5640
ccaacgtcgg ggcggcaggc cctgccatag cagatctgcg cagctggggc tctagggggt    5700
atccccacgc gccctgtagc ggcgcattaa gcgcggcggg tgtggtggtt acgcgcagcg    5760
tgaccgctac acttgccagc gccctagcgc ccgctccttt cgctttcttc ccttcctttc    5820
tcgccacgtt cgccggcttt ccccgtcaag ctctaaatcg gggcatccct ttagggttcc    5880
gatttagtgc tttacggcac ctcgacccca aaaaacttga ttagggtgat ggttcacgta    5940
gtgggccatc gccctgatag acggttttc gccctttgac gttggagtcc acgttcttta    6000
atagtggact cttgttccaa actggaacaa cactcaaccc tatctcggtc tattcttttg    6060
atttataagg gattttgggg atttcggcct attggttaaa aaatgagctg atttaacaaa    6120
aatttaacgc gaattaattc tgtggaatgt gtgtcagtta gggtgtggaa agtccccagg    6180
ctccccagca ggcagaagta tgcaaagcat gcatctcaat tagtcagcaa ccaggtgtgg    6240
aaagtcccca ggctccccag caggcagaag tatgcaaagc atgcatctca attagtcagc    6300
aaccatagtc ccgcccctaa ctccgcccat cccgcccta actccgccca gttccgccca    6360
ttctccgccc catggctgac taatttttt tatttatgca gaggccgagg ccgcctctgc    6420
ctctgagcta ttccagaagt agtgaggagg cttttttgga ggcctaggct tttgcaaaaa    6480
gctcccggga gcttgtatat ccatttcgg atctgatcag cacgtgttga caattaatca    6540
```

```
tcggcatagt atatcggcat agtataaatac gacaaggtga ggaactaaac catggccaag    6600
cctttgtctc aagaagaatc caccctcatt gaaagagcaa cggctacaat caacagcatc    6660
cccatctctg aagactacag cgtcgccagc gcagctctct ctagcgacgg ccgcatcttc    6720
actggtgtca atgtatatca ttttactggg ggaccttgtg cagaactcgt ggtgctgggc    6780
actgctgctg ctgcggcagc tggcaacctg acttgtatcg tcgcgatcgg aaatgagaac    6840
aggggcatct tgagcccctg cggacggtgc cgacaggtgc ttctcgatct gcatcctggg    6900
atcaaagcca tagtgaagga cagtgatgga cagccgacgg cagttgggat tcgtgaattg    6960
ctgccctctg gttatgtgtg ggagggctaa gcacttcgtg gccgaggagc aggactgaca    7020
cgtgctacga gatttcgatt ccaccgccgc cttctatgaa aggttgggct tcggaatcgt    7080
tttccgggac gccggctgga tgatcctcca gcgcggggat ctcatgctgg agttcttcgc    7140
ccaccccaac ttgtttattg cagcttataa tggttacaaa taaagcaata gcatcacaaa    7200
tttcacaaat aaagcatttt ttcactgca ttctagttgt ggtttgtcca aactcatcaa    7260
tgtatcttat catgtctgta taccgtcgac ctctagctag agcttggcgt aatcatggtc    7320
atagctgttt cctgtgtgaa attgttatcc gctcacaatt ccacacaaca tacgagccgg    7380
aagcataaag tgtaaagcct ggggtgccta atgagtgagc taactcacat taattgcgtt    7440
gcgctcactg cccgctttcc agtcgggaaa cctgtcgtgc cagctgcatt aatgaatcgg    7500
ccaacgcgcg gggagaggcg gtttgcgtat tgggcgctct tccgcttcct cgctcactga    7560
ctcgctgcgc tcggtcgttc ggctgcggcg agcggtatca gctcactcaa aggcggtaat    7620
acggttatcc acagaatcag gggataacgc aggaaagaac                         7660

<210> SEQ ID NO 42
<211> LENGTH: 6969
<212> TYPE: DNA
<213> ORGANISM: Artificial sequence
<220> FEATURE:
<223> OTHER INFORMATION: pCLS8518

<400> SEQUENCE: 42
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa atgaattcga ctcactgttg ggagacccaa gctggctagt     900
```

```
taagctatca acaagtttgt acaaaaaagc aggctggcgc gcctacacag cggccttgcc    960
accatgggtt ccgaggcacc ccgggccgag acctttgtct tcctggacct ggaagccact   1020
gggctcccca gtgtggagcc cgagattgcc gagctgtccc tctttgctgt ccaccgctcc   1080
tccctggaga acccggagca cgacgagtct ggtgccctag tattgccccg ggtcctggac   1140
aagctcacgc tgtgcatgtg cccggagcgc cccttcactg ccaaggccag cgagatcacc   1200
ggcctgagca gtgagggcct ggcgcgatgc cggaaggctg gctttgatgg cgccgtggtg   1260
cggacgctgc aggccttcct gagccgccag gcagggccca tctgccttgt ggcccacaat   1320
ggctttgatt atgatttccc cctgctgtgt gccgagctgc ggcgcctggg tgcccgcctg   1380
ccccgggaca ctgtctgcct ggacacgctg ccggccctgc ggggcctgga ccgcgcccac   1440
agccacggca cccgggcccg gggccgccag ggttacagcc tcggcagcct cttccaccgc   1500
tacttccggg cagagccaag cgcagcccac tcagccgagg gcgacgtgca caccctgctc   1560
ctgatcttcc tgcaccgcgc cgcagagctg ctcgcctggg ccgatgagca ggcccgtggg   1620
tgggcccaca tcgagcccat gtacttgccg cctgatgacc ccagcctgga ggcgggaggt   1680
ggaggttctg gaggtggagg ttccaatacc aaatataacg aagagttcct gctgtacctg   1740
gccggctttg tggacggtga cggtagcatc gttgctcaga ttaaaccaaa ccagcgtgct   1800
aagtttaaac atcagctaag cttgaccttt caggtgactc aaaagaccca gcgccgttgg   1860
ctgctggaca aactagtgga tgaaattggc gttggttacg tacaggattc tggtagcgtt   1920
tccaactacc gtttaagcga aatcaagccg ctgcacaact tcctgactca actgcagccg   1980
tttctggaac tgaaacagaa acaggcaaac ctggttctga aaattatcga acagctgccg   2040
tctgcaaaag aatccccgga caaattcctg gaagtttgta cctgggctga tcagattgca   2100
gctctgaacg attctaagac gcgtaaaacc acttctgaaa ccgttcgtgc tgtgctggac   2160
agcctgagcg agaagaagaa accgtccccg gcggccggtg gatctgataa gtataatcag   2220
gctctgtcta aatacaacca agcactgtcc aagtacaatc aggccctgtc tggtggaggc   2280
ggttccaaca aaaaattcct gctgtatctt gctggatttg tggattctga tggctccatc   2340
attgctcaga taaaaccacg tcaatcttac aagttcaaac accagctccg tttgaccttt   2400
tacgtcactc agaagacaca aagaaggtgg ttcttggaca aattggttga tcgtattggt   2460
gtgggctatg tcgaagactc tggctctgtg tcacgttacg ttctgtctga aattaagcct   2520
cttcataact ttctcaccca actgcaaccc ttcttgaagc tcaaacagaa gcaagcaaat   2580
ctggttttga aaatcatcga gcaactgcca tctgccaagg agtcccctga caagtttctt   2640
gaagtgtgta cttgggtgga tcaggttgct gccttgaatg actccaagac cagaaaaacc   2700
acctctgaga ctgtgagggc agttctggat agcctctctg agaagaaaaa gtcctctcct   2760
tagtaactcg agcgctagca cccagctttc ttgtacaaag tggtgatcta gagggcccgc   2820
ggttcgaagg taagcctatc cctaaccctc tcctcggtct cgattctacg cgtaccggtt   2880
agtaatgagt ttaaacgggg gaggctaact gaaacacgga aggagacaat accggaagga   2940
acccgcgcta tgacggcaat aaaaagacag aataaaacgc acgggtgttg ggtcgtttgt   3000
tcataaacgc ggggttcggt cccagggctg gcactctgtc gatacccacc gagaccccca   3060
ttggggccaa tacgcccgcg tttcttcctt ttccccaccc cacccccccaa gttcgggtga   3120
aggcccaggg ctcgcagcca acgtcggggc ggcaggccct gccatagcag atctgcgcag   3180
ctggggctct aggggtatcc ccacgcgccc tgtagcggc gcattaagcg cggcgggtgt   3240
ggtggttacg cgcagcgtga ccgctacact tgccagcgcc ctagcgcccg ctcctttcgc   3300
```

-continued

```
tttcttccct tcctttctcg ccacgttcgc cggctttccc cgtcaagctc taaatcgggg    3360
catcccttta gggttccgat ttagtgcttt acggcacctc gaccccaaaa aacttgatta    3420
gggtgatggt tcacgtagtg ggccatcgcc ctgatagacg ttttttcgcc ctttgacgtt    3480
ggagtccacg ttctttaata gtggactctt gttccaaact ggaacaacac tcaaccctat    3540
ctcggtctat tcttttgatt tataagggat tttggggatt tcggcctatt ggttaaaaaa    3600
tgagctgatt taacaaaaat ttaacgcgaa ttaattctgt ggaatgtgtg tcagttaggg    3660
tgtggaaagt ccccaggctc cccagcaggc agaagtatgc aaagcatgca tctcaattag    3720
tcagcaacca ggtgtggaaa gtccccaggc tccccagcag gcagaagtat gcaaagcatg    3780
catctcaatt agtcagcaac catagtcccg cccctaactc cgcccatccc gcccctaact    3840
ccgcccagtt ccgcccattc tccgccccat ggctgactaa ttttttttat ttatgcagag    3900
gccgaggccg cctctgcctc tgagctattc cagaagtagt gaggaggctt ttttggaggc    3960
ctaggctttt gcaaaaagct cccgggagct tgtatatcca ttttcggatc tgatcagcac    4020
gtgttgacaa ttaatcatcg gcatagtata tcggcatagt ataatacgac aaggtgagga    4080
actaaaccat ggccaagcct ttgtctcaag aagaatccac cctcattgaa agagcaacgg    4140
ctacaatcaa cagcatcccc atctctgaag actacagcgt cgccagcgca gctctctcta    4200
gcgacggccg catcttcact ggtgtcaatg tatatcattt tactggggga ccttgtgcag    4260
aactcgtggt gctgggcact gctgctgctg cggcagctgg caacctgact tgtatcgtcg    4320
cgatcggaaa tgagaacagg ggcatcttga gcccctgcgg acggtgccga caggtgcttc    4380
tcgatctgca tcctgggatc aaagccatag tgaaggacag tgatggacag ccgacggcag    4440
ttgggattcg tgaattgctg ccctctggtt atgtgtggga gggctaagca cttcgtggcc    4500
gaggagcagg actgacacgt gctacgagat ttcgattcca ccgccgcctt ctatgaaagg    4560
ttgggcttcg gaatcgtttt ccgggacgcc ggctggatga tcctccagcg cggggatctc    4620
atgctggagt tcttcgccca ccccaacttg tttattgcag cttataatgg ttacaaataa    4680
agcaatagca tcacaaattt cacaaataaa gcattttttt cactgcattc tagttgtggt    4740
ttgtccaaac tcatcaatgt atcttatcat gtctgtatac cgtcgacctc tagctagagc    4800
ttggcgtaat catggtcata gctgtttcct gtgtgaaatt gttatccgct cacaattcca    4860
cacaacatac gagccggaag cataaagtgt aaagcctggg gtgcctaatg agtgagctaa    4920
ctcacattaa ttgcgttgcg ctcactgccc gctttccagt cgggaaacct gtcgtgccag    4980
ctgcattaat gaatcggcca acgcgcgggg agaggcggtt tgcgtattgg gcgctcttcc    5040
gcttcctcgc tcactgactc gctgcgctcg gtcgttcggc tgcggcgagc ggtatcagct    5100
cactcaaagg cggtaatacg gttatccaca gaatcagggg ataacgcagg aaagaacatg    5160
tgagcaaaag gccagcaaaa ggccaggaac cgtaaaaagg ccgcgttgct ggcgtttttc    5220
cataggctcc gcccccctga cgagcatcac aaaaatcgac gctcaagtca gaggtggcga    5280
aacccgacag gactataaag ataccaggcg tttccccctg gaagctccct cgtgcgctct    5340
cctgttccga ccctgccgct taccggatac ctgtccgcct ttctcccttc gggaagcgtg    5400
gcgctttctc atagctcacg ctgtaggtat ctcagttcgg tgtaggtcgt tcgctccaag    5460
ctgggctgtg tgcacgaacc ccccgttcag cccgaccgct gcgccttatc cggtaactat    5520
cgtcttgagt ccaacccggt aagacacgac ttatcgccac tggcagcagc cactggtaac    5580
aggattagca gagcgaggta tgtaggcggt gctacagagt tcttgaagtg gtggcctaac    5640
```

| | |
|---|---|
| tacggctaca ctagaagaac agtatttggt atctgcgctc tgctgaagcc agttaccttc | 5700 |
| ggaaaaagag ttggtagctc ttgatccggc aaacaaacca ccgctggtag cggttttttt | 5760 |
| gtttgcaagc agcagattac gcgcagaaaa aaggatctc aagaagatcc tttgatcttt | 5820 |
| tctacggggt ctgacgctca gtggaacgaa aactcacgtt aagggatttt ggtcatgaga | 5880 |
| ttatcaaaaa ggatcttcac ctagatcctt ttaaattaaa aatgaagttt taaatcaatc | 5940 |
| taaagtatat atgagtaaac ttggtctgac agttaccaat gcttaatcag tgaggcacct | 6000 |
| atctcagcga tctgtctatt tcgttcatcc atagttgcct gactccccgt cgtgtagata | 6060 |
| actacgatac gggagggctt accatctggc cccagtgctg caatgatacc gcgagaccca | 6120 |
| cgctcaccgg ctccagattt atcagcaata aaccagccag ccggaagggc cgagcgcaga | 6180 |
| agtggtcctg caactttatc cgcctccatc cagtctatta attgttgccg ggaagctaga | 6240 |
| gtaagtagtt cgccagttaa tagtttgcgc aacgttgttg ccattgctac aggcatcgtg | 6300 |
| gtgtcacgct cgtcgtttgg tatggcttca ttcagctccg gttcccaacg atcaaggcga | 6360 |
| gttacatgat cccccatgtt gtgcaaaaaa gcggttagc ccttcggtcc tccgatcgtt | 6420 |
| gtcagaagta agttggccgc agtgttatca ctcatggtta tggcagcact gcataattct | 6480 |
| cttactgtca tgccatccgt aagatgcttt tctgtgactg gtgagtactc aaccaagtca | 6540 |
| ttctgagaat agtgtatgcg gcgaccgagt tgctcttgcc cggcgtcaat acgggataat | 6600 |
| accgcgccac atagcagaac tttaaaagtg ctcatcattg gaaaacgttc ttcggggcga | 6660 |
| aaactctcaa ggatcttacc gctgttgaga tccagttcga tgtaacccac tcgtgcaccc | 6720 |
| aactgatctt cagcatcttt tactttcacc agcgtttctg ggtgagcaaa aacaggaagg | 6780 |
| caaaatgccg caaaaaaggg aataagggcg acacggaaat gttgaatact catactcttc | 6840 |
| ctttttcaat attattgaag catttatcag ggttattgtc tcatgagcgg atacatattt | 6900 |
| gaatgtattt agaaaaataa acaaataggg gttccgcgca catttccccg aaaagtgcca | 6960 |
| cctgacgtc | 6969 |

<210> SEQ ID NO 43
<211> LENGTH: 7660
<212> TYPE: DNA
<213> ORGANISM: Artificial sequence
<220> FEATURE:
<223> OTHER INFORMATION: pCLS9571

<400> SEQUENCE: 43

| | |
|---|---|
| atgtgagcaa aaggccagca aaaggccagg aaccgtaaaa aggccgcgtt gctggcgttt | 60 |
| ttccataggc tccgcccccc tgacgagcat cacaaaaatc gacgctcaag tcagaggtgg | 120 |
| cgaaacccga caggactata aagataccag gcgtttcccc ctggaagctc cctcgtgcgc | 180 |
| tctcctgttc cgaccctgcc gcttaccgga tacctgtccg cctttctccc ttcgggaagc | 240 |
| gtggcgcttt ctcatagctc acgctgtagg tatctcagtt cggtgtaggt cgttcgctcc | 300 |
| aagctgggct gtgtgcacga accccccgtt cagcccgacc gctgcgcctt atccggtaac | 360 |
| tatcgtcttg agtccaaccc ggtaagacac gacttatcgc cactggcagc agccactggt | 420 |
| aacaggatta gcagagcgag gtatgtaggc ggtgctacag agttcttgaa gtggtggcct | 480 |
| aactacggct acactagaag aacagtattt ggtatctgcg ctctgctgaa gccagttacc | 540 |
| ttcggaaaaa gagttggtag ctcttgatcc ggcaaacaaa ccaccgctgg tagcggtttt | 600 |
| tttgtttgca gcagcagat tacgcgcaga aaaaaaggat ctcaagaaga tcctttgatc | 660 |
| ttttctacgg ggtctgacgc tcagtggaac gaaaactcac gttaagggat tttggtcatg | 720 |

-continued

```
agattatcaa aaaggatctt cacctagatc cttttaaatt aaaaatgaag ttttaaatca    780
atctaaagta tatatgagta aacttggtct gacagttacc aatgcttaat cagtgaggca    840
cctatctcag cgatctgtct atttcgttca tccatagttg cctgactccc cgtcgtgtag    900
ataactacga tacgggaggg cttaccatct ggccccagtg ctgcaatgat accgcgagac    960
ccacgctcac cggctccaga tttatcagca ataaaccagc cagccggaag ggccgagcgc   1020
agaagtggtc ctgcaacttt atccgcctcc atccagtcta ttaattgttg ccgggaagct   1080
agagtaagta gttcgccagt taatagtttg cgcaacgttg ttgccattgc tacaggcatc   1140
gtggtgtcac gctcgtcgtt tggtatggct tcattcagct ccggttccca acgatcaagg   1200
cgagttacat gatcccccat gttgtgcaaa aaagcggtta gctccttcgg tcctccgatc   1260
gttgtcagaa gtaagttggc cgcagtgtta tcactcatgg ttatggcagc actgcataat   1320
tctcttactg tcatgccatc cgtaagatgc ttttctgtga ctggtgagta ctcaaccaag   1380
tcattctgag aatagtgtat gcggcgaccg agttgctctt gcccggcgtc aatacgggat   1440
aataccgcgc cacatagcag aactttaaaa gtgctcatca ttggaaaacg ttcttcgggg   1500
cgaaaactct caaggatctt accgctgttg agatccagtt cgatgtaacc cactcgtgca   1560
cccaactgat cttcagcatc ttttactttc accagcgttt ctgggtgagc aaaaacagga   1620
aggcaaaatg ccgcaaaaaa gggaataagg gcgacacgga aatgttgaat actcatactc   1680
ttcctttttc aatattattg aagcatttat cagggttatt gtctcatgag cggatacata   1740
tttgaatgta tttagaaaaa taaacaaata ggggttccgc gcacatttcc ccgaaaagtg   1800
ccacctgacg tcgacggatc gggagatctc ccgatcccct atggtgcact ctcagtacaa   1860
tctgctctga tgccgcatag ttaagccagt atctgctccc tgcttgtgtg ttggaggtcg   1920
ctgagtagtg cgcgagcaaa atttaagcta caacaaggca aggcttgacc gacaattgca   1980
tgaagaatct gcttagggtt aggcgttttg cgctgcttcg cgatgtacgg gccagatata   2040
cgcgttgaca ttgattattg actagttatt aatagtaatc aattacgggg tcattagttc   2100
atagcccata tatggagttc cgcgttacat aacttacggt aaatggcccg cctggctgac   2160
cgcccaacga ccccgccca ttgacgtcaa taatgacgta tgttcccata gtaacgccaa   2220
tagggacttt ccattgacgt caatgggtgg agtatttacg gtaaactgcc cacttggcag   2280
tacatcaagt gtatcatatg ccaagtacgc cccctattga cgtcaatgac ggtaaatggc   2340
ccgcctggca ttatgcccag tacatgacct tatgggactt tcctacttgg cagtacatct   2400
acgtattagt catcgctatt accatggtga tgcggttttg gcagtacatc aatgggcgtg   2460
gatagcggtt tgactcacgg ggatttccaa gtctccaccc cattgacgtc aatgggagtt   2520
tgttttggca ccaaaatcaa cgggactttc caaaatgtcg taacaactcc gccccattga   2580
cgcaaatggg cggtaggcgt gtacggtggg aggtctatat aagcagagct ctctggctaa   2640
ctagagaacc cactgcttac tggcttatcg aaatgaattc gactcactgt gggagaccc   2700
aagctggcta gttaagctat cacaagtttg tacaaaaaag caggctggcg cgcctacaca   2760
gcggccttgc caccatgggt tccgaggcac ccgggccga dacctttgtc ttcctggacc   2820
tggaagccac tgggctcccc agtgtggagc ccgagattgc cgagctgtcc ctctttgctg   2880
tccaccgctc ctccctggag aacccggagc acgacgagtc tggtgcccta gtattgcccc   2940
gggtcctgga caagctcacg ctgtgcatgt gcccggagcg ccccttcact gccaaggca   3000
gcgagatcac cggcctgagc agtgagggcc tggcgcgatg ccggaaggct ggctttgatg   3060
```

```
gcgccgtggt gcggacgctg caggccttcc tgagccgcca ggcagggccc atctgccttg    3120
tggcccacaa tggctttgat tatgatttcc ccctgctgtg tgccgagctg cggcgcctgg    3180
gtgcccgcct gccccgggac actgtctgcc tggacacgct gccggccctg cggggcctgg    3240
accgcgccca cagccacggc acccgggccc ggggccgcca gggttacagc ctcggcagcc    3300
tcttccaccg ctacttccgg gcagagccaa gcgcagccca ctcagccgag ggcgacgtgc    3360 acacctgct cctgatcttc ctgcaccgcg ccgcagagct gctcgcctgg gccgatgagc     3420
aggcccgtgg gtgggcccac atcgagccca tgtacttgcc gcctgatgac cccagcctgg    3480
aggcgactcc tccacagacc ggtctggatg ttccttactc cgaggcaccc cgggccgaga    3540
cctttgtctt cctggacctg aagccactg ggctccccag tgtggagccc gagattgccg      3600
agctgtccct ctttgctgtc caccgctcct ccctggagaa cccggagcac gacgagtctg    3660
gtgccctagt attgccccgg gtcctggaca agctcacgct gtgcatgtgc ccggagcgcc    3720
ccttcactgc caaggccagc gagatcaccg gcctgagcag tgagggcctg gcgcgatgcc    3780
ggaaggctgg ctttgatggc gccgtggtgc ggacgctgca ggccttcctg agccgccagg    3840
cagggcccat ctgccttgtg cccacaatg gctttgatta tgatttcccc ctgctgtgtg     3900
ccgagctgcg cgcctgggt gcccgcctgc ccgggacac tgtctgcctg gacacgctgc      3960
cggccctgcg gggcctggac cgcgcccaca gccacggcac ccgggcccgg ggccgccagg    4020
gttacagcct cggcagcctc ttccaccgct acttccgggc agagccaagc gcagcccact    4080
cagccgaggg cgacgtgcac accctgctcc tgatcttcct gcaccgcgcc gcagagctgc    4140
tcgcctgggc cgatgagcag gccgtgggt gggcccacat cgagcccatg tacttgccgc      4200
ctgatgaccc cagcctggag gcggaggtg gaggttctgg aggtggaggt tccaatacca     4260
aatataacga agagttcctg ctgtacctgg ccggctttgt ggacggtgac ggtagcatcg    4320
ttgctcagat taaaccaaac cagcgtgcta agtttaaaca tcagctaagc ttgacctttc    4380
aggtgactca aaagacccag cgccgttggc tgctggacaa actagtggat gaaattggcg    4440
ttggttacgt acaggattct ggtagcgttt ccaactaccg tttaagcgaa atcaagccgc    4500
tgcacaactt cctgactcaa ctgcagccgt ttctggaact gaaacagaaa caggcaaacc    4560
tggttctgaa aattatcgaa cagctgccgt ctgcaaaaga tccccggac aaattcctgg     4620 aagtttgtac ctgggctgat cagattgcag ctctgaacga ttctaagacg cgtaaaacca    4680
cttctgaaac cgttcgtgct gtgctggaca gcctgagcga agaagaaaa ccgtccccgg     4740 cggccggtgg atctgataag tataatcagg ctctgtctaa atacaaccaa gcactgtcca    4800
agtacaatca ggccctgtct ggtggaggcg gttccaacaa aaaattcctg ctgtatcttg    4860
ctggatttgt ggattctgat ggctccatca ttgctcagat aaaaccacgt caatcttaca    4920
agttcaaaca ccagctccgt ttgacctttt acgtcactca gaagacacaa agaaggtggt    4980
tcttggacaa attggttgat cgtattggtg tgggctatgt cgaagactct ggctctgtgt    5040
cacgttacgt tctgtctgaa attaagcctc ttcataactt tctcacccaa ctgcaaccct    5100
tcttgaagct caaacagaag caagcaaatc tggttttgaa aatcatcgag caactgccat    5160
ctgccaagga gtcccctgac aagtttcttg aagtgtgtac ttgggtggat caggttgctg    5220
ccttgaatga ctccaagacc agaaaaacca cctctgagac tgtgagggca gttctggata    5280
gcctctctga gaagaaaag tcctctcctt agccatggcc cgcggttcga aggtaagcct     5340
atccctaacc ctctcctcgg tctcgattct acgcgtaccg gttagtaatg agtttaaacg    5400
ggggaggcta actgaaacac ggaaggagac aataccggaa ggaacccgcg ctatgacggc    5460
```

```
aataaaaaga cagaataaaa cgcacgggtg ttgggtcgtt tgttcataaa cgcggggttc    5520
ggtcccaggg ctggcactct gtcgatacce caccgagace ccattgggge caatacgcce    5580 gcgtttcttc cttttcccca ccccacccce caagttcggg tgaaggccca gggctcgcag    5640
ccaacgtcgg ggcggcaggc cctgccatag cagatctgcg cagctggggc tctaggggt     5700 atccccacgc gccctgtagc ggcgcattaa gcgcggcggg tgtggtggtt acgcgcagcg    5760
tgaccgctac acttgccagc gccctagcgc ccgctccttt cgctttcttc ccttcctttc    5820
tcgccacgtt cgccggcttt ccccgtcaag ctctaaatcg ggcatccct ttagggttcc     5880 gatttagtgc tttacggcac ctcgacccca aaaaacttga ttagggtgat ggttcacgta    5940
gtgggccatc gccctgatag acggttttc gcccttgac gttggagtcc acgttcttta     6000
atagtggact cttgttccaa actggaacaa cactcaaccc tatctcggtc tattcttttg    6060
atttataagg gattttgggg atttcggcct attggttaaa aaatgagctg atttaacaaa    6120
aatttaacgc gaattaattc tgtggaatgt gtgtcagtta gggtgtggaa agtccccagg    6180
ctccccagca ggcagaagta tgcaaagcat gcatctcaat tagtcagcaa ccaggtgtgg    6240
aaagtcccca ggctccccag caggcagaag tatgcaaagc atgcatctca attagtcagc    6300
aaccatagtc ccgcccctaa ctccgcccat cccgcccta actccgccca gttccgccca    6360
ttctccgccc catggctgac taattttttt tatttatgca gaggccgagg ccgcctctgc    6420
ctctgagcta ttccagaagt agtgaggagg cttttttgga ggcctaggct tttgcaaaaa    6480
gctcccggga gcttgtatat ccattttcgg atctgatcag cacgtgttga caattaatca    6540
tcggcatagt atatcggcat agtataatac gacaaggtga ggaactaaac catggccaag    6600
cctttgtctc aagaagaatc caccctcatt gaaagagcaa cggctacaat caacagcatc    6660
cccatctctg aagactacag cgtcgccagc gcagctctct ctagcgacgg ccgcatcttc    6720
actggtgtca atgtatatca ttttactggg ggaccttgtg cagaactcgt ggtgctgggc    6780
actgctgctg ctgcggcagc tggcaacctg acttgtatcg tcgcgatcgg aaatgagaac    6840 agggcatct tgagcccctg cggacggtgc cgacaggtgc ttctcgatct gcatcctggg    6900
atcaaagcca tagtgaagga cagtgatgga cagccgacgg cagttgggat tcgtgaattg    6960
ctgccctctg gttatgtgtg ggagggctaa gcacttcgtg gccgaggagc aggactgaca    7020
cgtgctacga gatttcgatt ccaccgccgc cttctatgaa aggttgggct tcggaatcgt    7080
tttccgggac gccggctgga tgatcctcca gcgcggggat ctcatgctgg agttcttcgc    7140 ccacccaac ttgtttattg cagcttataa tggttacaaa taaagcaata gcatcacaaa     7200
tttcacaaat aaagcatttt tttcactgca ttctagttgt ggtttgtcca aactcatcaa    7260
tgtatcttat catgtctgta taccgtcgac ctctagctag agcttggcgt aatcatggtc    7320
atagctgttt cctgtgtgaa attgttatcc gctcacaatt ccacacaaca tacgagccgg    7380
aagcataaag tgtaaagcct ggggtgccta atgagtgagc taactcacat taattgcgtt    7440
gcgctcactg cccgctttcc agtcgggaaa cctgtcgtgc cagctgcatt aatgaatcgg    7500
ccaacgcgcg gggagaggcg gtttgcgtat gggcgctct tccgcttcct cgctcactga    7560
ctcgctgcgc tcggtcgttc ggctgcggcg agcggtatca gctcactcaa aggcggtaat    7620
acggttatcc acagaatcag gggataacgc aggaaagaac                         7660
```

<210> SEQ ID NO 44
<211> LENGTH: 6234
<212> TYPE: DNA

<213> ORGANISM: Artificial sequence
<220> FEATURE:
<223> OTHER INFORMATION: pCLS6163

<400> SEQUENCE: 44

```
taactcgagc gctagcaccc agctttcttg tacaaagtgg tgatctagag ggcccgcggt    60
tcgaaggtaa gcctatccct aaccctctcc tcggtctcga ttctacgcgt accggttagt   120
aatgagttta acggggagg gctaactgaa acacggaagg agacaatacc ggaaggaacc   180
cgcgctatga cggcaataaa aagacagaat aaaacgcacg ggtgttgggt cgtttgttca   240
taaacgcggg gttcggtccc agggctggca ctctgtcgat accccaccga gaccccattg   300
gggccaatac gcccgcgttt cttccttttc cccaccccac cccccaagtt cgggtgaagg   360
cccagggctc gcagccaacg tcgggcggc aggccctgcc atagcagatc tgcgcagctg   420
gggctctagg gggtatcccc acgcgccctg tagcggcgca ttaagcgcgg cgggtgtggt   480
ggttacgcgc agcgtgaccg ctacacttgc cagcgcccta gcgcccgctc ctttcgcttt   540
cttcccttcc tttctcgcca cgttcgccgg ctttccccgt caagctctaa atcggggcat   600
cccttaggg ttccgattta gtgctttacg gcacctcgac cccaaaaaac ttgattaggg   660
tgatggttca cgtagtgggc catcgccctg atagacggtt tttcgccctt tgacgttgga   720
gtccacgttc tttaatagtg gactcttgtt ccaaactgga acaacactca accctatctc   780
ggtctattct tttgatttat aagggatttt ggggatttcg gcctattggt taaaaaatga   840
gctgatttaa caaaaattta acgcgaatta attctgtgga atgtgtgtca gttagggtgt   900
ggaaagtccc caggctcccc agcaggcaga agtatgcaaa gcatgcatct caattagtca   960
gcaaccaggt gtggaaagtc cccaggctcc ccagcaggca gaagtatgca aagcatgcat  1020
ctcaattagt cagcaaccat agtcccgccc ctaactccgc ccatcccgcc ctaactccg  1080
cccagttccg cccattctcc gccccatggc tgactaattt ttttatttat gcagaggcc   1140
gaggccgcct ctgcctctga gctattccag aagtagtgag gaggcttttt tggaggccta  1200
ggcttttgca aaaagctccc gggagcttgt atatccattt tcggatctga tcagcacgtg  1260
ttgacaatta atcatcggca tagtatatcg gcatagtata atacgacaag gtgaggaact  1320
aaaccatggc caagcctttg tctcaagaag aatccaccct cattgaaaga gcaacggcta  1380
caatcaacag catccccatc tctgaagact acagcgtcgc cagcgcagct ctctctagcg  1440
acggccgcat cttcactggt gtcaatgtat atcattttac tgggggacct tgtgcagaac  1500
tcgtggtgct gggcactgct gctgctgcgg cagctggcaa cctgacttgt atcgtcgcga  1560
tcggaaatga gaacaggggc atcttgagcc cctgcggacg gtgccgacag gtgcttctcg  1620
atctgcatcc tgggatcaaa gccatagtga aggacagtga tggacagccg acggcagttg  1680
ggattcgtga attgctgccc tctggttatg tgtgggaggg ctaagcactt cgtggccgag  1740
gagcaggact gacacgtgct acgagatttc gattccaccg ccgccttcta tgaaaggttg  1800
ggcttcggaa tcgttttccg gacgccggc tggatgatcc tccagcgcgg ggatctcatg  1860
ctggagttct tcgcccaccc caacttgttt attgcagctt ataatggtta caaataaagc  1920
aatagcatca caaatttcac aaataaagca tttttttcac tgcattctag ttgtggtttg  1980
tccaaactca tcaatgtatc ttatcatgtc tgtataccgt cgacctctag ctagagcttg  2040
gcgtaatcat ggtcatagct gtttcctgtg tgaaattgtt atccgctcac aattccacac  2100
aacatacgag ccggaagcat aaagtgtaaa gcctggggtg cctaatgagt gagctaactc  2160
acattaattg cgttgcgctc actgcccgct ttccagtcgg gaaacctgtc gtgccagctg  2220
```

```
cattaatgaa tcggccaacg cgcggggaga ggcggtttgc gtattgggcg ctcttccgct   2280
tcctcgctca ctgactcgct gcgctcggtc gttcggctgc ggcgagcggt atcagctcac   2340
tcaaaggcgg taatacggtt atccacagaa tcaggggata acgcaggaaa gaacatgtga   2400
gcaaaaggcc agcaaaaggc caggaaccgt aaaaaggccg cgttgctggc gttttttccat  2460
aggctccgcc cccctgacga gcatcacaaa aatcgacgct caagtcagag gtggcgaaac   2520
ccgacaggac tataaagata ccaggcgttt ccccctggaa gctccctcgt gcgctctcct   2580
gttccgaccc tgccgcttac cggatacctg tccgcctttc tcccttcggg aagcgtggcg   2640
ctttctcata gctcacgctg taggtatctc agttcggtgt aggtcgttcg ctccaagctg   2700
ggctgtgtgc acgaaccccc cgttcagccc gaccgctgcg ccttatccgg taactatcgt   2760
cttgagtcca acccggtaag acacgactta tcgccactgg cagcagccac tggtaacagg   2820
attagcagag cgaggtatgt aggcggtgct acagagttct tgaagtggtg cctaactac    2880
ggctacacta agaacagt atttggtatc tgcgctctgc tgaagccagt taccttcgga    2940
aaaagagttg gtagctcttg atccggcaaa caaaccaccg ctggtagcgg ttttttttgtt  3000
tgcaagcagc agattacgcg cagaaaaaaa ggatctcaag aagatccttt gatcttttct   3060
acggggtctg acgctcagtg aacgaaaac tcacgttaag ggattttggt catgagatta    3120
tcaaaaagga tcttcaccta gatccttttta aattaaaaat gaagttttaa atcaatctaa   3180
agtatatatg agtaaacttg gtctgacagt taccaatgct taatcagtga ggcacctatc   3240
tcagcgatct gtctatttcg ttcatccata gttgcctgac tccccgtcgt gtagataact   3300
acgatacggg agggcttacc atctggcccc agtgctgcaa tgataccgcg agacccacgc   3360
tcaccggctc cagatttatc agcaataaac cagccagccg aagggccga gcgcagaagt    3420
ggtcctgcaa ctttatccgc ctccatccag tctattaatt gttgccggga agctagagta   3480
agtagttcgc cagttaatag tttgcgcaac gttgttgcca ttgctacagg catcgtggtg   3540
tcacgctcgt cgtttggtat ggcttcattc agctccggtt cccaacgatc aaggcgagtt   3600
acatgatccc ccatgttgtg caaaaaagcg gttagctcct tcggtcctcc gatcgttgtc   3660
agaagtaagt tggccgcagt gttatcactc atggttatgg cagcactgca taattctctt   3720
actgtcatgc catccgtaag atgcttttct gtgactggtg agtactcaac caagtcattc   3780
tgagaatagt gtatgcggcg accgagttgc tcttgcccgg cgtcaatacg ggataatacc   3840
gcgccacata gcagaacttt aaaagtgctc atcattggaa aacgttcttc ggggcgaaaa   3900
ctctcaagga tcttaccgct gttgagatcc agttcgatgt aacccactcg tgcacccaac   3960
tgatcttcag catcttttac tttcaccagc gtttctgggt gagcaaaaac aggaaggcaa   4020
aatgccgcaa aaaagggaat aagggcgaca cggaaatgtt gaatactcat actcttcctt   4080
tttcaatatt attgaagcat ttatcagggt tattgtctca tgagcggata catatttgaa   4140
tgtatttaga aaataaaca ataggggtt ccgcgcacat ttccccgaaa agtgccacct     4200
gacgtcgacg gatcgggaga tctcccgatc ccctatggtg cactctcagt acaatctgct   4260
ctgatgccgc atagttaagc cagtatctgc tccctgcttg tgtgttggag gtcgctgagt   4320
agtgcgcgag caaaatttaa gctacaacaa ggcaaggctt gaccgacaat tgcatgaaga   4380
atctgcttag ggttaggcgt tttgcgctgc ttcgcgatgt acgggccaga tatacgcgtt   4440
gacattgatt attgactagt tattaatagt aatcaattac ggggtcatta gttcatagcc   4500
catatatgga gttccgcgtt acataactta cggtaaatgg cccgcctggc tgaccgccca   4560
```

```
acgacccccg cccattgacg tcaataatga cgtatgttcc catagtaacg ccaatagggα    4620 ctttccattg acgtcaatgg gtggagtatt tacggtaaac tgcccacttg gcagtacatc    4680
aagtgtatca tatgccaagt acgcccccta ttgacgtcaa tgacggtaaa tggcccgcct    4740
ggcattatgc ccagtacatg accttatggg actttcctac ttggcagtac atctacgtat    4800
tagtcatcgc tattaccatg gtgatgcggt tttggcagta catcaatggg cgtggatagc    4860
ggtttgactc acggggattt ccaagtctcc accccattga cgtcaatggg agtttgtttt    4920
ggcaccaaaa tcaacgggac tttccaaaat gtcgtaacaa ctccgcccca ttgacgcaaa    4980
tgggcggtag gcgtgtacgg tgggaggtct atataagcag agctctctgg ctaactagag    5040
aacccactgc ttactggctt atcgaaatga attcgactca ctgttgggag acccaagctg    5100
gctagttaag ctatcaacaa gtttgtacaa aaaagcaggc tggcgcgcct acacagcggc    5160
cttgccacca tggccaatac caaatataac gaagagttcc tgctgtacct ggccggcttt    5220
gtggacggtg acggtagcat cgttgctcag attaaaccaa accagcgtgc taagtttaaa    5280
catcagctaa gcttgacctt tcaggtgact caaaagaccc agcgccgttg gctgctggac    5340
aaactagtgg atgaaattgg cgttggttac gtacaggatt ctggtagcgt ttccaactac    5400
cgtttaagcg aaatcaagcc gctgcacaac ttcctgactc aactgcagcc gtttctggaa    5460
ctgaaacaga acaggcaaa cctggttctg aaaattatcg aacagctgcc gtctgcaaaa    5520
gaatccccgg acaaattcct ggaagtttgt acctgggctg atcagattgc agctctgaac    5580
gattctaaga cgcgtaaaac cacttctgaa accgttcgtg ctgtgctgga cagcctgagc    5640
gagaagaaga aaccgtcccc ggcggccggt ggatctgata agtataatca ggctctgtct    5700
aaatacaacc aagcactgtc caagtacaat caggccctgt ctggtggagg cggttccaac    5760
aaaaaattcc tgctgtatct tgctggattt gtggattctg atggctccat cattgctcag    5820
ataaaaccac gtcaatctta caagttcaaa caccagctcc gtttgacctt ttacgtcact    5880
cagaagacac aaagaaggtg gttcttggac aaattggttg atcgtattgg tgtgggctat    5940
gtcgaagact ctggctctgt gtcacgttac gttctgtctg aaattaagcc tcttcataac    6000
tttctcaccc aactgcaacc cttccttgaag ctcaaacaga agcaagcaaa tctggttttg    6060
aaaatcatcg agcaactgcc atctgccaag gagtcccctg acaagtttct tgaagtgtgt    6120
acttgggtgg atcaggttgc tgccttgaat gactccaaga ccagaaaaac cacctctgag    6180
actgtgaggg cagttctgga tagcctctct gagaagaaaa agtcctctcc ttag         6234
```

<210> SEQ ID NO 45
<211> LENGTH: 354
<212> TYPE: PRT
<213> ORGANISM: Artificial sequence
<220> FEATURE:
<223> OTHER INFORMATION: SC_CAPNS1

<400> SEQUENCE: 45

Met Ala Asn Thr Lys Tyr Asn Glu Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30

Arg Ala Lys Phe Lys His Gln Leu Ser Leu Thr Phe Gln Val Thr Gln
            35                  40                  45

Lys Thr Gln Arg Arg Trp Leu Leu Asp Lys Leu Val Asp Glu Ile Gly
        50                  55                  60

Val Gly Tyr Val Gln Asp Ser Gly Ser Val Ser Asn Tyr Arg Leu Ser

```
                65                  70                  75                  80
        Glu Ile Lys Pro Leu His Asn Phe Leu Thr Gln Leu Gln Pro Phe Leu
                        85                  90                  95
        Glu Leu Lys Gln Lys Gln Ala Asn Leu Val Leu Lys Ile Ile Glu Gln
                       100                 105                 110
        Leu Pro Ser Ala Lys Glu Ser Pro Asp Lys Phe Leu Glu Val Cys Thr
                       115                 120                 125
        Trp Ala Asp Gln Ile Ala Ala Leu Asn Asp Ser Lys Thr Arg Lys Thr
                130                 135                 140
        Thr Ser Glu Thr Val Arg Ala Val Leu Asp Ser Leu Ser Glu Lys Lys
        145                 150                 155                 160
        Lys Pro Ser Pro Ala Ala Gly Gly Ser Asp Lys Tyr Asn Gln Ala Leu
                        165                 170                 175
        Ser Lys Tyr Asn Gln Ala Leu Ser Lys Tyr Asn Gln Ala Leu Ser Gly
                       180                 185                 190
        Gly Gly Gly Ser Asn Lys Lys Phe Leu Leu Tyr Leu Ala Gly Phe Val
                       195                 200                 205
        Asp Ser Asp Gly Ser Ile Ile Ala Gln Ile Lys Pro Arg Gln Ser Tyr
                210                 215                 220
        Lys Phe Lys His Gln Leu Arg Leu Thr Phe Tyr Val Thr Gln Lys Thr
        225                 230                 235                 240
        Gln Arg Arg Trp Phe Leu Asp Lys Leu Val Asp Arg Ile Gly Val Gly
                        245                 250                 255
        Tyr Val Glu Asp Ser Gly Ser Val Ser Arg Tyr Val Leu Ser Glu Ile
                       260                 265                 270
        Lys Pro Leu His Asn Phe Leu Thr Gln Leu Gln Pro Phe Leu Lys Leu
                       275                 280                 285
        Lys Gln Lys Gln Ala Asn Leu Val Leu Lys Ile Ile Glu Gln Leu Pro
                290                 295                 300
        Ser Ala Lys Glu Ser Pro Asp Lys Phe Leu Glu Val Cys Thr Trp Val
        305                 310                 315                 320
        Asp Gln Val Ala Ala Leu Asn Asp Ser Lys Thr Arg Lys Thr Thr Ser
                        325                 330                 335
        Glu Thr Val Arg Ala Val Leu Asp Ser Leu Ser Glu Lys Lys Lys Ser
                       340                 345                 350
        Ser Pro

<210> SEQ ID NO 46
<211> LENGTH: 6089
<212> TYPE: DNA
<213> ORGANISM: Artificial sequence
<220> FEATURE:
<223> OTHER INFORMATION: pCLS2222

<400> SEQUENCE: 46
atggccaata ccaaatataa cgaagagttc ctgctgtacc tggccggctt tgtggacggt      60
gacggtagca tcatcgctca gattaatcca aaccagtctt ctaagtttaa acatcgtcta     120
cgtttgacct tttatgtgac tcaaaagacc cagcgccgtt ggtttctgga caaactagtg     180
gatgaaattg gcgttggtta cgtacgtgat tctggatccg tttcccagta cgttttaagc     240
gaaatcaagc cgctgcacaa cttcctgact caactgcagc cgtttctgga actgaaacag     300
aaacaggcaa acctggttct gaaaattatc gaacagctgc cgtctgcaaa agaatccccg     360
gacaaattcc tggaagtttg tacctgggtg gatcagattg cagctctgaa cgattctaag     420
```

```
acgcgtaaaa ccacttctga aaccgttcgt gctgtgctgg acagcctgag cgggaagaag      480
aaatcctccc cggcggccgg tggatctgat aagtataatc aggctctgtc taaatacaac      540
caagcactgt ccaagtacaa tcaggccctg tctggtggag gcggttccaa caaaaagttc      600
ctgctgtatc ttgctggatt tgtggattct gatggctcca tcattgctca gataaaacca      660
cgtcaatcta acaagttcaa acaccagctc tccttgactt ttgcagtcac tcagaagaca      720
caaagaaggt ggttcttgga caaattggtt gataggattg gtgtgggcta tgtctatgac      780
agtggctctg tgtcagacta ccgcctgtct gaaattaagc tcttcataa ctttctcacc       840
caactgcaac ccttcttgaa gctcaaacag aagcaagcaa atctggtttt gaaaatcatc      900
gagcaactgc catctgccaa ggagtcccct gacaagtttc ttgaagtgtg tacttgggtg      960
gatcagattg ctgccttgaa tgactccaag accagaaaaa ccacctctga gactgtgagg     1020
gcagttctgg atagcctctc tgagaagaaa aagtcctctc cttagtctag agggcccgcg     1080
gttcgaaggt aagcctatcc ctaaccctct cctcggtctc gattctacgc gtaccggtta     1140
gtaatgagtt taaacggggg aggctaactg aaacacggaa ggagacaata ccggaaggaa     1200
cccgcgctat gacggcaata aaaagacaga ataaaacgca cgggtgttgg gtcgtttgtt     1260
cataaacgcg gggttcggtc ccagggctgg cactctgtcg ataccccacc gagacccat      1320
tggggccaat acgcccgcgt ttcttccttt tcccccacccc accccccaag ttcgggtgaa     1380
ggcccagggc tcgcagccaa cgtcggggcg gcaggccctg ccatagcaga tctgcgcagc     1440
tggggctcta gggggtatcc ccacgcgccc tgtagcggcg cattaagcgc ggcgggtgtg     1500
gtggttacgc gcagcgtgac cgctacactt gccagcgccc tagcgcccgc tcctttcgct     1560
ttcttccctt cctttctcgc cacgttcgcc ggctttcccc gtcaagctct aaatcggggc     1620
atccctttag ggttccgatt tagtgcttta cggcacctcg accccaaaaa acttgattag     1680
ggtgatggtt cacgtagtgg gccatcgccc tgatagacgg ttttcgccc tttgacgttg      1740
gagtccacgt tctttaatag tggactcttg ttccaaactg gaacaacact caaccctatc     1800
tcggtctatt cttttgattt ataagggatt ttggggattt cggcctattg gttaaaaaat     1860
gagctgattt aacaaaaatt taacgcgaat taattctgtg aatgtgtgt cagttagggt      1920
gtggaaagtc cccaggctcc ccagcaggca gaagtatgca aagcatgcat ctcaattagt     1980
cagcaaccag gtgtggaaag tccccaggct ccccagcagg cagaagtatg caaagcatgc     2040
atctcaatta gtcagcaacc atagtcccgc ccctaactcc gcccatcccg cccctaactc     2100
cgcccagttc cgcccattct ccgccccatg gctgactaat tttttttatt tatgcagagg     2160
ccgaggccgc ctctgcctct gagctattcc agaagtagtg aggaggcttt tttggaggcc     2220
taggcttttg caaaaagctc ccgggagctt gtatatccat tttcggatct gatcagcacg     2280
tgttgacaat taatcatcgg catagtatat cggcatagta taatacgaca aggtgaggaa     2340
ctaaaccatg gccaagcctt tgtctcaaga agaatccacc ctcattgaaa gagcaacggc     2400
tacaatcaac agcatcccca tctctgaaga ctacagcgtc gccagcgcag ctctctctag     2460
cgacggccgc atcttcactg gtgtcaatgt atatcatttt actggggggac cttgtgcaga     2520
actcgtggtg ctgggcactg ctgctgctgc ggcagctggc aacctgactt gtatcgtcgc     2580
gatcggaaat gagaacaggg gcatcttgag cccctgcgga cggtgccgac aggtgcttct     2640
cgatctgcat cctgggatca aagccatagt gaaggacagt gatggacagc cgacggcagt     2700
tgggattcgt gaattgctgc cctctggtta tgtgtgggag ggctaagcac ttcgtggccg     2760
aggagcagga ctgacacgtg ctacgagatt tcgattccac cgccgccttc tatgaaaggt     2820
```

```
tgggcttcgg aatcgttttc cgggacgccg gctggatgat cctccagcgc ggggatctca  2880
tgctggagtt cttcgcccac cccaacttgt ttattgcagc ttataatggt tacaaataaa  2940
gcaatagcat cacaaatttc acaaataaag catttttttc actgcattct agttgtggtt  3000
tgtccaaact catcaatgta tcttatcatg tctgtatacc gtcgacctct agctagagct  3060
tggcgtaatc atggtcatag ctgtttcctg tgtgaaattg ttatccgctc acaattccac  3120
acaacatacg agccggaagc ataaagtgta aagcctgggg tgcctaatga gtgagctaac  3180
tcacattaat tgcgttgcgc tcactgcccg ctttccagtc gggaaacctg tcgtgccagc  3240
tgcattaatg aatcggccaa cgcgcgggga gaggcggttt gcgtattggg cgctcttccg  3300
cttcctcgct cactgactcg ctgcgctcgg tcgttcggct gcggcgagcg gtatcagctc  3360
actcaaaggc ggtaatacgg ttatccacag aatcagggga taacgcagga agaacatgt  3420
gagcaaaagg ccagcaaaag gccaggaacc gtaaaaaggc cgcgttgctg gcgttttcc  3480
ataggctccg cccccctgac gagcatcaca aaaatcgacg ctcaagtcag aggtggcgaa  3540
acccgacagg actataaaga taccaggcgt ttccccctgg aagctccctc gtgcgctctc  3600
ctgttccgac cctgccgctt accggatacc tgtccgcctt ctcccttcg ggaagcgtgg  3660
cgctttctca tagctcacgc tgtaggtatc tcagttcggt gtaggtcgtt cgctccaagc  3720
tgggctgtgt gcacgaaccc cccgttcagc ccgaccgctg cgccttatcc ggtaactatc  3780
gtcttgagtc caacccggta agacacgact tatcgccact ggcagcagcc actggtaaca  3840
ggattagcag agcgaggtat gtaggcggtg ctacagagtt cttgaagtgg tggcctaact  3900
acggctacac tagaagaaca gtatttggta tctgcgctct gctgaagcca gttaccttcg  3960
gaaaaagagt tggtagctct tgatccggca acaaaccac cgctggtagc ggttttttg  4020
tttgcaagca gcagattacg cgcagaaaaa aaggatctca agaagatcct ttgatctttt  4080
ctacggggtc tgacgctcag tggaacgaaa actcacgtta agggattttg gtcatgagat  4140
tatcaaaaag gatcttcacc tagatccttt taaattaaaa atgaagtttt aaatcaatct  4200
aaagtatata tgagtaaact tggtctgaca gttaccaatg cttaatcagt gaggcaccta  4260
tctcagcgat ctgtctattt cgttcatcca tagttgcctg actccccgtc gtgtagataa  4320
ctacgatacg ggagggctta ccatctggcc ccagtgctgc aatgataccg cgagacccac  4380
gctcaccggc tccagattta tcagcaataa accagccagc cggaagggcc gagcgcagaa  4440
gtggtcctgc aactttatcc gcctccatcc agtctattaa ttgttgccgg gaagctagag  4500
taagtagttc gccagttaat agtttgcgca acgttgttgc cattgctaca ggcatcgtgg  4560
tgtcacgctc gtcgtttggt atggcttcat tcagctccgg ttcccaacga tcaaggcgag  4620
ttacatgatc ccccatgttg tgcaaaaaag cggttagctc cttcggtcct ccgatcgttg  4680
tcagaagtaa gttggccgca gtgttatcac tcatggttat ggcagcactg cataattctc  4740
ttactgtcat gccatccgta agatgctttt ctgtgactgg tgagtactca accaagtcat  4800
tctgagaata gtgtatgcgg cgaccgagtt gctcttgccc ggcgtcaata cgggataata  4860
ccgcgccaca tagcagaact ttaaaagtgc tcatcattgg aaaacgttct cggggcgaa  4920
aactctcaag gatcttaccg ctgttgagat ccagttcgat gtaacccact cgtgcaccca  4980
actgatcttc agcatctttt actttcacca gcgtttctgg gtgagcaaaa acaggaaggc  5040
aaaatgccgc aaaaagggaa taagggcga cacggaaatg ttgaatactc atactcttcc  5100
tttttcaata ttattgaagc atttatcagg gttattgtct catgagcgga tacatatttg  5160
```

```
aatgtattta gaaaaataaa caaatagggg ttccgcgcac atttccccga aaagtgccac      5220
ctgacgtcga cggatcggga gatccccga tccctatgg tgcactctca gtacaatctg       5280
ctctgatgcc gcatagttaa gccagtatct gctccctgct tgtgtgttgg aggtcgctga     5340
gtagtgcgcg agcaaaattt aagctacaac aaggcaaggc ttgaccgaca attgcatgaa     5400
gaatctgctt agggttaggc gttttgcgct gcttcgcgat gtacgggcca gatatacgcg     5460
ttgacattga ttattgacta gttattaata gtaatcaatt acgggtcat tagttcatag      5520 cccatatatg gagttccgcg ttacataact tacggtaaat ggcccgcctg gctgaccgcc     5580
caacgacccc cgcccattga cgtcaataat gacgtatgtt cccatagtaa cgccaatagg     5640
gactttccat tgacgtcaat gggtggagta tttacggtaa actgcccact tggcagtaca    5700
tcaagtgtat catatgccaa gtacgccccc tattgacgtc aatgacggta aatggcccgc    5760
ctggcattat gcccagtaca tgaccttatg gactttcct acttggcagt acatctacgt     5820
attagtcatc gctattacca tggtgatgcg gttttggcag tacatcaatg ggcgtggata    5880
gcggtttgac tcacggggat ttccaagtct ccaccccatt gacgtcaatg ggagtttgtt    5940
ttggcaccaa aatcaacggg actttccaaa atgtcgtaac aactccgccc cattgacgca    6000
aatgggcggt aggcgtgtac ggtgggaggt ctatataagc agagctctct ggctaactag    6060
agaacccact gcttactggc ttatcgacc                                        6089
```

<210> SEQ ID NO 47
<211> LENGTH: 354
<212> TYPE: PRT
<213> ORGANISM: Artificial sequence
<220> FEATURE:
<223> OTHER INFORMATION: SC_RAG

<400> SEQUENCE: 47

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Asn Pro Asn Gln
                20                  25                  30

Ser Ser Lys Phe Lys His Arg Leu Arg Leu Thr Phe Tyr Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Gln Tyr Val Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Gly Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
```

```
                195                 200                 205
Asp Ser Asp Gly Ser Ile Ile Ala Gln Ile Lys Pro Arg Gln Ser Asn
    210                 215                 220

Lys Phe Lys His Gln Leu Ser Leu Thr Phe Ala Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 48
<211> LENGTH: 60
<212> TYPE: DNA
<213> ORGANISM: Artificial sequence
<220> FEATURE:
<223> OTHER INFORMATION: CAPNS1 locus specific forward primer
<220> FEATURE:
<221> NAME/KEY: misc_feature
<222> LOCATION: (31)..(40)
<223> OTHER INFORMATION: n is a or c or t or g

<400> SEQUENCE: 48
ccatctcatc cctgcgtgtc tccgactcag nnnnnnnnnn cgagtcaggg cgggattaag    60

<210> SEQ ID NO 49
<211> LENGTH: 67
<212> TYPE: DNA
<213> ORGANISM: Artificial sequence
<220> FEATURE:
<223> OTHER INFORMATION: RAG1 locus specific forward primer
<220> FEATURE:
<221> NAME/KEY: misc_feature
<222> LOCATION: (31)..(40)
<223> OTHER INFORMATION: n is a or c or t or g

<400> SEQUENCE: 49
ccatctcatc cctgcgtgtc tccgactcag nnnnnnnnnn ggcaaagatg aatcaaagat    60
tctgtcc                                                             67

<210> SEQ ID NO 50
<211> LENGTH: 50
<212> TYPE: DNA
<213> ORGANISM: Artificial sequence
<220> FEATURE:
<223> OTHER INFORMATION: CAPNS1 locus specific reverse primer

<400> SEQUENCE: 50
cctatcccct gtgtgccttg gcagtctcag cgagacttca cggtttcgcc              50

<210> SEQ ID NO 51
```

```
<211> LENGTH: 57
<212> TYPE: DNA
<213> ORGANISM: Artificial sequence
<220> FEATURE:
<223> OTHER INFORMATION: RAG1 locus specific reverse primer

<400> SEQUENCE: 51
cctatcccct gtgtgccttg gcagtctcag gatctcaccc ggaacagctt aaatttc      57

<210> SEQ ID NO 52
<211> LENGTH: 600
<212> TYPE: PRT
<213> ORGANISM: Artificial sequence
<220> FEATURE:
<223> OTHER INFORMATION: SC_GS-10_Trex

<400> SEQUENCE: 52
```

Met Ala Asn Thr Lys Tyr Asn Glu Glu Phe Leu Leu Tyr Leu Ala Gly
1               5                   10                  15

Phe Val Asp Ala Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Ala Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Gly Asp Gly Ser Ile Ile Ala Gln Ile Lys Pro Arg Gln Gly Tyr
    210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Leu Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro Gly Gly Gly Ser Gly Gly Gly Ser Glu Ala Pro Arg
        355                 360                 365

Ala Glu Thr Phe Val Phe Leu Asp Leu Glu Ala Thr Gly Leu Pro Ser
        370                 375                 380

Val Glu Pro Glu Ile Ala Glu Leu Ser Leu Phe Ala Val His Arg Ser
385                 390                 395                 400

Ser Leu Glu Asn Pro Glu His Asp Glu Ser Gly Ala Leu Val Leu Pro
            405                 410                 415

Arg Val Leu Asp Lys Leu Thr Leu Cys Met Cys Pro Glu Arg Pro Phe
            420                 425                 430

Thr Ala Lys Ala Ser Glu Ile Thr Gly Leu Ser Ser Glu Gly Leu Ala
            435                 440                 445

Arg Cys Arg Lys Ala Gly Phe Asp Gly Ala Val Val Arg Thr Leu Gln
        450                 455                 460

Ala Phe Leu Ser Arg Gln Ala Gly Pro Ile Cys Leu Val Ala His Asn
465                 470                 475                 480

Gly Phe Asp Tyr Asp Phe Pro Leu Leu Cys Ala Glu Leu Arg Arg Leu
            485                 490                 495

Gly Ala Arg Leu Pro Arg Asp Thr Val Cys Leu Asp Thr Leu Pro Ala
            500                 505                 510

Leu Arg Gly Leu Asp Arg Ala His Ser His Gly Thr Arg Ala Arg Gly
        515                 520                 525

Arg Gln Gly Tyr Ser Leu Gly Ser Leu Phe His Arg Tyr Phe Arg Ala
        530                 535                 540

Glu Pro Ser Ala Ala His Ser Ala Glu Gly Asp Val His Thr Leu Leu
545                 550                 555                 560

Leu Ile Phe Leu His Arg Ala Ala Glu Leu Leu Ala Trp Ala Asp Glu
            565                 570                 575

Gln Ala Arg Gly Trp Ala His Ile Glu Pro Met Tyr Leu Pro Pro Asp
        580                 585                 590

Asp Pro Ser Leu Glu Ala Ala Asp
        595                 600

<210> SEQ ID NO 53
<211> LENGTH: 599
<212> TYPE: PRT
<213> ORGANISM: Artificial sequence
<220> FEATURE:
<223> OTHER INFORMATION: Trex-10-SC_GS

<400> SEQUENCE: 53

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
            20                  25                  30

Leu Phe Ala Val His Arg Ser Ser Leu Glu Asn Pro Glu His Asp Glu
        35                  40                  45

Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
65                  70                  75                  80

```
Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Ile Phe Leu His Arg Ala Ala Glu
        195                 200                 205

Leu Leu Ala Trp Ala Asp Glu Gln Ala Arg Gly Trp Ala His Ile Glu
    210                 215                 220

Pro Met Tyr Leu Pro Pro Asp Asp Pro Ser Leu Glu Ala Gly Gly Gly
225                 230                 235                 240

Gly Ser Gly Gly Gly Ser Asn Thr Lys Tyr Asn Glu Glu Phe Leu
                245                 250                 255

Leu Tyr Leu Ala Gly Phe Val Asp Ala Asp Gly Ser Ile Ile Ala Gln
            260                 265                 270

Ile Lys Pro Arg Gln Ser Arg Lys Phe Lys His Glu Leu Ser Leu Thr
        275                 280                 285

Phe Asp Val Thr Gln Lys Thr Gln Arg Arg Trp Phe Leu Asp Lys Leu
    290                 295                 300

Val Asp Glu Ile Gly Val Gly Tyr Val Tyr Asp Ser Gly Ser Val Ser
305                 310                 315                 320

Tyr Tyr Gln Leu Ser Glu Ile Lys Pro Leu His Asn Phe Leu Thr Gln
                325                 330                 335

Leu Gln Pro Phe Leu Glu Leu Lys Gln Lys Gln Ala Asn Leu Val Leu
            340                 345                 350

Lys Ile Ile Glu Gln Leu Pro Ser Ala Lys Glu Ser Pro Ala Lys Phe
        355                 360                 365

Leu Glu Val Cys Thr Trp Val Asp Gln Ile Ala Ala Leu Asn Asp Ser
    370                 375                 380

Lys Thr Arg Lys Thr Thr Ser Glu Thr Val Arg Ala Val Leu Asp Ser
385                 390                 395                 400

Leu Ser Glu Lys Lys Lys Ser Ser Pro Ala Ala Gly Gly Ser Asp Lys
                405                 410                 415

Tyr Asn Gln Ala Leu Ser Lys Tyr Asn Gln Ala Leu Ser Lys Tyr Asn
            420                 425                 430

Gln Ala Leu Ser Gly Gly Gly Ser Asn Lys Lys Phe Leu Leu Tyr
        435                 440                 445

Leu Ala Gly Phe Val Asp Gly Asp Gly Ser Ile Ile Ala Gln Ile Lys
    450                 455                 460

Pro Arg Gln Gly Tyr Lys Phe Lys His Gln Leu Ser Leu Thr Phe Gln
465                 470                 475                 480

Val Thr Gln Lys Thr Gln Arg Arg Trp Phe Leu Asp Lys Leu Val Asp
                485                 490                 495
```

Arg Ile Gly Val Gly Tyr Val Ala Asp Arg Gly Ser Val Ser Asp Tyr
            500                 505                 510

Arg Leu Ser Glu Ile Lys Pro Leu His Asn Phe Leu Thr Gln Leu Gln
        515                 520                 525

Pro Phe Leu Lys Leu Lys Gln Lys Gln Ala Asn Leu Val Leu Lys Ile
    530                 535                 540

Ile Glu Gln Leu Pro Ser Ala Lys Glu Ser Leu Asp Lys Phe Leu Glu
545                 550                 555                 560

Val Cys Thr Trp Val Asp Gln Ile Ala Ala Leu Asn Asp Ser Lys Thr
                565                 570                 575

Arg Lys Thr Thr Ser Glu Thr Val Arg Ala Val Leu Asp Ser Leu Ser
            580                 585                 590

Glu Lys Lys Lys Ser Ser Pro
            595

<210> SEQ ID NO 54
<211> LENGTH: 599
<212> TYPE: PRT
<213> ORGANISM: Artificial sequence
<220> FEATURE:
<223> OTHER INFORMATION: Trex-SC_CAPNS1

<400> SEQUENCE: 54

Met Gly Ser Glu Ala Pro Arg Ala Glu Thr Phe Val Phe Leu Asp Leu
1               5                   10                  15

Glu Ala Thr Gly Leu Pro Ser Val Gly Pro Glu Ile Ala Glu Leu Ser
            20                  25                  30

Leu Phe Ala Val His Arg Ser Ser Leu Glu Asn Pro His Asp Glu
        35                  40                  45

Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
65                  70                  75                  80

Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
    130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Leu Ile Phe Leu His Arg Ala Ala Glu
        195                 200                 205

Leu Leu Ala Trp Ala Asp Glu Gln Ala Arg Gly Trp Ala His Ile Glu
    210                 215                 220

Pro Met Tyr Leu Pro Pro Asp Asp Pro Ser Leu Glu Ala Gly Gly Gly
225                 230                 235                 240

Gly Ser Gly Gly Gly Ser Asn Thr Lys Tyr Asn Glu Glu Phe Leu
                245                 250                 255

Leu Tyr Leu Ala Gly Phe Val Asp Gly Asp Gly Ser Ile Val Ala Gln
                260                 265                 270

Ile Lys Pro Asn Gln Arg Ala Lys Phe Lys His Gln Leu Ser Leu Thr
            275                 280                 285

Phe Gln Val Thr Gln Lys Thr Gln Arg Arg Trp Leu Leu Asp Lys Leu
        290                 295                 300

Val Asp Glu Ile Gly Val Gly Tyr Val Gln Asp Ser Gly Ser Val Ser
305                 310                 315                 320

Asn Tyr Arg Leu Ser Glu Ile Lys Pro Leu His Asn Phe Leu Thr Gln
                325                 330                 335

Leu Gln Pro Phe Leu Glu Leu Lys Gln Lys Gln Ala Asn Leu Val Leu
            340                 345                 350

Lys Ile Ile Glu Gln Leu Pro Ser Ala Lys Glu Ser Pro Asp Lys Phe
        355                 360                 365

Leu Glu Val Cys Thr Trp Ala Asp Gln Ile Ala Ala Leu Asn Asp Ser
370                 375                 380

Lys Thr Arg Lys Thr Thr Ser Glu Thr Val Arg Ala Val Leu Asp Ser
385                 390                 395                 400

Leu Ser Glu Lys Lys Lys Pro Ser Pro Ala Ala Gly Gly Ser Asp Lys
                405                 410                 415

Tyr Asn Gln Ala Leu Ser Lys Tyr Asn Gln Ala Leu Ser Lys Tyr Asn
            420                 425                 430

Gln Ala Leu Ser Gly Gly Gly Gly Ser Asn Lys Lys Phe Leu Leu Tyr
        435                 440                 445

Leu Ala Gly Phe Val Asp Ser Asp Gly Ser Ile Ile Ala Gln Ile Lys
450                 455                 460

Pro Arg Gln Ser Tyr Lys Phe Lys His Gln Leu Arg Leu Thr Phe Tyr
465                 470                 475                 480

Val Thr Gln Lys Thr Gln Arg Arg Trp Phe Leu Asp Lys Leu Val Asp
                485                 490                 495

Arg Ile Gly Val Gly Tyr Val Glu Asp Ser Gly Ser Val Ser Arg Tyr
            500                 505                 510

Val Leu Ser Glu Ile Lys Pro Leu His Asn Phe Leu Thr Gln Leu Gln
        515                 520                 525

Pro Phe Leu Lys Leu Lys Gln Lys Gln Ala Asn Leu Val Leu Lys Ile
530                 535                 540

Ile Glu Gln Leu Pro Ser Ala Lys Glu Ser Pro Asp Lys Phe Leu Glu
545                 550                 555                 560

Val Cys Thr Trp Val Asp Gln Val Ala Ala Leu Asn Asp Ser Lys Thr
                565                 570                 575

Arg Lys Thr Thr Ser Glu Thr Val Arg Ala Val Leu Asp Ser Leu Ser
            580                 585                 590

Glu Lys Lys Lys Ser Ser Pro
        595

<210> SEQ ID NO 55
<211> LENGTH: 599
<212> TYPE: PRT
<213> ORGANISM: Artificial sequence
<220> FEATURE:
<223> OTHER INFORMATION: Trex-SC_RAG

<400> SEQUENCE: 55

Met Gly Ser Glu Ala Pro Arg Ala Glu Thr Phe Val Phe Leu Asp Leu
1               5                   10                  15

```
Glu Ala Thr Gly Leu Pro Ser Val Glu Pro Glu Ile Ala Glu Leu Ser
                 20                  25                  30
Leu Phe Ala Val His Arg Ser Ser Leu Glu Asn Pro Glu His Asp Glu
             35                  40                  45
Ser Gly Ala Leu Val Leu Pro Arg Val Leu Asp Lys Leu Thr Leu Cys
         50                  55                  60
Met Cys Pro Glu Arg Pro Phe Thr Ala Lys Ala Ser Glu Ile Thr Gly
 65                  70                  75                  80
Leu Ser Ser Glu Gly Leu Ala Arg Cys Arg Lys Ala Gly Phe Asp Gly
                 85                  90                  95
Ala Val Val Arg Thr Leu Gln Ala Phe Leu Ser Arg Gln Ala Gly Pro
            100                 105                 110
Ile Cys Leu Val Ala His Asn Gly Phe Asp Tyr Asp Phe Pro Leu Leu
            115                 120                 125
Cys Ala Glu Leu Arg Arg Leu Gly Ala Arg Leu Pro Arg Asp Thr Val
            130                 135                 140
Cys Leu Asp Thr Leu Pro Ala Leu Arg Gly Leu Asp Arg Ala His Ser
145                 150                 155                 160
His Gly Thr Arg Ala Arg Gly Arg Gln Gly Tyr Ser Leu Gly Ser Leu
                165                 170                 175
Phe His Arg Tyr Phe Arg Ala Glu Pro Ser Ala Ala His Ser Ala Glu
            180                 185                 190
Gly Asp Val His Thr Leu Leu Leu Ile Phe Leu His Arg Ala Ala Glu
            195                 200                 205
Leu Leu Ala Trp Ala Asp Glu Gln Ala Arg Gly Trp Ala His Ile Glu
            210                 215                 220
Pro Met Tyr Leu Pro Pro Asp Asp Pro Ser Leu Glu Ala Gly Gly Gly
225                 230                 235                 240
Gly Ser Gly Gly Gly Ser Asn Thr Lys Tyr Asn Glu Glu Phe Leu
                245                 250                 255
Leu Tyr Leu Ala Gly Phe Val Asp Gly Asp Gly Ser Ile Ile Ala Gln
            260                 265                 270
Ile Asn Pro Asn Gln Ser Ser Lys Phe Lys His Arg Leu Arg Leu Thr
            275                 280                 285
Phe Tyr Val Thr Gln Lys Thr Gln Arg Arg Trp Phe Leu Asp Lys Leu
            290                 295                 300
Val Asp Glu Ile Gly Val Gly Tyr Val Arg Asp Ser Gly Ser Val Ser
305                 310                 315                 320
Gln Tyr Val Leu Ser Glu Ile Lys Pro Leu His Asn Phe Leu Thr Gln
                325                 330                 335
Leu Gln Pro Phe Leu Glu Leu Lys Gln Lys Gln Ala Asn Leu Val Leu
            340                 345                 350
Lys Ile Ile Glu Gln Leu Pro Ser Ala Lys Glu Ser Pro Asp Lys Phe
            355                 360                 365
Leu Glu Val Cys Thr Trp Val Asp Gln Ile Ala Ala Leu Asn Asp Ser
            370                 375                 380
Lys Thr Arg Lys Thr Thr Ser Glu Thr Val Arg Ala Val Leu Asp Ser
385                 390                 395                 400
Leu Ser Gly Lys Lys Ser Ser Pro Ala Ala Gly Gly Ser Asp Lys
                405                 410                 415
Tyr Asn Gln Ala Leu Ser Lys Tyr Asn Gln Ala Leu Ser Lys Tyr Asn
            420                 425                 430
Gln Ala Leu Ser Gly Gly Gly Gly Ser Asn Lys Lys Phe Leu Leu Tyr
```

```
            435                 440                 445
Leu Ala Gly Phe Val Asp Ser Asp Gly Ser Ile Ile Ala Gln Ile Lys
    450                 455                 460

Pro Arg Gln Ser Asn Lys Phe Lys His Gln Leu Ser Leu Thr Phe Ala
465                 470                 475                 480

Val Thr Gln Lys Thr Gln Arg Arg Trp Phe Leu Asp Lys Leu Val Asp
                485                 490                 495

Arg Ile Gly Val Gly Tyr Val Tyr Asp Ser Gly Ser Val Ser Asp Tyr
            500                 505                 510

Arg Leu Ser Glu Ile Lys Pro Leu His Asn Phe Leu Thr Gln Leu Gln
        515                 520                 525

Pro Phe Leu Lys Leu Lys Gln Lys Gln Ala Asn Leu Val Leu Lys Ile
    530                 535                 540

Ile Glu Gln Leu Pro Ser Ala Lys Glu Ser Pro Asp Lys Phe Leu Glu
545                 550                 555                 560

Val Cys Thr Trp Val Asp Gln Ile Ala Ala Leu Asn Asp Ser Lys Thr
                565                 570                 575

Arg Lys Thr Thr Ser Glu Thr Val Arg Ala Val Leu Asp Ser Leu Ser
            580                 585                 590

Glu Lys Lys Lys Ser Ser Pro
        595
```

<210> SEQ ID NO 56
<211> LENGTH: 845
<212> TYPE: PRT
<213> ORGANISM: Artificial sequence
<220> FEATURE:
<223> OTHER INFORMATION: scTrex2-10-SC_GS

<400> SEQUENCE: 56

```
Met Gly Ser Glu Ala Pro Arg Ala Glu Thr Phe Val Phe Leu Asp Leu
1               5                   10                  15

Glu Ala Thr Gly Leu Pro Ser Val Glu Pro Gly Ile Ala Glu Leu Ser
            20                  25                  30

Leu Phe Ala Val His Arg Ser Ser Leu Glu Asn Pro Glu His Asp Glu
        35                  40                  45

Ser Gly Ala Leu Val Leu Pro Arg Val Leu Asp Lys Leu Thr Leu Cys
    50                  55                  60

Met Cys Pro Glu Arg Pro Phe Thr Ala Lys Ala Ser Glu Ile Thr Gly
65                  70                  75                  80

Leu Ser Ser Glu Gly Leu Ala Arg Cys Arg Lys Ala Gly Phe Asp Gly
                85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
        115                 120                 125

Cys Ala Glu Leu Arg Arg Leu Gly Ala Arg Leu Pro Arg Asp Thr Val
    130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
            180                 185                 190

Gly Asp Val His Thr Leu Leu Leu Ile Phe Leu His Arg Ala Ala Glu
```

-continued

```
                195                 200                 205
Leu Leu Ala Trp Ala Asp Glu Gln Ala Arg Gly Trp Ala His Ile Glu
210                 215                 220
Pro Met Tyr Leu Pro Pro Asp Asp Pro Ser Leu Glu Ala Thr Pro Pro
225                 230                 235                 240
Gln Thr Gly Leu Asp Val Pro Tyr Ser Glu Ala Pro Arg Ala Glu Thr
                245                 250                 255
Phe Val Phe Leu Asp Leu Glu Ala Thr Gly Leu Pro Ser Val Glu Pro
                260                 265                 270
Glu Ile Ala Glu Leu Ser Leu Phe Ala Val His Arg Ser Ser Leu Glu
                275                 280                 285
Asn Pro Glu His Asp Glu Ser Gly Ala Leu Val Leu Pro Arg Val Leu
290                 295                 300
Asp Lys Leu Thr Leu Cys Met Cys Pro Glu Arg Pro Phe Thr Ala Lys
305                 310                 315                 320
Ala Ser Glu Ile Thr Gly Leu Ser Ser Glu Gly Leu Ala Arg Cys Arg
                325                 330                 335
Lys Ala Gly Phe Asp Gly Ala Val Val Arg Thr Leu Gln Ala Phe Leu
                340                 345                 350
Ser Arg Gln Ala Gly Pro Ile Cys Leu Val Ala His Asn Gly Phe Asp
                355                 360                 365
Tyr Asp Phe Pro Leu Leu Cys Ala Glu Leu Arg Arg Leu Gly Ala Arg
                370                 375                 380
Leu Pro Arg Asp Thr Val Cys Leu Asp Thr Leu Pro Ala Leu Arg Gly
385                 390                 395                 400
Leu Asp Arg Ala His Ser His Gly Thr Arg Ala Arg Gly Arg Gln Gly
                405                 410                 415
Tyr Ser Leu Gly Ser Leu Phe His Arg Tyr Phe Arg Ala Glu Pro Ser
                420                 425                 430
Ala Ala His Ser Ala Glu Gly Asp Val His Thr Leu Leu Leu Ile Phe
                435                 440                 445
Leu His Arg Ala Ala Glu Leu Leu Ala Trp Ala Asp Glu Gln Ala Arg
                450                 455                 460
Gly Trp Ala His Ile Glu Pro Met Tyr Leu Pro Pro Asp Asp Pro Ser
465                 470                 475                 480
Leu Glu Ala Gly Gly Gly Gly Ser Gly Gly Gly Ser Asn Thr Lys
                485                 490                 495
Tyr Asn Glu Glu Phe Leu Leu Tyr Leu Ala Gly Phe Val Asp Ala Asp
                500                 505                 510
Gly Ser Ile Ile Ala Gln Ile Lys Pro Arg Gln Ser Arg Lys Phe Lys
                515                 520                 525
His Glu Leu Ser Leu Thr Phe Asp Val Thr Gln Lys Thr Gln Arg Arg
                530                 535                 540
Trp Phe Leu Asp Lys Leu Val Asp Glu Ile Gly Val Gly Tyr Val Tyr
545                 550                 555                 560
Asp Ser Gly Ser Val Ser Tyr Tyr Gln Leu Ser Glu Ile Lys Pro Leu
                565                 570                 575
His Asn Phe Leu Thr Gln Leu Gln Pro Phe Leu Glu Leu Lys Gln Lys
                580                 585                 590
Gln Ala Asn Leu Val Leu Lys Ile Ile Glu Gln Leu Pro Ser Ala Lys
                595                 600                 605
Glu Ser Pro Ala Lys Phe Leu Glu Val Cys Thr Trp Val Asp Gln Ile
610                 615                 620
```

Ala Ala Leu Asn Asp Ser Lys Thr Arg Lys Thr Thr Ser Glu Thr Val
625                 630                 635                 640

Arg Ala Val Leu Asp Ser Leu Ser Glu Lys Lys Ser Ser Pro Ala
            645                 650                 655

Ala Gly Gly Ser Asp Lys Tyr Asn Gln Ala Leu Ser Lys Tyr Asn Gln
            660                 665                 670

Ala Leu Ser Lys Tyr Asn Gln Ala Leu Ser Gly Gly Gly Gly Ser Asn
        675                 680                 685

Lys Lys Phe Leu Leu Tyr Leu Ala Gly Phe Val Asp Gly Asp Gly Ser
        690                 695                 700

Ile Ile Ala Gln Ile Lys Pro Arg Gln Gly Tyr Lys Phe Lys His Gln
705                 710                 715                 720

Leu Ser Leu Thr Phe Gln Val Thr Gln Lys Thr Gln Arg Arg Trp Phe
                725                 730                 735

Leu Asp Lys Leu Val Asp Arg Ile Gly Val Gly Tyr Val Ala Asp Arg
            740                 745                 750

Gly Ser Val Ser Asp Tyr Arg Leu Ser Glu Ile Lys Pro Leu His Asn
        755                 760                 765

Phe Leu Thr Gln Leu Gln Pro Phe Leu Lys Leu Lys Gln Lys Gln Ala
        770                 775                 780

Asn Leu Val Leu Lys Ile Ile Glu Gln Leu Pro Ser Ala Lys Glu Ser
785                 790                 795                 800

Leu Asp Lys Phe Leu Glu Val Cys Thr Trp Val Asp Gln Ile Ala Ala
                805                 810                 815

Leu Asn Asp Ser Lys Thr Arg Lys Thr Thr Ser Glu Thr Val Arg Ala
            820                 825                 830

Val Leu Asp Ser Leu Ser Glu Lys Lys Ser Ser Pro
        835                 840                 845

<210> SEQ ID NO 57
<211> LENGTH: 846
<212> TYPE: PRT
<213> ORGANISM: Artificial sequence
<220> FEATURE:
<223> OTHER INFORMATION: SC_GS-10-scTrex2

<400> SEQUENCE: 57

Met Ala Asn Thr Lys Tyr Asn Glu Glu Phe Leu Leu Tyr Leu Ala Gly
1               5                   10                  15

Phe Val Asp Ala Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Ala Lys Phe Leu Glu Val Cys Thr
        115                 120                 125

Trp Val Asp Gln Ile Ala Ala Leu Asn Asp Ser Lys Thr Arg Lys Thr
    130                 135                 140

```
Thr Ser Glu Thr Val Arg Ala Val Leu Asp Ser Leu Ser Glu Lys Lys
145                 150                 155                 160

Lys Ser Ser Pro Ala Gly Gly Ser Asp Lys Tyr Asn Gln Ala Leu
            165                 170                 175

Ser Lys Tyr Asn Gln Ala Leu Ser Lys Tyr Asn Gln Ala Leu Ser Gly
                180                 185                 190

Gly Gly Gly Ser Asn Lys Lys Phe Leu Leu Tyr Leu Ala Gly Phe Val
        195                 200                 205

Asp Gly Asp Gly Ser Ile Ile Ala Gln Ile Lys Pro Arg Gln Gly Tyr
        210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Arg Leu Ser Glu Ile
                260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
        290                 295                 300

Ser Ala Lys Glu Ser Leu Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro Gly Gly Gly Ser Gly Gly Gly Ser Glu Ala Pro Arg
        355                 360                 365

Ala Glu Thr Phe Val Phe Leu Asp Leu Glu Ala Thr Gly Leu Pro Ser
        370                 375                 380

Val Glu Pro Glu Ile Ala Glu Leu Ser Leu Phe Ala Val His Arg Ser
385                 390                 395                 400

Ser Leu Glu Asn Pro Glu His Asp Glu Ser Gly Ala Leu Val Leu Pro
                405                 410                 415

Arg Val Leu Asp Lys Leu Thr Leu Cys Met Cys Pro Glu Arg Pro Phe
                420                 425                 430

Thr Ala Lys Ala Ser Glu Ile Thr Gly Leu Ser Ser Glu Gly Leu Ala
        435                 440                 445

Arg Cys Arg Lys Ala Gly Phe Asp Gly Ala Val Val Arg Thr Leu Gln
        450                 455                 460

Ala Phe Leu Ser Arg Gln Ala Gly Pro Ile Cys Leu Val Ala His Asn
465                 470                 475                 480

Gly Phe Asp Tyr Asp Phe Pro Leu Leu Cys Ala Glu Leu Arg Arg Leu
                485                 490                 495

Gly Ala Arg Leu Pro Arg Asp Thr Val Cys Leu Asp Thr Leu Pro Ala
        500                 505                 510

Leu Arg Gly Leu Asp Arg Ala His Ser His Gly Thr Arg Ala Arg Gly
        515                 520                 525

Arg Gln Gly Tyr Ser Leu Gly Ser Leu Phe His Arg Tyr Phe Arg Ala
        530                 535                 540

Glu Pro Ser Ala Ala His Ser Ala Glu Gly Asp Val His Thr Leu Leu
545                 550                 555                 560
```

```
Leu Ile Phe Leu His Arg Ala Ala Glu Leu Leu Ala Trp Ala Asp Glu
                565                 570                 575

Gln Ala Arg Gly Trp Ala His Ile Glu Pro Met Tyr Leu Pro Pro Asp
            580                 585                 590

Asp Pro Ser Leu Glu Ala Thr Pro Pro Gln Thr Gly Leu Asp Val Pro
        595                 600                 605

Tyr Ser Glu Ala Pro Arg Ala Glu Thr Phe Val Phe Leu Asp Leu Glu
    610                 615                 620

Ala Thr Gly Leu Pro Ser Val Glu Pro Glu Ile Ala Glu Leu Ser Leu
625                 630                 635                 640

Phe Ala Val His Arg Ser Ser Leu Glu Asn Pro Glu His Asp Glu Ser
                645                 650                 655

Gly Ala Leu Val Leu Pro Arg Val Leu Asp Lys Leu Thr Leu Cys Met
            660                 665                 670

Cys Pro Glu Arg Pro Phe Thr Ala Lys Ala Ser Glu Ile Thr Gly Leu
        675                 680                 685

Ser Ser Glu Gly Leu Ala Arg Cys Arg Lys Ala Gly Phe Asp Gly Ala
    690                 695                 700

Val Val Arg Thr Leu Gln Ala Phe Leu Ser Arg Gln Ala Gly Pro Ile
705                 710                 715                 720

Cys Leu Val Ala His Asn Gly Phe Asp Tyr Asp Phe Pro Leu Leu Cys
                725                 730                 735

Ala Glu Leu Arg Arg Leu Gly Ala Arg Leu Pro Arg Asp Thr Val Cys
            740                 745                 750

Leu Asp Thr Leu Pro Ala Leu Arg Gly Leu Asp Arg Ala His Ser His
        755                 760                 765

Gly Thr Arg Ala Arg Gly Arg Gln Gly Tyr Ser Leu Gly Ser Leu Phe
    770                 775                 780

His Arg Tyr Phe Arg Ala Glu Pro Ser Ala Ala His Ser Ala Glu Gly
785                 790                 795                 800

Asp Val His Thr Leu Leu Leu Ile Phe Leu His Arg Ala Ala Glu Leu
                805                 810                 815

Leu Ala Trp Ala Asp Glu Gln Ala Arg Gly Trp Ala His Ile Glu Pro
            820                 825                 830

Met Tyr Leu Pro Pro Asp Asp Pro Ser Leu Glu Ala Ala Asp
        835                 840                 845

<210> SEQ ID NO 58
<211> LENGTH: 845
<212> TYPE: PRT
<213> ORGANISM: Artificial sequence
<220> FEATURE:
<223> OTHER INFORMATION: scTrex2_SC_CAPNS1

<400> SEQUENCE: 58

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
                20                  25                  30

Leu Phe Ala Val His Arg Ser Ser Leu Glu Asn Pro Glu His Asp Glu
            35                  40                  45

Ser Gly Ala Leu Val Leu Pro Arg Val Leu Asp Lys Leu Thr Leu Cys
        50                  55                  60

Met Cys Pro Glu Arg Pro Phe Thr Ala Lys Ala Ser Glu Ile Thr Gly
65                  70                  75                  80
```

```
Leu Ser Ser Glu Gly Leu Ala Arg Cys Arg Lys Ala Gly Phe Asp Gly
             85                  90                  95

Ala Val Val Arg Thr Leu Gln Ala Phe Leu Ser Arg Gln Ala Gly Pro
            100                 105                 110

Ile Cys Leu Val Ala His Asn Gly Phe Asp Tyr Asp Phe Pro Leu Leu
            115                 120                 125

Cys Ala Glu Leu Arg Arg Leu Gly Ala Arg Leu Pro Arg Asp Thr Val
            130                 135                 140

Cys Leu Asp Thr Leu Pro Ala Leu Arg Gly Leu Asp Arg Ala His Ser
145                 150                 155                 160

His Gly Thr Arg Ala Arg Gly Arg Gln Gly Tyr Ser Leu Gly Ser Leu
                165                 170                 175

Phe His Arg Tyr Phe Arg Ala Glu Pro Ser Ala Ala His Ser Ala Glu
                180                 185                 190

Gly Asp Val His Thr Leu Leu Ile Phe Leu His Arg Ala Ala Glu
                195                 200                 205

Leu Leu Ala Trp Ala Asp Glu Gln Ala Arg Gly Trp Ala His Ile Glu
            210                 215                 220

Pro Met Tyr Leu Pro Pro Asp Asp Pro Ser Leu Glu Ala Thr Pro Pro
225                 230                 235                 240

Gln Thr Gly Leu Asp Val Pro Tyr Ser Glu Ala Pro Arg Ala Glu Thr
                245                 250                 255

Phe Val Phe Leu Asp Leu Glu Ala Thr Gly Leu Pro Ser Val Glu Pro
                260                 265                 270

Glu Ile Ala Glu Leu Ser Leu Phe Ala Val His Arg Ser Ser Leu Glu
            275                 280                 285

Asn Pro Glu His Asp Glu Ser Gly Ala Leu Val Leu Pro Arg Val Leu
            290                 295                 300

Asp Lys Leu Thr Leu Cys Met Cys Pro Glu Arg Pro Phe Thr Ala Lys
305                 310                 315                 320

Ala Ser Glu Ile Thr Gly Leu Ser Ser Glu Gly Leu Ala Arg Cys Arg
                325                 330                 335

Lys Ala Gly Phe Asp Gly Ala Val Val Arg Thr Leu Gln Ala Phe Leu
                340                 345                 350

Ser Arg Gln Ala Gly Pro Ile Cys Leu Val Ala His Asn Gly Phe Asp
            355                 360                 365

Tyr Asp Phe Pro Leu Leu Cys Ala Glu Leu Arg Arg Leu Gly Ala Arg
            370                 375                 380

Leu Pro Arg Asp Thr Val Cys Leu Asp Thr Leu Pro Ala Leu Arg Gly
385                 390                 395                 400

Leu Asp Arg Ala His Ser His Gly Thr Arg Ala Arg Gly Arg Gln Gly
                405                 410                 415

Tyr Ser Leu Gly Ser Leu Phe His Arg Tyr Phe Arg Ala Glu Pro Ser
                420                 425                 430

Ala Ala His Ser Ala Glu Gly Asp Val His Thr Leu Leu Leu Ile Phe
            435                 440                 445

Leu His Arg Ala Ala Glu Leu Leu Ala Trp Ala Asp Glu Gln Ala Arg
            450                 455                 460

Gly Trp Ala His Ile Glu Pro Met Tyr Leu Pro Asp Asp Pro Ser
465                 470                 475                 480

Leu Glu Ala Gly Gly Gly Gly Ser Gly Gly Gly Ser Asn Thr Lys
                485                 490                 495

Tyr Asn Glu Glu Phe Leu Leu Tyr Leu Ala Gly Phe Val Asp Gly Asp
```

```
            500                 505                 510
Gly Ser Ile Val Ala Gln Ile Lys Pro Asn Gln Arg Ala Lys Phe Lys
        515                 520                 525
His Gln Leu Ser Leu Thr Phe Gln Val Thr Gln Lys Thr Gln Arg Arg
        530                 535                 540
Trp Leu Leu Asp Lys Leu Val Asp Glu Ile Gly Val Gly Tyr Val Gln
545                 550                 555                 560
Asp Ser Gly Ser Val Ser Asn Tyr Arg Leu Ser Glu Ile Lys Pro Leu
                565                 570                 575
His Asn Phe Leu Thr Gln Leu Gln Pro Phe Leu Glu Leu Lys Gln Lys
        580                 585                 590
Gln Ala Asn Leu Val Leu Lys Ile Ile Glu Gln Leu Pro Ser Ala Lys
        595                 600                 605
Glu Ser Pro Asp Lys Phe Leu Glu Val Cys Thr Trp Ala Asp Gln Ile
        610                 615                 620
Ala Ala Leu Asn Asp Ser Lys Thr Arg Lys Thr Thr Ser Glu Thr Val
625                 630                 635                 640
Arg Ala Val Leu Asp Ser Leu Ser Glu Lys Lys Pro Ser Pro Ala
                645                 650                 655
Ala Gly Gly Ser Asp Lys Tyr Asn Gln Ala Leu Ser Lys Tyr Asn Gln
                660                 665                 670
Ala Leu Ser Lys Tyr Asn Gln Ala Leu Ser Gly Gly Gly Ser Asn
        675                 680                 685
Lys Lys Phe Leu Leu Tyr Leu Ala Gly Phe Val Asp Ser Asp Gly Ser
690                 695                 700
Ile Ile Ala Gln Ile Lys Pro Arg Gln Ser Tyr Lys Phe Lys His Gln
705                 710                 715                 720
Leu Arg Leu Thr Phe Tyr Val Thr Gln Lys Thr Gln Arg Arg Trp Phe
                725                 730                 735
Leu Asp Lys Leu Val Asp Arg Ile Gly Val Gly Tyr Val Glu Asp Ser
                740                 745                 750
Gly Ser Val Ser Arg Tyr Val Leu Ser Glu Ile Lys Pro Leu His Asn
        755                 760                 765
Phe Leu Thr Gln Leu Gln Pro Phe Leu Lys Leu Lys Gln Lys Gln Ala
        770                 775                 780
Asn Leu Val Leu Lys Ile Ile Glu Gln Leu Pro Ser Ala Lys Glu Ser
785                 790                 795                 800
Pro Asp Lys Phe Leu Glu Val Cys Thr Trp Val Asp Gln Val Ala Ala
                805                 810                 815
Leu Asn Asp Ser Lys Thr Arg Lys Thr Thr Ser Glu Thr Val Arg Ala
                820                 825                 830
Val Leu Asp Ser Leu Ser Glu Lys Lys Ser Ser Pro
        835                 840                 845

<210> SEQ ID NO 59
<211> LENGTH: 845
<212> TYPE: PRT
<213> ORGANISM: Artificial sequence
<220> FEATURE:
<223> OTHER INFORMATION: scTrex2_SC_RAG

<400> SEQUENCE: 59

Met Gly Ser Glu Ala Pro Arg Ala Glu Thr Phe Val Phe Leu Asp Leu
1               5                   10                  15

Glu Ala Thr Gly Leu Pro Ser Val Glu Pro Glu Ile Ala Glu Leu Ser
```

```
                20              25              30
Leu Phe Ala Val His Arg Ser Ser Leu Glu Asn Pro Glu His Asp Glu
            35                  40                  45
Ser Gly Ala Leu Val Leu Pro Arg Val Leu Asp Lys Leu Thr Leu Cys
        50                  55                  60
Met Cys Pro Glu Arg Pro Phe Thr Ala Lys Ala Ser Glu Ile Thr Gly
 65                  70                  75                  80
Leu Ser Ser Glu Gly Leu Ala Arg Cys Arg Lys Ala Gly Phe Asp Gly
                85                  90                  95
Ala Val Val Arg Thr Leu Gln Ala Phe Leu Ser Arg Gln Ala Gly Pro
            100                 105                 110
Ile Cys Leu Val Ala His Asn Gly Phe Asp Tyr Asp Phe Pro Leu Leu
            115                 120                 125
Cys Ala Glu Leu Arg Arg Leu Gly Ala Arg Leu Pro Arg Asp Thr Val
            130                 135                 140
Cys Leu Asp Thr Leu Pro Ala Leu Arg Gly Leu Asp Arg Ala His Ser
145                 150                 155                 160
His Gly Thr Arg Ala Arg Gly Arg Gln Gly Tyr Ser Leu Gly Ser Leu
                165                 170                 175
Phe His Arg Tyr Phe Arg Ala Glu Pro Ser Ala Ala His Ser Ala Glu
            180                 185                 190
Gly Asp Val His Thr Leu Leu Leu Ile Phe Leu His Arg Ala Ala Glu
            195                 200                 205
Leu Leu Ala Trp Ala Asp Glu Gln Ala Arg Gly Trp Ala His Ile Glu
210                 215                 220
Pro Met Tyr Leu Pro Pro Asp Asp Pro Ser Leu Glu Ala Thr Pro Pro
225                 230                 235                 240
Gln Thr Gly Leu Asp Val Pro Tyr Ser Glu Ala Pro Arg Ala Glu Thr
                245                 250                 255
Phe Val Phe Leu Asp Leu Glu Ala Thr Gly Leu Pro Ser Val Glu Pro
                260                 265                 270
Glu Ile Ala Glu Leu Ser Leu Phe Ala Val His Arg Ser Ser Leu Glu
            275                 280                 285
Asn Pro Glu His Asp Glu Ser Gly Ala Leu Val Leu Pro Arg Val Leu
        290                 295                 300
Asp Lys Leu Thr Leu Cys Met Cys Pro Glu Arg Pro Phe Thr Ala Lys
305                 310                 315                 320
Ala Ser Glu Ile Thr Gly Leu Ser Ser Glu Gly Leu Ala Arg Cys Arg
                325                 330                 335
Lys Ala Gly Phe Asp Gly Ala Val Val Arg Thr Leu Gln Ala Phe Leu
            340                 345                 350
Ser Arg Gln Ala Gly Pro Ile Cys Leu Val Ala His Asn Gly Phe Asp
            355                 360                 365
Tyr Asp Phe Pro Leu Leu Cys Ala Glu Leu Arg Arg Leu Gly Ala Arg
            370                 375                 380
Leu Pro Arg Asp Thr Val Cys Leu Asp Thr Leu Pro Ala Leu Arg Gly
385                 390                 395                 400
Leu Asp Arg Ala His Ser His Gly Thr Arg Ala Arg Gly Arg Gln Gly
                405                 410                 415
Tyr Ser Leu Gly Ser Leu Phe His Arg Tyr Phe Arg Ala Glu Pro Ser
            420                 425                 430
Ala Ala His Ser Ala Glu Gly Asp Val His Thr Leu Leu Leu Ile Phe
            435                 440                 445
```

Leu His Arg Ala Ala Glu Leu Ala Trp Ala Asp Glu Gln Ala Arg
    450                 455                 460

Gly Trp Ala His Ile Glu Pro Met Tyr Leu Pro Asp Asp Pro Ser
465                 470                 475                 480

Leu Glu Ala Gly Gly Gly Ser Gly Gly Gly Ser Asn Thr Lys
                485                 490                 495

Tyr Asn Glu Glu Phe Leu Leu Tyr Leu Ala Gly Phe Val Asp Gly Asp
                500                 505                 510

Gly Ser Ile Ile Ala Gln Ile Asn Pro Asn Gln Ser Ser Lys Phe Lys
            515                 520                 525

His Arg Leu Arg Leu Thr Phe Tyr Val Thr Gln Lys Thr Gln Arg Arg
        530                 535                 540

Trp Phe Leu Asp Lys Leu Val Asp Glu Ile Gly Val Gly Tyr Val Arg
545                 550                 555                 560

Asp Ser Gly Ser Val Ser Gln Tyr Val Leu Ser Glu Ile Lys Pro Leu
                565                 570                 575

His Asn Phe Leu Thr Gln Leu Gln Pro Phe Leu Glu Leu Lys Gln Lys
            580                 585                 590

Gln Ala Asn Leu Val Leu Lys Ile Ile Glu Gln Leu Pro Ser Ala Lys
        595                 600                 605

Glu Ser Pro Asp Lys Phe Leu Glu Val Cys Thr Trp Val Asp Gln Ile
610                 615                 620

Ala Ala Leu Asn Asp Ser Lys Thr Arg Lys Thr Thr Ser Glu Thr Val
625                 630                 635                 640

Arg Ala Val Leu Asp Ser Leu Ser Gly Lys Lys Ser Ser Pro Ala
                645                 650                 655

Ala Gly Gly Ser Asp Lys Tyr Asn Gln Ala Leu Ser Lys Tyr Asn Gln
                660                 665                 670

Ala Leu Ser Lys Tyr Asn Gln Ala Leu Ser Gly Gly Gly Gly Ser Asn
        675                 680                 685

Lys Lys Phe Leu Leu Tyr Leu Ala Gly Phe Val Asp Ser Asp Gly Ser
    690                 695                 700

Ile Ile Ala Gln Ile Lys Pro Arg Gln Ser Asn Lys Phe Lys His Gln
705                 710                 715                 720

Leu Ser Leu Thr Phe Ala Val Thr Gln Lys Thr Gln Arg Arg Trp Phe
                725                 730                 735

Leu Asp Lys Leu Val Asp Arg Ile Gly Val Gly Tyr Val Tyr Asp Ser
            740                 745                 750

Gly Ser Val Ser Asp Tyr Arg Leu Ser Glu Ile Lys Pro Leu His Asn
        755                 760                 765

Phe Leu Thr Gln Leu Gln Pro Phe Leu Lys Leu Lys Gln Lys Gln Ala
    770                 775                 780

Asn Leu Val Leu Lys Ile Ile Glu Gln Leu Pro Ser Ala Lys Glu Ser
785                 790                 795                 800

Pro Asp Lys Phe Leu Glu Val Cys Thr Trp Val Asp Gln Ile Ala Ala
                805                 810                 815

Leu Asn Asp Ser Lys Thr Arg Lys Thr Thr Ser Glu Thr Val Arg Ala
            820                 825                 830

Val Leu Asp Ser Leu Ser Glu Lys Lys Lys Ser Ser Pro
        835                 840                 845

<210> SEQ ID NO 60
<211> LENGTH: 354

```
<212> TYPE: PRT
<213> ORGANISM: Artificial sequence
<220> FEATURE:
<223> OTHER INFORMATION: SC_GS

<400> SEQUENCE: 60
```

Met Ala Asn Thr Lys Tyr Asn Glu Glu Phe Leu Leu Tyr Leu Ala Gly
1               5                   10                  15

Phe Val Asp Ala Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Ala Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Gly Asp Gly Ser Ile Ile Ala Gln Ile Lys Pro Arg Gln Gly Tyr
    210                 215                 220

Lys Phe Lys His Gln Leu Ser Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Ala Asp Arg Gly Ser Val Ser Asp Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Leu Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

```
<210> SEQ ID NO 61
<211> LENGTH: 8180
<212> TYPE: DNA
```

<213> ORGANISM: Artificial sequence
<220> FEATURE:
<223> OTHER INFORMATION: pCLS9027

<400> SEQUENCE: 61

```
gtttgtttaa acttggtacc ataactagtt cggcgcgcca ctagcgctgt cacgcgtctc    60
catgggcgat cctaaaaaga aacgtaaggt catcgattac ccatacgatg ttccagatta   120
cgctatcgat atcgccgacc ccattcgttc gcgcacacca agtcctgccc gcgagcttct   180
gcccggaccc caacccgatg gggttcagcc gactgcagat cgtggggtgt ctccgcctgc   240
cggcggcccc ctggatggct tgccggctcg gcggacgatg tcccggaccc ggctgccatc   300
tccccctgcc ccctcacctg cgttctcggc gggcagcttc agtgacctgt tacgtcagtt   360
cgatccgtca cttttttaata catcgctttt tgattcattg cctcccttcg gcgctcacca   420
tacagaggct gccacaggcg agtgggatga ggtgcaatcg ggtctgcggg cagccgacgc   480
cccccacccc accatgcgcg tggctgtcac tgccgcgcgg ccccgcgcg ccaagccggc    540
gccgcgacga cgtgctgcgc aaccctccga cgcttcgccg gcggcgcagg tggatctacg   600
cacgctcggc tacagccagc agcaacagga gaagatcaaa ccgaaggttc gttcgacagt   660
ggcgcagcac cacgaggcac tggtcggcca cgggtttaca cacgcgcaca tcgttgcgtt   720
aagccaacac ccggcagcgt tagggaccgt cgctgtcaag tatcaggaca tgatcgcagc   780
gttgccagag gcgacacacg aagcgatcgt tggcgtcggc aaacagtggt ccggcgcacg   840
cgctctggag gccttgctca cggtggcggg agagttgaga ggtccaccgt tacagttgga   900
cacaggccaa cttctcaaga ttgcaaaacg tggcggcgtg accgcagtgg aggcagtgca   960
tgcatggcgc aatgcactga cgggtgcccc gctcaacttg accccccagc aggtggtggc  1020
catcgccagc aataatggtg gcaagcaggc gctggagacg tccagcggc tgttgccggt   1080
gctgtgccag gcccacggct tgacccccca gcaggtggtg gccatcgcca gcaatggcgg  1140
tggcaagcag gcgctggaga cggtccagcg gctgttgccg gtgctgtgcc aggcccacgg  1200
cttgaccccg agcaggtgg tggccatcgc cagcaatatt ggtggcaagc aggcgctgga  1260
gacggtgcag gcgctgttgc cggtgctgtg ccaggcccac ggcttgaccc ccagcaggt   1320
ggtggccatc gccagcaatg gcggtggcaa gcaggcgctg gagacggtcc agcggctgtt  1380
gccggtgctg tgccaggccc acggcttgac cccccagcag gtggtggcca tcgcagcaa   1440
tggcggtggc aagcaggcgc tggagacggt ccagcggctg ttgccggtgc tgtgccaggc  1500
ccacggcttg accccggagc aggtggtggc catcgccagc cacgatgcg gcaagcaggc   1560
gctggagacg gtccagcggc tgttgccggt gctgtgccag gcccacggct tgaccccgga  1620
gcaggtggtg gccatcgcca gccacgatgg cggcaagcag gcgctggaga cggtccagcg  1680
gctgttgccg gtgctgtgcc aggcccacgg cttgaccccc agcaggtgg tggccatcgc  1740
cagcaatggc ggtggcaagc aggcgctgga gacggtccag cggctgttgc cggtgctgtg  1800
ccaggcccac ggcttgaccc cccagcaggt ggtggccatc gccagcaatg gcggtggcaa  1860
gcaggcgctg gagacggtcc agcggctgtt gccggtgctg tgccaggccc acggcttgac  1920
cccccagcag gtggtggcca tcgcagcaa tggcggtggc aagcaggcgc tggagacggt  1980
ccagcggctg ttgccggtgc tgtgccaggc ccacggcttg accccggagc aggtggtggc  2040
catcgccagc aatattggtg gcaagcaggc gctggagacg gtgcaggcgc tgttgccggt  2100
gctgtgccag gcccacggct tgaccccca gcaggtggtg gccatcgcca gcaatggcgg  2160
tggcaagcag gcgctggaga cggtccagcg gctgttgccg gtgctgtgcc aggcccacgg  2220
```

```
cttgaccccc cagcaggtgg tggccatcgc cagcaataat ggtggcaagc aggcgctgga    2280
gacggtccag cggctgttgc cggtgctgtg ccaggcccac ggcttgaccc cccagcaggt    2340
ggtggccatc gccagcaata atggtggcaa gcaggcgctg agacggtcc agcggctgtt    2400 gccggtgctg tgccaggccc acggcttgac cccggagcag gtggtggcca tcgccagcaa    2460
tattggtggc aagcaggcgc tggagacggt gcaggcgctg ttgccggtgc tgtgccaggc    2520
ccacggcttg acccctcagc aggtggtggc catcgccagc aatggcggcg gcaggccggc    2580
gctggagagc attgttgccc agttatctcg ccctgatccg gcgttggccg cgttgaccaa    2640
cgaccacctc gtcgccttgg cctgcctcgg cgggcgtcct cgcgctggatg cagtgaaaaa    2700 gggattgggg gatcctatca gccgttccca gctggtgaag tccgagctgg aggagaagaa    2760
atccgagttg aggcacaagc tgaagtacgt gccccacgag tacatcgagc tgatcgagat    2820
cgcccggaac agcacccagg accgtatcct ggagatgaag gtgatggagt tcttcatgaa    2880
ggtgtacggc tacaggggca agcacctggg cggctccagg aagcccgacg cgccatcta    2940 caccgtgggc tcccccatcg actacggcgt gatcgtggac accaaggcct actccggcgg    3000
ctacaacctg cccatcggcc aggccgacga aatgcagagg tacgtggagg agaaccagac    3060
caggaacaag cacatcaacc ccaacgagtg gtggaaggtg taccccctcca gcgtgaccga    3120 gttcaagttc ctgttcgtgt ccggccactt caagggcaac tacaaggccc agctgaccag    3180
gctgaaccac atcaccaact gcaacggcgc cgtgctgtcc gtggaggagc tcctgatcgg    3240
cggcgagatg atcaaggccg gcaccctgac cctggaggag gtgaggagga gttcaacaa    3300 cggcgagatc aacttcgcgg ccgcttgata actcgagcgc tagcacccag ctttcttgta    3360
caaagtggtg atctaggaaa gcggccgcgg agctccagga attctgcaga tcgactgtgc    3420
cttctagttg ccagccatct gttgtttgcc cctcccccgt gccttccttg accctggaag    3480
gtgccactcc cactgtcctt tcctaataaa atgaggaaat tgcatcgcat tgtctgagta    3540
ggtgtcattc tattctgggg gtgggggtgg ggcaggacag caaggggag gattgggaag    3600 acaatagcag gcatgctggg gatgcggtgg gctctatgga tcctctagag tcgacctgca    3660
ggcatgcaag cttggcgtaa tcatggtcat agctgttcc tgtgtgaaat tgttatccgc    3720
tcacaattcc acacaacata cgagccgaa gcataaagtg taaagcctgg ggtgcctaat    3780
gagtgagcta actcacatta attgcgttgc gctcactgcc cgctttccag tcgggaaacc    3840
tgtcgtgcca gctgcattaa tgaatcggcc aacgcgcggg gagaggcggt ttgcgtattg    3900
ggcgctcttc cgcttcctcg ctcactgact cgctgcgctc ggtcgttcgg ctgcggcgag    3960
cggtatcagc tcactcaaag gcggtaatac ggttatccac agaatcaggg gataacgcag    4020
gaaagaacat gtgagcaaaa ggccagcaaa aggccaggaa ccgtaaaaag gccgcgttgc    4080
tggcgttttt ccataggctc cgcccccctg acgagcatca caaaaatcga cgctcaagtc    4140
agaggtggcg aaacccgaca ggactataaa gataccaggc gtttccccct ggaagctccc    4200
tcgtgcgctc tcctgttccg accctgccgc ttaccggata cctgtccgcc tttctccctt    4260
cgggaagcgt ggcgctttct catagctcac gctgtaggta tctcagttcg gtgtaggtcg    4320
ttcgctccaa gctgggctgt gtgcacgaac cccccgttca gcccgaccgc tgcgccttat    4380
ccggtaacta tcgtcttgag tccaacccgg taagacacga cttatcgcca ctggcagcag    4440
ccactggtaa caggattagc agagcgaggt atgtaggcgg tgctacagag ttcttgaagt    4500
ggtggcctaa ctacggctac actagaagga cagtatttgg tatctgcgct ctgctgaagc    4560
```

```
cagttacctt cggaaaaaga gttggtagct cttgatccgg caaacaaacc accgctggta    4620
gcggtggttt ttttgtttgc aagcagcaga ttacgcgcag aaaaaaagga tctcaagaag    4680
atcctttgat cttttctacg gggtctgacg ctcagtggaa cgaaaactca cgttaaggga    4740
ttttggtcat gagattatca aaaggatct tcacctagat ccttttaaat taaaaatgaa    4800
gttttaaatc aatctaaagt atatatgagt aaacttggtc tgacagttac caatgcttaa    4860
tcagtgaggc acctatctca gcgatctgtc tatttcgttc atccatagtt gcctgactcc    4920
ccgtcgtgta gataactacg atacgggagg gcttaccatc tggccccagt gctgcaatga    4980
taccgcgaga cccacgctca ccggctccag atttatcagc aataaaccag ccagccggaa    5040
gggccgagcg cagaagtggt cctgcaactt tatccgcctc catccagtct attaattgtt    5100
gccgggaagc tagagtaagt agttcgccag ttaatagttt gcgcaacgtt gttgccattg    5160
ctacaggcat cgtggtgtca cgctcgtcgt ttggtatggc ttcattcagc tccggttccc    5220
aacgatcaag gcgagttaca tgatccccca tgttgtgcaa aaaagcggtt agctccttcg    5280
gtcctccgat cgttgtcaga agtaagttgg ccgcagtgtt atcactcatg gttatggcag    5340
cactgcataa ttctcttact gtcatgccat ccgtaagatg cttttctgtg actggtgagt    5400
actcaaccaa gtcattctga atagtgta tgcggcgacc gagttgctct tgcccggcgt    5460
caatacggga taataccgcg ccacatagca gaactttaaa agtgctcatc attggaaaac    5520
gttcttcggg gcgaaaactc tcaaggatct taccgctgtt gagatccagt tcgatgtaac    5580
ccactcgtgc acccaactga tcttcagcat cttttacttt caccagcgtt tctgggtgag    5640
caaaaacagg aaggcaaaat gccgcaaaaa agggaataag ggcgacacgg aaatgttgaa    5700
tactcatact cttcctttt caatattatt gaagcattta tcagggttat tgtctcatga    5760
gcggatacat atttgaatgt atttagaaaa ataaacaaat aggggttccg cgcacatttc    5820
cccgaaaagt gccacctgac gtctaagaaa ccattattat catgacatta acctataaaa    5880
ataggcgtat cacgaggccc tttcgtctcg cgcgtttcgg tgatgacggt gaaaacctct    5940
gacacatgca gctcccggag acggtcacag cttgtctgta agcggatgcc gggagcagac    6000
aagcccgtca gggcgcgtca gcgggtgttg gcgggtgtcg gggctggctt aactatgcgg    6060
catcagagca gattgtactg agagtgcacc atatgcggtg tgaaataccg cacagatgcg    6120
taaggagaaa ataccgcatc aggcgccatt cgccattcag gctgcgcaac tgttgggaag    6180
ggcgatcggt gcgggcctct tcgctattac gccagctggc gaaagggggga tgtgctgcaa    6240
ggcgattaag ttgggtaacg ccagggtttt cccagtcacg acgttgtaaa acgacggcca    6300
gtgaattcgc gccaaagcta actgtaggac tgagtctatt ctaaactgaa agcctggaca    6360
tctggagtac caggggggaga tgacgtgtta cgggcttcca taaaagcagc tggctttgaa    6420
tggaaggagc caagaggcca gcacaggagc ggattcgtcg ctttcacggc catcgagccg    6480
aacctctcgc aagtccgtga gccgttaagg aggcccccag tcccgaccct tcgcccaag    6540
cccctcgggg tccccgggcc tggtactcct tgccacacgg gagggggcgcg gaagccgggg    6600
cggaggagga gccaaccccg ggctgggctg agacccgcag aggaagacgc tctagggatt    6660
tgtcccggac tagcgagatg gcaaggctga ggacgggagg ctgattgaga ggcgaaggta    6720
cacctaatc tcaatacaac ctttggagct aagccagcaa tggtagaggg aagattctgc    6780
acgtcccttc caggcggcct cccgtcacc ccccccccca acccgcccccg accggagctg    6840
agagtaattc atacaaaagg actcgcccct gccttgggga atcccaggga ccgtcgttaa    6900
actcccacta acgtagaacc cagagatcgc tgcgttcccg cccctcacc cgcccgctct    6960
```

```
cgtcatcact gaggtggaga agagcatgcg tgaggctccg gtgcccgtca gtgggcagag     7020
cgcacatcgc ccacagtccc cgagaagttg ggggagggg  tcggcaattg aaccggtgcc     7080
tagagaaggt ggcgcggggt aaactgggaa agtgatgtcg tgtactggct ccgccttttt     7140
cccgagggtg ggggagaacc gtatataagt gcagtagtcg ccgtgaacgt tcttttttcgc    7200 aacgggtttg ccgccagaac acaggtaagt gccgtgtgtg gttcccgcgg gcctggcctc     7260
tttacgggtt atggcccttg cgtgccttga attacttcca cgcccctggc tgcagtacgt     7320
gattcttgat cccgagcttc gggttggaag tgggtgggag agttcgaggc cttgcgctta     7380
aggagcccct tcgcctcgtg cttgagttga ggcctggctt gggcgctggg gccgccgcgt     7440
gcgaatctgg tggcaccttc gcgcctgtct cgctgctttc gataagtctc tagccattta     7500 aaattttga tgacctgctg cgacgctttt tttctggcaa gatagtcttg taaatgcggg      7560
ccaagatcga tctgcacact ggtatttcgg ttttgggc cgcgggcggc gacggggccc       7620
gtgcgtccca gcgcacatgt tcggcgaggc ggggcctgcg agcgcggcca ccgagaatcg     7680 gacggggta  gtctcaagct ggccggcctg ctctggtgcc tggcctcgcg ccgccgtgta    7740
tcgccccgcc ctgggcggca aggctggccc ggtcggcacc agttgcgtga gcggaaagat    7800
ggccgcttcc cggccctgct gcagggagct caaaatggag gacgcggcgc tcgggagagc    7860
gggcgggtga gtcacccaca caaaggaaaa gggccttccc gtcctcagcc gtcgcttcat    7920
gtgactccac ggagtaccgg gcgccgtcca ggcacctcga ttagttctcg agcttttgga   7980
gtacgtcgtc tttaggttgg ggggagggggt tttatgcgat ggagtttccc cacactgagt   8040
gggtggagac tgaagttagg ccagcttggc acttgatgta attctccttg gaatttgccc    8100 ttttgagtt tggatcttgg ttcattctca agcctcagac agtggttcaa agttttttc     8160 ttccatttca ggtgtcgtgg                                                8180
```

<210> SEQ ID NO 62
<211> LENGTH: 8198
<212> TYPE: DNA
<213> ORGANISM: Artificial sequence
<220> FEATURE:
<223> OTHER INFORMATION: pCLS9028

<400> SEQUENCE: 62

```
gtttgtttaa acttggtacc ataactagtt cggcgcgcca ctagcgctgt cacgcgtctc       60
catgggcgat cctaaaaaga aacgtaaggt catcgataag gagaccgccg ctgccaagtt      120
cgagagacag cacatggaca gcatcgatat cgccgacccc attcgttcgc gcacaccaag     180
tcctgcccgc gagcttctgc ccggacccca acccgatggg gttcagccga ctgcagatcg     240
tggggtgtct ccgcctgccg gcggcccct  ggatggcttg ccggctcggc ggacgatgtc     300
ccggacccgg ctgccatctc ccctgcccc  ctcacctgcg ttctcggcgg gcagcttcag    360
tgacctgtta cgtcagttcg atccgtcact ttttaataca tcgcttttg attcattgcc     420 tccttcggc gctcaccata cagaggctgc cacaggcgag tgggatgagg tgcaatcggg     480
tctgcgggca gccgacgccc ccccacccac catgcgcgtg gctgtcactg ccgcgcggcc     540
cccgcgcgcc aagccggcgc cgcgacgacg tgctgcgcaa ccctccgacg cttcgccggc     600
ggcgcaggtg gatctacgca cgctcggcta cagccagcag caacaggaga agatcaaacc     660
gaaggttcgt tcgacagtgg cgcagcacca cgaggcactg gtcggccacg ggtttacaca    720
cgcgcacatc gttgcgttaa gccaacaccc ggcagcgtta gggaccgtcg ctgtcaagta     780
```

-continued

```
tcaggacatg atcgcagcgt tgccagaggc gacacacgaa gcgatcgttg gcgtcggcaa    840
acagtggtcc ggcgcacgcg ctctggaggc cttgctcacg gtggcggag agttgagagg     900 tccaccgtta cagttggaca caggccaact tctcaagatt gcaaaacgtg gcggcgtgac   960
cgcagtggag gcagtgcatg catggcgcaa tgcactgacg ggtgcccgc tcaacttgac    1020 cccccagcag gtggtggcca tcgccagcaa taatggtggc aagcaggcgc tggagacggt    1080
ccagcggctg ttgccggtgc tgtgccaggc ccacggcttg accccggagc aggtggtggc    1140
catcgccagc aatattggtg gcaagcaggc gctggagacg gtgcaggcgc tgttgccggt    1200
gctgtgccag gcccacggct tgaccccca gcaggtggtg ccatcgcca gcaataatgg     1260 tggcaagcag gcgctggaga cggtccagcg gctgttgccg gtgctgtgcc aggcccacgg    1320
cttgaccccg gagcaggtgg tggccatcgc cagccacgat ggcggcaagc aggcgctgga    1380
gacggtccag cggctgttgc cggtgctgtg ccaggcccac ggcttgaccc ccagcaggt    1440 ggtggccatc gccagcaatg gcggtggcaa caggcgctg gagacggtcc agcggctgtt    1500
gccggtgctg tgccaggccc acggcttgac cccgagcag gtggtggcca tcgccagcaa    1560
tattggtggc aagcaggcgc tggagacggt gcaggcgctg ttgccggtgc tgtgccaggc    1620
ccacggcttg accccggagc aggtggtggc catcgccagc aatattggtg gcaagcaggc    1680
gctggagacg gtgcaggcgc tgttgccggt gctgtgccag gcccacggct tgaccccgga    1740
gcaggtggtg gccatcgcca gcaatattgg tggcaagcag gcgctggaga cggtgcaggc    1800
gctgttgccg gtgctgtgcc aggcccacgg cttgaccccc agcaggtgg tggccatcgc    1860 cagcaataat ggtggcaagc aggcgctgga acggtccag cggctgttgc cggtgctgtg    1920
ccaggcccac ggcttgaccc ccagcaggt ggtggccatc gccagcaatg gcggtggcaa    1980
gcaggcgctg gagacggtcc agcggctgtt gccggtgctg tgccaggccc acggcttgac    2040 ccccagcag gtggtggcca tcgccagcaa tggcggtggc aagcaggcgc tggagacggt    2100
ccagcggctg ttgccggtgc tgtgccaggc ccacggcttg accccggagc aggtggtggc    2160
catcgccagc aatattggtg gcaagcaggc gctggagacg gtgcaggcgc tgttgccggt    2220
gctgtgccag gcccacggct tgaccccca gcaggtggtg ccatcgcca gcaatggcgg    2280 tggcaagcag gcgctggaga cggtccagcg gctgttgccg gtgctgtgcc aggcccacgg    2340
cttgaccccg gagcaggtgg tggccatcgc cagccacgat ggcggcaagc aggcgctgga    2400
gacggtccag cggctgttgc cggtgctgtg ccaggcccac ggcttgaccc cggagcaggt    2460
ggtggccatc gccagcaata ttggtggcaa gcaggcgctg gagacggtgc aggcgctgtt    2520
gccggtgctg tgccaggccc acggcttgac ccctcagcag gtggtggcca tcgccagcaa    2580
tggcggcggc aggccggcgc tggagagcat tgttgcccag ttatctcgcc ctgatccggc    2640
gttggccgcg ttgaccaacg accacctcgt cgccttggcc tgcctcggcg ggcgtcctgc    2700
gctggatgca gtgaaaaagg gattgggga tcctatcagc cgttcccagc tggtgaagtc    2760
cgagctggag gagaagaaat ccgagttgag gcacaagctg aagtacgtgc ccacgagta    2820 catcgagctg atcgagatcg cccggaacag cacccaggac cgtatcctgg agatgaaggt    2880
gatggagttc ttcatgaagg tgtacggcta caggggcaag cacctgggcg gctccaggaa    2940
gcccgacggc gccatctaca ccgtgggctc ccccatcgac tacggcgtga tcgtggacac    3000
caaggcctac tccggcggct acaacctgcc catcggccag gccgacgaaa tgcagaggta    3060
cgtggaggag aaccagacca ggaacaagca catcaacccc aacagtggt ggaaggtgta    3120 cccctccagc gtgaccgagt tcaagttcct gttcgtgtcc ggccacttca agggcaacta    3180
```

```
caaggcccag ctgaccaggc tgaaccacat caccaactgc aacgcgccg tgctgtccgt   3240 ggaggagctc ctgatcggcg gcgagatgat caaggccggc accctgaccc tggaggaggt   3300
gaggaggaag ttcaacaacg gcgagatcaa cttcgcggcc gcttgataac tcgagcgcta   3360
gcacccagct ttcttgtaca aagtggtgat ctaggaaagc ggccgcggag ctccaggaat   3420
tctgcagatc gactgtgcct tctagttgcc agccatctgt tgtttgcccc tcccccgtgc   3480
cttccttgac cctggaaggt gccactccca ctgtcctttc ctaataaaat gaggaaattg   3540
catcgcattg tctgagtagg tgtcattcta ttctgggggg tggggtgggg caggacagca   3600
agggggagga ttgggaagac aatagcaggc atgctgggga tgcggtgggc tctatggatc   3660
ctctagagtc gacctgcagg catgcaagct tggcgtaatc atggtcatag ctgtttcctg   3720
tgtgaaattg ttatccgctc acaattccac acaacatacg agccgaagc ataaagtgta    3780 aagcctgggg tgcctaatga gtgagctaac tcacattaat tgcgttgcgc tcactgcccg   3840
ctttccagtc gggaaacctg tcgtgccagc tgcattaatg aatcggccaa cgcgcgggga   3900
gaggcggttt gcgtattggg cgctcttccg cttcctcgct cactgactcg ctgcgctcgg   3960
tcgttcggct gcggcgagcg gtatcagctc actcaaaggc ggtaatacgg ttatccacag   4020
aatcagggga taacgcagga agaacatgt  gagcaaaagg ccagcaaaag gccaggaacc   4080
gtaaaaaggc cgcgttgctg gcgttttttcc ataggctccg cccccctgac gagcatcaca   4140
aaaatcgacg ctcaagtcag aggtggcgaa acccgacagg actataaaga taccaggcgt   4200
ttccccctgg aagctccctc gtgcgctctc ctgttccgac cctgccgctt accggatacc   4260
tgtccgcctt tctcccttcg ggaagcgtgg cgctttctca tagctcacgc tgtaggtatc   4320
tcagttcggt gtaggtcgtt cgctccaagc tgggctgtgt gcacgaaccc cccgttcagc   4380
ccgaccgctg cgccttatcc ggtaactatc gtcttgagtc aacccggta agacacgact    4440 tatcgccact ggcagcagcc actggtaaca ggattagcag agcgaggtat gtaggcggtg   4500
ctacagagtt cttgaagtgg tggcctaact acggctacac tagaaggaca gtatttggta   4560
tctgcgctct gctgaagcca gttaccttcg gaaaaagagt tggtagctct tgatccggca   4620
aacaaaccac cgctggtagc ggtggttttt tgtttgcaa gcagcagatt acgcgcagaa    4680
aaaaaggatc tcaagaagat cctttgatct tttctacggg gtctgacgct cagtggaacg   4740
aaaactcacg ttaagggatt ttggtcatga gattatcaaa aaggatcttc acctagatcc   4800
ttttaaatta aaaatgaagt tttaaatcaa tctaaagtat atatgagtaa acttggtctg   4860
acagttacca atgcttaatc agtgaggcac ctatctcagc gatctgtcta tttcgttcat   4920
ccatagttgc ctgactcccc gtcgtgtaga taactacgat acgggagggc ttaccatctg   4980
gccccagtgc tgcaatgata ccgcgagacc cacgctcacc ggctccagat ttatcagcaa   5040
taaaccagcc agccggaagg gccgagcgca gaagtggtcc tgcaacttta tccgcctcca   5100
tccagtctat taattgttgc cgggaagcta gagtaagtag ttcgccagtt aatagtttgc   5160
gcaacgttgt tgccattgct acaggcatcg tggtgtcacg ctcgtcgttt ggtatggctt   5220
cattcagctc cggttcccaa cgatcaaggc gagttacatg atcccccatg ttgtgcaaaa   5280
aagcggttag ctccttcggt cctccgatcg ttgtcagaag taagttggcc gcagtgttat   5340
cactcatggt tatggcagca ctgcataatt ctcttactgt catgccatcc gtaagatgct   5400
tttctgtgac tggtgagtac tcaaccaagt cattctgaga atagtgtatg cggcgaccga   5460
gttgctcttg cccggcgtca atacgggata ataccgcgcc acatagcaga actttaaaag   5520
```

```
tgctcatcat tggaaaacgt tcttcggggc gaaaactctc aaggatctta ccgctgttga   5580
gatccagttc gatgtaaccc actcgtgcac ccaactgatc ttcagcatct tttactttca   5640
ccagcgtttc tgggtgagca aaaacaggaa ggcaaaatgc cgcaaaaaag gaataagggg   5700
cgacacggaa atgttgaata ctcatactct tcctttttca atattattga agcatttatc   5760
agggttattg tctcatgagc ggatacatat ttgaatgtat ttagaaaaat aaacaaatag   5820
gggttccgcg cacatttccc cgaaaagtgc cacctgacgt ctaagaaacc attattatca   5880
tgacattaac ctataaaaat aggcgtatca cgaggccctt tcgtctcgcg cgtttcggtg   5940
atgacggtga aaacctctga cacatgcagc tcccggagac ggtcacagct tgtctgtaag   6000
cggatgccgg gagcagacaa gcccgtcagg gcgcgtcagc gggtgttggc gggtgtcggg   6060
gctggcttaa ctatgcggca tcagagcaga ttgtactgag agtgcaccat atgcggtgtg   6120
aaataccgca cagatgcgta aggagaaaat accgcatcag gcgccattcg ccattcaggc   6180
tgcgcaactg ttgggaaggg cgatcggtgc gggcctcttc gctattacgc cagctggcga   6240
aagggggatg tgctgcaagg cgattaagtt gggtaacgcc agggttttcc cagtcacgac   6300
gttgtaaaac gacggccagt gaattcgcgc caaagctaac tgtaggactg agtctattct   6360
aaactgaaag cctggacatc tggagtacca ggggagatg acgtgttacg gcttccata   6420 aaagcagctg gctttgaatg gaaggagcca agaggccagc acaggagcgg attcgtcgct   6480
ttcacggcca tcgagccgaa cctctcgcaa gtccgtgagc cgttaaggag gccccagtc   6540 ccgaccttc gccccaagcc cctcggggtc cccgggcctg gtactccttg ccacacggga   6600
ggggcgcgga agccggggcg gaggaggagc caaccccggg ctgggctgag accgcagag   6660 gaagacgctc tagggatttg tcccggacta gcgagatggc aaggctgagg acgggaggct   6720
gattgagagg cgaaggtaca ccctaatctc aatacaacct ttggagctaa gccagcaatg   6780
gtagagggaa gattctgcac gtcccttcca ggcggcctcc ccgtcaccac cccccccaac   6840
ccgccccgac cggagctgag agtaattcat acaaaaggac tcgcccctgc cttggggaat   6900
cccagggacc gtcgttaaac tcccactaac gtagaaccca gagatcgctg cgttcccgcc   6960
ccctcacccg cccgctctcg tcatcactga ggtggagaag agcatgcgtg aggctccggt   7020
gcccgtcagt gggcagagcg cacatcgccc acagtccccg agaagttggg gggagggtc   7080 ggcaattgaa ccggtgccta gagaaggtgg cgcggggtaa actgggaaag tgatgtcgtg   7140
tactggctcc gccttttttcc cgagggtggg ggagaaccgt atataagtgc agtagtcgcc   7200
gtgaacgttc tttttcgcaa cgggtttgcc gccagaacac aggtaagtgc cgtgtgtggt   7260
tcccgcgggc ctggcctctt tacgggttat ggcccttgcg tgccttgaat tacttccacg   7320 ccctggctg cagtacgtga ttcttgatcc cgagcttcgg gttggaagtg ggtgggagag   7380
ttcgaggcct tgcgcttaag gagccccttc gcctcgtgct tgagttgagg cctggcttgg   7440
gcgctggggc cgccgcgtgc gaatctggtg gcaccttcgc gcctgtctcg ctgctttcga   7500
taagtctcta gccatttaaa attttttgatg acctgctgcg acgcttttt tctgcaagga   7560 tagtcttgta aatgcgggcc aagatcgatc tgcacactgg tatttcggtt tttggggccg   7620
cgggcggcga cggggcccgt gcgtcccagc gcacatgttc ggcgaggcgg ggcctgcgag   7680
cgcggccacc gagaatcgga cggggggtagt ctcaagctgg ccggcctgct ctggtgcctg   7740
gcctcgcgcc gccgtgtatc gccccgccct gggcggcaag gctggccgg tcggcaccag   7800 ttgcgtgagc ggaaagatgg ccgcttcccg gccctgctgc agggagctca aaatggagga   7860
cgcggcgctc gggagagcgg gcgggtgagt cacccacaca aaggaaaagg gcctttccgt   7920
```

```
cctcagccgt cgcttcatgt gactccacgg agtaccgggc gccgtccagg cacctcgatt    7980
agttctcgag cttttggagt acgtcgtctt taggttgggg ggaggggttt tatgcgatgg    8040
agtttcccca cactgagtgg gtggagactg aagttaggcc agcttggcac ttgatgtaat    8100
tctccttgga atttgccctt tttgagtttg gatcttggtt cattctcaag cctcagacag    8160
tggttcaaag ttttttctt ccatttcagg tgtcgtgg                             8198
```

<210> SEQ ID NO 63
<211> LENGTH: 7901
<212> TYPE: DNA
<213> ORGANISM: Artificial sequence
<220> FEATURE:
<223> OTHER INFORMATION: pCLS9235

<400> SEQUENCE: 63

```
catgggcgat cctaaaaaga aacgtaaggt catcgattac ccatacgatg ttccagatta      60
cgctatcgat atcgccgacc ccattcgttc gcgcacacca agtcctgccc gcgagcttct     120
gcccggaccc caacccgatg gggttcagcc gactgcagat cgtgggtgt ctccgcctgc      180
cggcggcccc ctggatggct tgccggctcg gcggacgatg tcccggaccc ggctgccatc     240
tcccctgcc ccctcacctg cgttctcggc gggcagcttc agtgacctgt acgtcagtt       300
cgatccgtca cttttaata catcgctttt tgattcattg cctcccttcg gcgctcacca      360
tacagaggct gccacaggcg agtgggatga ggtgcaatcg ggtctgcggg cagccgacgc     420
ccccccaccc accatgcgcg tggctgtcac tgccgcgcgg ccccgcgcg ccaagccggc      480
gccgcgacga cgtgctgcgc aaccctccga cgcttcgccg gcggcgcagg tggatctacg     540
cacgctcggc tacagccagc agcaacagga gaagatcaaa ccgaaggttc gttcgacagt     600
ggcgcagcac cacgaggcac tggtcggcca cgggtttaca cacgcgcaca tcgttgcgtt     660
aagccaacac ccggcagcgt tagggaccgt cgctgtcaag tatcaggaca tgatcgcagc     720
gttgccagag gcgacacacg aagcgatcgt tggcgtcggc aaacagtggt ccggcgcacg     780
cgctctggag gccttgctca cggtggcggg agagttgaga ggtccaccgt tacagttgga     840
cacaggccaa cttctcaaga ttgcaaaacg tggcggcgtg accgcagtgg aggcagtgca     900
tgcatggcgc aatgcactga cgggtgcccc gctcaacttg accccggagc aggtggtggc     960
catcgccagc cacgatggcg gcaagcaggc gctggagacg tccagcggc tgttgccggt     1020
gctgtgccag gcccacggct tgacccccca gcaggtggtg gccatcgcca gcaatggcgg    1080
tggcaagcag gcgctggaga cggtccagcg gctgttgccg gtgctgtgcc aggcccacgg    1140
cttgaccccc cagcaggtgg tggccatcgc cagcaataat ggtggcaagc aggcgctgga    1200
gacggtccag cggctgttgc cggtgctgtg ccaggcccac ggcttgaccc cggagcaggt    1260
ggtggccatc gccagcaata ttggtggcaa gcaggcgctg agacggtgc aggcgctgtt    1320
gccggtgctg tgccaggccc acggcttgac cccggagcag gtggtggcca tcgccagcca    1380
cgatggcggc aagcaggcgc tggagacggt ccagcggctg ttgccggtgc tgtgccaggc    1440
ccacggcttg accccggagc aggtggtggc catcgccagc aatattggtg gcaagcaggc    1500
gctggagacg tgcaggcgc tgttgccggt gctgtgccag gcccacggct tgaccccgga    1560
gcaggtggtg gccatcgcca ccacgatgg cggcaagcag gcgctggaga cggtccagcg    1620
gctgttgccg gtgctgtgcc aggcccacgg cttgaccccg gagcaggtgg tggccatcgc    1680
cagcaatatt ggtggcaagc aggcgctgga gacggtgcag gcgctgttgc cggtgctgtg    1740
```

```
ccaggcccac ggcttgaccc cggagcaggt ggtggccatc gccagcaata ttggtggcaa    1800
gcaggcgctg gagacggtgc aggcgctgtt gccggtgctg tgccaggccc acggcttgac    1860
cccggagcag gtggtggcca tcgccagcca cgatggcggc aagcaggcgc tggagacggt    1920
ccagcggctg ttgccggtgc tgtgccaggc ccacggcttg accccccagc aggtggtggc    1980
catcgccagc aatggcggtg gcaagcaggc gctggagacg gtccagcggc tgttgccggt    2040
gctgtgccag gcccacggct tgaccccca gcaggtggtg gccatcgcca gcaataatgg    2100
tggcaagcag gcgctggaga cggtccagcg gctgttgccg gtgctgtgcc aggcccacgg    2160
cttgaccccc cagcaggtgg tggccatcgc cagcaatggc ggtggcaagc aggcgctgga    2220
gacggtccag cggctgttgc cggtgctgtg ccaggcccac ggcttgaccc ccagcaggt    2280
ggtggccatc gccagcaata atggtggcaa gcaggcgctg gagacggtcc agcggctgtt    2340
gccggtgctg tgccaggccc acggcttgac cccccagcag gtggtggcca tcgccagcaa    2400
tggcggtggc aagcaggcgc tggagacggt ccagcggctg ttgccggtgc tgtgccaggc    2460
ccacggcttg acccctcagc aggtggtggc catcgccagc aatggcggcg gcaggccggc    2520
gctggagagc attgttgccc agttatctcg ccctgatccg gcgttggccg cgttgaccaa    2580
cgaccacctc gtcgccttgg cctgcctcgg cgggcgtcct gcgctggatg cagtgaaaaa    2640
gggattgggg gatcctatca gccgttccca gctggtgaag tccgagctgg aggagaagaa    2700
atccgagttg aggcacaagc tgaagtacgt gccccacgag tacatcgagc tgatcgagat    2760
cgcccggaac agcacccagg accgtatcct ggagatgaag gtgatggagt tcttcatgaa    2820
ggtgtacggg tacaggggca agcacctggg cggctccagg aagcccgacg cgccatcta    2880
caccgtgggc tcccccatcg actacggcgt gatcgtggac accaaggcct actccggcgg    2940
ctacaacctg cccatcggcc aggccgacga aatgcagagg tacgtggagg agaaccagac    3000
caggaacaag cacatcaacc ccaacgagtg gtggaaggtg tacccctcca gcgtgaccga    3060
gttcaagttc ctgttcgtgt ccggccactt caagggcaac tacaaggccc agctgaccag    3120
gctgaaccac atcaccaact gcaacggcgc cgtgctgtcc gtggaggagc tcctgatcgg    3180
cggcgagatg atcaaggccg gcaccctgac cctggaggag gtgaggagga gttcaacaa    3240
cggcgagatc aacttcgcgg ccgactgata actcgagcga tcctctagac gagctcctcg    3300
agcctgcagc agctgaagct tcgactgtgc cttctagttg ccagccatct gttgtttgcc    3360
cctcccccgt gccttccttg accctggaag gtgccactcc cactgtcctt tcctaataaa    3420
atgaggaaat tgcatcgcat tgtctgagta ggtgtcattc tattctgggg ggtggggtgg    3480
ggcaggacag caagggggag gattgggaag acaatagcag gcatgctggg gatgcggtgg    3540
gctctatggg atatcttctt aattaagacc tagagcttgg cgtaatcatg gtcatagctg    3600
tttcctgtgt gaaattgtta tccgctcaca attccacaca acatacgagc cggaagcata    3660
aagtgtaaag cctggggtgc ctaatgagtg agctaactca cattaattgc gttgcgctca    3720
ctgcccgctt tccagtcggg aaacctgtcg tgccagctgc attaatgaat cggccaacgc    3780
gcggggagag gcggtttgcg tattgggcgc tcttccgctt cctcgctcac tgactcgctg    3840
cgctcggtcg ttcggctgcg gcgagcggta tcagctcact caaaggcggt aatacggtta    3900
tccacagaat caggggataa cgcaggaaag aacatgtgag caaaaggcca gcaaaaggcc    3960
aggaaccgta aaaaggccgc gttgctggcg ttttccata ggctccgccc ccctgacgag    4020
catcacaaaa atcgacgctc aagtcagagg tggcgaaacc cgacaggact ataaagatac    4080
caggcgtttc ccccctggaag ctccctcgtg cgctctcctg ttccgaccct gccgcttacc    4140
```

```
ggatacctgt ccgcctttct cccttcggga agcgtggcgc tttctcatag ctcacgctgt    4200
aggtatctca gttcggtgta ggtcgttcgc tccaagctgg gctgtgtgca cgaacccccc    4260
gttcagcccg accgctgcgc cttatccggt aactatcgtc ttgagtccaa cccggtaaga    4320
cacgacttat cgccactggc agcagccact ggtaacagga ttagcagagc gaggtatgta    4380
ggcggtgcta cagagttctt gaagtggtgg cctaactacg gctacactag aaggacagta    4440
tttggtatct gcgctctgct gaagccagtt accttcggaa aaagagttgg tagctcttga    4500
tccggcaaac aaaccaccgc tggtagcggt ggttttttg tttgcaagca gcagattacg    4560
cgcagaaaaa aaggatctca agaagatcct ttgatctttt ctacggggtc tgacgctcag    4620
tggaacgaaa actcacgtta agggattttg gtcatgagat tatcaaaaag gatcttcacc    4680
tagatccttt taaattaaaa atgaagtttt aaatcaatct aaagtatata tgagtaaact    4740
tggtctgaca gttaccaatg cttaatcagt gaggcaccta tctcagcgat ctgtctattt    4800
cgttcatcca tagttgcctg actccccgtc gtgtagataa ctacgatacg ggagggctta    4860
ccatctggcc ccagtgctgc aatgataccg cgagacccac gctcaccggc tccagattta    4920
tcagcaataa accagccagc cggaagggcc gagcgcagaa gtggtcctgc aactttatcc    4980
gcctccatcc agtctattaa ttgttgccgg gaagctagag taagtagttc gccagttaat    5040
agtttgcgca acgttgttgc cattgctaca ggcatcgtgg tgtcacgctc gtcgtttggt    5100
atggcttcat tcagctccgg ttcccaacga tcaaggcgag ttacatgatc ccccatgttg    5160
tgcaaaaaag cggttagctc cttcggtcct ccgatcgttg tcagaagtaa gttggccgca    5220
gtgttatcac tcatggttat ggcagcactg cataattctc ttactgtcat gccatccgta    5280
agatgctttt ctgtgactgg tgagtactca accaagtcat tctgagaata gtgtatgcgg    5340
cgaccgagtt gctcttgccc ggcgtcaata cgggataata ccgcgccaca tagcagaact    5400
ttaaaagtgc tcatcattgg aaaacgttct cggggcgaaa actctcaag gatcttaccg    5460 ctgttgagat ccagttcgat gtaacccact cgtgcaccca actgatcttc agcatctttt    5520
actttcacca gcgtttctgg gtgagcaaaa acaggaaggc aaaatgccgc aaaaaaggga    5580
ataagggcga cacggaaatg ttgaatactc atactcttcc tttttcaata ttattgaagc    5640
atttatcagg gttattgtct catgagcgga tacatatttg aatgtattta gaaaaataaa    5700
caaatagggg ttccgcgcac atttccccga aaagtgccac ctgactatgc ggtgtgaaat    5760
accgcacaga tgcgtaagga gaaaataccg catcaggcgc cattcgccat tcaggctgcg    5820
caactgttgg aagggcgat cggtgcgggc ctcttcgcta ttacgccagc tggcgaaagg    5880
gggatgtgct gcaaggcgat taagttgggt aacgccaggg ttttcccagt cacgacgttg    5940
taaaacgacg gccagtgaat cgcgccaaag ctaactgtag gactgagtct attctaaact    6000
gaaagcctgg acatctggag taccaggggg agatgacgtg ttacgggctt ccataaaagc    6060
agctggcttt gaatgaagg agccaagagg ccagcacagg agcggattcg tcgctttcac    6120
ggccatcgag ccgaacctct cgcaagtccg tgagccgtta aggaggcccc cagtcccgac    6180
ccttcgcccc aagcccctcg gggtccccgg gcctggtact ccttgccaca cgggaggggc    6240
gcggaagccg gggcggagga ggagccaacc ccgggctggg ctgagacccg cagaggaaga    6300
cgctctaggg atttgtcccg gactagcgag atggcaaggc tgaggacggg aggctgattg    6360
agaggcgaag gtacacccta atctcaatac aaccctttgga gctaagccag caatggtaga    6420
gggaagattc tgcacgtccc ttccaggcgg cctccccgtc accaccccccc ccaacccgcc    6480
```

| | |
|---|---|
| ccgaccggag ctgagagtaa ttcatacaaa aggactcgcc cctgccttgg ggaatcccag | 6540 |
| ggaccgtcgt taaactccca ctaacgtaga acccagagat cgctgcgttc ccgcccctc | 6600 |
| acccgcccgc tctcgtcatc actgaggtgg agaagagcat gcgtgaggct ccggtgcccg | 6660 |
| tcagtgggca gagcgcacat cgcccacagt ccccagaaag ttgggggggag gggtcggcaa | 6720 |
| ttgaaccggt gcctagagaa ggtggcgcgg ggtaaactgg gaaagtgatg tcgtgtactg | 6780 |
| gctccgcctt tttcccgagg gtgggggaga accgtatata agtgcagtag tcgccgtgaa | 6840 |
| cgttcttttt cgcaacgggt ttgccgccag aacacaggta agtgccgtgt gtggttcccg | 6900 |
| cgggcctggc ctctttacgg gttatggccc ttgcgtgcct tgaattactt ccacgcccct | 6960 |
| ggctgcagta cgtgattctt gatcccgagc ttcgggttgg aagtgggtgg gagagttcga | 7020 |
| ggccttgcgc ttaaggagcc ccttcgcctc gtgcttgagt tgaggcctgg cttgggcgct | 7080 |
| ggggccgccg cgtgcgaatc tggtggcacc ttcgcgcctg tctcgctgct ttcgataagt | 7140 |
| ctctagccat ttaaaatttt tgatgacctg ctgcgacgct ttttttctgg caagatagtc | 7200 |
| ttgtaaatgc gggccaagat cgatctgcac actggtattt cggttttgg ggccgcgggc | 7260 |
| ggcgacgggg cccgtgcgtc ccagcgcaca tgttcggcga gcggggcct gcgagcgcgg | 7320 |
| ccaccgagaa tcgacggggg gtagtctcaa gctggccggc ctgctctggt gcctggcctc | 7380 |
| gcgccgccgt gtatcgcccc gccctgggcg gcaaggctgg cccggtcggc accagttgcg | 7440 |
| tgagcggaaa gatggccgct tcccggccct gctgcaggga gctcaaaatg gaggacgcgg | 7500 |
| cgctcgggag agcgggcggg tgagtcaccc acacaaagga aaagggcctt tccgtcctca | 7560 |
| gccgtcgctt catgtgactc cacggagtac cgggcgccgt ccaggcacct cgattagttc | 7620 |
| tcgagctttt ggagtacgtc gtctttaggt tgggggagg ggttttatgc gatggagttt | 7680 |
| ccccacactg agtgggtgga gactgaagtt aggccagctt ggcacttgat gtaattctcc | 7740 |
| ttggaatttg ccctttttga gtttggatct tggttcattc tcaagcctca gacagtggtt | 7800 |
| caaagttttt tcttccatt tcaggtgtcg tgggtttgtt taaacttggt accataacta | 7860 |
| gttcggcgcg ccactagcgc tgtcacgcgc caagccgcca c | 7901 |

<210> SEQ ID NO 64
<211> LENGTH: 7901
<212> TYPE: DNA
<213> ORGANISM: Artificial sequence
<220> FEATURE:
<223> OTHER INFORMATION: pCLS9241

<400> SEQUENCE: 64

| | |
|---|---|
| catgggcgat cctaaaaaga aacgtaaggt catcgattac ccatacgatg ttccagatta | 60 |
| cgctatcgat atcgccgacc ccattcgttc gcgcacacca agtcctgccc gcgagcttct | 120 |
| gcccggaccc caacccgatg gggttcagcc gactgcagat cgtggggtgt ctccgcctgc | 180 |
| cggcggcccc ctggatggct tgccggctcg gcggacgatg tcccggaccc ggctgccatc | 240 |
| tccccctgcc ccctcacctg cgttctcggc gggcagcttc agtgacctgt tacgtcagtt | 300 |
| cgatccgtca cttttttaata catcgctttt tgattcattg cctcccttcg gcgctcacca | 360 |
| tacagaggct gccacaggcg agtgggatga ggtgcaatcg ggtctgcggg cagccgacgc | 420 |
| cccccaccc accatgcgcg tggctgtcac tgccgcgcgg ccccgcgcg ccaagccggc | 480 |
| gccggacga cgtgctgcgc aaccctccga cgcttgccg gcggcgcagg tggatctacg | 540 |
| cacgctcggc tacagccagc agcaacagga gaagatcaaa ccgaaggttc gttcgacagt | 600 |
| ggcgcagcac cacgaggcac tggtcggcca cgggtttaca cacgcgcaca tcgttgcgtt | 660 |

```
aagccaacac ccggcagcgt tagggaccgt cgctgtcaag tatcaggaca tgatcgcagc    720
gttgccagag gcgacacacg aagcgatcgt tggcgtcggc aaacagtggt ccggcgcacg    780
cgctctggag gccttgctca cggtggcggg agagttgaga ggtccaccgt tacagttgga    840
cacaggccaa cttctcaaga ttgcaaaacg tggcggcgtg accgcagtgg aggcagtgca    900
tgcatggcgc aatgcactga cgggtgcccc gctcaacttg accccccagc aggtggtggc    960
catcgccagc aataatggtg gcaagcaggc gctggagacg gtccagcggc tgttgccggt   1020
gctgtgccag gcccacggct tgaccccgga gcaggtggtg ccatcgcca gccacgatgg    1080 cggcaagcag gcgctggaga cggtccagcg gctgttgccg gtgctgtgcc aggcccacgg   1140
cttgaccccg gagcaggtgg tggccatcgc cagcaatatt ggtggcaagc aggcgctgga   1200
gacggtgcag gcgctgttgc cggtgctgtg ccaggcccac ggcttgaccc cggagcaggt   1260
ggtggccatc gccagccacg atggcggcaa gcaggcgctg gagacggtcc agcggctgtt   1320
gccggtgctg tgccaggccc acggcttgac cccggagcag gtggtggcca tcgccagcca   1380
cgatggcggc aagcaggcgc tggagacggt ccagcggctg ttgccggtgc tgtgccaggc   1440
ccacggcttg accccggagc aggtggtggc catcgccagc aatattggtg gcaagcaggc   1500
gctggagacg gtgcaggcgc tgttgccggt gctgtgccag gcccacggct tgaccccca    1560 gcaggtggtg gccatcgcca gcaatggcgg tggcaagcag gcgctggaga cggtccagcg   1620
gctgttgccg gtgctgtgcc aggcccacgg cttgaccccc cagcaggtgg tggccatcgc   1680
cagcaataat ggtggcaagc aggcgctgga gacggtccag cggctgttgc cggtgctgtg   1740
ccaggcccac ggcttgaccc cccagcaggt ggtggccatc gccagcaata atggtggcaa   1800
gcaggcgctg gagacggtcc agcggctgtt gccggtgctg tgccaggccc acggcttgac   1860
cccccagcag gtggtggcca tcgccagcaa tggcggtggc aagcaggcgc tggagacggt   1920
ccagcggctg ttgccggtgc tgtgccaggc ccacggcttg accccccagc aggtggtggc   1980
catcgccagc aataatggtg gcaagcaggc gctggagacg gtccagcggc tgttgccggt   2040
gctgtgccag gcccacggct tgacccccca gcaggtggtg gccatcgcca gcaatggcgg   2100
tggcaagcag gcgctggaga cggtccagcg gctgttgccg gtgctgtgcc aggcccacgg   2160
cttgaccccg gagcaggtgg tggccatcgc cagccacgat ggcggcaagc aggcgctgga   2220
gacggtccag cggctgttgc cggtgctgtg ccaggcccac ggcttgaccc ccagcaggt   2280 ggtggccatc gccagcaatg gcggtggcaa gcaggcgctg gagacggtcc agcggctgtt   2340
gccggtgctg tgccaggccc acggcttgac cccccagcag gtggtggcca tcgccagcaa   2400
taatggtggc aagcaggcgc tggagacggt ccagcggctg ttgccggtgc tgtgccaggc   2460
ccacggcttg acccctcagc aggtggtggc catcgccagc aatggcggcg gcaggccggc   2520
gctggagagc attgttgccc agttatctcg ccctgatccg gcgttggccg cgttgaccaa   2580
cgaccacctc gtcgccttgg cctgcctcgg cgggcgtcct gcgctggatg cagtgaaaaa   2640
gggattgggg gatcctatca gccgttccca gctggtgaag tccgagctgg aggagaagaa   2700
atccgagttg aggcacaagc tgaagtacgt gccccacgag tacatcgagc tgatcgagat   2760
cgcccggaac agcacccagg accgtatcct ggagatgaag gtgatggagt tcttcatgaa   2820
ggtgtacggc tacaggggca agcacctggg cggctccagg aagcccgacg gcgccatcta   2880
caccgtgggc tcccccatcg actacggcgt gatcgtggac accaaggcct actccggcgg   2940
ctacaacctg cccatcggcc aggccgacga aatgcagagg tacgtggagg agaaccagac   3000
```

```
caggaacaag cacatcaacc ccaacgagtg gtggaaggtg taccoctcca gcgtgaccga    3060 gttcaagttc ctgttcgtgt ccggccactt caagggcaac tacaaggccc agctgaccag    3120
gctgaaccac atcaccaact gcaacggcgc cgtgctgtcc gtggaggagc tcctgatcgg    3180
cggcgagatg atcaaggccg gcaccctgac cctggaggag gtgaggagga agttcaacaa    3240
cggcgagatc aacttcgcgg ccgactgata actcgagcga tcctctagac gagctcctcg    3300
agcctgcagc agctgaagct tcgactgtgc cttctagttg ccagccatct gttgtttgcc    3360
cctcccccgt gccttccttg accctggaag gtgccactcc cactgtcctt tcctaataaa    3420
atgaggaaat tgcatcgcat tgtctgagta ggtgtcattc tattctgggg ggtgggggtgg   3480 ggcaggacag caaggggggag gattgggaag acaatagcag gcatgctggg gatgcggtgg   3540
gctctatggg atatcttctt aattaagacc tagagcttgg cgtaatcatg gtcatagctg    3600
tttcctgtgt gaaattgtta tccgctcaca attccacaca acatacgagc cggaagcata    3660
aagtgtaaag cctggggtgc ctaatgagtg agctaactca cattaattgc gttgcgctca    3720
ctgcccgctt tccagtcggg aaacctgtcg tgccagctgc attaatgaat cggccaacgc    3780
gcggggagag gcggttttgcg tattgggcgc tcttccgctt cctcgctcac tgactcgctg    3840
cgctcggtcg ttcggctgcg gcgagcggta tcagctcact caaaggcggt aatacggtta    3900
tccacagaat caggggataa cgcaggaaag aacatgtgag caaaaggcca gcaaaaggcc    3960
aggaaccgta aaaaggccgc gttgctggcg ttttttccata ggctccgccc ccctgacgag    4020
catcacaaaa atcgacgctc aagtcagagg tggcgaaacc cgacaggact ataaagatac    4080
caggcgtttc cccctggaag ctccctcgtg cgctctcctg ttccgaccct gccgcttacc    4140
ggatacctgt ccgcctttct cccttcggga agcgtggcgc tttctcatag ctcacgctgt    4200
aggtatctca gttcggtgta ggtcgttcgc tccaagctgg gctgtgtgca cgaaccccc    4260 gttcagcccg accgctgcgc cttatccggt aactatcgtc ttgagtccaa cccggtaaga    4320
cacgacttat cgccactggc agcagccact ggtaacagga ttagcagagc gaggtatgta    4380
ggcggtgcta cagagttctt gaagtggtgg cctaactacg gctacactag aaggacagta    4440
tttggtatct gcgctctgct gaagccagtt accttcggaa aaagagttgg tagctcttga    4500
tccggcaaac aaaccaccgc tggtagcggt ggtttttttg tttgcaagca gcagattacg    4560
cgcagaaaaa aaggatctca agaagatcct ttgatctttt ctacgggtc tgacgctcag    4620 tggaacgaaa actcacgtta agggattttg gtcatgagat tatcaaaaag gatcttcacc    4680
tagatccttt taaattaaaa atgaagtttt aaatcaatct aaagtatata tgagtaaact    4740
tggtctgaca gttaccaatg cttaatcagt gaggcaccta tctcagcgat ctgtctattt    4800
cgttcatcca tagttgcctg actccccgtc gtgtagataa ctacgatacg ggagggctta    4860
ccatctggcc ccagtgctgc aatgataccg cgagacccac gctcaccggc tccagattta    4920
tcagcaataa accagccagc cggaagggcc gagcgcagaa gtggtcctgc aactttatcc    4980
gcctccatcc agtctattaa ttgttgccgg gaagctagag taagtagttc gccagttaat    5040
agtttgcgca acgttgttgc cattgctaca ggcatcgtgg tgtcacgctc gtcgtttggt    5100
atggcttcat tcagctccgg ttcccaacga tcaaggcgag ttacatgatc ccccatgttg    5160
tgcaaaaaag cggttagctc cttcggtcct ccgatcgttg tcagaagtaa gttggccgca    5220
gtgttatcac tcatggttat ggcagcactg cataattctc ttactgtcat gccatccgta    5280
agatgctttt ctgtgactgg tgagtactca accaagtcat tctgagaata gtgtatgcgg    5340
cgaccgagtt gctcttgccc ggcgtcaata cgggataata ccgcgccaca tagcagaact    5400
```

```
ttaaaagtgc tcatcattgg aaaacgttct tcggggcgaa aactctcaag gatcttaccg    5460
ctgttgagat ccagttcgat gtaacccact cgtgcaccca actgatcttc agcatctttt    5520
actttcacca gcgtttctgg gtgagcaaaa acaggaaggc aaaatgccgc aaaaaaggga    5580
ataagggcga cacggaaatg ttgaatactc atactcttcc tttttcaata ttattgaagc    5640
atttatcagg gttattgtct catgagcgga tacatatttg aatgtattta gaaaaataaa    5700
caaatagggg ttccgcgcac atttccccga aaagtgccac ctgactatgc ggtgtgaaat    5760
accgcacaga tgcgtaagga gaaaataccg catcaggcgc cattcgccat tcaggctgcg    5820
caactgttgg gaagggcgat cggtgcgggc ctcttcgcta ttacgccagc tggcgaaagg    5880
gggatgtgct gcaaggcgat taagttgggt aacgccaggg ttttcccagt cacgacgttg    5940
taaaacgacg gccagtgaat cgcgccaaag ctaactgtag gactgagtct attctaaact    6000
gaaagcctgg acatctggag taccaggggg agatgacgtg ttacgggctt ccataaaagc    6060
agctggcttt gaatgaagg agccaagagg ccagcacagg agcggattcg tcgctttcac    6120
ggccatcgag ccgaacctct cgcaagtccg tgagccgtta aggaggcccc cagtcccgac    6180
ccttcgcccc aagcccctcg gggtcccgg gcctggtact ccttgccaca cgggaggggc    6240
gcggaagccg gggcggagga ggagccaacc ccgggctggg ctgagacccg cagaggaaga    6300
cgctctaggg atttgtcccg gactagcgag atggcaaggc tgaggacggg aggctgattg    6360
agaggcgaag gtacacccta atctcaatac aacctttgga gctaagccag caatggtaga    6420
gggaagattc tgcacgtccc ttccaggcgg cctccccgtc accacccccc caacccgcc    6480 ccgaccggag ctgagagtaa ttcatacaaa aggactcgcc cctgccttgg ggaatcccag    6540
ggaccgtcgt taaactccca ctaacgtaga acccagagat cgctgcgttc ccgccccctc    6600
acccgcccgc tctcgtcatc actgaggtgg agaagagcat gcgtgaggct ccggtgcccg    6660
tcagtgggca gagcgcacat cgcccacagt ccccagaaag ttgggggag gggtcggcaa    6720 ttgaaccggt gcctagagaa ggtggcgcgg ggtaaactgg gaaagtgatg tcgtgtactg    6780
gctccgcctt ttccccgagg gtgggggaga accgtatata agtgcagtag tcgccgtgaa    6840
cgttcttttt cgcaacgggt ttgccgccag aacacaggta agtgccgtgt gtggttcccg    6900
cgggcctggc ctctttacgg gttatggccc ttgcgtgcct tgaattactt ccacgcccct    6960
ggctgcagta cgtgattctt gatcccgagc ttcgggttgg aagtgggtgg gagagttcga    7020
ggccttgcgc ttaaggagcc ccttcgcctc gtgcttgagt tgaggcctgg cttgggcgct    7080
ggggccgccg cgtgcgaatc tggtggcacc ttcgcgcctg tctcgctgct ttcgataagt    7140
ctctagccat ttaaaatttt tgatgacctg ctgcgacgct ttttttctgg caagatagtc    7200
ttgtaaatgc gggccaagat cgatctgcac actggtattt cggttttggg ggccgcgggc    7260
ggcgacgggg cccgtgcgtc ccagcgcaca tgttcggcga ggcggggcct gcgagcgcgg    7320
ccaccgagaa tcgacggggg gtagtctcaa gctggccggc ctgctctggt gcctggcctc    7380
gcgccgccgt gtatcgcccc gccctgggcg gcaaggctgg cccggtcggc accagttgcg    7440
tgagcggaaa gatggccgct tcccggcccc gctgcaggga gctcaaaatg gaggacgcgg    7500
cgctcgggag agcgggcggg tgagtcaccc acacaaagga aaagggcctt tccgtcctca    7560
gccgtcgctt catgtgactc cacggagtac cgggcgccgt ccaggcacct cgattagttc    7620
tcgagctttt ggagtacgtc gtctttaggt tggggggagg ggtttatgc gatggagttt    7680 ccccacactg agtgggtgga gactgaagtt aggccagctt ggcacttgat gtaattctcc    7740
```

```
ttggaatttg ccctttttga gtttggatct tggttcattc tcaagcctca gacagtggtt      7800
caaagttttt ttcttccatt tcaggtgtcg tgggtttgtt taaacttggt accataacta      7860
gttcggcgcg ccactagcgc tgtcacgcgc aagccgcca c                           7901

<210> SEQ ID NO 65
<211> LENGTH: 8198
<212> TYPE: DNA
<213> ORGANISM: Artificial sequence
<220> FEATURE:
<223> OTHER INFORMATION: pCLS9025

<400> SEQUENCE: 65
gtttgtttaa acttggtacc ataactagtt cggcgcgcca ctagcgctgt cacgcgtctc        60
catgggcgat cctaaaaaga aacgtaaggt catcgataag gagaccgccg ctgccaagtt       120
cgagagacag cacatggaca gcatcgatat cgccgacccc attcgttcgc gcacaccaag       180
tcctgcccgc gagcttctgc ccggacccca acccgatggg gttcagccga ctgcagatcg       240
tggggtgtct ccgcctgccg gcggcccct ggatggcttg ccggctcggc ggacgatgtc        300
ccggacccgg ctgccatctc ccctgcccc ctcacctgcg ttctcggcgg gcagcttcag        360
tgacctgtta cgtcagttcg atccgtcact ttttaataca tcgcttttg attcattgcc       420 tcccttcggc gctcaccata cagaggctgc acaggcgag tgggatgagg tgcaatcggg        480
tctgcgggca gccgacgccc cccacccac catgcgcgtg ctgtcactg ccgcgcggcc         540 cccgcgcgcc aagccggcgc cgcgacgacg tgctgcgcaa ccctccgacg cttcgccggc       600
ggcgcaggtg gatctacgca cgctcggcta cagccagcag caacaggaga agatcaaacc       660
gaaggttcgt tcgacagtgg cgcagcacca cgaggcactg gtcggccacg ggtttacaca       720
cgcgcacatc gttgcgttaa gccaacaccc ggcagcgtta gggaccgtcg ctgtcaagta       780
tcaggacatg atcgcagcgt tgccagaggc gacacacgaa gcgatcgttg cgtcggcaa        840 acagtggtcc ggcgcacgcg ctctggaggc cttgctcacg gtggcgggag agttgagagg       900
tccaccgtta cagttggaca caggccaact tctcaagatt gcaaaacgtg gcggcgtgac       960
cgcagtggag gcagtgcatg catggcgcaa tgcactgacg ggtgccccgc tcaacttgac      1020
cccggagcag gtggtggcca tcgccagcca cgatggcggc aagcaggcgc tggagacggt      1080
ccagcggctg ttgccggtgc tgtgccaggc ccacggcttg acccccagc aggtggtggc       1140 catcgccagc aatggcggtg gcaagcaggc gctggagacg tccagcggc tgttgccggt       1200 gctgtgccag gccacggct tgaccccca gcaggtggtg gccatcgcca gcaataatgg        1260
tggcaagcag gcgctggaga cggtccagcg gctgttgccg gtgctgtgcc aggcccacgg      1320 cttgacccc cagcaggtgg tggccatcgc cagcaatggc ggtggcaagc aggcgctgga       1380
gacggtccag cggctgttgc cggtgctgtg ccaggcccac ggcttgaccc ccagcaggt       1440 ggtggccatc gccagcaata atggtggcaa gcaggcgctg gagacggtcc agcggctgtt      1500
gccggtgctg tgccaggccc acggcttgac ccccagcag gtggtggcca tcgccagcaa       1560
taatggtggc aagcaggcgc tggagacggt ccagcggctg ttgccggtgc tgtgccaggc      1620
ccacggcttg acccccagc aggtggtggc catcgccagc aataatggtg gcaagcaggc       1680
gctggagacg tccagcggc tgttgccggt gctgtgccag gcccacggct tgaccccgga       1740
gcaggtggtg gccatcgcca gcacgatggt cggcaagcag gcgctggaga cggtccagcg      1800
gctgttgccg gtgctgtgcc aggcccacg cttgaccccc cagcaggtgg tggccatcgc       1860
cagcaatggc ggtggcaagc aggcgctgga gacggtccag cggctgttgc cggtgctgtg      1920
```

```
ccaggcccac ggcttgaccc cggagcaggt ggtggccatc gccagccacg atggcggcaa    1980
gcaggcgctg gagacggtcc agcggctgtt gccggtgctg tgccaggccc acggcttgac    2040
cccccagcag gtggtggcca tcgccagcaa taatggtggc aagcaggcgc tggagacggt    2100
ccagcggctg ttgccggtgc tgtgccaggc ccacggcttg accccccagc aggtggtggc    2160
catcgccagc aataatggtg gcaagcaggc gctggagacg gtccagcggc tgttgccggt    2220
gctgtgccag gccacggct tgaccccca gcaggtggtg gccatcgcca gcaataatgg    2280
tggcaagcag gcgctggaga cggtccagcg gctgttgccg gtgctgtgcc aggcccacgg    2340 cttgacccc cagcaggtgg tggccatcgc cagcaatggc ggtggcaagc aggcgctgga    2400
gacggtccag cggctgttgc cggtgctgtg ccaggcccac ggcttgaccc cggagcaggt    2460
ggtggccatc gccagccacg atggcggcaa gcaggcgctg gagacggtcc agcggctgtt    2520
gccggtgctg tgccaggccc acggcttgac ccctcagcag gtggtggcca tcgccagcaa    2580
tggcggcggc aggccggcgc tggagagcat gttgcccag ttatctcgcc ctgatccggc    2640
gttggccgcg ttgaccaacg accacctcgt cgccttggcc tgcctcggcg ggcgtcctgc    2700
gctggatgca gtgaaaaagg gattgggga tcctatcagc cgttcccagc tggtgaagtc    2760
cgagctggag gagaagaaat ccgagttgag gcacaagctg aagtacgtgc ccacgagta    2820 catcgagctg atcgagatcg cccggaacag cacccaggac cgtatcctgg agatgaaggt    2880
gatggagttc ttcatgaagg tgtacggcta caggggcaag cacctgggcg gctccaggaa    2940
gcccgacggc gccatctaca ccgtgggctc ccccatcgac tacggcgtga tcgtggacac    3000
caaggcctac tccggcggct acaacctgcc catcggccag gccgacgaaa tgcagaggta    3060
cgtggaggag aaccagacca ggaacaagca catcaacccc aacgagtggt ggaaggtgta    3120
cccctccagc gtgaccgagt tcaagttcct gttcgtgtcc ggccacttca agggcaacta    3180
caaggcccag ctgaccaggc tgaaccacat caccaactgc aacggcgccg tgctgtccgt    3240
ggaggagctc ctgatcggcg gcgagatgat caaggccggc accctgaccc tggaggaggt    3300
gaggaggaag ttcaacaacg gcgagatcaa cttcgcggcc gcttgataac tcgagcgcta    3360
gcacccagct ttcttgtaca aagtggtgat ctaggaaagc ggccgcggag ctccaggaat    3420
tctgcagatc gactgtgcct tctagttgcc agccatctgt tgtttgcccc tcccccgtgc    3480
cttccttgac cctggaaggt gccactccca ctgtcctttc ctaataaaat gaggaaattg    3540
catcgcattg tctgagtagg tgtcattcta ttctgggggg tggggtgggg caggacagca    3600
agggggagga ttgggaagac aatagcaggc atgctgggga tgcggtgggc tctatggatc    3660
ctctagagtc gacctgcagg catgcaagct ggcgtaatc atggtcatag ctgtttcctg    3720
tgtgaaattg ttatccgctc acaattccac acaacatacg agccggaagc ataaagtgta    3780
aagcctgggg tgcctaatga gtgagctaac tcacattaat tgcgttgcgc tcactgcccg    3840
ctttccagtc gggaaacctg tcgtgccagc tgcattaatg aatcggccaa cgcgcgggga    3900
gaggcggttt gcgtattggg cgctcttccg cttcctcgct cactgactcg ctgcgctcgg    3960
tcgttcggct gcggcgagcg gtatcagctc actcaaaggc ggtaatacgg ttatccacag    4020
aatcagggga taacgcagga agaacatgt gagcaaaagg ccagcaaaag gccaggaacc    4080
gtaaaaaggc cgcgttgctg gcgtttttcc ataggctccg cccccctgac gagcatcaca    4140
aaaatcgacg ctcaagtcag aggtggcgaa acccgacagg actataaaga taccaggcgt    4200 ttcccctgg aagctccctc gtgcgctctc ctgttccgac cctgccgctt accggatacc    4260
```

| | |
|---|---|
| tgtccgcctt tctcccttcg ggaagcgtgg cgctttctca tagctcacgc tgtaggtatc | 4320 |
| tcagttcggt gtaggtcgtt cgctccaagc tgggctgtgt gcacgaaccc cccgttcagc | 4380 |
| ccgaccgctg cgccttatcc ggtaactatc gtcttgagtc caacccggta agacacgact | 4440 |
| tatcgccact ggcagcagcc actggtaaca ggattagcag agcgaggtat gtaggcggtg | 4500 |
| ctacagagtt cttgaagtgg tggcctaact acggctacac tagaaggaca gtatttggta | 4560 |
| tctgcgctct gctgaagcca gttaccttcg gaaaaagagt tggtagctct tgatccggca | 4620 |
| aacaaaccac cgctggtagc ggtggttttt tgtttgcaa gcagcagatt acgcgcagaa | 4680 |
| aaaaaggatc tcaagaagat cctttgatct tttctacggg gtctgacgct cagtggaacg | 4740 |
| aaaactcacg ttaagggatt ttggtcatga gattatcaaa aaggatcttc acctagatcc | 4800 |
| ttttaaatta aaaatgaagt tttaaatcaa tctaaagtat atatgagtaa acttggtctg | 4860 |
| acagttacca atgcttaatc agtgaggcac ctatctcagc gatctgtcta tttcgttcat | 4920 |
| ccatagttgc ctgactcccc gtcgtgtaga taactacgat acgggagggc ttaccatctg | 4980 |
| gccccagtgc tgcaatgata ccgcgagacc cacgctcacc ggctccagat ttatcagcaa | 5040 |
| taaaccagcc agccggaagg gccgagcgca gaagtggtcc tgcaacttta tccgcctcca | 5100 |
| tccagtctat taattgttgc cgggaagcta gagtaagtag ttcgccagtt aatagtttgc | 5160 |
| gcaacgttgt tgccattgct acaggcatcg tggtgtcacg ctcgtcgttt ggtatggctt | 5220 |
| cattcagctc cggttcccaa cgatcaaggc gagttacatg atcccccatg ttgtgcaaaa | 5280 |
| aagcggttag ctccttcggt cctccgatcg ttgtcagaag taagttggcc gcagtgttat | 5340 |
| cactcatggt tatggcagca ctgcataatt ctcttactgt catgccatcc gtaagatgct | 5400 |
| tttctgtgac tggtgagtac tcaaccaagt cattctgaga atagtgtatg cggcgaccga | 5460 |
| gttgctcttg cccggcgtca atacgggata ataccgcgcc acatagcaga actttaaaag | 5520 |
| tgctcatcat tggaaaacgt tcttcgggc gaaaactctc aaggatctta ccgctgttga | 5580 |
| gatccagttc gatgtaaccc actcgtgcac ccaactgatc ttcagcatct tttactttca | 5640 |
| ccagcgtttc tgggtgagca aaaacaggaa ggcaaaatgc cgcaaaaaag ggaataaggg | 5700 |
| cgacacggaa atgttgaata ctcatactct ccttttttca atattattga agcatttatc | 5760 |
| agggttattg tctcatgagc ggatacatat ttgaatgtat ttagaaaaat aaacaaatag | 5820 |
| gggttccgcg cacatttccc cgaaaagtgc cacctgacgt ctaagaaacc attattatca | 5880 |
| tgacattaac ctataaaaat aggcgtatca cgaggccctt tcgtctcgcg cgtttcggtg | 5940 |
| atgacggtga aaacctctga cacatgcagc tcccggagac ggtcacagct tgtctgtaag | 6000 |
| cggatgccgg gagcagacaa gcccgtcagg gcgcgtcagc gggtgttggc gggtgtcggg | 6060 |
| gctggcttaa ctatgcggca tcagagcaga ttgtactgag agtgcaccat atgcggtgtg | 6120 |
| aaataccgca cagatgcgta aggagaaaat accgcatcag gcgccattcg ccattcaggc | 6180 |
| tgcgcaactg ttgggaaggg cgatcggtgc gggcctcttc gctattacgc cagctggcga | 6240 |
| aagggggatg tgctgcaagg cgattaagtt gggtaacgcc agggttttcc cagtcacgac | 6300 |
| gttgtaaaac gacggccagt gaattcgcgc caaagctaac tgtaggactg agtctattct | 6360 |
| aaactgaaag cctggacatc tggagtacca ggggagatg acgtgttacg gcttccata | 6420 |
| aaagcagctg gctttgaatg gaaggagcca agaggccagc acaggagcgg attcgtcgct | 6480 |
| ttcacggcca tcgagccgaa cctctcgcaa gtccgtgagc cgttaaggag gcccccagtc | 6540 |
| ccgacccttc gccccaagcc cctcggggtc cccgggcctg gtactccttg ccacacggga | 6600 |
| ggggcgcgga agccggggcg gaggaggagc caaccccggg ctgggctgag accgcagag | 6660 |

| | |
|---|---:|
| gaagacgctc tagggatttg tcccggacta gcgagatggc aaggctgagg acgggaggct | 6720 |
| gattgagagg cgaaggtaca ccctaatctc aatacaacct ttggagctaa gccagcaatg | 6780 |
| gtagagggaa gattctgcac gtcccttcca ggcggcctcc ccgtcaccac ccccccaac | 6840 |
| ccgccccgac cggagctgag agtaattcat acaaaaggac tcgcccctgc cttggggaat | 6900 |
| cccagggacc gtcgttaaac tcccactaac gtagaaccca gagatcgctg cgttcccgcc | 6960 |
| ccctcacccg cccgctctcg tcatcactga ggtggagaag agcatgcgtg aggctccggt | 7020 |
| gcccgtcagt gggcagagcg cacatcgccc acagtccccg agaagttggg gggaggggtc | 7080 |
| ggcaattgaa ccggtgccta gagaaggtgg cgcggggtaa actgggaaag tgatgtcgtg | 7140 |
| tactggctcc gccttttcc cgagggtggg ggagaaccgt atataagtgc agtagtcgcc | 7200 |
| gtgaacgttc tttttcgcaa cgggtttgcc gccagaacac aggtaagtgc cgtgtgtggt | 7260 |
| tcccgcgggc ctggcctctt tacgggttat ggcccttgcg tgccttgaat tacttccacg | 7320 |
| cccctggctg cagtacgtga ttcttgatcc cgagcttcgg gttggaagtg ggtgggagag | 7380 |
| ttcgaggcct tgcgcttaag gagccccttc gcctcgtgct tgagttgagg cctggcttgg | 7440 |
| gcgctggggc cgccgcgtgc gaatctggtg gcaccttcgc gcctgtctcg ctgctttcga | 7500 |
| taagtctcta gccatttaaa attttttgatg acctgctgcg acgcttttt tctggcaaga | 7560 |
| tagtcttgta aatgcgggcc aagatcgatc tgcacactgg tatttcggtt tttggggccg | 7620 |
| cgggcggcga cggggcccgt gcgtcccagc gcacatgttc ggcgaggcgg ggcctgcgag | 7680 |
| cgcggccacc gagaatcgga cggggggtagt ctcaagctgg ccggcctgct ctggtgcctg | 7740 |
| gcctcgcgcc gccgtgtatc gccccgccct gggcggcaag gctggcccgg tcggcaccag | 7800 |
| ttgcgtgagc ggaaagatgg ccgcttcccg gccctgctgc agggagctca aaatggagga | 7860 |
| cgcggcgctc gggagagcgg gcgggtgagt cacccacaca aaggaaaagg gcctttccgt | 7920 |
| cctcagccgt cgcttcatgt gactccacgg agtaccgggc gccgtccagg cacctcgatt | 7980 |
| agttctcgag cttttggagt acgtcgtctt taggttgggg ggaggggttt tatgcgatgg | 8040 |
| agtttcccca cactgagtgg gtggagactg aagttaggcc agcttggcac ttgatgtaat | 8100 |
| tctccttgga atttgccctt tttgagtttg gatcttggtt cattctcaag cctcagacag | 8160 |
| tggttcaaag ttttttttctt ccatttcagg tgtcgtgg | 8198 |

<210> SEQ ID NO 66
<211> LENGTH: 8180
<212> TYPE: DNA
<213> ORGANISM: Artificial sequence
<220> FEATURE:
<223> OTHER INFORMATION: pCLS9026

<400> SEQUENCE: 66

| | |
|---|---:|
| gtttgtttaa acttggtacc ataactagtt cggcgcgcca ctagcgctgt cacgcgtctc | 60 |
| catgggcgat cctaaaaaga aacgtaaggt catcgattac ccatacgatg ttccagatta | 120 |
| cgctatcgat atcgccgacc ccattcgttc gcgcacacca agtcctgccc gcgagcttct | 180 |
| gcccggaccc caacccgatg gggttcagcc gactgcagat cgtggggtgt ctccgcctgc | 240 |
| cggcggcccc ctggatggct tgccggctcg gcggacgatg tcccgacccc ggctgccatc | 300 |
| tccccctgcc ccctcacctg cgttctcggc gggcagcttc agtgacctgt tacgtcagtt | 360 |
| cgatccgtca cttttttaata catcgctttt tgattcattg cctcccttcg gcgctcacca | 420 |
| tacagaggct gccacaggcg agtgggatga ggtgcaatcg ggtctgcggg cagccgacgc | 480 |

-continued

```
cccccacc   accatgcgcg  tggctgtcac  tgccgcgcgg  ccccgcgcg   ccaagccggc    540
gccgcgacga  cgtgctgcgc  aaccctccga  cgcttcgccg  gcggcgcagg  tggatctacg    600
cacgctcggc  tacagccagc  agcaacagga  gaagatcaaa  ccgaaggttc  gttcgacagt    660
ggcgcagcac  cacgaggcac  tggtcggcca  cgggtttaca  cacgcgcaca  tcgttgcgtt    720
aagccaacac  ccggcagcgt  tagggaccgt  cgctgtcaag  tatcaggaca  tgatcgcagc    780
gttgccagag  cgacacacg   aagcgatcgt  tggcgtcggc  aaacagtggt  ccggcgcacg    840
cgctctggag  gccttgctca  cggtggcggg  agagttgaga  ggtccaccgt  tacagttgga    900
cacaggccaa  cttctcaaga  ttgcaaaacg  tggcggcgtg  accgcagtgg  aggcagtgca    960
tgcatggcgc  aatgcactga  cgggtgcccc  gctcaacttg  accccggagc  aggtggtggc   1020
catcgccagc  cacgatggcg  gcaagcaggg  gctggagacg  tccagcggc   tgttgccggt   1080
gctgtgccag  gcccacggct  tgaccccgga  gcaggtggtg  gccatcgcca  gccacgatgg   1140
cggcaagcag  gcgctggaga  cggtccagcg  gctgttgccg  gtgctgtgcc  aggcccacgg   1200
cttgaccccc  cagcaggtgg  tggccatcgc  cagcaataat  ggtggcaagc  aggcgctgga   1260
gacggtccag  cggctgttgc  cggtgctgtg  ccaggcccac  ggcttgaccc  cccagcaggt   1320
ggtggccatc  gccagcaata  atggtggcaa  gcaggcgctg  gagacggtcc  agcggctgtt   1380
gccggtgctg  tgccaggccc  acggcttgac  cccccagcag  gtggtggcca  tcgccagcaa   1440
taatggtggc  aagcaggcgc  tggagacggt  ccagcggctg  ttgccggtgc  tgtgccaggc   1500
ccacggcttg  accccggagc  aggtggtggc  catcgccagc  aatattggtg  gcaagcaggc   1560
gctggagacg  tgcaggcgc   tgttgccggt  gctgtgccag  gcccacggct  tgaccccgga   1620
gcaggtggtg  gccatcgcca  gcaatattgg  tggcaagcag  gcgctggaga  cggtgcaggc   1680
gctgttgccg  gtgctgtgcc  aggcccacgg  cttgaccccg  gagcaggtgg  tggccatcgc   1740
cagccacgat  ggcggcaagc  aggcgctgga  gacggtccag  cggctgttgc  cggtgctgtg   1800
ccaggcccac  ggcttgaccc  cggagcaggt  ggtggccatc  gccagccacg  atggcggcaa   1860
gcaggcgctg  gagacggtcc  agcggctgtt  gccggtgctg  tgccaggccc  acggcttgac   1920
cccggagcag  gtggtggcca  tcgccagcca  cgatggcggc  aagcaggcgc  tggagacggt   1980
ccagcggctg  ttgccggtgc  tgtgccaggc  ccacggcttg  accccggagc  aggtggtggc   2040
catcgccagc  aatattggtg  gcaagcaggc  gctggagacg  tgcaggcgc   tgttgccggt   2100
gctgtgccag  gcccacggct  tgaccccca   gcaggtggtg  gccatcgcca  gcaataatgg   2160
tggcaagcag  gcgctggaga  cggtccagcg  gctgttgccg  gtgctgtgcc  aggcccacgg   2220
cttgaccccg  gagcaggtgg  tggccatcgc  cagcaatatt  ggtggcaagc  aggcgctgga   2280
gacggtgcag  gcgctgttgc  cggtgctgtg  ccaggcccac  ggcttgaccc  cccagcaggt   2340
ggtggccatc  gccagcaata  atggtggcaa  gcaggcgctg  gagacggtcc  agcggctgtt   2400
gccggtgctg  tgccaggccc  acggcttgac  cccggagcag  gtggtggcca  tcgccagcca   2460
cgatggcggc  aagcaggcgc  tggagacggt  ccagcggctg  ttgccggtgc  tgtgccaggc   2520
ccacggcttg  accccctcagc  aggtggtggc  catcgccagc  aatggcggcg  gcaggccggc   2580
gctggagagc  attgttgccc  agttatctcg  ccctgatccg  gcgttggccg  cgttgaccaa   2640
cgaccacctc  gtcgccttgg  cctgcctcgg  cgggcgtcct  gcgctggatg  cagtgaaaaa   2700
gggattgggg  gatcctatca  gccgttccca  gctggtgaag  tccgagctgg  aggagaagaa   2760
atccgagttg  aggcacaagc  tgaagtacgt  gccccacgag  tacatcgagc  tgatcgagat   2820
cgcccggaac  agcacccagg  accgtatcct  ggagatgaag  gtgatggagt  tcttcatgaa   2880
```

```
ggtgtacggc tacaggggca agcacctggg cggctccagg aagcccgacg gcgccatcta    2940
caccgtgggc tccccatcg actacggcgt gatcgtggac accaaggcct actccggcgg    3000
ctacaacctg cccatcggcc aggccgacga aatgcagagg tacgtggagg agaaccagac    3060
caggaacaag cacatcaacc ccaacgagtg gtggaaggtg tacccctcca gcgtgaccga    3120
gttcaagttc ctgttcgtgt ccggccactt caagggcaac tacaaggccc agctgaccag    3180
gctgaaccac atcaccaact gcaacggcgc cgtgctgtcc gtggaggagc tcctgatcgg    3240
cggcgagatg atcaaggccg gcaccctgac cctggaggag gtgaggagga agttcaacaa    3300
cggcgagatc aacttcgcgg ccgcttgata actcgagcgc tagcacccag ctttcttgta    3360
caaagtggtg atctaggaaa gcggccgcgg agctccagga attctgcaga tcgactgtgc    3420
cttctagttg ccagccatct gttgtttgcc cctcccccgt gccttccttg accctggaag    3480
gtgccactcc cactgtcctt tcctaataaa atgaggaaat tgcatcgcat tgtctgagta    3540
ggtgtcattc tattctgggg ggtggggtgg ggcaggacag caaggggag gattgggaag    3600
acaatagcag gcatgctggg gatgcggtgg gctctatgga tcctctagag tcgacctgca    3660
ggcatgcaag cttggcgtaa tcatggtcat agctgtttcc tgtgtgaaat tgttatccgc    3720
tcacaattcc acacaacata cgagccggaa gcataaagtg taaagcctgg ggtgcctaat    3780
gagtgagcta actcacatta attgcgttgc gctcactgcc cgctttccag tcgggaaacc    3840
tgtcgtgcca gctgcattaa tgaatcggcc aacgcgcggg gagaggcggt ttgcgtattg    3900
ggcgctcttc cgcttcctcg ctcactgact cgctgcgctc ggtcgttcgg ctgcggcgag    3960
cggtatcagc tcactcaaag gcggtaatac ggttatccac agaatcaggg gataacgcag    4020
gaaagaacat gtgagcaaaa ggccagcaaa aggccaggaa ccgtaaaaag gccgcgttgc    4080
tggcgttttt ccataggctc cgcccccctg acgagcatca caaaaatcga cgctcaagtc    4140
agaggtggcg aaacccgaca ggactataaa gataccaggc gtttccccct ggaagctccc    4200
tcgtgcgctc tcctgttccg accctgccgc ttaccggata cctgtccgcc tttctccctt    4260
cgggaagcgt ggcgctttct catagctcac gctgtaggta tctcagttcg gtgtaggtcg    4320
ttcgctccaa gctgggctgt gtgcacgaac cccccgttca gcccgaccgc tgcgccttat    4380
ccggtaacta tcgtcttgag tccaacccgg taagacacga cttatcgcca ctggcagcag    4440
ccactggtaa caggattagc agagcgaggt atgtaggcgg tgctacagag ttcttgaagt    4500
ggtggcctaa ctacggctac actagaagga cagtatttgg tatctgcgct ctgctgaagc    4560
cagttacctt cggaaaaaga gttggtagct cttgatccgg caaacaaacc accgctggta    4620
gcggtggttt ttttgtttgc aagcagcaga ttacgcgcag aaaaaaagga tctcaagaag    4680
atcctttgat cttttctacg gggtctgacg ctcagtggaa cgaaaactca cgttaaggga    4740
ttttggtcat gagattatca aaaaggatct tcacctagat ccttttaaat taaaaatgaa    4800
gttttaaatc aatctaaagt atatatgagt aaacttggtc tgacagttac caatgcttaa    4860
tcagtgaggc acctatctca gcgatctgtc tatttcgttc atccatagtt gcctgactcc    4920
ccgtcgtgta gataactacg atacgggagg gcttaccatc tggccccagt gctgcaatga    4980
taccgcgaga cccacgctca ccggctccag atttatcagc aataaaccag ccagccggaa    5040
gggccgagcg cagaagtggt cctgcaactt tatccgcctc catccagtct attaattgtt    5100
gccgggaagc tagagtaagt agttcgccag ttaatagttt gcgcaacgtt gttgccattg    5160
ctacaggcat cgtggtgtca cgctcgtcgt ttggtatggc ttcattcagc tccggttccc    5220
```

```
aacgatcaag gcgagttaca tgatccccca tgttgtgcaa aaaagcggtt agctccttcg    5280
gtcctccgat cgttgtcaga agtaagttgg ccgcagtgtt atcactcatg gttatggcag    5340
cactgcataa ttctcttact gtcatgccat ccgtaagatg cttttctgtg actggtgagt    5400
actcaaccaa gtcattctga gaatagtgta tgcggcgacc gagttgctct tgcccggcgt    5460
caatacggga taataccgcg ccacatagca gaactttaaa agtgctcatc attggaaaac    5520
gttcttcggg gcgaaaactc tcaaggatct taccgctgtt gagatccagt tcgatgtaac    5580
ccactcgtgc acccaactga tcttcagcat cttttacttt caccagcgtt tctgggtgag    5640
caaaaacagg aaggcaaaat gccgcaaaaa agggaataag ggcgacacgg aaatgttgaa    5700
tactcatact cttccttttt caatattatt gaagcattta tcagggttat tgtctcatga    5760
gcggatacat atttgaatgt atttagaaaa ataaacaaat aggggttccg cgcacatttc    5820
cccgaaaagt gccacctgac gtctaagaaa ccattattat catgacatta acctataaaa    5880
ataggcgtat cacgaggccc tttcgtctcg cgcgtttcgg tgatgacggt gaaaacctct    5940
gacacatgca gctcccggag acggtcacag cttgtctgta agcggatgcc gggagcagac    6000
aagcccgtca gggcgcgtca gcgggtgttg gcgggtgtcg ggctggctt  aactatgcgg    6060
catcagagca gattgtactg agagtgcacc atatgcggtg tgaaataccg cacagatgcg    6120
taaggagaaa ataccgcatc aggcgccatt cgccattcag gctgcgcaac tgttgggaag    6180
ggcgatcggt gcgggcctct tcgctattac gccagctggc gaaagggga  tgtgctgcaa    6240
ggcgattaag ttgggtaacg ccagggtttt cccagtcacg acgttgtaaa acgacggcca    6300
gtgaattcgc gccaaagcta actgtaggac tgagtctatt ctaaactgaa agcctggaca    6360
tctggagtac caggggagag tgacgtgtta cgggcttcca taaaagcagc tggctttgaa    6420
tggaaggagc caagaggcca gcacaggagc ggattcgtcg cttt cacggc catcgagccg    6480
aacctctcgc aagtccgtga gccgttaagg aggcccccag tcccgaccct tcgcccaag    6540
cccctcgggg tccccgggcc tggtactcct tgccacacgg gaggggcgcg gaagccgggg    6600
cggaggagga gccaaccccg ggctgggctg agaccgcag  aggaagacgc tctagggatt    6660
tgtcccggac tagcgagatg gcaaggctga ggacgggagg ctgattgaga ggcgaaggta    6720
caccctaatc tcaatacaac cttt ggagct aagccagcaa tggtagaggg aagattctgc    6780
acgtcccttc caggcggcct ccccgtcacc acccccccca acccgccccg accggagctg    6840
agagtaattc atacaaaagg actcgcccct gccttgggga atcccaggga ccgtcgttaa    6900
actcccacta acgtagaacc cagagatcgc tgcgttcccg cccctcacc  cgcccgctct    6960
cgtcatcact gaggtggaga agagcatgcg tgaggctccg gtgcccgtca gtgggcagag    7020
cgcacatcgc ccacagtccc cgagaagttg ggggagggg  tcggcaattg aaccggtgcc    7080
tagagaaggt ggcgcggggt aaactgggaa agtgatgtcg tgtactggct ccgcctttt    7140
cccgagggtg ggggagaacc gtatataagt gcagtagtcg ccgtgaacgt tcttttt cgc    7200
aacgggtttg ccgccagaac acaggtaagt gccgtgtgtg gttcccgcgg gcctggcctc    7260
tttacgggtt atggcccttg cgtgccttga attacttcca cgcccctggc tgcagtacgt    7320
gattcttgat cccgagcttc gggttggaag tgggtgggag agttcgaggc cttgcgctta    7380
aggagcccct tcgcctcgtg cttgagttga ggcctggctt gggcgctggg gccgccgcgt    7440
gcgaatctgg tggcaccttc gcgcctgtct cgctgctttc gataagtctc tagccattta    7500
aaatttttga tgacctgctg cgacgctttt tttctggcaa gatagtcttg taaatgcggg    7560
ccaagatcga tctgcacact ggtatttcgg tttttggggc cgcgggcggc gacggggccc    7620
```

```
gtgcgtccca gcgcacatgt tcggcgaggc ggggcctgcg agcgcggcca ccgagaatcg    7680 gacggggta gtctcaagct ggccggcctg ctctggtgcc tggcctcgcg ccgccgtgta     7740
tcgccccgcc ctgggcggca aggctggccc ggtcggcacc agttgcgtga gcggaaagat    7800
ggccgcttcc cggccctgct gcaggagct caaaatggag gacgcggcgc tcgggagagc     7860
gggcgggtga gtcacccaca caaaggaaaa gggccttttcc gtcctcagcc gtcgcttcat   7920
gtgactccac ggagtaccgg gcgccgtcca ggcacctcga ttagttctcg agcttttgga   7980
gtacgtcgtc tttaggttgg ggggaggggt tttatgcgat ggagtttccc cacactgagt    8040
gggtggagac tgaagttagg ccagcttggc acttgatgta attctccttg gaatttgccc    8100
tttttgagtt tggatcttgg ttcattctca agcctcagac agtggttcaa agttttttc     8160 ttccatttca ggtgtcgtgg                                                8180
```

<210> SEQ ID NO 67
<211> LENGTH: 49
<212> TYPE: DNA
<213> ORGANISM: Artificial sequence
<220> FEATURE:
<223> OTHER INFORMATION: DMD target

<400> SEQUENCE: 67

```
tgtattcctt tatggatcag ttaacattat aaatgataac tttagctca               49
```

<210> SEQ ID NO 68
<211> LENGTH: 49
<212> TYPE: DNA
<213> ORGANISM: Artificial sequence
<220> FEATURE:
<223> OTHER INFORMATION: HBB target

<400> SEQUENCE: 68

```
tctgacacaa ctgtgttcac tagcaacctc aaacagacac catggtgca               49
```

<210> SEQ ID NO 69
<211> LENGTH: 49
<212> TYPE: DNA
<213> ORGANISM: Artificial sequence
<220> FEATURE:
<223> OTHER INFORMATION: CAPT1 target

<400> SEQUENCE: 69

```
tccgggaacc cagagctcac agccacgatc ttagacccga gcccacaga               49
```

<210> SEQ ID NO 70
<211> LENGTH: 4263
<212> TYPE: DNA
<213> ORGANISM: Artificial sequence
<220> FEATURE:
<223> OTHER INFORMATION: pCLS8940

<400> SEQUENCE: 70

```
gcccctgcag ccgaattata ttatttttgc caaataattt ttaacaaaag ctctgaagtc    60
ttcttcattt aaattcttag atgatacttc atctggaaaa ttgtcccaat tagtagcatc    120
acgctgtgag taagttctaa accattttt tattgttgta ttatctctaa tcttactact     180
cgatgagttt tcggtattat ctctattttt aacttggagc aggttccatt cattgttttt    240
ttcatcatag tgaataaaat caactgcttt aacacttgtg cctgaacacc atatccatcc    300
ggcgtaatac gactcactat agggagagcg gccgccagat cttccggatg gctcgagttt    360
```

```
ttcagcaaga ttacacacat acaaatactt gtgacttttg aaatttatta tttgttttcc    420
ttatgtcatc agtgtacctt gagtaccatt acaatgtgag actacttgat acaaagtttt    480
cacattctga gttgaaagaa agaaaactaa aggtgaaaaa tcacatggtc atatatgcga    540
ctatattaga ccagcattta ttcaaaacat tttatttcta agtaaagaaa attaagatat    600
tgttcttgca gcctaaagga acaaaatacc cattgaaaat gtttaaagcc attttccagt    660
ccatatttta gtattatttg atcgtattta aattaacatg catatatgac atattttaga    720
aattatttga tggtaactta gcacatgatt tttattaata tcctgatatt tctcctatta    780
atattgagca tttaggtttc agaaatgaag caggagttat tagataggaa ttagtgtaca    840
tttaaatcaa aatattttca tgtagttgtg tgttaatatt ttcagatttg ctgttatctc    900
agtcacaaat acacatctgt attcctttat ggatcagtta attaaggcgc gccggaccgc    960
ggccgcaatt cattataaat gataacttta gctcatttct ctaatgtttt aatttctaga   1020
actacactaa aaaagccaaa agaatacttt cacagtaatt catgacttgt ctgacatgat   1080
gaagtaccac actcccccat ctttctacag gtgcccctaa aaatgtgttc tttacaacta   1140
gatgggagga aacttatttt gaaacctcaa gtaccaaatg taaaagaaag gctatgagca   1200
cagtatctta taatagcatt ccatgaaagt tttaaattgg attttgtgt gtgtttaaat    1260
aacatgtctt attatctctg ttaacaatgt acagcttttt aaaaaccaaa atgaagactg   1320
tacttgttgt ttttgatcag aatgaagaca atgagggtac tgtaaaagaa ttgttgcaaa   1380
gaggagacaa cttacaacaa agaatcacag atgagagaaa gcgagaggaa ataaagataa   1440
aacagcagct gttacagaca aaacataatg ctctcaaggt attagagcta aaattataat   1500
ataccttgcc tgtggttttt ttttaatata tagggtaaaa tataatgtgc attaataaaa   1560
tctgcttcag acttagtcat cagaaactca ctttttctgt tcaatgtgta tgctttattt   1620
aacattttg agtggtattt gattttgaac gatgtgttgc atctttctag aagatctcct    1680
acaatattct cagctgccat ggaaaatcga tgttcttctt ttattctctc aagattttca   1740
ggctgtatat taaaacttat attaagaact atgctaacca cctcatcagg aaccgttgta   1800
ggtggcgtgg gttttcttgg caatcgactc tcatgaaaac tacgagctaa atattcaata   1860
tgttcctctt gaccaacttt attctgcatt ttttttgaac gaggtttaga gcaagcttca   1920
ggaaactgag acaggaattt tattaaaaat ttaaattttg aagaaagttc agggttaata   1980
gcatccattt tttgctttgc aagttcctca gcattcttaa caaaagacgt ctcttttgac   2040
atgtttaaag tttaaacctc ctgtgtgaaa ttattatccg ctcataattc cacacattat   2100
acgagccgga agcataaagt gtaaagcctg ggtgcctaa tgagtgagct aactcacatt    2160
aattgcgttg cgctcactgc caattgcttt ccagtcggga aacctgtcgt gccagctgca   2220
ttaatgaatc ggccaacgcg cggggagagg cggtttgcgt attgggcgct cttccgcttc   2280
ctcgctcact gactcgctgc gctcggtcgt tcggctgcgg cgagcggtat cagctcactc   2340
aaaggcggta atacggttat ccacagaatc agggataac gcaggaaaga acatgtgagc    2400
aaaaggccag caaaaggcca ggaaccgtaa aaaggccgcg ttgctggcgt ttttccatag   2460
gctccgcccc cctgacgagc atcacaaaaa tcgacgctca gtcagaggt ggcgaaaccc    2520
gacaggacta taaagatacc aggcgtttcc ccctggaagc tccctcgtgc gctctcctgt   2580
tccgaccctg ccgcttaccg gatacctgtc gcccttctc ccttcgggaa gcgtggcgct   2640
ttctcatagc tcacgctgta ggtatctcag ttcggtgtag tcgttcgct ccaagctggg    2700
ctgtgtgcac gaaccccccg ttcagcccga ccgctgcgcc ttatccggta actatcgtct   2760
```

| | |
|---|---|
| tgagtccaac ccggtaagac acgacttatc gccactggca gcagccactg gtaacaggat | 2820 |
| tagcagagcg aggtatgtag gcggtgctac agagttcttg aagtggtggc ctaactacgg | 2880 |
| ctacactaga aggacagtat ttggtatctg cgctctgctg aagccagtta ccttcggaaa | 2940 |
| aagagttggt agctcttgat ccggcaaaca accaccgct ggtagcggtg gttttttttgt | 3000 |
| ttgcaagcag cagattacgc gcagaaaaaa aggatctcaa gaagatcctt tgatcttttc | 3060 |
| tacgggtct gacgctcagt ggaacgaaaa ctcacgttaa gggattttgg tcatgagatt | 3120 |
| atcaaaaagg atcttcacct agatcctttt aaattaaaaa tgaagtttta aatcaatcta | 3180 |
| aagtatatat gagtaaactt ggtctgacag ttaccaatgc ttaatcagtg aggcaccctat | 3240 |
| ctcagcgatc tgtctatttc gttcatccat agttgcctga ctccccgtcg tgtagataac | 3300 |
| tacgatacgg gagggcttac catctggccc cagtgctgca atgataccgc gagacccacg | 3360 |
| ctcaccggct ccagatttat cagcaataaa ccagccagcc ggaagggccg agcgcagaag | 3420 |
| tggtcctgca actttatccg cctccatcca gtctattaat tgttgccggg aagctagagt | 3480 |
| aagtagttcg ccagttaata gtttgcgcaa cgttgttgcc attgctacag gcatcgtggt | 3540 |
| gtcacgctcg tcgtttggta tggcttcatt cagctccggt tcccaacgat caaggcgagt | 3600 |
| tacatgatcc cccatgttgt gcaaaaaagc ggttagctcc ttcggtcctc cgatcgttgt | 3660 |
| cagaagtaag ttggccgcag tgttatcact catggttatg gcagcactgc ataattctct | 3720 |
| tactgtcatg ccatccgtaa gatgcttttc tgtgactggt gagtactcaa ccaagtcatt | 3780 |
| ctgagaatag tgtatgcggc gaccgagttg ctcttgcccg gcgtcaatac gggataatac | 3840 |
| cgcgccacat agcagaactt taaaagtgct catcattgga aaacgttctt cggggcgaaa | 3900 |
| actctcaagg atcttaccgc tgttgagatc cagttcgatg taacccactc gtgcacccaa | 3960 |
| ctgatcttca gcatctttta ctttcaccag cgtttctggg tgagcaaaaa caggaaggca | 4020 |
| aaatgccgca aaaaagggaa taagggcgac acggaaatgt tgaatactca tactcttcct | 4080 |
| ttttcaatat tattgaagca tttatcaggg ttattgtctc atgagcggat acatatttga | 4140 |
| atgtatttag aaaaataaac aaataggggt tccgcgcaca tttccccgaa aagtgccacc | 4200 |
| tgacgtctaa gaaaccatta ttatcatgac attaacctat aaaaataggc gtatcacgag | 4260 |
| gcc | 4263 |

<210> SEQ ID NO 71
<211> LENGTH: 5155
<212> TYPE: DNA
<213> ORGANISM: Artificial sequence
<220> FEATURE:
<223> OTHER INFORMATION: pCLS8943

<400> SEQUENCE: 71

| | |
|---|---|
| gcccctgcag ccgaattata ttatttttgc caaataattt ttaacaaaag ctctgaagtc | 60 |
| ttcttcattt aaattcttag atgatacttc atctggaaaa ttgtcccaat tagtagcatc | 120 |
| acgctgtgag taagttctaa accattttt tattgttgta ttatctctaa tcttactact | 180 |
| cgatgagttt tcggtattat ctctattttt aacttggagc aggttccatt cattgttttt | 240 |
| ttcatcatag tgaataaaat caactgcttt aacacttgtg cctgaacacc atatccatcc | 300 |
| ggcgtaatac gactcactat agggagagcg gccgccagat cttccggatg gctcgagttt | 360 |
| ttcagcaaga tgtagaagac cttttcccct cctaccccta cttttctaagt cacagaggct | 420 |
| ttttgttccc ccagacactc ttgcagatta gtccaggcag aaacagttag atgtccccag | 480 |

```
ttaacctcct atttgacacc actgattacc ccattgatag tcacactttg ggttgtaagt    540
gactttttat ttatttgtat ttttgactgc attaagaggt ctctagtttt ttatctcttg    600
tttcccaaaa cctaataagt aactaatgca cagagcacat tgatttgtat ttattctatt    660
tttagacata atttattagc atgcatgagc aaattaagaa aaacaacaac aaatgaatgc    720
atatatatgt atatgtatgt gtgtatatat acacacatat atatatatat ttttctttt     780 cttaccagaa ggttttaatc caaataagga gaagatatgc ttagaaccga ggtagagttt    840
tcatccattc tgtcctgtaa gtattttgca tattctggag acgcaggaag agatccatct    900
acatatccca aagctgaatt atggtagaca aaactcttcc acttttagtg catcaacttc    960
ttatttgtgt aataagaaaa ttgggaaaac gatcttcaat atgcttacca agctgtgatt   1020
ccaaatatta cgtaaataca cttgcaaagg aggatgtttt tagtagcaat ttgtactgat   1080
ggtatggggc caagagatat atcttagagg gagggctgag ggtttgaagt ccaactccta   1140
agccagtgcc agaagagcca aggacaggta cggctgtcat cacttagacc tcaccctgtg   1200
gagccacacc ctagggttgg ccaatctact cccaggagca gggagggcag gagccagggc   1260
tgggcataaa agtcagggca gagccatcta ttgcttacat ttgcttctga cacaactgtg   1320
ttcactagca ttaaggcgcg ccggaccgcg gccgcaatta cctcaaacag acaccatggt   1380
gcatctgact cctgtggaga agtctgccgt tactgccctg tggggcaagg tgaacgtgga   1440
tgaagttggt ggtgaggccc tgggcaggtt ggtatcaagg ttacaagaca ggtttaagga   1500
gaccaataga aactgggcat gtggagacag agaagactct tgggtttctg ataggcactg   1560
actctctctg cctattggtc tattttccca cccttaggct gctggtggtc tacccttgga   1620
cccagaggtt ctttgagtcc tttggggatc tgtccactcc tgatgctgtt atgggcaacc   1680
ctaaggtgaa ggctcatggc aagaaagtgc tcggtgcctt tagtgatggc ctggctcacc   1740
tggacaacct caagggcacc tttgccacac tgagtgagct gcactgtgac aagctgcacg   1800
tggatcctga gaacttcagg gtgagtctat gggacgcttg atgttttctt tccccttctt   1860
ttctatggtt aagttcatgt cataggaagg ggataagtaa cagggtacag tttagaatgg   1920
gaaacagacg aatgattgca tcagtgtgga agtctcagga tcgttttagt ttcttttatt   1980
tgctgttcat aacaattgtt ttcttttgtt taattcttgc tttctttttt tttcttctcc   2040 gcaatttttta ctattatact taatgcctta acattgtgta taacaaaagg aaatatctct   2100
gagatacatt aagtaactta aaaaaaaact ttacacagtc tgcctagtac attactatt    2160 ggaatatatg tgtgcttatt tgcatattca taatctccct actttatttt cttttatttt   2220
taattgatac ataatcatta tacatattta tggttaaag tgtaatgttt taatatgtgt    2280
acacatattg accaaatcag ggtaattttg catttgtaat tttaaaaaat gctttcttct   2340
tttaatatac ttttttgttt atcttatttc taatactttc cctaatctct ttctttcagg   2400
gcaataatga tacaatgtat catgcctctt tgcaccattc taaagaataa cagtgataat   2460
ttctgggtta aggcaatagc aatatctctg catataaata tttctgcata taaattgtaa   2520
ctgatgtaag aggtttcata ttgctaatag caatctttct agaagatctc ctacaatatt   2580
ctcagctgcc atgaaaaatc gatgttcttc ttttattctc tcaagatttt caggctgtat   2640
attaaaactt atattaagaa ctatgctaac cacctcatca ggaaccgttg taggtggcgt   2700
gggttttctt ggcaatcgac tctcatgaaa actacgagct aaatattcaa tatgttcctc   2760
ttgaccaact ttattctgca ttttttttga acgaggttta gagcaagctt caggaaactg   2820
agacaggaat tttattaaaa atttaaattt tgaagaaagt tcagggttaa tagcatccat   2880
```

```
tttttgcttt gcaagttcct cagcattctt aacaaaagac gtctcttttg acatgtttaa   2940
agtttaaacc tcctgtgtga aattattatc cgctcataat tccacacatt atacgagccg   3000
gaagcataaa gtgtaaagcc tggggtgcct aatgagtgag ctaactcaca ttaattgcgt   3060
tgcgctcact gccaattgct ttccagtcgg gaaacctgtc gtgccagctg cattaatgaa   3120
tcggccaacg cgcggggaga ggcggtttgc gtattgggcg ctcttccgct tcctcgctca   3180
ctgactcgct gcgctcggtc gttcggctgc ggcgagcggt atcagctcac tcaaaggcgg   3240
taatacggtt atccacagaa tcaggggata acgcaggaaa gaacatgtga gcaaaaggcc   3300
agcaaaaggc caggaaccgt aaaaaggccg cgttgctggc gtttttccat aggctccgcc   3360
cccctgacga gcatcacaaa aatcgacgct caagtcagag gtggcgaaac ccgacaggac   3420
tataaagata ccaggcgttt ccccctggaa gctccctcgt gcgctctcct gttccgaccc   3480
tgccgcttac cggatacctg tccgcctttc tcccttcggg aagcgtggcg ctttctcata   3540
gctcacgctg taggtatctc agttcggtgt aggtcgttcg ctccaagctg ggctgtgtgc   3600
acgaaccccc cgttcagccc gaccgctgcg ccttatccgg taactatcgt cttgagtcca   3660
acccggtaag acacgactta tcgccactgg cagcagccac tggtaacagg attagcagag   3720
cgaggtatgt aggcggtgct acagagttct tgaagtggtg gcctaactac ggctacacta   3780
gaaggacagt atttggtatc tgcgctctgc tgaagccagt taccttcgga aaaagagttg   3840
gtagctcttg atccggcaaa caaaccaccg ctggtagcgg tggtttttttt gtttgcaagc   3900 agcagattac gcgcagaaaa aaggatctca agaagatcc tttgatcttt tctacggggt   3960
ctgacgctca gtggaacgaa aactcacgtt aagggatttt ggtcatgaga ttatcaaaaa   4020
ggatcttcac ctagatcctt ttaaattaaa aatgaagttt taaatcaatc taagtatat   4080 atgagtaaac ttggtctgac agttaccaat gcttaatcag tgaggcacct atctcagcga   4140
tctgtctatt tcgttcatcc atagttgcct gactccccgt cgtgtagata actacgatac   4200
gggagggctt accatctggc cccagtgctg caatgatacc gcgagaccca cgctcaccgg   4260
ctccagattt atcagcaata aaccagccag ccggaagggc cgagcgcaga agtggtcctg   4320
caactttatc cgcctccatc cagtctatta attgttgccg ggaagctaga gtaagtagtt   4380
cgccagttaa tagtttgcgc aacgttgttg ccattgctac aggcatcgtg gtgtcacgct   4440
cgtcgtttgg tatggcttca ttcagctccg gttcccaacg atcaaggcga gttacatgat   4500
cccccatgtt gtgcaaaaaa gcggttagct ccttcggtcc tccgatcgtt gtcagaagta   4560
agttggccgc agtgttatca ctcatggtta tggcagcact gcataattct cttactgtca   4620
tgccatccgt aagatgcttt tctgtgactg gtgagtactc aaccaagtca ttctgagaat   4680
agtgtatgcg gcgaccgagt tgctcttgcc cggcgtcaat acgggataat accgcgccac   4740
atagcagaac tttaaaagtg ctcatcattg gaaaacgttc ttcggggcga aaactctcaa   4800
ggatcttacc gctgttgaga tccagttcga tgtaacccac tcgtgcaccc aactgatctt   4860
cagcatcttt tactttcacc agcgtttctg ggtgagcaaa aacaggaagg caaaatgccg   4920
caaaaaaggg aataagggcg acacggaaat gttgaatact catactcttc ctttttcaat   4980
attattgaag catttatcag ggttattgtc tcatgagcgg atacatattt gaatgtattt   5040
agaaaaataa acaaataggg gttccgcgca catttccccg aaaagtgcca cctgacgtct   5100
aagaaaccat tattatcatg acattaacct ataaaaatag gcgtatcacg aggcc         5155
```

<210> SEQ ID NO 72

<211> LENGTH: 4258
<212> TYPE: DNA
<213> ORGANISM: Artificial sequence
<220> FEATURE:
<223> OTHER INFORMATION: pCLS9893

<400> SEQUENCE: 72

| | |
|---|---:|
| gcccctgcag ccgaattata ttatttttgc caaataattt ttaacaaaag ctctgaagtc | 60 |
| ttcttcattt aaattcttag atgatacttc atctggaaaa ttgtcccaat tagtagcatc | 120 |
| acgctgtgag taagttctaa accatttttt tattgttgta ttatctctaa tcttactact | 180 |
| cgatgagttt tcggtattat ctctattttt aacttggagc aggttccatt cattgttttt | 240 |
| ttcatcatag tgaataaaat caactgcttt aacacttgtg cctgaacacc atatccatcc | 300 |
| ggcgtaatac gactcactat agggagagcg gccgccagat cttccggatg gctcgagttt | 360 |
| ttcagcaaga tgaaggatat tggcatgccc tagggtgaaa attcacacta cgacactcgg | 420 |
| ggggtgggtc ccctccgagt tctcgtccgc gggtgcctcc acccagacct gaggggtgtc | 480 |
| gggaagaccc ccgcctaccg agtcagggcg ggattaagac ctccggcgct ggaaacgcgt | 540 |
| agggcggggc ccagacctgg atccagctag ccgggcggtg tggggtgcgc atgcgcaatg | 600 |
| tccgcttcgg ctctaggacc gcgcgggcga cagcagggcc gcggtgcagt gtccgacccg | 660 |
| agagttgcgg cctgagtcac cggccccgcc ctccggagcc ggacgctgcg ggaggcccgg | 720 |
| gagcggcagt ggaaccgact cccagaactc cggacgtgtg cggcggtaag cgcccggccc | 780 |
| gtaccccctc cgcaccccgc aactccgact ttggcggccc ccagaccccgg cgaaaccgtg | 840 |
| aagtctcggc tcaggagcc ccccagatcc atggtctcag attcgaaccc tcagacctgt | 900 |
| tcgatctcct tttatgccgt cccggggacc cttctccacc ctctgtctca tgatccaaaa | 960 |
| tacaggccca taggtttcag agataccctg tgaattcttc cttggggtgt cctgaaccgc | 1020 |
| gatcgtagat ctgtgccccc agttccagcg gggaacccca ttgtccggga acccagagct | 1080 |
| cacagccatt aaggcgcgcc ggaccgcggc cgcaattcga tcttagaccc gagcccacag | 1140 |
| agccagaggt gacactggaa tcctgccgct gggaatacct aaattctcaa gcccacattt | 1200 |
| gggatttcct aaaccccgcc ctggggccct ttaggccgtg gatgtttgct ccgcgcccat | 1260 |
| gacctgccaa ggacctctac attcaggctg gctctggat ctcacattct agcgcccaga | 1320 |
| catgtcggga acgccttacg ccaacttggg gtccccacca agagaacccc caccagatct | 1380 |
| gcaccctccc cttcacgcgt gcacccagtc caggctccct caagcccac gggtgccttt | 1440 |
| tagacctgag gaggttgcaa acctgatccc ccatacctgc cccacccatc cgcggacaac | 1500 |
| ccgccctcgc aaactcagac ccccacccgg aggcttcaga ttcctcccag gtccagctgc | 1560 |
| cggaaatgcg tgtttgaagg gagggtgtgg gctcagggc gaagcaccca ctggtcccct | 1620 |
| tttttccccc cagcagtgag tcgcagccat gttccatctt tctagaagat ctcctacaat | 1680 |
| attctcagct gccatggaaa atcgatgttc ttcttttatt ctctcaagat tttcaggctg | 1740 |
| tatattaaaa cttatattaa gaactatgct aaccacctca tcaggaaccg ttgtaggtgg | 1800 |
| cgtgggtttt cttggcaatc gactctcatg aaaactacga gctaaatatt caatatgttc | 1860 |
| ctcttgacca actttattct gcattttttt tgaacgaggt ttagagcaag cttcaggaaa | 1920 |
| ctgagacagg aattttatta aaatttaaa ttttgaagaa agttcagggt taatagcatc | 1980 |
| cattttttgc tttgcaagtt cctcagcatt cttaacaaaa gacgtctctt ttgacatgtt | 2040 |
| taaagtttaa acctcctgtg tgaaattatt atccgctcat aattccacac attatacgag | 2100 |
| ccggaagcat aaagtgtaaa gcctggggtg cctaatgagt gagctaactc acattaattg | 2160 |

```
cgttgcgctc actgccaatt gctttccagt cgggaaacct gtcgtgccag ctgcattaat    2220
gaatcggcca acgcgcgggg agaggcggtt tgcgtattgg gcgctcttcc gcttcctcgc    2280
tcactgactc gctgcgctcg gtcgttcggc tgcggcgagc ggtatcagct cactcaaagg    2340
cggtaatacg gttatccaca gaatcagggg ataacgcagg aaagaacatg tgagcaaaag    2400
gccagcaaaa ggccaggaac cgtaaaaagg ccgcgttgct ggcgtttttc cataggctcc    2460
gcccccctga cgagcatcac aaaaatcgac gctcaagtca gaggtggcga acccgacag    2520 gactataaag ataccaggcg tttccccctg gaagctccct cgtgcgctct cctgttccga    2580
ccctgccgct taccggatac ctgtccgcct ttctcccttc gggaagcgtg gcgctttctc    2640
atagctcacg ctgtaggtat ctcagttcgg tgtaggtcgt tcgctccaag ctgggctgtg    2700
tgcacgaacc ccccgttcag cccgaccgct gcgccttatc cggtaactat cgtcttgagt    2760
ccaacccggt aagacacgac ttatcgccac tggcagcagc cactggtaac aggattagca    2820
gagcgaggta tgtaggcggt gctacagagt tcttgaagtg gtggcctaac tacggctaca    2880
ctagaaggac agtatttggt atctgcgctc tgctgaagcc agttaccttc ggaaaaagag    2940
ttggtagctc ttgatccggc aaacaaacca ccgctggtag cggtggtttt tttgtttgca    3000
agcagcagat tacgcgcaga aaaaaggat ctcaagaaga tcctttgatc ttttctacgg    3060
ggtctgacgc tcagtggaac gaaaactcac gttaagggat tttggtcatg agattatcaa    3120
aaaggatctt cacctagatc cttttaaatt aaaaatgaag ttttaaatca atctaaagta    3180
tatatgagta aacttggtct gacagttacc aatgcttaat cagtgaggca cctatctcag    3240
cgatctgtct atttcgttca tccatagttg cctgactccc cgtcgtgtag ataactacga    3300
tacgggaggg cttaccatct ggccccagtg ctgcaatgat accgcgagac ccacgctcac    3360
cggctccaga tttatcagca ataaaccagc cagccggaag ggccgagcgc agaagtggtc    3420
ctgcaacttt atccgcctcc atccagtcta ttaattgttg ccgggaagct agagtaagta    3480
gttcgccagt taatagtttg cgcaacgttg ttgccattgc tacaggcatc gtggtgtcac    3540
gctcgtcgtt tggtatggct tcattcagct ccggttccca acgatcaagg cgagttacat    3600 gatccccat gttgtgcaaa aaagcggtta gctccttcgg tcctccgatc gttgtcagaa    3660
gtaagttggc cgcagtgtta tcactcatgg ttatggcagc actgcataat tctcttactg    3720
tcatgccatc cgtaagatgc ttttctgtga ctggtgagta ctcaaccaag tcattctgag    3780
aatagtgtat gcggcgaccg agttgctctt gcccggcgtc aatacgggat aataccgcgc    3840
cacatagcag aactttaaaa gtgctcatca ttggaaaacg ttcttcgggg cgaaaactct    3900
caaggatctt accgctgttg agatccagtt cgatgtaacc cactcgtgca cccaactgat    3960
cttcagcatc ttttactttc accagcgttt ctgggtgagc aaaaacagga aggcaaaatg    4020
ccgcaaaaaa gggaataagg gcgacacgga atgttgaat actcatactc ttcctttttc    4080
aatattattg aagcatttat cagggttatt gtctcatgag cggatacata tttgaatgta    4140
tttagaaaaa taaacaaata ggggttccgc gcacatttcc ccgaaaagtg ccacctgacg    4200
tctaagaaac cattattatc atgacattaa cctataaaaa taggcgtatc acgaggcc     4258
```

<210> SEQ ID NO 73
<211> LENGTH: 27
<212> TYPE: DNA
<213> ORGANISM: Artificial sequence
<220> FEATURE:
<223> OTHER INFORMATION: DMDT F1

<400> SEQUENCE: 73
aggcctccat tcctttgaag gaattgg                                   27

<210> SEQ ID NO 74
<211> LENGTH: 31
<212> TYPE: DNA
<213> ORGANISM: Artificial sequence
<220> FEATURE:
<223> OTHER INFORMATION: DMDT R1

<400> SEQUENCE: 74
ttaaacactg ctattcagta ggacacacac c                              31

<210> SEQ ID NO 75
<211> LENGTH: 58
<212> TYPE: DNA
<213> ORGANISM: Artificial sequence
<220> FEATURE:
<223> OTHER INFORMATION: DMDT F2

<400> SEQUENCE: 75
ccatctcatc cctgcgtgtc tccgactcag tagcctgata tttctcctat taatattg  58

<210> SEQ ID NO 76
<211> LENGTH: 56
<212> TYPE: DNA
<213> ORGANISM: Artificial sequence
<220> FEATURE:
<223> OTHER INFORMATION: DMDT R2

<400> SEQUENCE: 76
cctatcccct gtgtgccttg gcagtctcag ggagtgtggt acttcatcat gtcaga    56

<210> SEQ ID NO 77
<211> LENGTH: 25
<212> TYPE: DNA
<213> ORGANISM: Artificial sequence
<220> FEATURE:
<223> OTHER INFORMATION: HBBT F1

<400> SEQUENCE: 77
gaagagtaaa ttttagtaaa ggagg                                     25

<210> SEQ ID NO 78
<211> LENGTH: 24
<212> TYPE: DNA
<213> ORGANISM: Artificial sequence
<220> FEATURE:
<223> OTHER INFORMATION: HBBT R1

<400> SEQUENCE: 78
gcctagcttg gactcagaat aatc                                      24

<210> SEQ ID NO 79
<211> LENGTH: 63
<212> TYPE: DNA
<213> ORGANISM: Artificial sequence
<220> FEATURE:
<223> OTHER INFORMATION: HBBT F2

<400> SEQUENCE: 79
ccatctcatc cctgcgtgtc tccgactcag tagccacacc ctagggttgg ccaatctact  60
ccc                                                             63

-continued

<210> SEQ ID NO 80
<211> LENGTH: 57
<212> TYPE: DNA
<213> ORGANISM: Artificial sequence
<220> FEATURE:
<223> OTHER INFORMATION: HBBT R2

<400> SEQUENCE: 80
cctatcccct gtgtgccttg gcagtctcag cccacccctta ggctgctggt ggtctac    57

<210> SEQ ID NO 81
<211> LENGTH: 25
<212> TYPE: DNA
<213> ORGANISM: Artificial sequence
<220> FEATURE:
<223> OTHER INFORMATION: CAPT F1

<400> SEQUENCE: 81
cttctccacc ctctgtctca tgatc    25

<210> SEQ ID NO 82
<211> LENGTH: 25
<212> TYPE: DNA
<213> ORGANISM: Artificial sequence
<220> FEATURE:
<223> OTHER INFORMATION: CAPT R1

<400> SEQUENCE: 82
ccttggcagg tcatgggcgc ggagc    25

<210> SEQ ID NO 83
<211> LENGTH: 58
<212> TYPE: DNA
<213> ORGANISM: Artificial sequence
<220> FEATURE:
<223> OTHER INFORMATION: CAPT F2

<400> SEQUENCE: 83
ccatctcatc cctgcgtgtc tccgactcag tagcttctcc accctctgtc tcatgatc    58

<210> SEQ ID NO 84
<211> LENGTH: 55
<212> TYPE: DNA
<213> ORGANISM: Artificial sequence
<220> FEATURE:
<223> OTHER INFORMATION: CAPT R2

<400> SEQUENCE: 84
cctatcccct gtgtgccttg gcagtctcag ccttggcagg tcatgggcgc ggagc    55

<210> SEQ ID NO 85
<211> LENGTH: 1065
<212> TYPE: PRT
<213> ORGANISM: Artificial sequence
<220> FEATURE:
<223> OTHER INFORMATION: protein encoded by pCLS9027

<400> SEQUENCE: 85

```
Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
                20                  25                  30

Val Ser Pro Pro Ala Gly Gly Pro Leu Asp Gly Leu Pro Ala Arg Arg
            35                  40                  45

Thr Met Ser Arg Thr Arg Leu Pro Ser Pro Pro Ala Pro Ser Pro Ala
```

-continued

```
                50                  55                  60
Phe Ser Ala Gly Ser Phe Ser Asp Leu Leu Arg Gln Phe Asp Pro Ser
 65                  70                  75                  80
Leu Phe Asn Thr Ser Leu Phe Asp Ser Leu Pro Pro Phe Gly Ala His
                     85                  90                  95
His Thr Glu Ala Ala Thr Gly Glu Trp Asp Glu Val Gln Ser Gly Leu
                100                 105                 110
Arg Ala Ala Asp Ala Pro Pro Thr Met Arg Val Ala Val Thr Ala
                115                 120                 125
Ala Arg Pro Pro Arg Ala Lys Pro Ala Pro Arg Arg Ala Ala Gln
            130                 135                 140
Pro Ser Asp Ala Ser Pro Ala Ala Gln Val Asp Leu Arg Thr Leu Gly
145                 150                 155                 160
Tyr Ser Gln Gln Gln Glu Lys Ile Lys Pro Lys Val Arg Ser Thr
                165                 170                 175
Val Ala Gln His His Glu Ala Leu Val Gly His Gly Phe Thr His Ala
                180                 185                 190
His Ile Val Ala Leu Ser Gln His Pro Ala Ala Leu Gly Thr Val Ala
                195                 200                 205
Val Lys Tyr Gln Asp Met Ile Ala Ala Leu Pro Glu Ala Thr His Glu
        210                 215                 220
Ala Ile Val Gly Val Gly Lys Gln Trp Ser Gly Ala Arg Ala Leu Glu
225                 230                 235                 240
Ala Leu Leu Thr Val Ala Gly Glu Leu Arg Gly Pro Pro Leu Gln Leu
                245                 250                 255
Asp Thr Gly Gln Leu Leu Lys Ile Ala Lys Arg Gly Gly Val Thr Ala
                260                 265                 270
Val Glu Ala Val His Ala Trp Arg Asn Ala Leu Thr Gly Ala Pro Leu
                275                 280                 285
Asn Leu Thr Pro Gln Gln Val Val Ala Ile Ala Ser Asn Asn Gly Gly
                290                 295                 300
Lys Gln Ala Leu Glu Thr Val Gln Arg Leu Leu Pro Val Leu Cys Gln
305                 310                 315                 320
Ala His Gly Leu Thr Pro Gln Gln Val Val Ala Ile Ala Ser Asn Gly
                325                 330                 335
Gly Gly Lys Gln Ala Leu Glu Thr Val Gln Arg Leu Leu Pro Val Leu
                340                 345                 350
Cys Gln Ala His Gly Leu Thr Pro Glu Gln Val Val Ala Ile Ala Ser
                355                 360                 365
Asn Ile Gly Gly Lys Gln Ala Leu Glu Thr Val Gln Ala Leu Leu Pro
                370                 375                 380
Val Leu Cys Gln Ala His Gly Leu Thr Pro Gln Gln Val Val Ala Ile
385                 390                 395                 400
Ala Ser Asn Gly Gly Lys Gln Ala Leu Glu Thr Val Gln Arg Leu
                405                 410                 415
Leu Pro Val Leu Cys Gln Ala His Gly Leu Thr Pro Gln Gln Val Val
                420                 425                 430
Ala Ile Ala Ser Asn Gly Gly Lys Gln Ala Leu Glu Thr Val Gln
                435                 440                 445
Arg Leu Leu Pro Val Leu Cys Gln Ala His Gly Leu Thr Pro Glu Gln
                450                 455                 460
Val Val Ala Ile Ala Ser His Asp Gly Gly Lys Gln Ala Leu Glu Thr
465                 470                 475                 480
```

```
Val Gln Arg Leu Leu Pro Val Leu Cys Gln Ala His Gly Leu Thr Pro
                485                 490                 495

Glu Gln Val Val Ala Ile Ala Ser His Asp Gly Gly Lys Gln Ala Leu
            500                 505                 510

Glu Thr Val Gln Arg Leu Leu Pro Val Leu Cys Gln Ala His Gly Leu
        515                 520                 525

Thr Pro Gln Gln Val Val Ala Ile Ala Ser Asn Gly Gly Lys Gln
    530                 535                 540

Ala Leu Glu Thr Val Gln Arg Leu Leu Pro Val Leu Cys Gln Ala His
545                 550                 555                 560

Gly Leu Thr Pro Gln Gln Val Val Ala Ile Ala Ser Asn Gly Gly Gly
                565                 570                 575

Lys Gln Ala Leu Glu Thr Val Gln Arg Leu Leu Pro Val Leu Cys Gln
                580                 585                 590

Ala His Gly Leu Thr Pro Gln Gln Val Val Ala Ile Ala Ser Asn Gly
            595                 600                 605

Gly Gly Lys Gln Ala Leu Glu Thr Val Gln Arg Leu Leu Pro Val Leu
        610                 615                 620

Cys Gln Ala His Gly Leu Thr Pro Glu Gln Val Val Ala Ile Ala Ser
625                 630                 635                 640

Asn Ile Gly Gly Lys Gln Ala Leu Glu Thr Val Gln Ala Leu Leu Pro
                645                 650                 655

Val Leu Cys Gln Ala His Gly Leu Thr Pro Gln Gln Val Val Ala Ile
                660                 665                 670

Ala Ser Asn Gly Gly Gly Lys Gln Ala Leu Glu Thr Val Gln Arg Leu
            675                 680                 685

Leu Pro Val Leu Cys Gln Ala His Gly Leu Thr Pro Gln Gln Val Val
        690                 695                 700

Ala Ile Ala Ser Asn Asn Gly Gly Lys Gln Ala Leu Glu Thr Val Gln
705                 710                 715                 720

Arg Leu Leu Pro Val Leu Cys Gln Ala His Gly Leu Thr Pro Gln Gln
                725                 730                 735

Val Val Ala Ile Ala Ser Asn Asn Gly Gly Lys Gln Ala Leu Glu Thr
                740                 745                 750

Val Gln Arg Leu Leu Pro Val Leu Cys Gln Ala His Gly Leu Thr Pro
            755                 760                 765

Glu Gln Val Val Ala Ile Ala Ser Asn Ile Gly Gly Lys Gln Ala Leu
        770                 775                 780

Glu Thr Val Gln Ala Leu Leu Pro Val Leu Cys Gln Ala His Gly Leu
785                 790                 795                 800

Thr Pro Gln Gln Val Val Ala Ile Ala Ser Asn Gly Gly Gly Arg Pro
                805                 810                 815

Ala Leu Glu Ser Ile Val Ala Gln Leu Ser Arg Pro Asp Pro Ala Leu
                820                 825                 830

Ala Ala Leu Thr Asn Asp His Leu Val Ala Leu Ala Cys Leu Gly Gly
            835                 840                 845

Arg Pro Ala Leu Asp Ala Val Lys Lys Gly Leu Gly Asp Pro Ile Ser
        850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895
```

-continued

```
Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 86
<211> LENGTH: 1065
<212> TYPE: PRT
<213> ORGANISM: Artificial sequence
<220> FEATURE:
<223> OTHER INFORMATION: protein encoded by pCLS9028

<400> SEQUENCE: 86

Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
            20                  25                  30

Val Ser Pro Pro Ala Gly Gly Pro Leu Asp Gly Leu Pro Ala Arg Arg
        35                  40                  45

Thr Met Ser Arg Thr Arg Leu Pro Ser Pro Pro Ala Pro Ser Pro Ala
    50                  55                  60

Phe Ser Ala Gly Ser Phe Ser Asp Leu Leu Arg Gln Phe Asp Pro Ser
65                  70                  75                  80

Leu Phe Asn Thr Ser Leu Phe Asp Ser Leu Pro Pro Phe Gly Ala His
                85                  90                  95

His Thr Glu Ala Ala Thr Gly Glu Trp Asp Glu Val Gln Ser Gly Leu
            100                 105                 110

Arg Ala Ala Asp Ala Pro Pro Thr Met Arg Val Ala Val Thr Ala
        115                 120                 125

Ala Arg Pro Pro Arg Ala Lys Pro Ala Pro Arg Arg Arg Ala Ala Gln
    130                 135                 140

Pro Ser Asp Ala Ser Pro Ala Ala Gln Val Asp Leu Arg Thr Leu Gly
145                 150                 155                 160

Tyr Ser Gln Gln Gln Gln Glu Lys Ile Lys Pro Lys Val Arg Ser Thr
                165                 170                 175

Val Ala Gln His His Glu Ala Leu Val Gly His Gly Phe Thr His Ala
            180                 185                 190
```

```
His Ile Val Ala Leu Ser Gln His Pro Ala Ala Leu Gly Thr Val Ala
            195                 200                 205

Val Lys Tyr Gln Asp Met Ile Ala Ala Leu Pro Glu Ala Thr His Glu
210                 215                 220

Ala Ile Val Gly Val Gly Lys Gln Trp Ser Gly Ala Arg Ala Leu Glu
225                 230                 235                 240

Ala Leu Leu Thr Val Ala Gly Glu Leu Arg Gly Pro Pro Leu Gln Leu
            245                 250                 255

Asp Thr Gly Gln Leu Leu Lys Ile Ala Lys Arg Gly Gly Val Thr Ala
            260                 265                 270

Val Glu Ala Val His Ala Trp Arg Asn Ala Leu Thr Gly Ala Pro Leu
        275                 280                 285

Asn Leu Thr Pro Gln Gln Val Ala Ile Ala Ser Asn Asn Gly Gly
290                 295                 300

Lys Gln Ala Leu Glu Thr Val Gln Arg Leu Leu Pro Val Leu Cys Gln
305                 310                 315                 320

Ala His Gly Leu Thr Pro Glu Gln Val Val Ala Ile Ala Ser Asn Ile
            325                 330                 335

Gly Gly Lys Gln Ala Leu Glu Thr Val Gln Ala Leu Leu Pro Val Leu
            340                 345                 350

Cys Gln Ala His Gly Leu Thr Pro Gln Gln Val Val Ala Ile Ala Ser
            355                 360                 365

Asn Asn Gly Gly Lys Gln Ala Leu Glu Thr Val Gln Arg Leu Leu Pro
370                 375                 380

Val Leu Cys Gln Ala His Gly Leu Thr Pro Glu Gln Val Val Ala Ile
385                 390                 395                 400

Ala Ser His Asp Gly Gly Lys Gln Ala Leu Glu Thr Val Gln Arg Leu
            405                 410                 415

Leu Pro Val Leu Cys Gln Ala His Gly Leu Thr Pro Gln Gln Val Val
            420                 425                 430

Ala Ile Ala Ser Asn Gly Gly Lys Gln Ala Leu Glu Thr Val Gln
            435                 440                 445

Arg Leu Leu Pro Val Leu Cys Gln Ala His Gly Leu Thr Pro Glu Gln
450                 455                 460

Val Val Ala Ile Ala Ser Asn Ile Gly Gly Lys Gln Ala Leu Glu Thr
465                 470                 475                 480

Val Gln Ala Leu Leu Pro Val Leu Cys Gln Ala His Gly Leu Thr Pro
            485                 490                 495

Glu Gln Val Val Ala Ile Ala Ser Asn Ile Gly Gly Lys Gln Ala Leu
            500                 505                 510

Glu Thr Val Gln Ala Leu Leu Pro Val Leu Cys Gln Ala His Gly Leu
            515                 520                 525

Thr Pro Glu Gln Val Val Ala Ile Ala Ser Asn Ile Gly Gly Lys Gln
530                 535                 540

Ala Leu Glu Thr Val Gln Ala Leu Leu Pro Val Leu Cys Gln Ala His
545                 550                 555                 560

Gly Leu Thr Pro Gln Gln Val Val Ala Ile Ala Ser Asn Asn Gly Gly
            565                 570                 575

Lys Gln Ala Leu Glu Thr Val Gln Arg Leu Leu Pro Val Leu Cys Gln
            580                 585                 590

Ala His Gly Leu Thr Pro Gln Gln Val Val Ala Ile Ala Ser Asn Gly
            595                 600                 605

Gly Gly Lys Gln Ala Leu Glu Thr Val Gln Arg Leu Leu Pro Val Leu
```

-continued

```
              610                 615                 620

Cys Gln Ala His Gly Leu Thr Pro Gln Gln Val Val Ala Ile Ala Ser
625                 630                 635                 640

Asn Gly Gly Gly Lys Gln Ala Leu Glu Thr Val Gln Arg Leu Leu Pro
                645                 650                 655

Val Leu Cys Gln Ala His Gly Leu Thr Pro Glu Gln Val Val Ala Ile
            660                 665                 670

Ala Ser Asn Ile Gly Gly Lys Gln Ala Leu Glu Thr Val Gln Ala Leu
        675                 680                 685

Leu Pro Val Leu Cys Gln Ala His Gly Leu Thr Pro Gln Gln Val Val
    690                 695                 700

Ala Ile Ala Ser Asn Gly Gly Gly Lys Gln Ala Leu Glu Thr Val Gln
705                 710                 715                 720

Arg Leu Leu Pro Val Leu Cys Gln Ala His Gly Leu Thr Pro Glu Gln
                725                 730                 735

Val Val Ala Ile Ala Ser His Asp Gly Gly Lys Gln Ala Leu Glu Thr
            740                 745                 750

Val Gln Arg Leu Leu Pro Val Leu Cys Gln Ala His Gly Leu Thr Pro
        755                 760                 765

Glu Gln Val Val Ala Ile Ala Ser Asn Ile Gly Gly Lys Gln Ala Leu
    770                 775                 780

Glu Thr Val Gln Ala Leu Leu Pro Val Leu Cys Gln Ala His Gly Leu
785                 790                 795                 800

Thr Pro Gln Gln Val Val Ala Ile Ala Ser Asn Gly Gly Gly Arg Pro
                805                 810                 815

Ala Leu Glu Ser Ile Val Ala Gln Leu Ser Arg Pro Asp Pro Ala Leu
            820                 825                 830

Ala Ala Leu Thr Asn Asp His Leu Val Ala Leu Ala Cys Leu Gly Gly
        835                 840                 845

Arg Pro Ala Leu Asp Ala Val Lys Lys Gly Leu Gly Asp Pro Ile Ser
    850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040
```

-continued

Ile Lys Ala Gly Thr Leu Thr Leu Glu Glu Val Arg Arg Lys Phe Asn
              1045                1050                1055

Asn Gly Glu Ile Asn Phe Ala Ala Asp
              1060            1065

<210> SEQ ID NO 87
<211> LENGTH: 1065
<212> TYPE: PRT
<213> ORGANISM: Artificial sequence
<220> FEATURE:
<223> OTHER INFORMATION: protein encoded by pCLS9235

<400> SEQUENCE: 87

Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
                20                  25                  30

Val Ser Pro Pro Ala Gly Gly Pro Leu Asp Gly Leu Pro Ala Arg Arg
            35                  40                  45

Thr Met Ser Arg Thr Arg Leu Pro Ser Pro Ala Pro Ser Pro Ala
    50                  55                  60

Phe Ser Ala Gly Ser Phe Ser Asp Leu Leu Arg Gln Phe Asp Pro Ser
65                  70                  75                  80

Leu Phe Asn Thr Ser Leu Phe Asp Ser Leu Pro Pro Phe Gly Ala His
                85                  90                  95

His Thr Glu Ala Ala Thr Gly Glu Trp Asp Glu Val Gln Ser Gly Leu
            100                 105                 110

Arg Ala Ala Asp Ala Pro Pro Thr Met Arg Val Ala Val Thr Ala
        115                 120                 125

Ala Arg Pro Pro Arg Ala Lys Pro Ala Pro Arg Arg Ala Ala Gln
    130                 135                 140

Pro Ser Asp Ala Ser Pro Ala Ala Gln Val Asp Leu Arg Thr Leu Gly
145                 150                 155                 160

Tyr Ser Gln Gln Gln Gln Glu Lys Ile Lys Pro Lys Val Arg Ser Thr
                165                 170                 175

Val Ala Gln His His Glu Ala Leu Val Gly His Gly Phe Thr His Ala
            180                 185                 190

His Ile Val Ala Leu Ser Gln His Pro Ala Ala Leu Gly Thr Val Ala
        195                 200                 205

Val Lys Tyr Gln Asp Met Ile Ala Ala Leu Pro Glu Ala Thr His Glu
    210                 215                 220

Ala Ile Val Gly Val Gly Lys Gln Trp Ser Gly Ala Arg Ala Leu Glu
225                 230                 235                 240

Ala Leu Leu Thr Val Ala Gly Glu Leu Arg Gly Pro Pro Leu Gln Leu
                245                 250                 255

Asp Thr Gly Gln Leu Leu Lys Ile Ala Lys Arg Gly Gly Val Thr Ala
            260                 265                 270

Val Glu Ala Val His Ala Trp Arg Asn Ala Leu Thr Gly Ala Pro Leu
        275                 280                 285

Asn Leu Thr Pro Glu Gln Val Val Ala Ile Ala Ser His Asp Gly Gly
    290                 295                 300

Lys Gln Ala Leu Glu Thr Val Gln Arg Leu Leu Pro Val Leu Cys Gln
305                 310                 315                 320

Ala His Gly Leu Thr Pro Gln Gln Val Val Ala Ile Ala Ser Asn Gly
                325                 330                 335

-continued

```
Gly Gly Lys Gln Ala Leu Glu Thr Val Gln Arg Leu Leu Pro Val Leu
            340                 345                 350

Cys Gln Ala His Gly Leu Thr Pro Gln Gln Val Val Ala Ile Ala Ser
            355                 360                 365

Asn Asn Gly Gly Lys Gln Ala Leu Glu Thr Val Gln Arg Leu Leu Pro
            370                 375                 380

Val Leu Cys Gln Ala His Gly Leu Thr Pro Glu Gln Val Val Ala Ile
385                 390                 395                 400

Ala Ser Asn Ile Gly Gly Lys Gln Ala Leu Glu Thr Val Gln Ala Leu
                405                 410                 415

Leu Pro Val Leu Cys Gln Ala His Gly Leu Thr Pro Glu Gln Val Val
            420                 425                 430

Ala Ile Ala Ser His Asp Gly Gly Lys Gln Ala Leu Glu Thr Val Gln
            435                 440                 445

Arg Leu Leu Pro Val Leu Cys Gln Ala His Gly Leu Thr Pro Glu Gln
            450                 455                 460

Val Val Ala Ile Ala Ser Asn Ile Gly Gly Lys Gln Ala Leu Glu Thr
465                 470                 475                 480

Val Gln Ala Leu Leu Pro Val Leu Cys Gln Ala His Gly Leu Thr Pro
                485                 490                 495

Glu Gln Val Val Ala Ile Ala Ser His Asp Gly Gly Lys Gln Ala Leu
            500                 505                 510

Glu Thr Val Gln Arg Leu Leu Pro Val Leu Cys Gln Ala His Gly Leu
            515                 520                 525

Thr Pro Glu Gln Val Val Ala Ile Ala Ser Asn Ile Gly Gly Lys Gln
            530                 535                 540

Ala Leu Glu Thr Val Gln Ala Leu Leu Pro Val Leu Cys Gln Ala His
545                 550                 555                 560

Gly Leu Thr Pro Glu Gln Val Val Ala Ile Ala Ser Asn Ile Gly Gly
                565                 570                 575

Lys Gln Ala Leu Glu Thr Val Gln Ala Leu Leu Pro Val Leu Cys Gln
            580                 585                 590

Ala His Gly Leu Thr Pro Glu Gln Val Val Ala Ile Ala Ser His Asp
            595                 600                 605

Gly Gly Lys Gln Ala Leu Glu Thr Val Gln Arg Leu Leu Pro Val Leu
            610                 615                 620

Cys Gln Ala His Gly Leu Thr Pro Gln Gln Val Val Ala Ile Ala Ser
625                 630                 635                 640

Asn Gly Gly Gly Lys Gln Ala Leu Glu Thr Val Gln Arg Leu Leu Pro
                645                 650                 655

Val Leu Cys Gln Ala His Gly Leu Thr Pro Gln Gln Val Val Ala Ile
            660                 665                 670

Ala Ser Asn Asn Gly Gly Lys Gln Ala Leu Glu Thr Val Gln Arg Leu
            675                 680                 685

Leu Pro Val Leu Cys Gln Ala His Gly Leu Thr Pro Gln Gln Val Val
            690                 695                 700

Ala Ile Ala Ser Asn Gly Gly Gly Lys Gln Ala Leu Glu Thr Val Gln
705                 710                 715                 720

Arg Leu Leu Pro Val Leu Cys Gln Ala His Gly Leu Thr Pro Gln Gln
                725                 730                 735

Val Val Ala Ile Ala Ser Asn Asn Gly Gly Lys Gln Ala Leu Glu Thr
            740                 745                 750
```

Val Gln Arg Leu Leu Pro Val Leu Cys Gln Ala His Gly Leu Thr Pro
            755                 760                 765

Gln Gln Val Val Ala Ile Ala Ser Asn Gly Gly Gly Lys Gln Ala Leu
    770                 775                 780

Glu Thr Val Gln Arg Leu Leu Pro Val Leu Cys Gln Ala His Gly Leu
785                 790                 795                 800

Thr Pro Gln Gln Val Val Ala Ile Ala Ser Asn Gly Gly Gly Arg Pro
                805                 810                 815

Ala Leu Glu Ser Ile Val Ala Gln Leu Ser Arg Pro Asp Pro Ala Leu
            820                 825                 830

Ala Ala Leu Thr Asn Asp His Leu Val Ala Leu Ala Cys Leu Gly Gly
        835                 840                 845

Arg Pro Ala Leu Asp Ala Val Lys Lys Gly Leu Gly Asp Pro Ile Ser
850                 855                 860

Arg Ser Gln Leu Val Lys Ser Glu Leu Glu Glu Lys Lys Ser Glu Leu
865                 870                 875                 880

Arg His Lys Leu Lys Tyr Val Pro His Glu Tyr Ile Glu Leu Ile Glu
                885                 890                 895

Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
        915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
        995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
            1060                1065

<210> SEQ ID NO 88
<211> LENGTH: 1065
<212> TYPE: PRT
<213> ORGANISM: Artificial sequence
<220> FEATURE:
<223> OTHER INFORMATION: protein encoded by pCLS9241

<400> SEQUENCE: 88

Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
            20                  25                  30

Val Ser Pro Pro Ala Gly Gly Pro Leu Asp Gly Leu Pro Ala Arg Arg
        35                  40                  45

```
Thr Met Ser Arg Thr Arg Leu Pro Ser Pro Pro Ala Pro Ser Pro Ala
    50                  55                  60

Phe Ser Ala Gly Ser Phe Ser Asp Leu Leu Arg Gln Phe Asp Pro Ser
65                  70                  75                  80

Leu Phe Asn Thr Ser Leu Phe Asp Ser Leu Pro Pro Phe Gly Ala His
                85                  90                  95

His Thr Glu Ala Ala Thr Gly Glu Trp Asp Glu Val Gln Ser Gly Leu
            100                 105                 110

Arg Ala Ala Asp Ala Pro Pro Thr Met Arg Val Ala Val Thr Ala
            115                 120                 125

Ala Arg Pro Pro Arg Ala Lys Pro Ala Pro Arg Arg Ala Ala Gln
    130                 135                 140

Pro Ser Asp Ala Ser Pro Ala Ala Gln Val Asp Leu Arg Thr Leu Gly
145                 150                 155                 160

Tyr Ser Gln Gln Gln Glu Lys Ile Lys Pro Lys Val Arg Ser Thr
                165                 170                 175

Val Ala Gln His His Glu Ala Leu Val Gly His Gly Phe Thr His Ala
            180                 185                 190

His Ile Val Ala Leu Ser Gln His Pro Ala Ala Leu Gly Thr Val Ala
            195                 200                 205

Val Lys Tyr Gln Asp Met Ile Ala Ala Leu Pro Glu Ala Thr His Glu
    210                 215                 220

Ala Ile Val Gly Val Gly Lys Gln Trp Ser Gly Ala Arg Ala Leu Glu
225                 230                 235                 240

Ala Leu Leu Thr Val Ala Gly Glu Leu Arg Gly Pro Pro Leu Gln Leu
                245                 250                 255

Asp Thr Gly Gln Leu Leu Lys Ile Ala Lys Arg Gly Gly Val Thr Ala
            260                 265                 270

Val Glu Ala Val His Ala Trp Arg Asn Ala Leu Thr Gly Ala Pro Leu
    275                 280                 285

Asn Leu Thr Pro Gln Gln Val Val Ala Ile Ala Ser Asn Asn Gly Gly
    290                 295                 300

Lys Gln Ala Leu Glu Thr Val Gln Arg Leu Leu Pro Val Leu Cys Gln
305                 310                 315                 320

Ala His Gly Leu Thr Pro Glu Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Ala His Gly Leu Thr Pro Glu Gln Val Val Ala Ile Ala Ser
    355                 360                 365

Asn Ile Gly Gly Lys Gln Ala Leu Glu Thr Val Gln Ala Leu Leu Pro
    370                 375                 380

Val Leu Cys Gln Ala His Gly Leu Thr Pro Glu Gln Val Val Ala Ile
385                 390                 395                 400

Ala Ser His Asp Gly Gly Lys Gln Ala Leu Glu Thr Val Gln Arg Leu
                405                 410                 415

Leu Pro Val Leu Cys Gln Ala His Gly Leu Thr Pro Glu Gln Val Val
            420                 425                 430

Ala Ile Ala Ser His Asp Gly Gly Lys Gln Ala Leu Glu Thr Val Gln
    435                 440                 445

Arg Leu Leu Pro Val Leu Cys Gln Ala His Gly Leu Thr Pro Glu Gln
    450                 455                 460

Val Val Ala Ile Ala Ser Asn Ile Gly Gly Lys Gln Ala Leu Glu Thr
```

```
            465                 470                 475                 480
        Val Gln Ala Leu Leu Pro Val Leu Cys Gln Ala His Gly Leu Thr Pro
                        485                 490                 495

Gln Gln Val Val Ala Ile Ala Ser Asn Gly Gly Lys Gln Ala Leu
                    500                 505                 510

Glu Thr Val Gln Arg Leu Leu Pro Val Leu Cys Gln Ala His Gly Leu
                        515                 520                 525

Thr Pro Gln Gln Val Val Ala Ile Ala Ser Asn Asn Gly Gly Lys Gln
                    530                 535                 540

Ala Leu Glu Thr Val Gln Arg Leu Leu Pro Val Leu Cys Gln Ala His
        545                 550                 555                 560

Gly Leu Thr Pro Gln Gln Val Val Ala Ile Ala Ser Asn Asn Gly Gly
                        565                 570                 575

Lys Gln Ala Leu Glu Thr Val Gln Arg Leu Leu Pro Val Leu Cys Gln
                    580                 585                 590

Ala His Gly Leu Thr Pro Gln Gln Val Val Ala Ile Ala Ser Asn Gly
                    595                 600                 605

Gly Gly Lys Gln Ala Leu Glu Thr Val Gln Arg Leu Leu Pro Val Leu
                    610                 615                 620

Cys Gln Ala His Gly Leu Thr Pro Gln Gln Val Val Ala Ile Ala Ser
        625                 630                 635                 640

Asn Asn Gly Gly Lys Gln Ala Leu Glu Thr Val Gln Arg Leu Leu Pro
                        645                 650                 655

Val Leu Cys Gln Ala His Gly Leu Thr Pro Gln Gln Val Val Ala Ile
                        660                 665                 670

Ala Ser Asn Gly Gly Gly Lys Gln Ala Leu Glu Thr Val Gln Arg Leu
                    675                 680                 685

Leu Pro Val Leu Cys Gln Ala His Gly Leu Thr Pro Glu Gln Val Val
                    690                 695                 700

Ala Ile Ala Ser His Asp Gly Gly Lys Gln Ala Leu Glu Thr Val Gln
        705                 710                 715                 720

Arg Leu Leu Pro Val Leu Cys Gln Ala His Gly Leu Thr Pro Gln Gln
                        725                 730                 735

Val Val Ala Ile Ala Ser Asn Gly Gly Gly Lys Gln Ala Leu Glu Thr
                        740                 745                 750

Val Gln Arg Leu Leu Pro Val Leu Cys Gln Ala His Gly Leu Thr Pro
                    755                 760                 765

Gln Gln Val Val Ala Ile Ala Ser Asn Asn Gly Gly Lys Gln Ala Leu
                    770                 775                 780

Glu Thr Val Gln Arg Leu Leu Pro Val Leu Cys Gln Ala His Gly Leu
        785                 790                 795                 800

Thr Pro Gln Gln Val Val Ala Ile Ala Ser Asn Gly Gly Gly Arg Pro
                        805                 810                 815

Ala Leu Glu Ser Ile Val Ala Gln Leu Ser Arg Pro Asp Pro Ala Leu
                        820                 825                 830

Ala Ala Leu Thr Asn Asp His Leu Val Ala Leu Ala Cys Leu Gly Gly
                    835                 840                 845

Arg Pro Ala Leu Asp Ala Val Lys Lys Gly Leu Gly Asp Pro Ile Ser
                    850                 855                 860

Arg Ser Gln Leu Val Lys Ser Glu Leu Glu Glu Lys Ser Glu Leu
        865                 870                 875                 880

Arg His Lys Leu Lys Tyr Val Pro His Glu Tyr Ile Glu Leu Ile Glu
                        885                 890                 895
```

-continued

```
Ile Ala Arg Asn Ser Thr Gln Asp Arg Ile Leu Glu Met Lys Val Met
            900                 905                 910

Glu Phe Phe Met Lys Val Tyr Gly Tyr Arg Gly Lys His Leu Gly Gly
            915                 920                 925

Ser Arg Lys Pro Asp Gly Ala Ile Tyr Thr Val Gly Ser Pro Ile Asp
    930                 935                 940

Tyr Gly Val Ile Val Asp Thr Lys Ala Tyr Ser Gly Gly Tyr Asn Leu
945                 950                 955                 960

Pro Ile Gly Gln Ala Asp Glu Met Gln Arg Tyr Val Glu Glu Asn Gln
                965                 970                 975

Thr Arg Asn Lys His Ile Asn Pro Asn Glu Trp Trp Lys Val Tyr Pro
            980                 985                 990

Ser Ser Val Thr Glu Phe Lys Phe Leu Phe Val Ser Gly His Phe Lys
            995                 1000                1005

Gly Asn Tyr Lys Ala Gln Leu Thr Arg Leu Asn His Ile Thr Asn Cys
    1010                1015                1020

Asn Gly Ala Val Leu Ser Val Glu Glu Leu Leu Ile Gly Gly Glu Met
1025                1030                1035                1040

Ile Lys Ala Gly Thr Leu Thr Leu Glu Glu Val Arg Arg Lys Phe Asn
                1045                1050                1055

Asn Gly Glu Ile Asn Phe Ala Ala Asp
                1060                1065
```

<210> SEQ ID NO 89
<211> LENGTH: 1065
<212> TYPE: PRT
<213> ORGANISM: Artificial sequence
<220> FEATURE:
<223> OTHER INFORMATION: protein encoded by pCLS9025

<400> SEQUENCE: 89

```
Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
            20                  25                  30

Val Ser Pro Pro Ala Gly Gly Pro Leu Asp Gly Leu Pro Ala Arg Arg
        35                  40                  45

Thr Met Ser Arg Thr Arg Leu Pro Ser Pro Ala Pro Ser Pro Ala
    50                  55                  60

Phe Ser Ala Gly Ser Phe Ser Asp Leu Leu Arg Gln Phe Asp Pro Ser
65                  70                  75                  80

Leu Phe Asn Thr Ser Leu Phe Asp Ser Leu Pro Pro Phe Gly Ala His
                85                  90                  95

His Thr Glu Ala Ala Thr Gly Glu Trp Asp Glu Val Gln Ser Gly Leu
            100                 105                 110

Arg Ala Ala Asp Ala Pro Pro Pro Thr Met Arg Val Ala Val Thr Ala
        115                 120                 125

Ala Arg Pro Pro Arg Ala Lys Pro Ala Pro Arg Arg Arg Ala Ala Gln
    130                 135                 140

Pro Ser Asp Ala Ser Pro Ala Ala Gln Val Asp Leu Arg Thr Leu Gly
145                 150                 155                 160

Tyr Ser Gln Gln Gln Gln Glu Lys Ile Lys Pro Lys Val Arg Ser Thr
                165                 170                 175

Val Ala Gln His His Glu Ala Leu Val Gly His Gly Phe Thr His Ala
            180                 185                 190
```

```
His Ile Val Ala Leu Ser Gln His Pro Ala Ala Leu Gly Thr Val Ala
            195                 200                 205

Val Lys Tyr Gln Asp Met Ile Ala Ala Leu Pro Glu Ala Thr His Glu
210                 215                 220

Ala Ile Val Gly Val Gly Lys Gln Trp Ser Gly Ala Arg Ala Leu Glu
225                 230                 235                 240

Ala Leu Leu Thr Val Ala Gly Glu Leu Arg Gly Pro Pro Leu Gln Leu
                245                 250                 255

Asp Thr Gly Gln Leu Leu Lys Ile Ala Lys Arg Gly Gly Val Thr Ala
            260                 265                 270

Val Glu Ala Val His Ala Trp Arg Asn Ala Leu Thr Gly Ala Pro Leu
            275                 280                 285

Asn Leu Thr Pro Glu Gln Val Ala Ile Ala Ser His Asp Gly Gly
            290                 295                 300

Lys Gln Ala Leu Glu Thr Val Gln Arg Leu Leu Pro Val Leu Cys Gln
305                 310                 315                 320

Ala His Gly Leu Thr Pro Gln Gln Val Val Ala Ile Ala Ser Asn Gly
                325                 330                 335

Gly Gly Lys Gln Ala Leu Glu Thr Val Gln Arg Leu Leu Pro Val Leu
                340                 345                 350

Cys Gln Ala His Gly Leu Thr Pro Gln Gln Val Val Ala Ile Ala Ser
            355                 360                 365

Asn Asn Gly Gly Lys Gln Ala Leu Glu Thr Val Gln Arg Leu Leu Pro
            370                 375                 380

Val Leu Cys Gln Ala His Gly Leu Thr Pro Gln Gln Val Val Ala Ile
385                 390                 395                 400

Ala Ser Asn Gly Gly Lys Gln Ala Leu Glu Thr Val Gln Arg Leu
                405                 410                 415

Leu Pro Val Leu Cys Gln Ala His Gly Leu Thr Pro Gln Gln Val Val
                420                 425                 430

Ala Ile Ala Ser Asn Asn Gly Gly Lys Gln Ala Leu Glu Thr Val Gln
            435                 440                 445

Arg Leu Leu Pro Val Leu Cys Gln Ala His Gly Leu Thr Pro Gln Gln
            450                 455                 460

Val Val Ala Ile Ala Ser Asn Asn Gly Gly Lys Gln Ala Leu Glu Thr
465                 470                 475                 480

Val Gln Arg Leu Leu Pro Val Leu Cys Gln Ala His Gly Leu Thr Pro
                485                 490                 495

Gln Gln Val Val Ala Ile Ala Ser Asn Asn Gly Gly Lys Gln Ala Leu
            500                 505                 510

Glu Thr Val Gln Arg Leu Leu Pro Val Leu Cys Gln Ala His Gly Leu
            515                 520                 525

Thr Pro Glu Gln Val Val Ala Ile Ala Ser His Asp Gly Gly Lys Gln
            530                 535                 540

Ala Leu Glu Thr Val Gln Arg Leu Leu Pro Val Leu Cys Gln Ala His
545                 550                 555                 560

Gly Leu Thr Pro Gln Gln Val Val Ala Ile Ala Ser Asn Gly Gly Gly
                565                 570                 575

Lys Gln Ala Leu Glu Thr Val Gln Arg Leu Leu Pro Val Leu Cys Gln
            580                 585                 590

Ala His Gly Leu Thr Pro Glu Gln Val Val Ala Ile Ala Ser His Asp
            595                 600                 605
```

-continued

```
Gly Gly Lys Gln Ala Leu Glu Thr Val Gln Arg Leu Leu Pro Val Leu
        610                 615                 620
Cys Gln Ala His Gly Leu Thr Pro Gln Gln Val Val Ala Ile Ala Ser
625                 630                 635                 640
Asn Asn Gly Gly Lys Gln Ala Leu Glu Thr Val Gln Arg Leu Leu Pro
                645                 650                 655
Val Leu Cys Gln Ala His Gly Leu Thr Pro Gln Gln Val Val Ala Ile
            660                 665                 670
Ala Ser Asn Asn Gly Gly Lys Gln Ala Leu Glu Thr Val Gln Arg Leu
        675                 680                 685
Leu Pro Val Leu Cys Gln Ala His Gly Leu Thr Pro Gln Gln Val Val
    690                 695                 700
Ala Ile Ala Ser Asn Asn Gly Gly Lys Gln Ala Leu Glu Thr Val Gln
705                 710                 715                 720
Arg Leu Leu Pro Val Leu Cys Gln Ala His Gly Leu Thr Pro Gln Gln
                725                 730                 735
Val Val Ala Ile Ala Ser Asn Gly Gly Gly Lys Gln Ala Leu Glu Thr
            740                 745                 750
Val Gln Arg Leu Leu Pro Val Leu Cys Gln Ala His Gly Leu Thr Pro
        755                 760                 765
Glu Gln Val Val Ala Ile Ala Ser His Asp Gly Gly Lys Gln Ala Leu
    770                 775                 780
Glu Thr Val Gln Arg Leu Leu Pro Val Leu Cys Gln Ala His Gly Leu
785                 790                 795                 800
Thr Pro Gln Gln Val Val Ala Ile Ala Ser Asn Gly Gly Gly Arg Pro
                805                 810                 815
Ala Leu Glu Ser Ile Val Ala Gln Leu Ser Arg Pro Asp Pro Ala Leu
            820                 825                 830
Ala Ala Leu Thr Asn Asp His Leu Val Ala Leu Ala Cys Leu Gly Gly
        835                 840                 845
Arg Pro Ala Leu Asp Ala Val Lys Lys Gly Leu Gly Asp Pro Ile Ser
    850                 855                 860
Arg Ser Gln Leu Val Lys Ser Glu Leu Glu Glu Lys Lys Ser Glu Leu
865                 870                 875                 880
Arg His Lys Leu Lys Tyr Val Pro His Glu Tyr Ile Glu Leu Ile Glu
                885                 890                 895
Ile Ala Arg Asn Ser Thr Gln Asp Arg Ile Leu Glu Met Lys Val Met
            900                 905                 910
Glu Phe Phe Met Lys Val Tyr Gly Tyr Arg Gly Lys His Leu Gly Gly
        915                 920                 925
Ser Arg Lys Pro Asp Gly Ala Ile Tyr Thr Val Gly Ser Pro Ile Asp
    930                 935                 940
Tyr Gly Val Ile Val Asp Thr Lys Ala Tyr Ser Gly Gly Tyr Asn Leu
945                 950                 955                 960
Pro Ile Gly Gln Ala Asp Glu Met Gln Arg Tyr Val Glu Glu Asn Gln
                965                 970                 975
Thr Arg Asn Lys His Ile Asn Pro Asn Glu Trp Trp Lys Val Tyr Pro
            980                 985                 990
Ser Ser Val Thr Glu Phe Lys Phe Leu Phe Val Ser Gly His Phe Lys
        995                 1000                1005
Gly Asn Tyr Lys Ala Gln Leu Thr Arg Leu Asn His Ile Thr Asn Cys
    1010                1015                1020
Asn Gly Ala Val Leu Ser Val Glu Glu Leu Leu Ile Gly Gly Glu Met
```

-continued

```
1025                1030                1035                1040
Ile Lys Ala Gly Thr Leu Thr Leu Glu Glu Val Arg Arg Lys Phe Asn
                    1045                1050                1055

Asn Gly Glu Ile Asn Phe Ala Ala Asp
            1060                1065

<210> SEQ ID NO 90
<211> LENGTH: 1065
<212> TYPE: PRT
<213> ORGANISM: Artificial sequence
<220> FEATURE:
<223> OTHER INFORMATION: protein encoded by pCLS9026

<400> SEQUENCE: 90

Met Ala Asp Pro Ile Arg Ser Arg Thr Pro Ser Pro Ala Arg Glu Leu
1               5                   10                  15

Leu Pro Gly Pro Gln Pro Asp Gly Val Gln Pro Thr Ala Asp Arg Gly
                20                  25                  30

Val Ser Pro Pro Ala Gly Gly Pro Leu Asp Gly Leu Pro Ala Arg Arg
            35                  40                  45

Thr Met Ser Arg Thr Arg Leu Pro Ser Pro Ala Pro Ser Pro Ala
    50                  55                  60

Phe Ser Ala Gly Ser Phe Ser Asp Leu Leu Arg Gln Phe Asp Pro Ser
65              70                  75                  80

Leu Phe Asn Thr Ser Leu Phe Asp Ser Leu Pro Pro Phe Gly Ala His
                85                  90                  95

His Thr Glu Ala Ala Thr Gly Glu Trp Asp Glu Val Gln Ser Gly Leu
            100                 105                 110

Arg Ala Ala Asp Ala Pro Pro Thr Met Arg Val Ala Val Thr Ala
            115                 120                 125

Ala Arg Pro Pro Arg Ala Lys Pro Ala Pro Arg Arg Arg Ala Ala Gln
            130                 135                 140

Pro Ser Asp Ala Ser Pro Ala Ala Gln Val Asp Leu Arg Thr Leu Gly
145                 150                 155                 160

Tyr Ser Gln Gln Gln Gln Glu Lys Ile Lys Pro Lys Val Arg Ser Thr
                165                 170                 175

Val Ala Gln His His Glu Ala Leu Val Gly His Gly Phe Thr His Ala
            180                 185                 190

His Ile Val Ala Leu Ser Gln His Pro Ala Ala Leu Gly Thr Val Ala
            195                 200                 205

Val Lys Tyr Gln Asp Met Ile Ala Ala Leu Pro Glu Ala Thr His Glu
    210                 215                 220

Ala Ile Val Gly Val Gly Lys Gln Trp Ser Gly Ala Arg Ala Leu Glu
225                 230                 235                 240

Ala Leu Leu Thr Val Ala Gly Glu Leu Arg Gly Pro Pro Leu Gln Leu
                245                 250                 255

Asp Thr Gly Gln Leu Leu Lys Ile Ala Lys Arg Gly Gly Val Thr Ala
            260                 265                 270

Val Glu Ala Val His Ala Trp Arg Asn Ala Leu Thr Gly Ala Pro Leu
    275                 280                 285

Asn Leu Thr Pro Glu Gln Val Val Ala Ile Ala Ser His Asp Gly Gly
            290                 295                 300

Lys Gln Ala Leu Glu Thr Val Gln Arg Leu Leu Pro Val Leu Cys Gln
305                 310                 315                 320

Ala His Gly Leu Thr Pro Glu Gln Val Val Ala Ile Ala Ser His Asp
```

-continued

```
                325                 330                 335
Gly Gly Lys Gln Ala Leu Glu Thr Val Gln Arg Leu Leu Pro Val Leu
            340                 345                 350
Cys Gln Ala His Gly Leu Thr Pro Gln Gln Val Val Ala Ile Ala Ser
        355                 360                 365
Asn Asn Gly Gly Lys Gln Ala Leu Glu Thr Val Gln Arg Leu Leu Pro
    370                 375                 380
Val Leu Cys Gln Ala His Gly Leu Thr Pro Gln Gln Val Val Ala Ile
385                 390                 395                 400
Ala Ser Asn Asn Gly Gly Lys Gln Ala Leu Glu Thr Val Gln Arg Leu
                405                 410                 415
Leu Pro Val Leu Cys Gln Ala His Gly Leu Thr Pro Gln Gln Val Val
            420                 425                 430
Ala Ile Ala Ser Asn Asn Gly Gly Lys Gln Ala Leu Glu Thr Val Gln
        435                 440                 445
Arg Leu Leu Pro Val Leu Cys Gln Ala His Gly Leu Thr Pro Glu Gln
    450                 455                 460
Val Val Ala Ile Ala Ser Asn Ile Gly Gly Lys Gln Ala Leu Glu Thr
465                 470                 475                 480
Val Gln Ala Leu Leu Pro Val Leu Cys Gln Ala His Gly Leu Thr Pro
                485                 490                 495
Glu Gln Val Val Ala Ile Ala Ser Asn Ile Gly Gly Lys Gln Ala Leu
            500                 505                 510
Glu Thr Val Gln Ala Leu Leu Pro Val Leu Cys Gln Ala His Gly Leu
        515                 520                 525
Thr Pro Glu Gln Val Val Ala Ile Ala Ser His Asp Gly Gly Lys Gln
    530                 535                 540
Ala Leu Glu Thr Val Gln Arg Leu Leu Pro Val Leu Cys Gln Ala His
545                 550                 555                 560
Gly Leu Thr Pro Glu Gln Val Val Ala Ile Ala Ser His Asp Gly Gly
                565                 570                 575
Lys Gln Ala Leu Glu Thr Val Gln Arg Leu Leu Pro Val Leu Cys Gln
            580                 585                 590
Ala His Gly Leu Thr Pro Glu Gln Val Val Ala Ile Ala Ser His Asp
        595                 600                 605
Gly Gly Lys Gln Ala Leu Glu Thr Val Gln Arg Leu Leu Pro Val Leu
    610                 615                 620
Cys Gln Ala His Gly Leu Thr Pro Glu Gln Val Val Ala Ile Ala Ser
625                 630                 635                 640
Asn Ile Gly Gly Lys Gln Ala Leu Glu Thr Val Gln Ala Leu Leu Pro
                645                 650                 655
Val Leu Cys Gln Ala His Gly Leu Thr Pro Gln Gln Val Val Ala Ile
            660                 665                 670
Ala Ser Asn Asn Gly Gly Lys Gln Ala Leu Glu Thr Val Gln Arg Leu
        675                 680                 685
Leu Pro Val Leu Cys Gln Ala His Gly Leu Thr Pro Glu Gln Val Val
    690                 695                 700
Ala Ile Ala Ser Asn Ile Gly Gly Lys Gln Ala Leu Glu Thr Val Gln
705                 710                 715                 720
Ala Leu Leu Pro Val Leu Cys Gln Ala His Gly Leu Thr Pro Gln Gln
                725                 730                 735
Val Val Ala Ile Ala Ser Asn Asn Gly Gly Lys Gln Ala Leu Glu Thr
            740                 745                 750
```

-continued

```
Val Gln Arg Leu Leu Pro Val Leu Cys Gln Ala His Gly Leu Thr Pro
        755             760             765

Glu Gln Val Val Ala Ile Ala Ser His Asp Gly Gly Lys Gln Ala Leu
    770             775             780

Glu Thr Val Gln Arg Leu Leu Pro Val Leu Cys Gln Ala His Gly Leu
785             790             795             800

Thr Pro Gln Gln Val Val Ala Ile Ala Ser Asn Gly Gly Arg Pro
            805             810             815

Ala Leu Glu Ser Ile Val Ala Gln Leu Ser Arg Pro Asp Pro Ala Leu
            820             825             830

Ala Ala Leu Thr Asn Asp His Leu Val Ala Leu Ala Cys Leu Gly Gly
            835             840             845

Arg Pro Ala Leu Asp Ala Val Lys Lys Gly Leu Gly Asp Pro Ile Ser
850             855             860

Arg Ser Gln Leu Val Lys Ser Glu Leu Glu Glu Lys Lys Ser Glu Leu
865             870             875             880

Arg His Lys Leu Lys Tyr Val Pro His Glu Tyr Ile Glu Leu Ile Glu
                885             890             895

Ile Ala Arg Asn Ser Thr Gln Asp Arg Ile Leu Glu Met Lys Val Met
            900             905             910

Glu Phe Phe Met Lys Val Tyr Gly Tyr Arg Gly Lys His Leu Gly Gly
            915             920             925

Ser Arg Lys Pro Asp Gly Ala Ile Tyr Thr Val Gly Ser Pro Ile Asp
    930             935             940

Tyr Gly Val Ile Val Asp Thr Lys Ala Tyr Ser Gly Gly Tyr Asn Leu
945             950             955             960

Pro Ile Gly Gln Ala Asp Glu Met Gln Arg Tyr Val Glu Glu Asn Gln
            965             970             975

Thr Arg Asn Lys His Ile Asn Pro Asn Glu Trp Trp Lys Val Tyr Pro
            980             985             990

Ser Ser Val Thr Glu Phe Lys Phe Leu Phe Val Ser Gly His Phe Lys
    995             1000            1005

Gly Asn Tyr Lys Ala Gln Leu Thr Arg Leu Asn His Ile Thr Asn Cys
    1010            1015            1020

Asn Gly Ala Val Leu Ser Val Glu Glu Leu Leu Ile Gly Gly Glu Met
1025            1030            1035            1040

Ile Lys Ala Gly Thr Leu Thr Leu Glu Glu Val Arg Arg Lys Phe Asn
            1045            1050            1055

Asn Gly Glu Ile Asn Phe Ala Ala Asp
            1060            1065
```